(12) United States Patent
Dockendorff et al.

(10) Patent No.: US 9,951,055 B2
(45) Date of Patent: Apr. 24, 2018

(54) THIAZOLE-BASED INHIBITORS OF SCAVENGER RECEPTOR BI

(71) Applicants: THE BROAD INSTITUTE, INC., Cambridge, MA (US); MASSACHUSETTS INSTITUTE OF TECHNOLOGY, Cambridge, MA (US)

(72) Inventors: Chris Dockendorff, Milwaukee, WI (US); Willmen Youngsaye, Cumberland, RI (US); Partha Pratim Nag, Somerville, MA (US); Timothy A. Lewis, Marlborough, MA (US); Sivaraman Dandapani, Malden, MA (US); Benito Munoz, Newtonville, MA (US); Patrick Faloon, Cambridge, MA (US); Thomas Nieland, Somerville, MA (US); Monty Krieger, Needham, MA (US); Miao Yu, Quincy, MA (US)

(73) Assignees: Massachusetts Institute of Technology, Cambridge, MA (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 14/436,626

(22) PCT Filed: Oct. 21, 2013

(86) PCT No.: PCT/US2013/065988
§ 371 (c)(1),
(2) Date: Apr. 17, 2015

(87) PCT Pub. No.: WO2014/063167
PCT Pub. Date: Apr. 24, 2014

(65) Prior Publication Data
US 2016/0060254 A1 Mar. 3, 2016

Related U.S. Application Data

(60) Provisional application No. 61/716,136, filed on Oct. 19, 2012.

(51) Int. Cl.
*C07D 277/44* (2006.01)
*C07D 417/12* (2006.01)
*C07D 417/14* (2006.01)
*C07D 417/04* (2006.01)
*C07D 491/048* (2006.01)

(52) U.S. Cl.
CPC .......... *C07D 417/04* (2013.01); *C07D 277/44* (2013.01); *C07D 417/12* (2013.01); *C07D 417/14* (2013.01); *C07D 491/048* (2013.01)

(58) Field of Classification Search
CPC ... C07D 277/44; C07D 417/12; C07D 417/14

USPC ........................................................ 548/195
See application file for complete search history.

(56) References Cited

U.S. PATENT DOCUMENTS 5,491,159 A 2/1996 Malamas
2012/0202794 A1 8/2012 Sofia et al.

FOREIGN PATENT DOCUMENTS

| WO | 2006122011 A2 | 11/2006 |
| WO | 2007070600 A2 | 6/2007 |
| WO | WO-2007/076055 A2 * | 7/2007 |
| WO | 2008124000 A2 | 10/2008 |

OTHER PUBLICATIONS

Chemical Abstracts Registry No. 847731-88-8, indexed in the Registry file on STN CAS Online Mar. 31, 2005.*
Chemical Abstracts Registry No. 794575-89-6, indexed in the Registry file on STN CAS Online Dec. 8, 2004.*
Chemical Abstracts Registry No. 837419-84-8, indexed in the Registry file on STN CAS Online Feb. 25, 2005.*
Chemical Abstracts Registry No. 838087-09-5, indexed in the Registry file on STN CAS Online Feb. 27, 2005.*
PubChem CID 1458848—National Center for Biotechnology Information. PubChem Compound Database; CID=1458848, https://pubchem.ncbi.nlm.nih.gov/compound/1458848 (accessed May 4, 2016), create date Jul. 11, 2005.*
PubChem CID 28861334—National Center for Biotechnology Information. PubChem Compound Database; CID=28861334, https://pubchem.ncbi.nlm.nih.gov/compound/28861334 (accessed May 4, 2016), create date May 28, 2009.*
PubChem CID 36288428—National Center for Biotechnology Information. PubChem Compound Database; CID=36288428, https://pubchem.ncbi.nlm.nih.gov/compound/36288428 (accessed May 4, 2016), create date May 29, 2009.*
PubChem CID 53347984—National Center for Biotechnology Information. PubChem Compound Database; CID=53347984, https://pubchem.ncbi.nlm.nih.gov/compound/53347984 (accessed Oct. 7, 2016), create date Sep. 2, 2011.*
PubChem CID 53347941—National Center for Biotechnology Information. PubChem Compound Database; CID=53347941, https://pubchem.ncbi.nlm.nih.gov/compound/53347941 (accessed Oct. 7, 2016), create date Sep. 2, 2011.*
PubChem CID 53377439—National Center for Biotechnology Information. PubChem Compound Database; CID=53377439, https://pubchem.ncbi.nlm.nih.gov/compound/53377439 (accessed Oct. 7, 2016), create date Oct. 4, 2011.*
PubChem CID 1451020—National Center for Biotechnology Information. PubChem Compound Database; CID=1451020, https://pubchem.ncbi.nlm.nih.gov/compound/1451020 (accessed Oct. 7, 2016), create date Jul. 11, 2005.*
PubChem CID 1458353—National Center for Biotechnology Information. PubChem Compound Database; CID=1458353, https://pubchem.ncbi.nlm.nih.gov/compound/1458353 (accessed Oct. 7, 2016), create date Jul. 11, 2005.*

(Continued)

*Primary Examiner* — Laura L. Stockton
(74) *Attorney, Agent, or Firm* — Thomas J. Engellenner; Reza Mollaaghababa; Pepper Hamilton LLP

(57) ABSTRACT

This application describes compounds and methods that can inhibit Scavenger receptor class B, type I (SR-BI) activity, which compounds and methods can used, for example, to mediate high-density lipoprotein (HDL) lipid uptake and treat hepatitis C viral infections.

10 Claims, 128 Drawing Sheets

(56) References Cited

OTHER PUBLICATIONS

PubChem CID 1458888—National Center for Biotechnology Information. PubChem Compound Database; CID=1458888, https://pubchem.ncbi.nlm.nih.gov/compound/1458888 (accessed Oct. 7, 2016), create date Jul. 11, 2005.*

PubChem CID 43816469—National Center for Biotechnology Information. PubChem Compound Database; CID=43816469, https://pubchem.ncbi.nlm.nih.gov/compound/43816469 (accessed Oct. 7, 2016), create date Jul. 21, 2009.*

PubChem CID 53347940—National Center for Biotechnology Information. PubChem Compound Database; CID=53347940, https://pubchem.ncbi.nlm.nih.gov/compound/53347940 (accessed Oct. 7, 2016), create date Sep. 2, 2011.*

PubChem CID 53347958—National Center for Biotechnology Information. PubChem Compound Database; CID=53347958, https://pubchem.ncbi.nlm.nih.gov/compound/53347958 (accessed Oct. 7, 2016), create date Sep. 2, 2011.*

Chemical Abstracts Registry No. 837418-96-9, indexed in the Registry file on STN CAS Online Feb. 25, 2005.*

Chemical Abstracts Registry No. 837418-97-0, indexed in the Registry file on STN CAS Online Feb. 25, 2005.*

PubChem CID 1458965—National Center for Biotechnology Information. PubChem Compound Database; CID=1458965, https://pubchem.ncbi.nlm.nih.gov/compound/1458965 (accessed Mar. 2, 2017), create date Jul. 11, 2005.*

PubChem CID 1459074—National Center for Biotechnology Information. PubChem Compound Database; CID=1459074, https://pubchem.ncbi.nlm.nih.gov/compound/1459074 (accessed Mar. 2, 2017), create date Jul. 11, 2005.*

PubChem CID 1459077—National Center for Biotechnology Information. PubChem Compound Database; CID=1459077, https://pubchem.ncbi.nlm.nih.gov/compound/1459077 (accessed Mar. 2, 2017), create date Jul. 11, 2005.*

PubChem CID 1458885—National Center for Biotechnology Information. PubChem Compound Database; CID=1458885, https://pubchem.ncbi.nlm.nih.gov/compound/1458885 (accessed Mar. 2, 2017), create date Jul. 11, 2005.*

PubChem CID 1458868—National Center for Biotechnology Information. PubChem Compound Database; CID=1458868, https://pubchem.ncbi.nlm.nih.gov/compound/1458868 (accessed Mar. 2, 2017), create date Jul. 11, 2005.*

Chemical Abstracts Registry No. 846573-92-0, indexed in the Registry file on STN CAS Online Mar. 22, 2005.*

Chemical Abstracts Registry No. 838090-02-1, indexed in the Registry file on STN CAS Online Feb. 27, 2005.*

Chemical Abstracts Registry No. 838089-78-4, indexed in the Registry file on STN CAS Online Feb. 27, 2005.*

Chemical Abstracts Registry No. 838089-12-6, indexed in the Registry file on STN CAS Online Feb. 27, 2005.*

Wiley, http://www.wiley.com/legacy/Australia/Landing_Pages/Chem_1_VCE_U1&2_c08_web.pdf, Chapter 8 "Organic Chemistry", pp. 153-157, accessed Mar. 3, 2017.*

Chemical Abstracts Registry No. 838089-60-4, indexed in the Registry file on STN CAS Online Feb. 27, 2005.*

International Search Report, PCT/US2013/065988, dated Nov. 22, 2013 (3 sheets).

Andrew J. Syder et al. "Small Molecule Scavenger Receptor BI Antagonists are Potent HCV Entry Inhibitors", Journal of Hepatology, vol. 54, No. pp. 48-55 (2011).

Kazuya Yoshiizumi et al., "Studies on Scavenger Receptor Inhibitors, Part 1: Synthesis and Structure-Activity Relationships of Novel Derivatives of Sulfatides", Bioorganic & Medicinal Chemistry, vol. 10, No. 8, 2002, pp. 2445-2460 (2002).

International Search Report for PCT/US2013/065991 dated Dec. 13, 2013.

National Center for Biotechnology Information. PubChemSubstance Database; SID-14404423, https://pubchem.ncbi.nlm.nih.gov/substance/124404423 (accessed Sep. 24, 2015) available date Aug. 1, 2012.

Office Action for related U.S. Appl. No. 14/436,610 dated Oct. 7, 2015.

* cited by examiner

| CID/ ML No. | Target | IC$_{50}$ (µM) [SID, AID] | Antitarget | IC$_{50}$ (µM) [SID, AID] | Fold Selective | Secondary Assay(s): IC$_{50}$ (µM) [SID, AID] |
|---|---|---|---|---|---|---|
| 53377439/ ML278 | mSR-BI-mediated HDL uptake | IC$_{50}$= 0.00093 [125299400, 588828] | 24-hour cytotoxicity | IC$_{50}$ >35 µM [125299400, 588829] | >1000x | 1) 3 hour cytotoxicity >35 µM [115950070, 588830] 2) [ldlA7] Dil-HDL uptake >35 µM [125299400, 588825] |

Percent (%) Recovered is relative to the undissolved solid recovered at T = 0 (100%), quantified by LC-MS.

| | |
|---|---|
| IUPAC chemical name | 3,5-dimethoxy-*N*-(4-(1-(2-methoxyacetyl)-1H-indol-5-yl)thiazol-2-yl)benzamide |
| PubChem CID | 53377439 |
| Molecular Weight | 453.51082 [g/mol] |
| Molecular Formula | $C_{23}H_{23}N_3O_5S$ |
| Clog P* | 3.3 |
| H-Bond Donor | 1 |
| H-Bond Acceptor | 5 |
| Rotatable Bond Count | 7 |
| Exact Mass | 453.135842 |
| Topological Polar Surface Area | 118 |

*Properties calculated with ChemDraw, Version 12.0.

Scheme 1. Synthesis of Probe (ML278)

MLS001217863

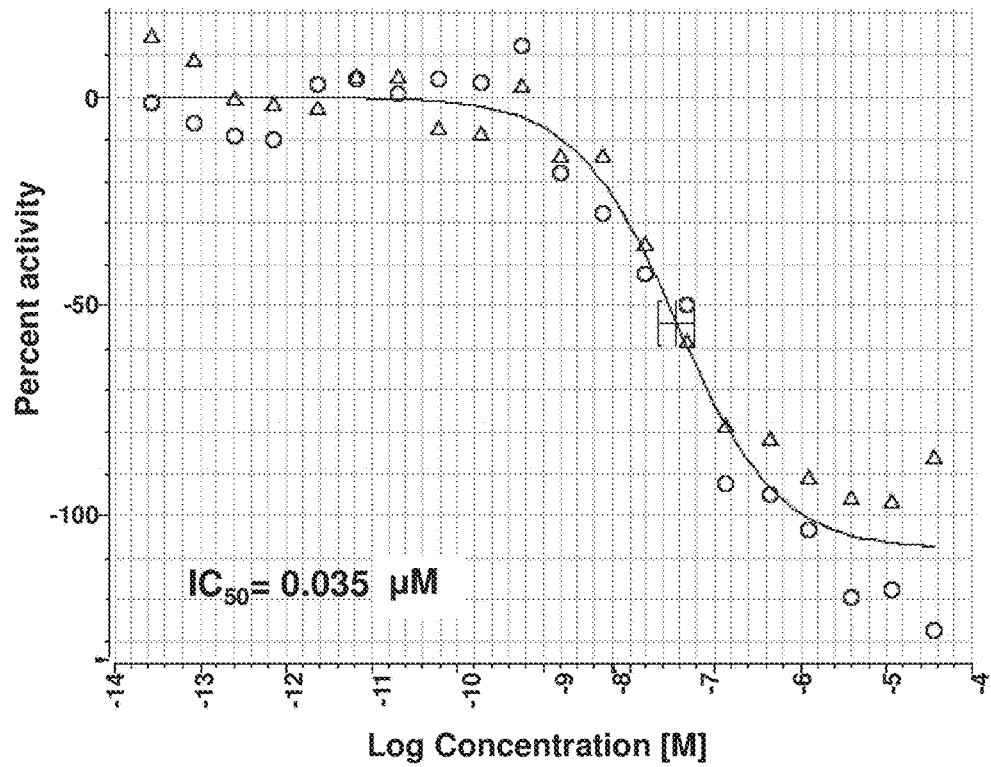

MLS001217863 (SID49678600, CID24761960) was used over a range of concentrations up to 35 μM in the primary assay and several secondary assays. Dose curves were generated with Genedata Condeseo and show normalized percent activity for the individual doses. DiI-HDL Uptake (AID 540354), $IC_{50}$= 0.035 μM (A); Alexa 488 HDL binding (AID 588810), $AC_{50}$=0.282 μM (B); 3h CellTiter-Glo (AID 588830), $AC_{50}$>35 μM (C) and 24h CellTiter-Glo (AID 540246), $IC_{50}$ >35 μM (D). o=replicate 1, Δ=replicate 2

*FIG. 8A*

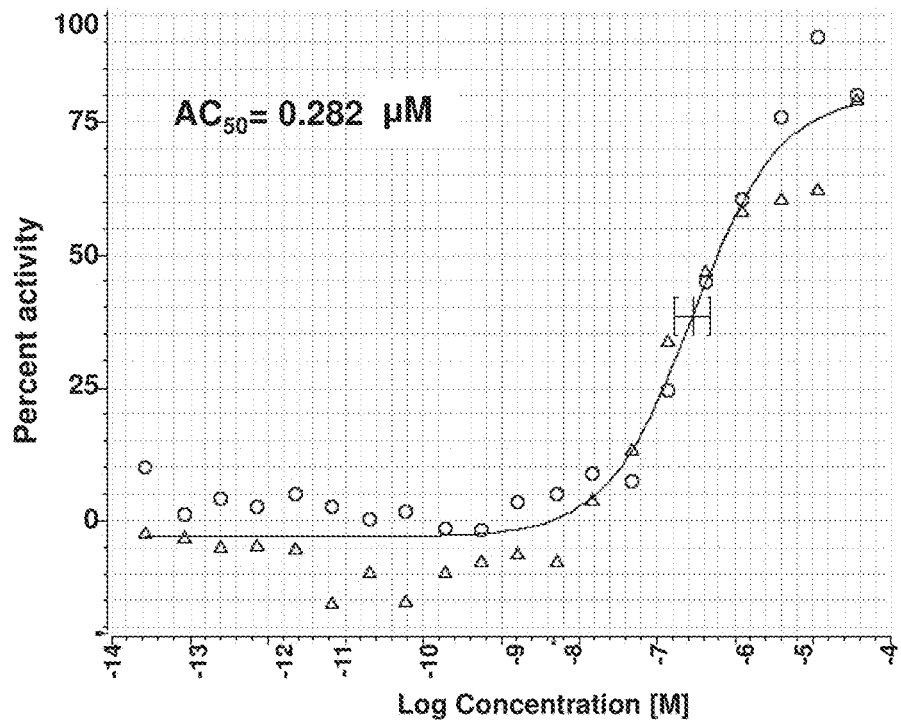

MLS001217863 (SID49678600, CID24761960) was used over a range of concentrations up to 35 μM in the primary assay and several secondary assays. Dose curves were generated with Genedata Condeseo and show normalized percent activity for the individual doses. DiI-HDL Uptake (AID 540354), $IC_{50}$= 0.035 μM (A); Alexa 488 HDL binding (AID 588810), $AC_{50}$=0.282 μM (B); 3h CellTiter-Glo (AID 588830), $AC_{50}$>35 μM (C) and 24h CellTiter-Glo (AID 540246), $IC_{50}$ >35 μM (D). o=replicate 1, Δ=replicate 2

*FIG. 8B*

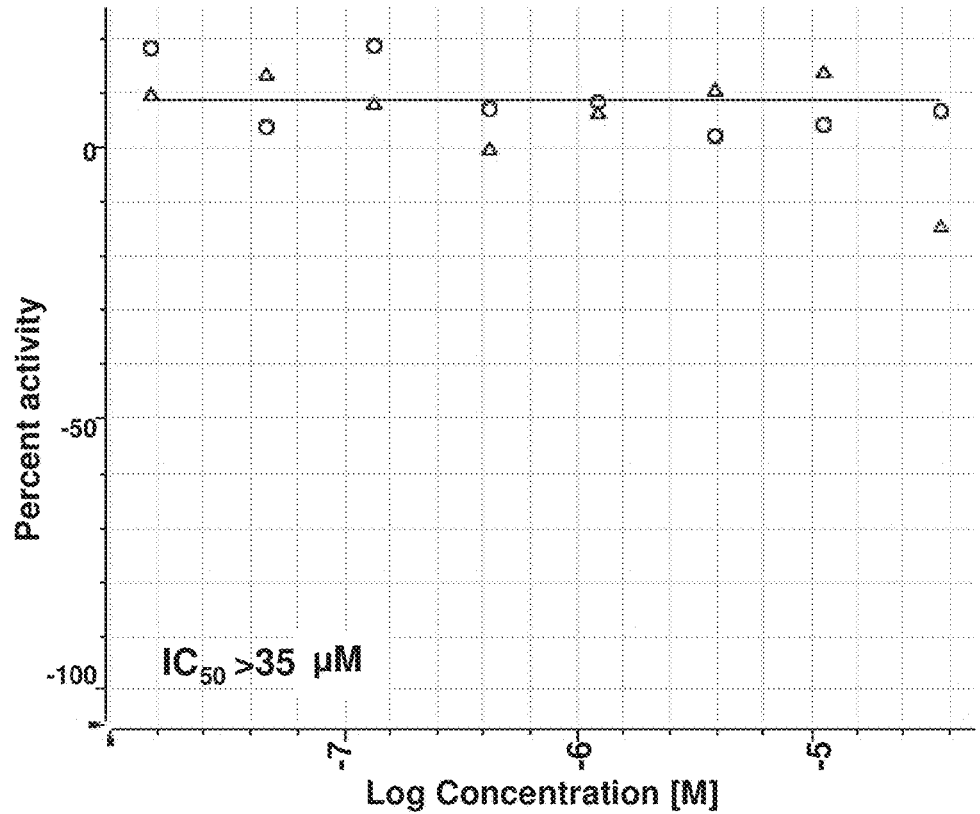

MLS001217863 (SID49678600, CID24761960) was used over a range of concentrations up to 35 μM in the primary assay and several secondary assays. Dose curves were generated with Genedata Condeseo and show normalized percent activity for the individual doses. DiI-HDL Uptake (AID 540354), $IC_{50}$= 0.035 μM (A); Alexa 488 HDL binding (AID 588810), $AC_{50}$=0.282 μM (B); 3h CellTiter-Glo (AID 588830), $AC_{50}$>35 μM (C) and 24h CellTiter-Glo (AID 540246), $IC_{50}$ >35 μM (D). o=replicate 1, Δ=replicate 2

*FIG. 8C*

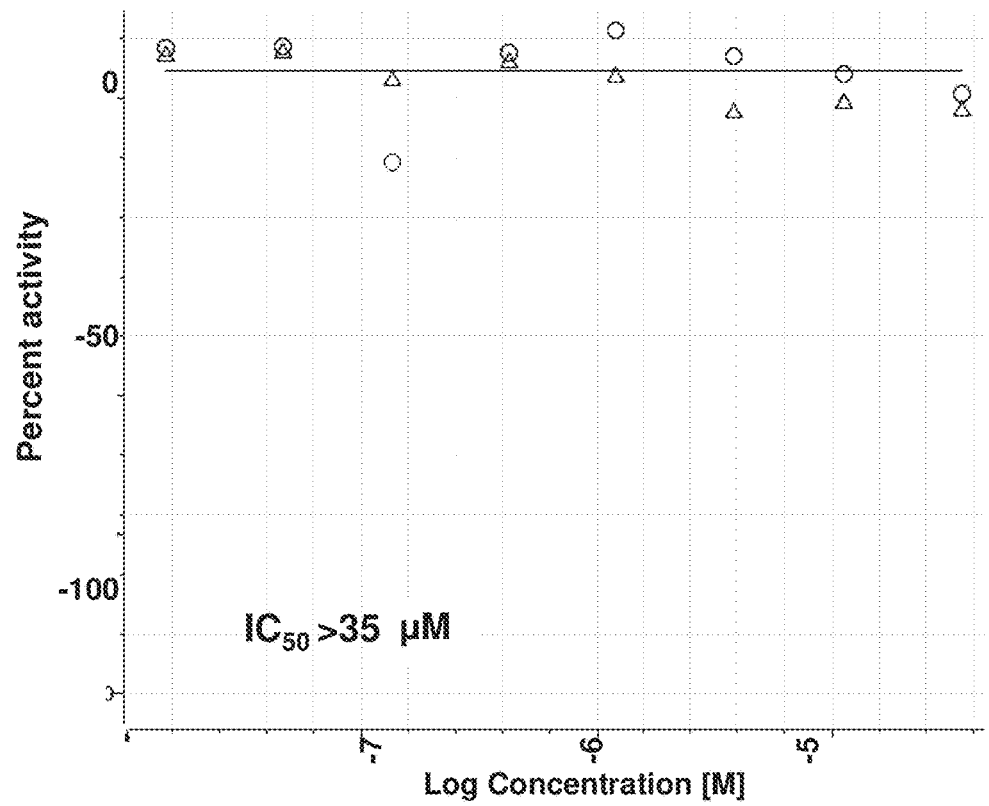

MLS001217863 (SID49678600, CID24761960) was used over a range of concentrations up to 35 μM in the primary assay and several secondary assays. Dose curves were generated with Genedata Condeseo and show normalized percent activity for the individual doses. DiI-HDL Uptake (AID 540354), $IC_{50}=$ 0.035 μM (A); Alexa 488 HDL binding (AID 588810), $AC_{50}=0.282$ μM (B); 3h CellTiter-Glo (AID 588830), $AC_{50}>35$ μM (C) and 24h CellTiter-Glo (AID 540246), $IC_{50} >35$ μM (D). o=replicate 1, Δ=replicate 2

*FIG. 8D*

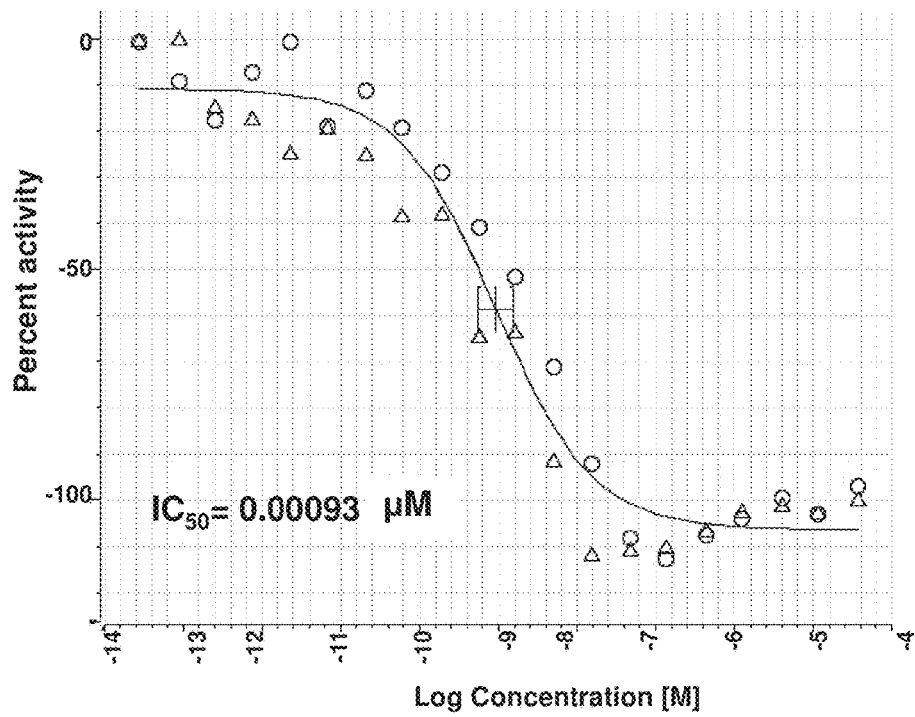

ML278 was used over a range of concentrations up to 35 μM in the primary DiI-HDL uptake assay, $IC_{50}$=0.00093 μM (AID 588828) (A), Alexa-488 HDL binding assay, $AC_{50}$ = 0.035 μM (AID 588810) (B), 24-h CellTiter-Glo cytotoxicity, $IC_{50}$ > 35 μM (AID 588829) (C), and the DiI-HDL ldlA7 counterscreen, $IC_{50}$ >35 μM (AID 588825) (D). Dose curves were generated with Genedata Condeseo and shows normalized percent activity for the individual doses. O=replicate 1, Δ=replicate 2

*FIG. 10A*

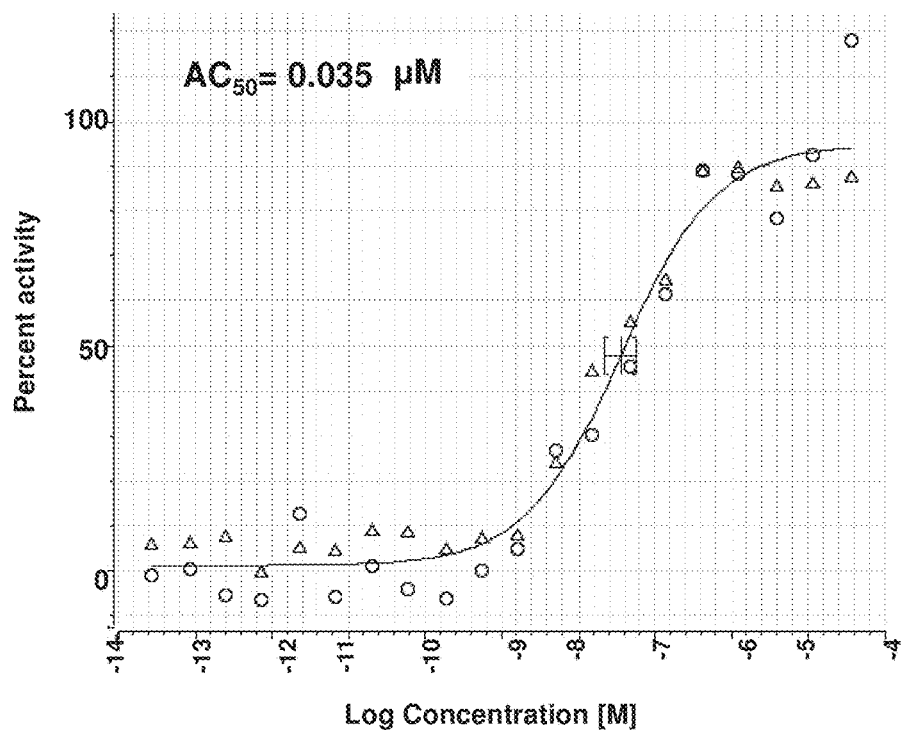

ML278 was used over a range of concentrations up to 35 µM in the primary DiI-HDL uptake assay, $IC_{50}$=0.00093 µM (AID 588828) (A), Alexa-488 HDL binding assay, $AC_{50}$ = 0.035 µM (AID 588810) (B), 24-h CellTiter-Glo cytotoxicity, $IC_{50}$ > 35 µM (AID 588829) (C), and the DiI-HDL ldlA7 counterscreen, $IC_{50}$ >35 µM (AID 588825) (D). Dose curves were generated with Genedata Condeseo and shows normalized percent activity for the individual doses. O=replicate 1, Δ=replicate 2

*FIG. 10B*

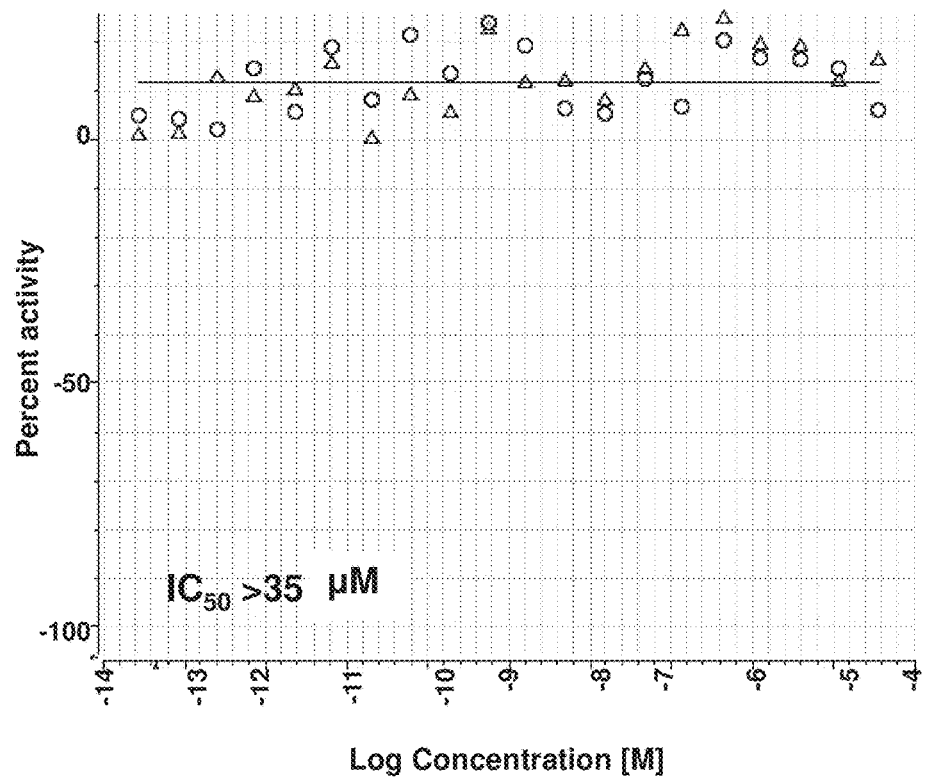

ML278 was used over a range of concentrations up to 35 μM in the primary DiI-HDL uptake assay, $IC_{50}$=0.00093 μM (AID 588828) (A), Alexa-488 HDL binding assay, $AC_{50}$ = 0.035 μM (AID 588810) (B), 24-h CellTiter-Glo cytotoxicity, $IC_{50}$ > 35 μM (AID 588829) (C), and the DiI-HDL ldlA7 counterscreen, $IC_{50}$ >35 μM (AID 588825) (D). Dose curves were generated with Genedata Condeseo and shows normalized percent activity for the individual doses. O=replicate 1, Δ=replicate 2

*FIG. 10C*

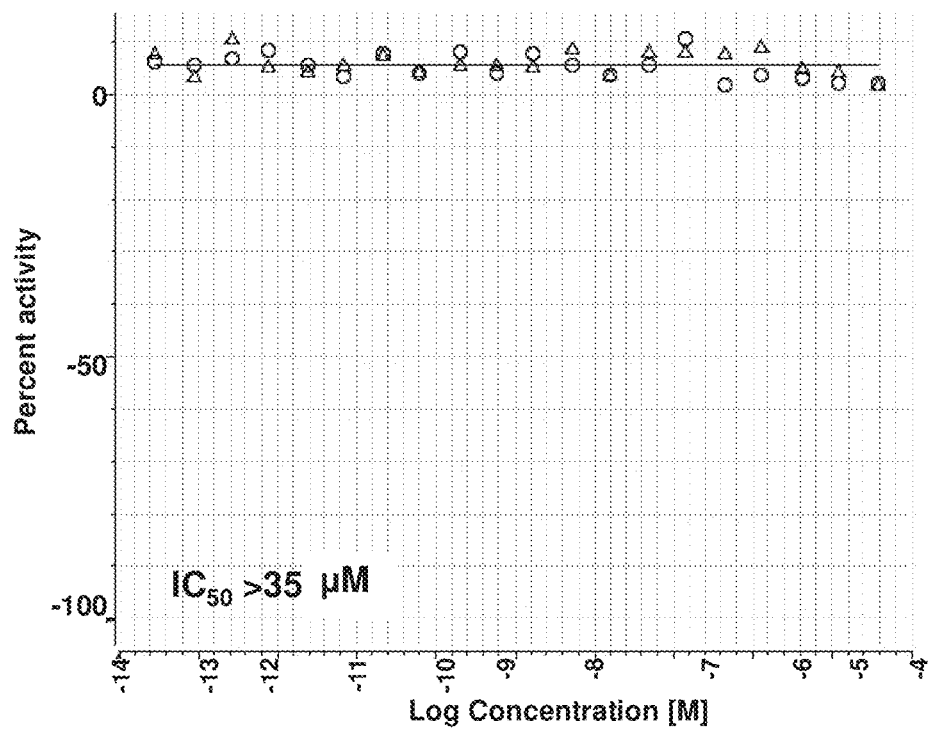

ML278 was used over a range of concentrations up to 35 μM in the primary DiI-HDL uptake assay, $IC_{50}$=0.00093 μM (AID 588828) (A), Alexa-488 HDL binding assay, $AC_{50}$ = 0.035 μM (AID 588810) (B), 24-h CellTiter-Glo cytotoxicity, $IC_{50}$ > 35 μM (AID 588829) (C), and the DiI-HDL ldlA7 counterscreen, $IC_{50}$ >35 μM (AID 588825) (D). Dose curves were generated with Genedata Condeseo and shows normalized percent activity for the individual doses. ○=replicate 1, △=replicate 2

*FIG. 10D*

Table 2. SAR Analysis of Probe 1 Western Amide: 5-Membered Heterocycles
| Entry No. | CID / SID / Broad ID | * | Structure | Potency (µM) SR-BI-mediated lipid uptake | | Potency (µM) 24-hour Cytotoxicity | | Toxicity /Activity |
|---|---|---|---|---|---|---|---|---|
| | | | | n | IC$_{50}$ | n | IC$_{50}$ | |
| 1 | 24761960 / 49678600 / K10405667-001 | P | 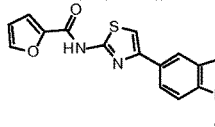 | 4 | 0.057 | 2 | >35 | >600 |
| 2 | 53262914 / 124404426 / K44559894-001 | S | 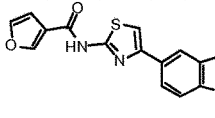 | 4 | 9.8 | 2 | >35 | >3.5 |
| 3 | 53347982 / 125082007 / A49856563-001 | S | 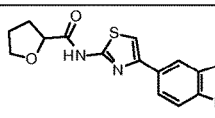 | 4 | 5.4 | 2 | >35 | >6.5 |
| 4 | 53348009 / 125082008 / K69660403-001 | S | 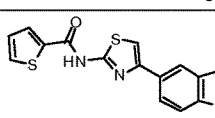 | 4 | 2.1 | 2 | >35 | >17 |
| 5 | 53262916 / 124404425 / K55327617-001 | S | 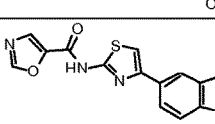 | 4 | 0.90 | 2 | >35 | >39 |
| 6 | 53347968 / 125082010 / K12056740-001 | S | 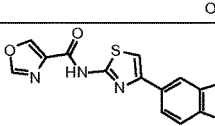 | 2 | 14.1 | 2 | >35 | >2.5 |
| 7 | 53347974 / 125082020 / K64985467-001 | S | 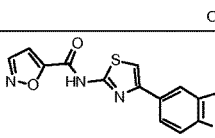 | 2 | 1.6 | 2 | >35 | >22 |
NT=not tested
FIG. 11

Table 3. SAR Analysis of Probe 1 Western Amide: Other Heteroarenes

| Entry No. | CID / SID / Broad ID | * | Structure | Potency (µM) SR-BI-mediated lipid uptake | | Potency (µM) 24-hour Cytotoxicity | | Toxicity /Activity |
|---|---|---|---|---|---|---|---|---|
| | | | | n | IC$_{50}$ | n | IC$_{50}$ | |
| 1 | 53348003 / 12508199 / K02489819-001 | S | 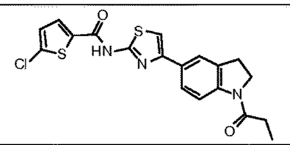 | 2 | 0.58 | 2 | >35 | >60 |
| 2 | 53262919 / 124404427 / K35016301-001 | S | 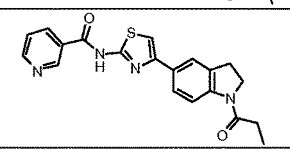 | 4 | 0.26 | 2 | >35 | >135 |
| 3 | 53262921 / 124404428 / K27796191-001 | S | 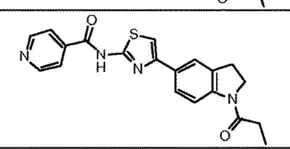 | 4 | 0.29 | 2 | >35 | >120 |
| 4 | -- / -- / K87022490-001 | S | 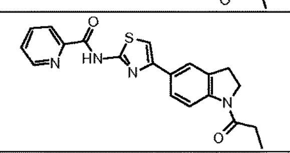 | -- | NT | | NT | NT |
| 5 | 53393838 / 125333445 / K07787731-001 | S | 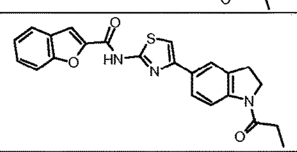 | 2 | 0.26 | | NT | NT |
| 6 | 53377424 / 125299413 / K25657317-001 | S | 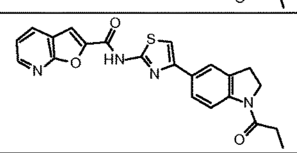 | 2 | 0.14 | 2 | >35 | >18 |
| 7 | 53347952 / 125082031 / K38653113-001 | S | 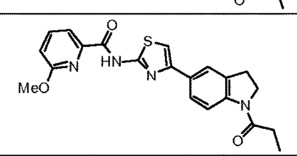 | 2 | 0.53 | 2 | >35 | >18 |

NT=Not tested; S=synthesized

*FIG. 12*

Table 4. SAR Analysis of Probe 1 Western Amide: Selected Arene Analogs

| Entry No. | CID / SID / Broad ID | * | Structure | Potency (µM) SR-BI-mediated lipid uptake | | Potency (µM) 24-hour Cytotoxicity | | Toxicity /Activity |
|---|---|---|---|---|---|---|---|---|
| | | | | n | $IC_{50}$ | n | $IC_{50}$ | |
| 1 | 53262918 / 124404421 / K63769158-001 | S | 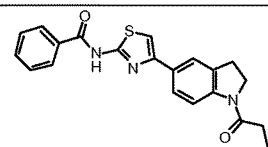 | 4 | 2.2 | 2 | >35 | >18 |
| 2 | 1458888 / 124404430 / K39070571-001 | S | 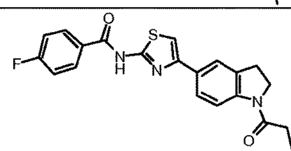 | 4 | 1.4 | 2 | >35 | >25 |
| 3 | 53347958 / 125081998 / K83202212-001 | S | 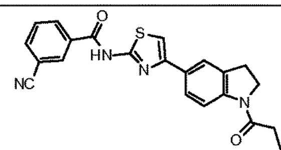 | 2 | 1.5 | 2 | >35 | >23 |
| 4 | 53262913 / 124404429 / K25116319-001 | S | 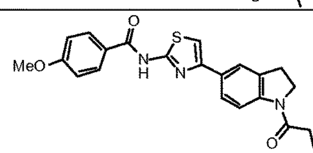 | 4 | 0.17 | 2 | >35 | >200 |
| 5 | 1458885 / 125082005 / K25412576-001 | S | 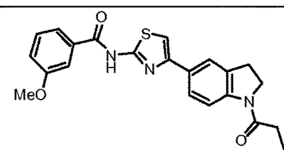 | 4 | 0.038 | 2 | >35 | >920 |
| 6 | 53347940 / 25082027 / K18773012-001 | S | 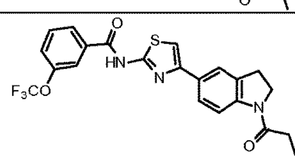 | 4 | 0.11 | 2 | >35 | >320 |
| 7 | 53347941 / 125082028 / K93724056-001 | S | 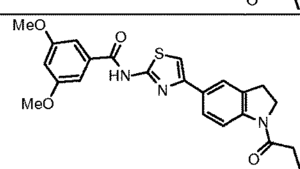 | 6 | 0.033 | 2 | >35 | >1000 |

S=synthesized

*FIG. 13*

Table 5. SAR Analysis of Probe 1: Functional Group Modifications and Central Ring SAR

| Entry No. | CID / SID / Broad ID | * | Structure | Potency (μM) SR-BI-mediated lipid uptake | | Potency (μM) 24-hour Cytotoxicity | | Toxicity /Activity |
|---|---|---|---|---|---|---|---|---|
| | | | | n | $IC_{50}$ | n | $IC_{50}$ | |
| 1 | 53377425 / 125299409 / K56909279-001 | S | 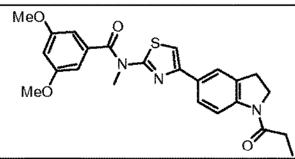 | 2 | 0.18 | 2 | 15 | >200 |
| 2 | 53393842 / 12533449 / K61652319-003 | S | 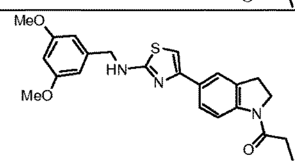 | 2 | 0.37 | | NT | NT |
| 3 | 53347969 / 125082032 / K48555455-001 | S | 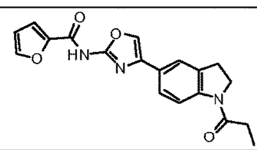 | 2 | 18.9 | 2 | >35 | >2 |
| 4 | 53347964 / 125082025 / K32819859-001 | S | 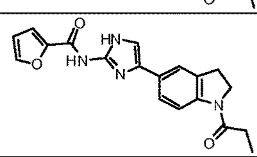 | 2 | 10.1 | 2 | >35 | >3.5 |
| 5 | 53377423 / 125299405 / K94701818-001 | S | 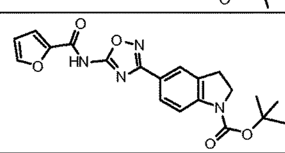 | 2 | 13.9 | 2 | >35 | >2.5 |
| 6 | 53393834 / 125333450 / K62979870-001 | S | 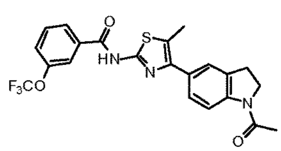 | 4 | 0.040 | 2 | >35 | >875 |

NT=not tested; S=synthesized

*FIG. 14*

Table 6. SAR Analysis of Probe 1: Modifications to Indoline Ring

| Entry No. | CID / SID / Broad ID | * | Structure | Potency (μM) SR-BI-mediated lipid uptake | | Potency (μM) 24-hour Cytotoxicity | | Toxicity /Activity |
|---|---|---|---|---|---|---|---|---|
| | | | | n | IC$_{50}$ | n | IC$_{50}$ | |
| 1 | 53377450 / 125299408 / K55587176-019 | S | 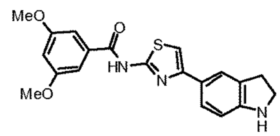 | 2 | 0.11 | 2 | >35 | >318 |
| 2 | 53377427 / 125299415 / K31439710-001 | S | 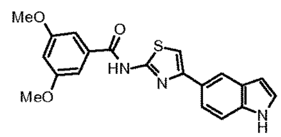 | 2 | 0.28 | 2 | 15.7 | >125 |
| 3 | 53393833 / 125333447 / K26007143-001 | S | 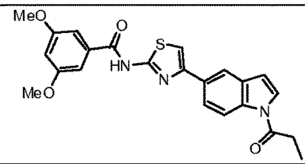 | 4 | 0.10 | | NT | NT |
| 4 | 53377433 / 125299412 / K14769165-001 | S | 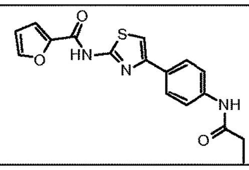 | 2 | 2.0 | 2 | >35 | >18 |
| 5 | 53377426 / 125299398 / K84589623-001 | S | 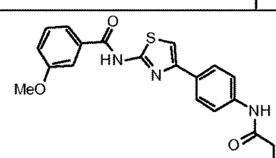 | 6 | 0.066 | 2 | >35 | >530 |
| 6 | 53393841 / 125333448 / K47808164-001 | S | 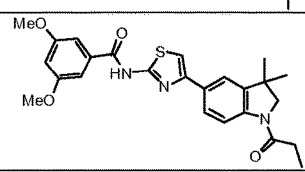 | 4 | 0.008 | 2 | >35 | >4375 |
| 7 | 53393840 / 125333444 / K01424506-001 | S | 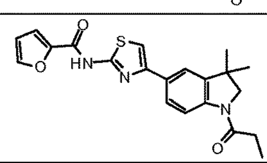 | 4 | 0.023 | | NT | NT |

S=synthesized, NT = Not Tested

*FIG. 15A*

Further modifications to indoline ring[a]
| Cmp | Structure | IC$_{50}$ (µM)[a] | Cmp | Structure | IC$_{50}$ (µM)[a] |
|---|---|---|---|---|---|
| 18 | 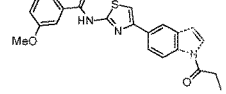 | 0.10 | 23 | 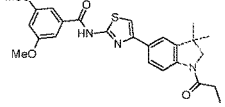 | 0.008 |
| 19 | 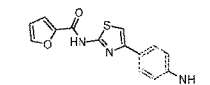 | 2.0 | 24 | 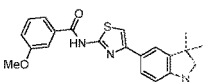 | 0.2 |
| 20 | 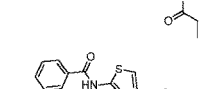 | 0.066 | 25 | 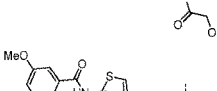 | 0.09 |
| 21 | 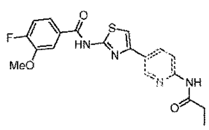 | 0.2 | 26 | 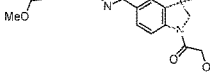 | 0.4 |
| 22 | 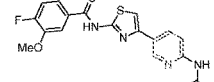 | 0.023 | 27 | 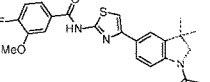 | 0.07 |
|  |  |  | 28 | 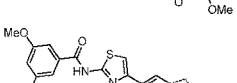 | 0.09 |
[a] Average of at least two measurements in SR-BI-mediated diI uptake assay.
*FIG. 15B*

Table 7. SAR Analysis of Probe 1 Eastern N-substitutent: Select Analogs
| Entry No. | CID | * | Structure | Potency (µM) | | | | Toxicity/ Activity |
| --- | --- | --- | --- | --- | --- | --- | --- | --- |
| | SID | | | SR-BI-mediated lipid uptake | | 24-hour Cytotoxicity | | |
| | Broad ID | | | n | IC$_{50}$ | n | IC$_{50}$ | |
| 1 | 53347949 | S | 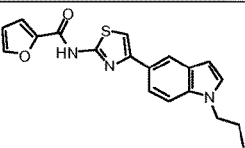 | 4 | 8.6 | 2 | >35 | >4 |
| | 125082003 | | | | | | | |
| | K79550860-001 | | | | | | | |
| 2 | 53348001 | S | 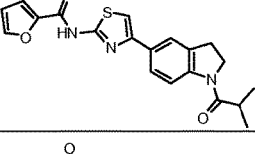 | 2 | 0.24 | 2 | >35 | >146 |
| | 125082026 | | | | | | | |
| | K84172559-001 | | | | | | | |
| 3 | 43816465 | S | 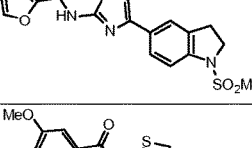 | 2 | 0.39 | 2 | >35 | >88 |
| | 125082042 | | | | | | | |
| | K58130477-001 | | | | | | | |
| 4 | 53377441 | S | 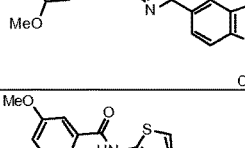 | 6 | 0.095 | 2 | >35 | >368 |
| | 125299401 | | | | | | | |
| | K78901905-001 | | | | | | | |
| 5 | 53377444 | S | 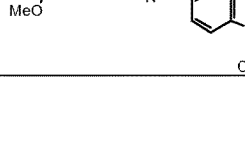 | 6 | 0.028 | 2 | >35 | >1250 |
| | 125299397 | | | | | | | |
| | K81155109-001 | | | | | | | |
FIG. 16A Table 7. SAR Analysis of Probe 1 Eastern N-substitutent: Select Analogs (cont'd)

Table 8. Comparison of the Probe to Project Criteria

| No. | Property | CPDP Requirement | Probe |
|---|---|---|---|
| 1 | Inhibition of DiI-HDL uptake in ldlA[mSR-BI] cells | $IC_{50}$<10 µM | Avg. $IC_{50}$= 0.002 µM |
| 2 | Selectivity; receptor mediated endocytosis | No effect at effective $IC_{50}$ (0.002 µM) | No effect at up to 35 µM |
| 3 | Biological Mode of Action | Reversible inhibition of SR-BI mediated uptake | Reversible |
| 4 | Cellular toxicity | Non-toxic at >30 µM at 3 h | Non-toxic with $IC_{50}$ >35 µM at 24 h |
| 5 | Functional groups | Avoid chemically reactive groups, metabolically labile groups, pH sensitive or hydrolytically unstable groups | No reactive functionality |
| 6 | Solubility | Soluble in aqueous buffer | 0.57 µM in PBS (pH 7.4, 23 °C) |

FIG. 18

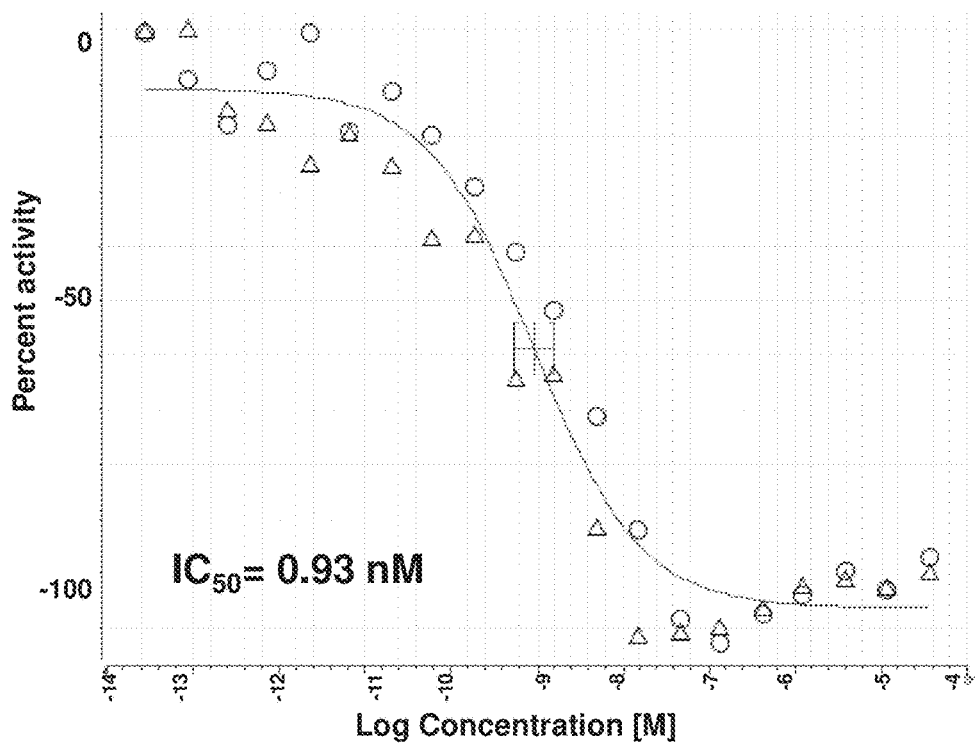

ML278 was tested against two compounds (BLT-1 and ITX-5061) in the DiI-HDL uptake assay. Each compound was used over a range of concentrations up to 35 µM. Concentration response curves were generated using Genedata Condeseo and show normalized percent activity for the individual doses (AID 588828). ML278, $IC_{50}$ = 0.93 nM (A); BLT-1 $IC_{50}$ = 10.8 nM (B); ITX-5061, $IC_{50}$ = 254 nM (C); and ML279, $IC_{50}$ = 16.2 nM. Note: Single 1 µM BLT-1 data points appear as a tight column because this dose of BLT-1 was used as the positive control and tested in dose in separate wells. ○=replicate 1, △=replicate 2

*FIG. 19A*

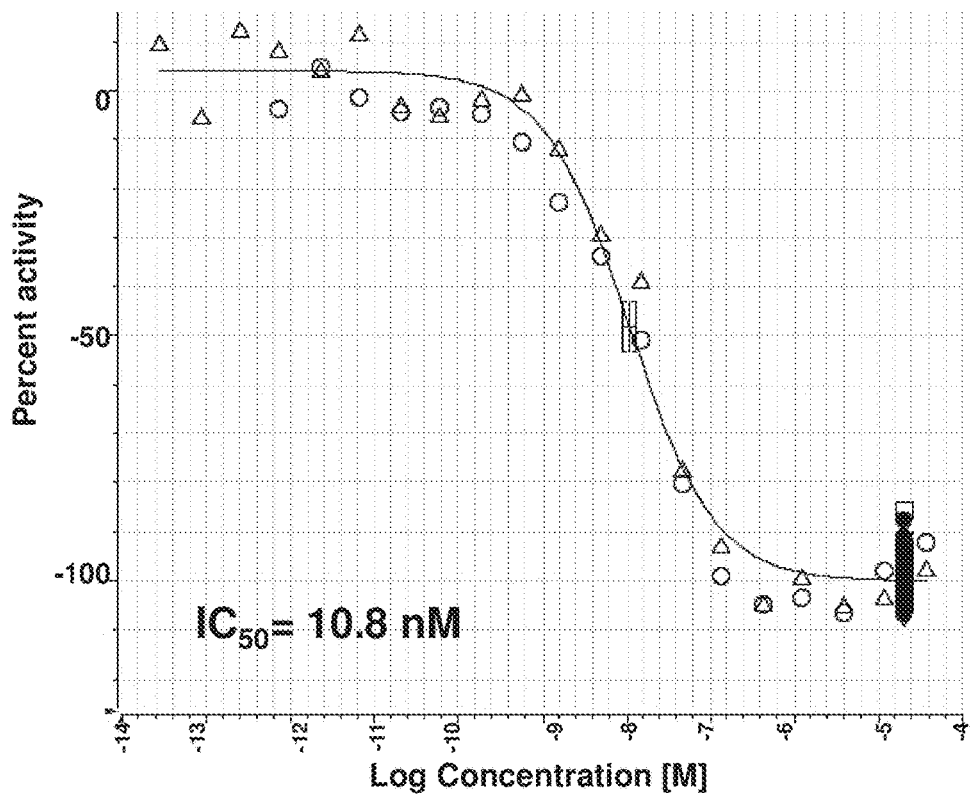

ML278 was tested against two compounds (BLT-1 and ITX-5061) in the DiI-HDL uptake assay. Each compound was used over a range of concentrations up to 35 μM. Concentration response curves were generated using Genedata Condeseo and show normalized percent activity for the individual doses (AID 588828), ML278, $IC_{50}$ = 0.93 nM (A); BLT-1 $IC_{50}$ = 10.8 nM (B); ITX-5061, $IC_{50}$ = 254 nM (C); and ML279, $IC_{50}$ = 16.2 nM. Note: Single 1 μM BLT-1 data points appear as a tight column because this dose of BLT-1 was used as the positive control and tested in dose in separate wells. ○=replicate 1, △=replicate 2

*FIG. 19B*

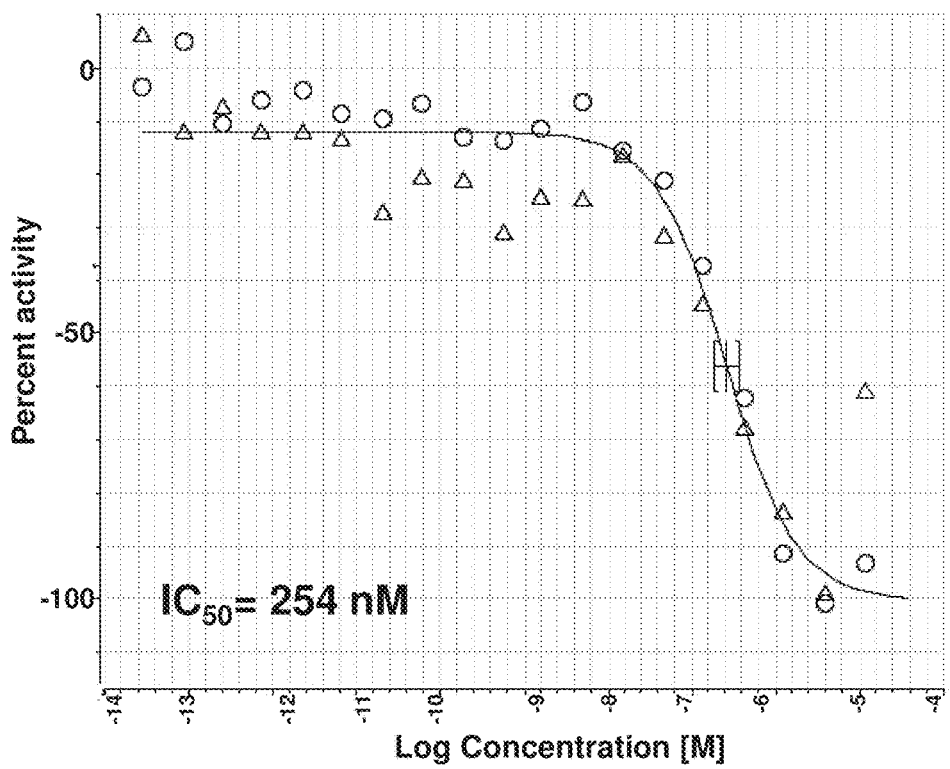

ML278 was tested against two compounds (BLT-1 and ITX-5061) in the DiI-HDL uptake assay. Each compound was used over a range of concentrations up to 35 µM. Concentration response curves were generated using Genedata Condeseo and show normalized percent activity for the individual doses (AID 588828), ML278, $IC_{50}$ = 0.93 nM (A); BLT-1 $IC_{50}$ = 10.8 nM (B); ITX-5061, $IC_{50}$ = 254 nM (C); and ML279, $IC_{50}$ = 16.2 nM. Note: Single 1 µM BLT-1 data points appear as a tight column because this dose of BLT-1 was used as the positive control and tested in dose in separate wells. O=replicate 1, Δ=replicate 2

*FIG. 19C*

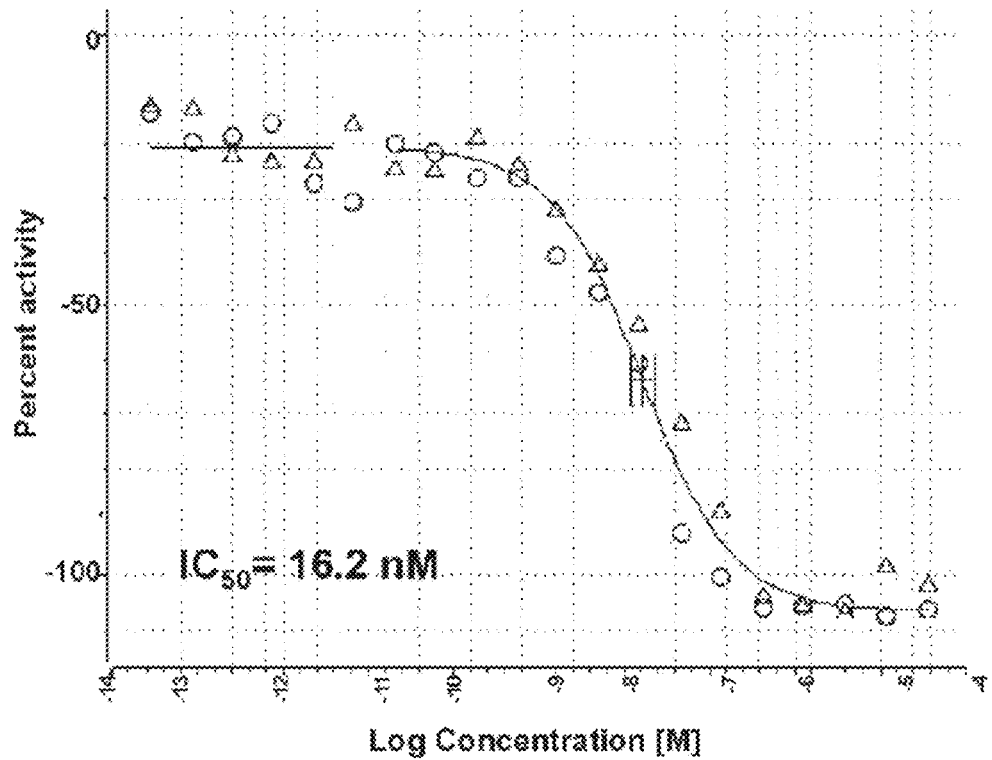

ML278 was tested against two compounds (BLT-1 and ITX-5061) in the DiI-HDL uptake assay. Each compound was used over a range of concentrations up to 35 µM. Concentration response curves were generated using Genedata Condeseo and show normalized percent activity for the individual doses (AID 588828), ML278, $IC_{50}$ = 0.93 nM (A); BLT-1 $IC_{50}$ = 10.8 nM (B); ITX-5061, $IC_{50}$ = 254 nM (C); and ML279, $IC_{50}$ = 16.2 nM. Note: Single 1 µM BLT-1 data points appear as a tight column because this dose of BLT-1 was used as the positive control and tested in dose in separate wells. ○=replicate 1, △=replicate 2

*FIG. 19D*

Table 9. Comparison of Probes to Select Prior Art Compounds.

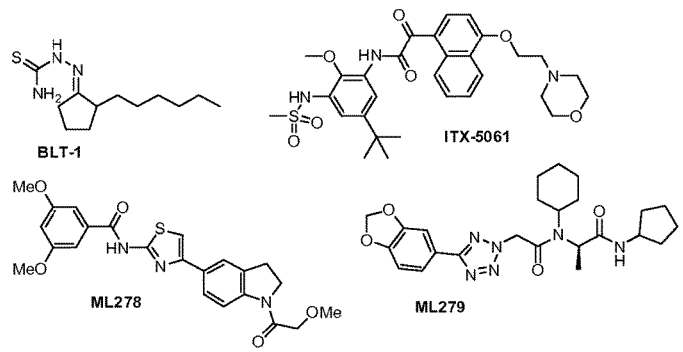

| Property | BLT-1 | ITX-5061 | ML278 | ML279 |
|---|---|---|---|---|
| Inhibition of DiI-HDL uptake in ldlA[mSR-BI] cells: $IC_{50}$ | 0.011 µM | 0.254 µM | 0.002 µM (avg.) | 0.016 µM (avg.) |
| Selectivity; receptor mediated endocytosis | No effect at up to 35 µM | No effect at up to 35 µM | No effect at up to 35 µM | No effect at up to 35 µM |
| Reversible? | No. See ref (16) | NT* | Yes | Yes |
| Cellular toxicity in ldlA[mSR-BI] | Toxic: $IC_{50}$ = 2.1 µM at 24 h | Non-toxic with $IC_{50}$ >35 µM at 24 h | Non-toxic with $IC_{50}$ >35 µM at 24 h | Non-toxic with $IC_{50}$ >35 µM at 24 h |
| Reactive functional groups? | Semithiocarbazone | α-ketoamide | No reactive functionality | No reactive functionality |
| PBS Solubility (pH 7.4, 23 °C) | NT | NT | 0.57 µM | 28 µM |

*NT = not tested

FIG. 20

ML278 was tested in a radiolabeled version of the uptake assay in wild type cells (A) (AID 588836), in free cholesterol efflux in wild type and C384S mutant cells (B) (AID No. 602152 and AID No. 602138, respectively), and SR-BI liposome assay (C) (AID No. 602155).

Table A4. SAR Analysis of Additional Analogs
| Entry No. | CID / SID / Broad ID | * | Structure | Potency (µM) SR-BI-mediated lipid uptake | | Potency (µM) 24-hour Cytotoxicity | | Toxicity /Activity |
|---|---|---|---|---|---|---|---|---|
| | | | | n | $IC_{50}$ | n | $IC_{50}$ | |
| 1 | 53347996 / 125082022 / K69876511-001 | S | 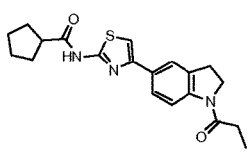 | 2 | 0.97 | 2 | >35 | >36 |
| 2 | 53262915 / 124404424 / K63473206-001 | S | 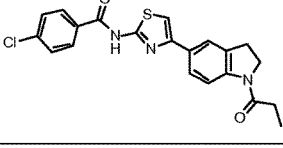 | 2 | 0.77 | 2 | >35 | >46 |
| 3 | 53347991 / 125081999 / K48446066-001 | S | 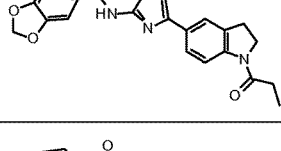 | 2 | 0.22 | 2 | NT | |
| 4 | 53347984 / 125082043 / K20254972-001 | S | 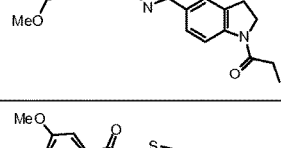 | 6 | 0.027 | 2 | >35 | >1,296 |
| 5 | 1458944 / 125299410 / K14625494-001 | S | 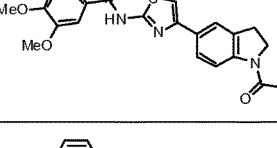 | 2 | 0.003 | 2 | >35 | >11,667 |
| 6 | 53347997 / 125082018 / K96691852-001 | S | 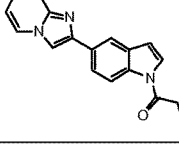 | 2 | 9.5 | 2 | 16 | 1.7 |
NT=not tested
FIG. 26A Table A4. SAR Analysis of Additional Analogs (cont'd)

| Entry No. | CID / SID / Broad ID | * | Structure | Potency (µM) | | | | Toxicity /Activity |
|---|---|---|---|---|---|---|---|---|
| | | | | SR-BI-mediated lipid uptake | | 24-hour Cytotoxicity | | |
| | | | | n | IC$_{50}$ | n | IC$_{50}$ | |
| 7 | 53262911 / 124404420 / K69616769-001 | S | 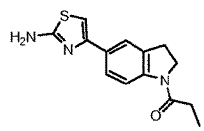 | 2 | 16.5 | 1 | NT | |
| 8 | 53347993 / 125082044 / K40579149-001 | S | 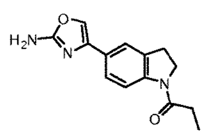 | 2 | 20 | 2 | >35 | 1.75 |
| 9 | 53347972 / 125082033 / K44839491-001 | S | 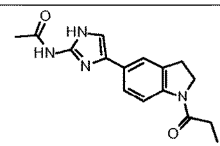 | 2 | 1.7 | 2 | >35 | >21 |
| 10 | 896768 / 125299399 / K91899274-003 | S | 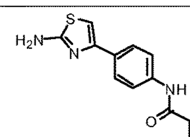 | 2 | 8.8 | 2 | >35 | >4 |
| 11 | 53347962 / 125082034 / K07456992-001 | S | 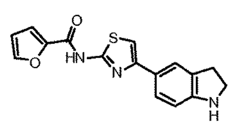 | 6 | 0.033 | 2 | >35 | >1060 |
| 12 | 53347944 / 125082021 / K50896000-001 | S | 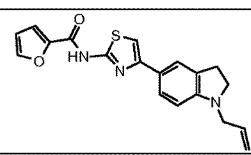 | 2 | 4.1 | | >35 | >8.5 |
| 13 | 53262917 / 124404422 / K99478179-001 | S | 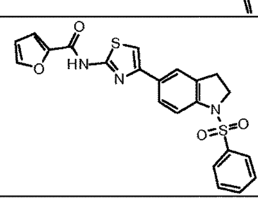 | 2 | 0.44 | | NT | |

*FIG. 26B*

Table A4. SAR Analysis of Additional Analogs (cont'd)

| Entry No. | CID | * | Structure | Potency (µM) | | | | Toxicity /Activity |
|---|---|---|---|---|---|---|---|---|
| | SID | | | SR-BI-mediated lipid uptake | | 24-hour Cytotoxicity | | |
| | Broad ID | | | n | $IC_{50}$ | n | $IC_{50}$ | |
| 14 | 44754606 | S | 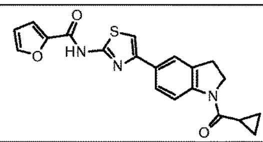 | 2 | 0.19 | 2 | >35 | >184 |
| | 125082030 | | | | | | | |
| | K63080565-001 | | | | | | | |
| 15 | 53347960 | S | 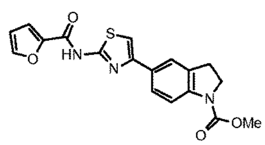 | 2 | 6.8 | 2 | >35 | >5 |
| | 125082029 | | | | | | | |
| | K43566795-001 | | | | | | | |

NT=not tested; S= synthesized

Additional Analogs

¹H NMR Spectrum (300 MHz, DMSO-d₆) of Analog CID 53262914
(Solubility was too low to obtain a reasonable spectrum)

Molecular Weight: 367.42

¹H NMR Spectrum (300 MHz, DMSO-d₆) of Analog CID 53262913
(Solubility was too low to obtain a reasonable spectrum)

Molecular weight: 407.49

|  | $EC_{50}$ | $EC_{90}$ |
|---|---|---|
| SRB1-1 | n.a. | n.a. |
| SRB1-2 | 2.8 uM | n.a. |
| SRB1-3 | n.a. | n.a. |
| SRB1-4 | n.a. | n.a. |
| SRB1-5 | 2.2 uM | n.a. |
| SRB1-6 | 0.9 uM | n.a. |
| SRB1-7 | 52 nM | > 500 nM |
| SRB1-8 | 118 nM | > 1 uM |
| SRB1-9 | 1.2 nM | 57 nM |

THIAZOLE-BASED INHIBITORS OF SCAVENGER RECEPTOR BI

REFERENCE TO RELATED APPLICATIONS

This application is based upon and claims the priority of U.S. Provisional Patent Application No. 61/716,136, entitled "Small Molecule Inhibitors Of Scavenger Receptor BI" filed Oct. 19, 2012, which is hereby incorporated in its entirety by reference.

U.S. GOVERNMENT RIGHTS

This invention was made with Government support under Grant Nos. R01 HL052212 and P01 HL066105 awarded by the National Institutes of Health. The Government has certain rights in the invention.

FIELD OF THE INVENTION

The present invention relates generally to the field of small molecule inhibitors of Scavenger receptors, and in particular to inhibitors of Scavenger receptor class B, type I (SR-BI) and their use.

BACKGROUND

Scavenger receptor class B, type I (SR-BI) is a member of the CD36 superfamily. Each member contains a large extracellular domain flanked by two membrane-spanning domains with short amino and carboxy-terminal intracellular tails. CD36 family members maintain about 30% amino acid sequence identity. They can differ in subcellular localization and ligand preference. For example, CD36/SCARB3 is 29% identical to SR-BI and can bind HDL but is incapable of efficient uptake of HDL cholesterol via selective lipid uptake. There are several isoforms of SR-BI with the predominant one being isoform 1 (NP_058021). Isoform 2 (called SR-BII) differs by a 40 amino acid sequence in the C-terminus that is encoded by an alternative exon and has a reduced efficiency in selective uptake of HDL lipids.

SR-BI mediates selective uptake of cholesterol from high-density lipoprotein (HDL) particles through a poorly understood process that is dramatically different from classic cellular endocytic uptake of lipoproteins (e.g., the uptake of low-density lipoprotein (LDL) via LDL receptors). Among other things, SR-BI serves as a co-receptor for Hepatitis C Virus (HCV) viral entry. Thus, compounds that can interfere with the interaction of the HCV and SR-BI may block or reduce HCV infection. New tools are required to enhance our understanding of SR-BI function and mechanism of action, both in vitro and in vivo as well as new pharmaceutical agents for use in diseases or conditions involving the inhibition of SR-BI function, such as in the inhibition of pathogen (e.g., HCV) cell entry.

SUMMARY

Novel compounds are disclosed that inhibit the activity of Scavenger receptor class B, type I (SR-BI). High-density lipoprotein (HDL)-focused pharmaceutical agents and methods of treatment based on such compounds are also disclosed.

In one aspect, the present invention provides small-molecule compounds described by Formula (I) below or a salt or solvate thereof. These compounds can inhibit the transfer of lipids mediated by the scavenger receptor class B, type I (SR-BI). These compounds can also increase the strength of binding of high-density lipoprotein (HDL) to cells expressing SR-BI, inhibit SR-BI transport of cholesteryl ester or other lipids from HDL into cells, inhibit SR-BI transport of cholesterol or other lipids from cells into HDL, and treat a hepatitis C viral infection.

Among other things, SR-BI serves as a co-receptor for Hepatitis C Virus (HCV) viral entry. Thus, in some embodiments of this invention, the compounds of Formula (I) can be administered to inhibit HCV or treat and/or block HCV infection. For example, a compound of Formula (I) may be administered in a dose sufficient to reduce, inhibit or block HCV infection or in combination with other inhibitors of HCV binding, entry, replication and/or release to treat or prevent HCV-based disease.

These and other features of the embodiments as will be apparent are set forth and described herein.

BRIEF DESCRIPTION OF DRAWINGS

FIG. 8A is a drawing showing the concentration response curve for the initial hit MLS001217863 in assay AID 540354;

FIG. 8B is a drawing showing the concentration response curve for the initial hit MLS001217863 in assay AID 588810;

FIG. 8C is a drawing showing the concentration response curve for the initial hit MLS001217863 in assay AID 588830;

FIG. 8D is a drawing showing the concentration response curve for the initial hit MLS001217863 in assay AID 540246;

FIG. 10A is a drawing showing the concentration response curve for the probe (ML278) in assay AID 588828;

FIG. 10B is a drawing showing the concentration response curve for the probe (ML278) in assay AID 588810;

FIG. 10C is a drawing showing the concentration response curve for the probe (ML278) in assay AID 588829;

FIG. 10D is a drawing showing the concentration response curve for the probe (ML278) in assay AID 588825;

FIG. 11 is a table showing the SAR analysis of probe 1 western amide (5-membered heterocycles);

FIG. 12 is a table showing the SAR analysis of probe 1 western amide (other heteroarenes);

FIG. 13 is a table showing the SAR analysis of probe 1 western amide (selected arene analogs);

FIG. 14 is a table showing the SAR analysis of probe 1 (functional group modifications and central ring SAR);

FIG. 15A is a table showing the SAR analysis of probe 1 (modifications to indoline ring);

FIG. 15B is a table showing further modifications to indoline ring;

FIG. 16A is a table showing the SAR analysis of probe 1 eastern N-substituent (select analogs);

FIG. 18 is a table showing the comparison of the probe to project criteria;

FIG. 19A is a drawing showing the concentration response curve for the probe (ML278) in assay AID 588828;

FIG. 19B is a drawing showing the concentration response curve for the compound BLT-1;

FIG. 19C is a drawing showing the concentration response curve for the compound ITX-5061;

FIG. 19D is a drawing showing the concentration response curve for the compound ML279;

FIG. 20 is a table showing the comparison of the probes to select prior art compounds;

FIG. 26A is a table showing the SAR analysis of additional analogs;

FIG. 26B is a table showing the SAR analysis of additional analogs (cont'd);

FIG. 104 is a graph showing the chemical characterization data for analog CID 53377409, UPLC-MS chromatogram;

FIG. 105 is a graph showing the chemical characterization data for analog CID 53377428, $^1$H-NMR spectrum;

FIG. 106 is a graph showing the chemical characterization data for analog CID 53377428, UPLC-MS chromatogram;

FIG. 107 is a histogram showing the percentage of HCV positive cells for three different infection set-ups with SR-BI compounds and controls;

FIG. 108 is a histogram showing the percentage of HCV positive cells for two independent experiments with SR-BI compounds and controls;

FIG. 109 is a histogram showing the MFI of HCV positive cells for three different infection set-ups with SR-BI compounds and controls;

FIG. 110 is a histogram showing the MFI of HCV positive cells for two independent experiments with SR-BI compounds and controls;

FIG. 111 is a graph showing the MFI of the HCV positive cells in function of the compound concentration for SRB1-2 and SRB1-8;

FIG. 112 is a graph showing the MFI of the HCV positive cells in function of the compound concentration for SRB1-7 and SRB1-9;

FIG. 113 is a graph showing the percentage of HCV positive cells in function of the compound SRB1-1 concentration for no-wash and 1x wash experimental conditions;

FIG. 114 is a graph showing the normalized to DMSO control in function of the compound SRB1-1 concentration for cell viability and viral replication;

FIG. 115 is a graph showing the percentage of HCV positive cells in function of the compound SRB1-2 concentration for no-wash and 1x wash experimental conditions;

Figure 116:
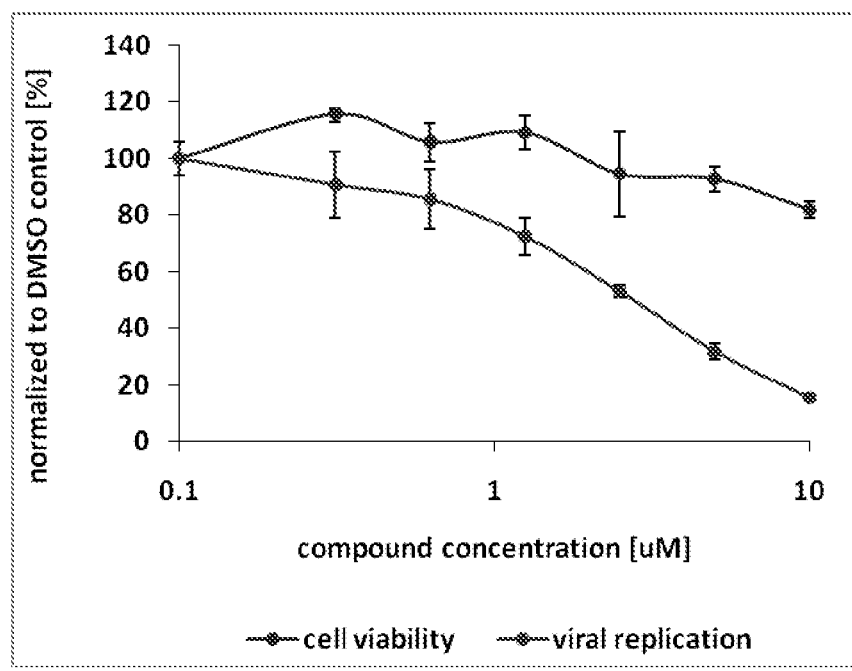
Figure 117:
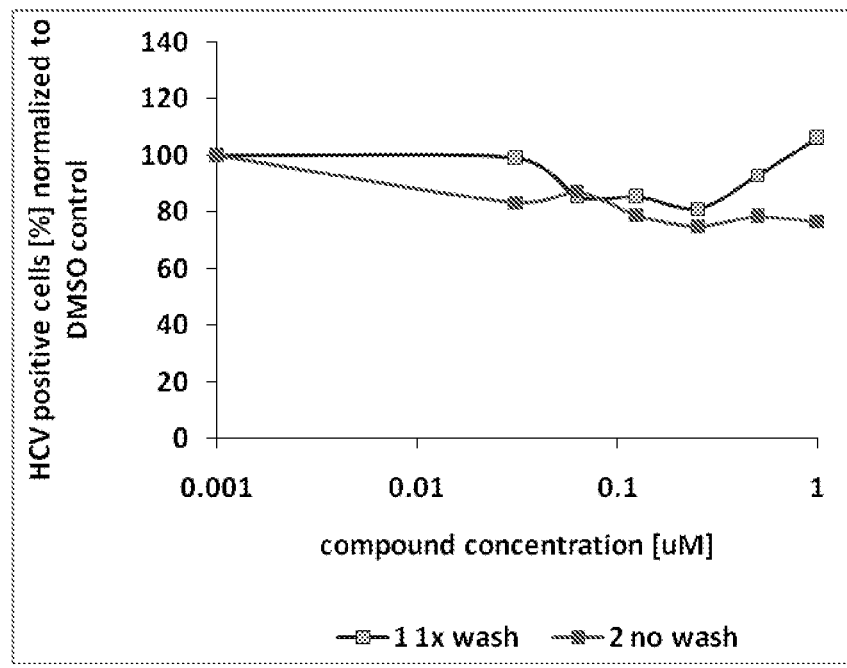
Figure 118:
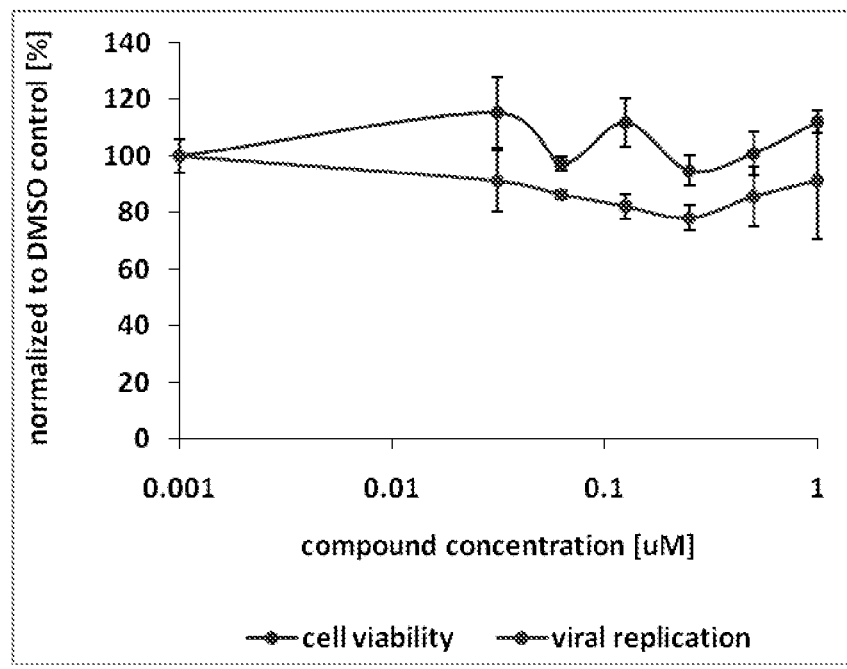
Figure 119:
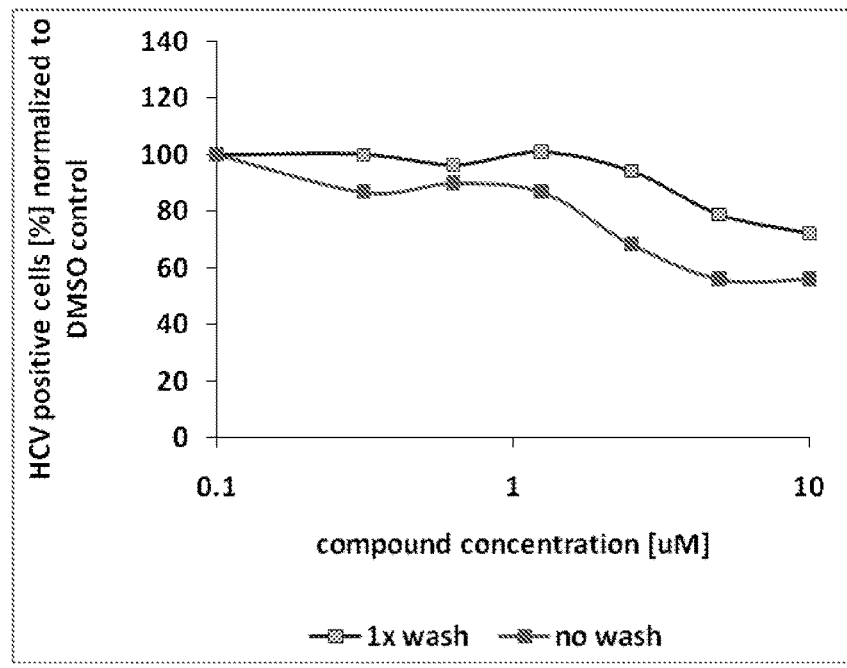
Figure 120:
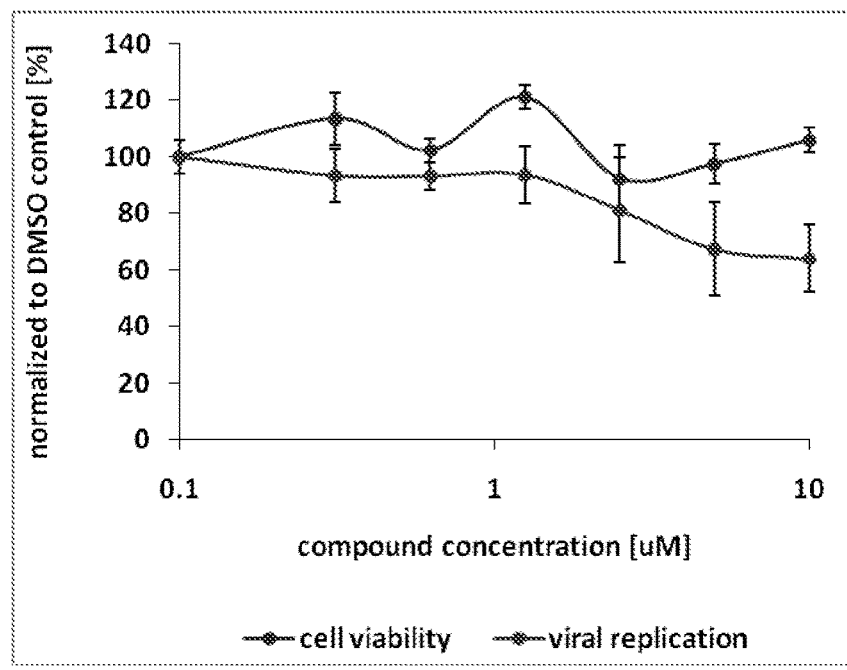
Figure 121:
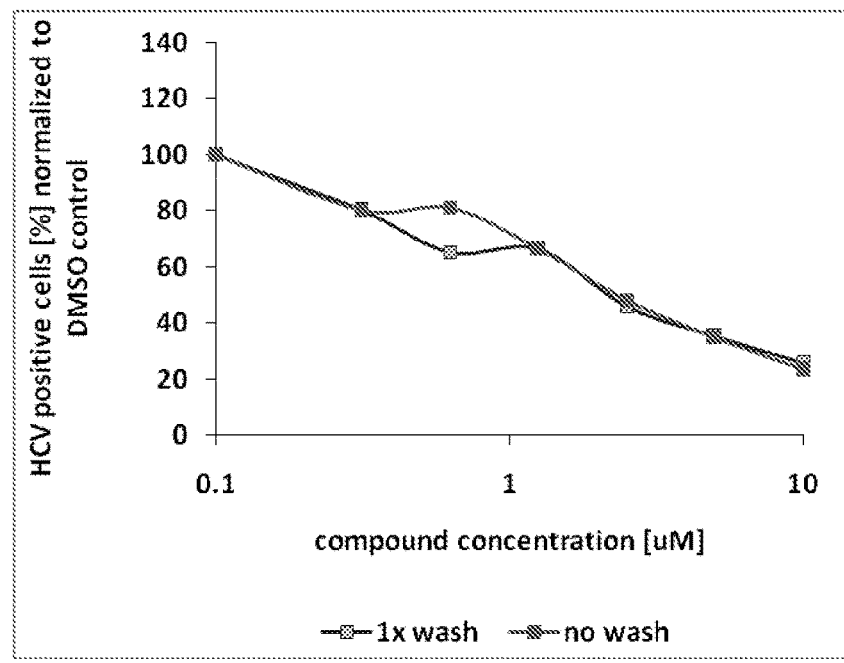
Figure 122:
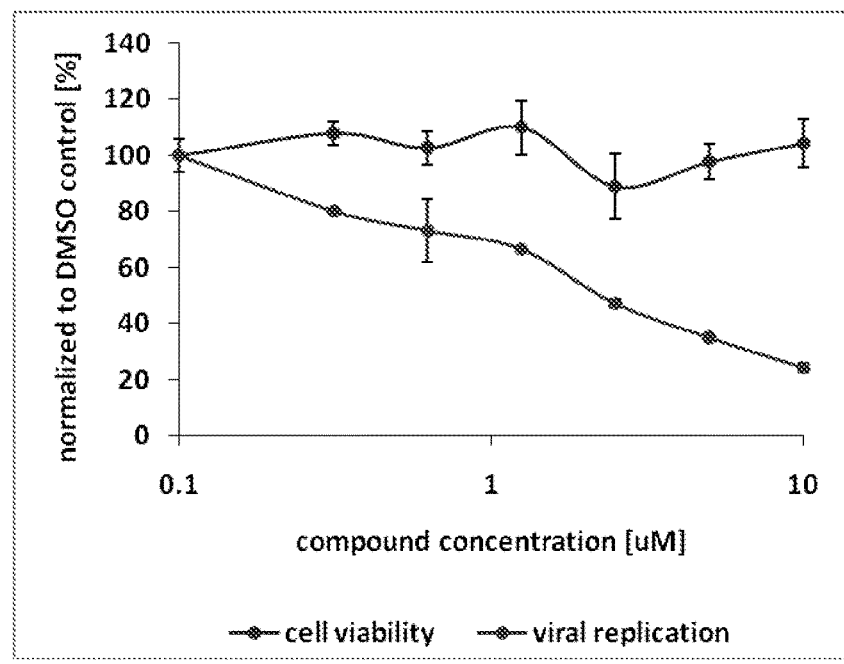
Figure 123:
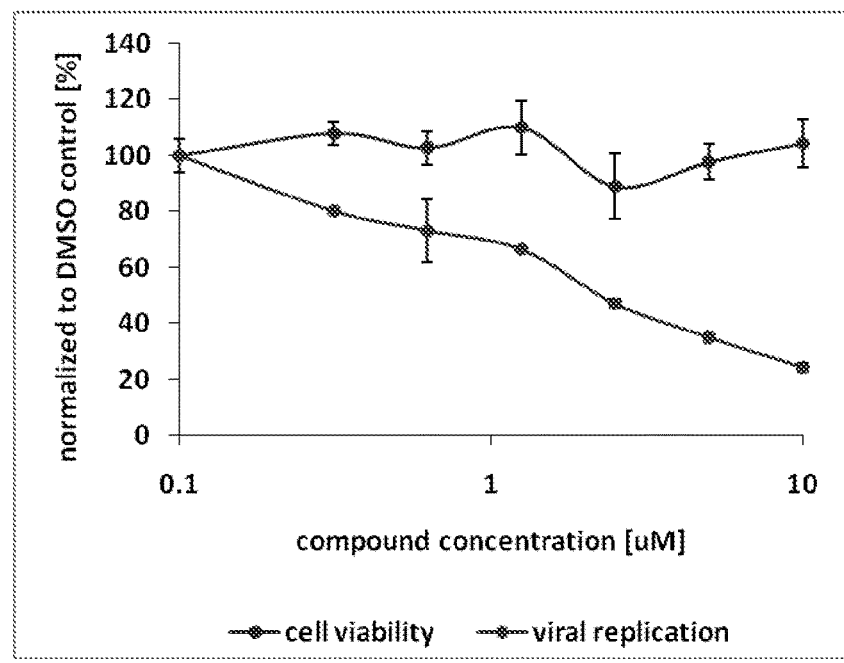
Figure 124:
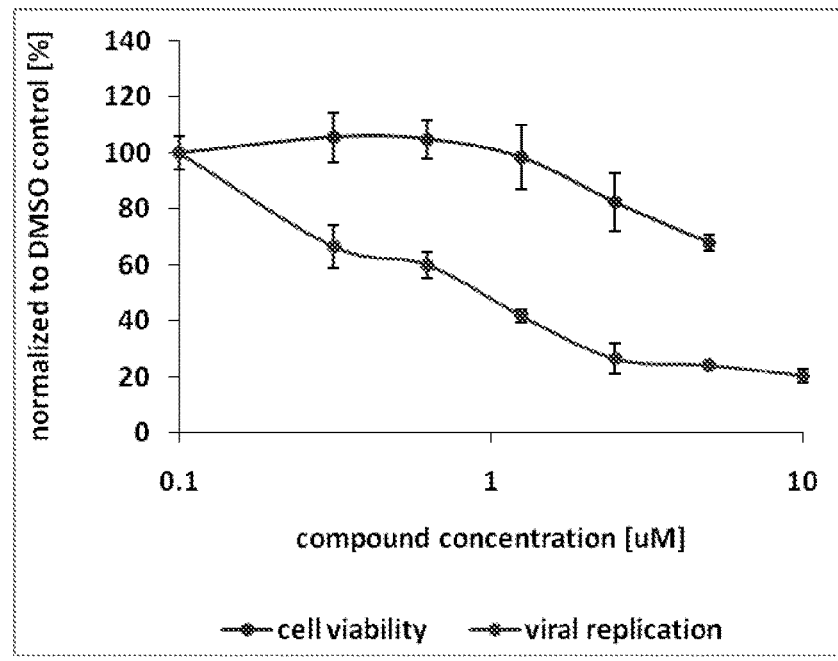
Figure 125:
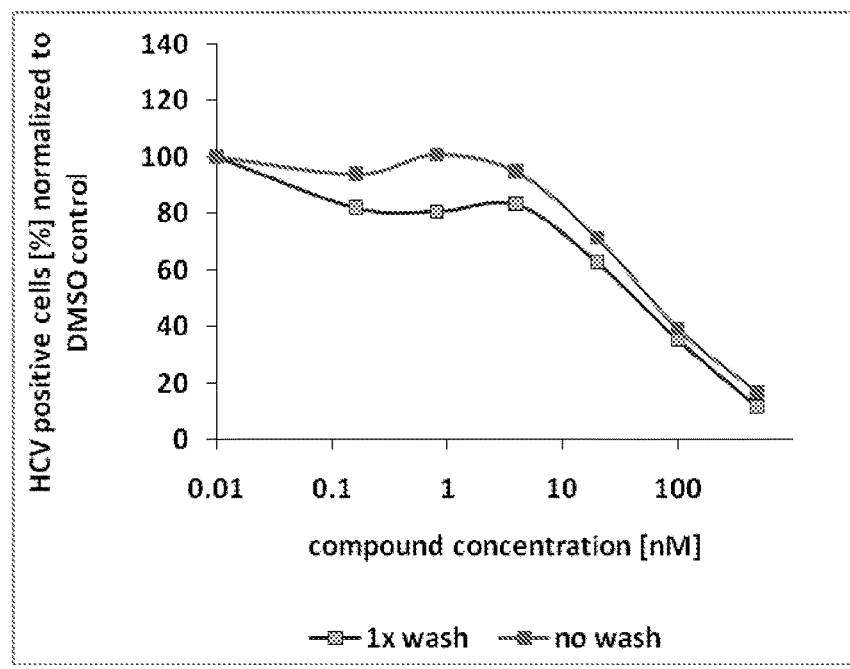
Figure 126:
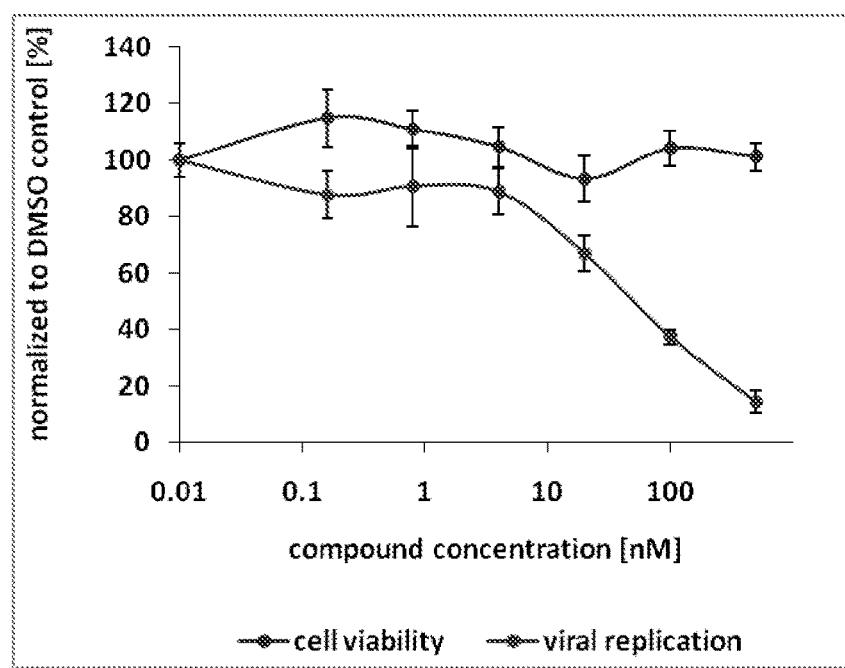
Figure 127:
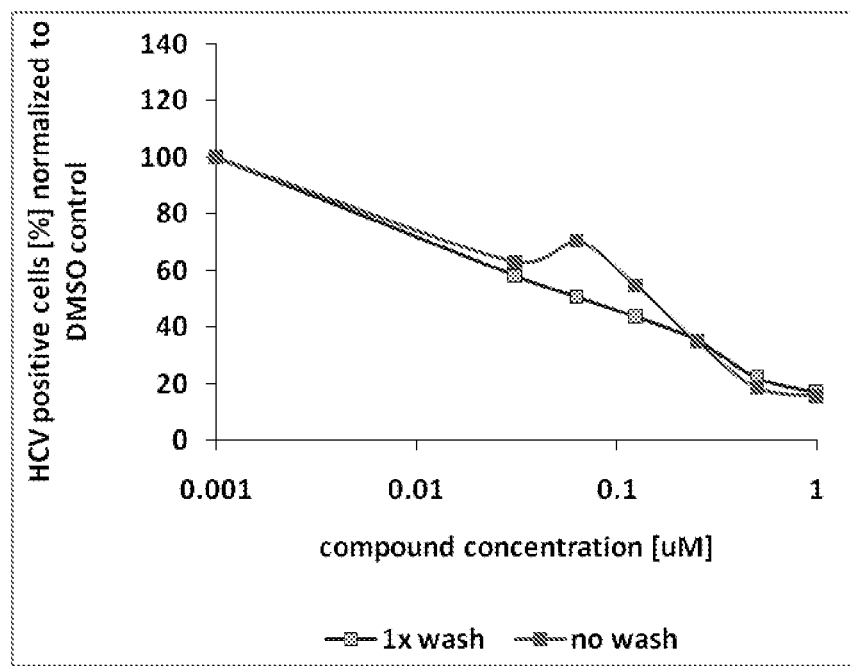
Figure 128:
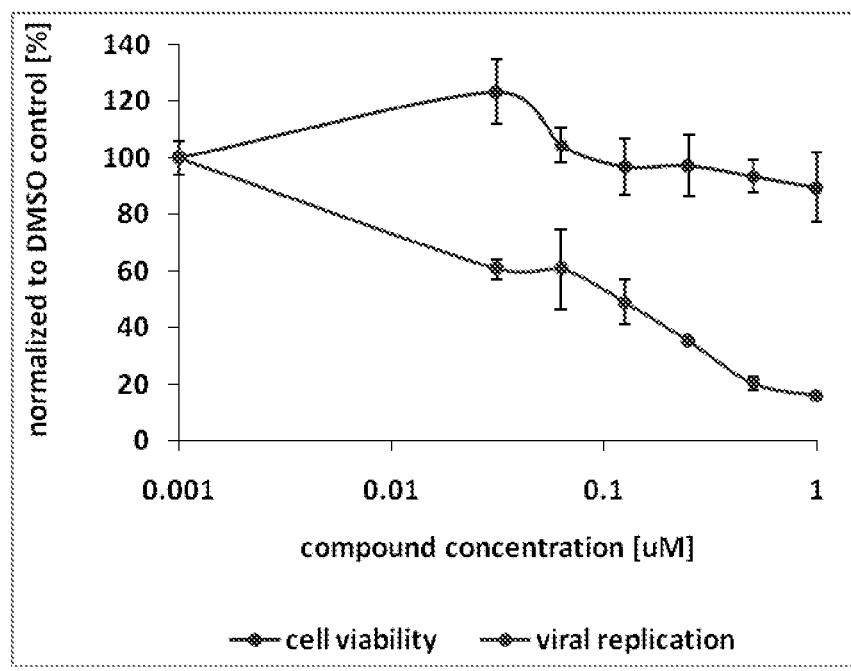
Figure 129:
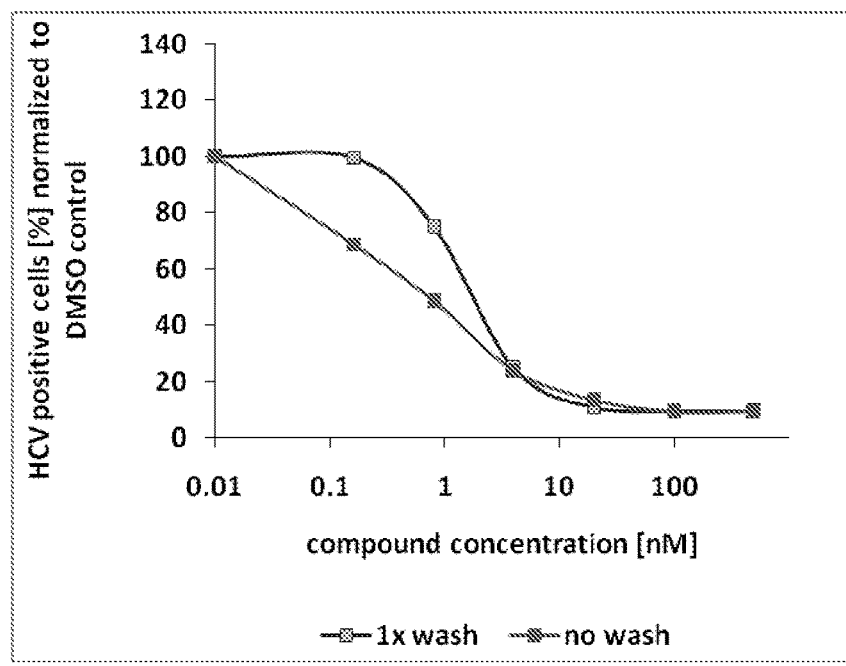
Figure 130:
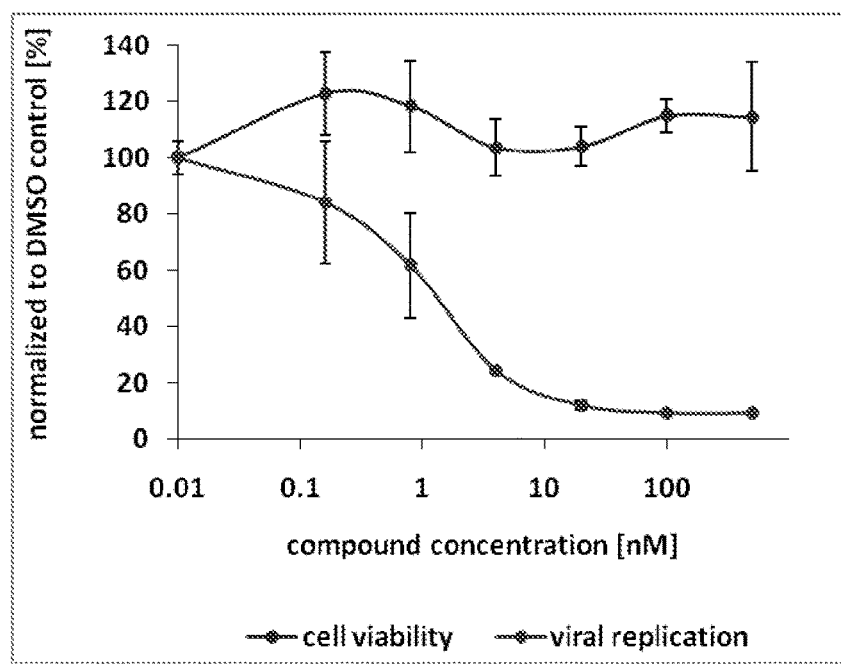

FIG. 116 is a graph showing the normalized to DMSO control in function of the compound SRB1-2 concentration for cell viability and viral replication;

FIG. 117 is a graph showing the percentage of HCV positive cells in function of the compound SRB1-3 concentration for no-wash and 1x wash experimental conditions;

FIG. 118 is a graph showing the normalized to DMSO control in function of the compound SRB1-3 concentration for cell viability and viral replication;

FIG. 119 is a graph showing the percentage of HCV positive cells in function of the compound SRB1-4 concentration for no-wash and 1x wash experimental conditions;

FIG. 120 is a graph showing the normalized to DMSO control in function of the compound SRB1-4 concentration for cell viability and viral replication;

FIG. 121 is a graph showing the percentage of HCV positive cells in function of the compound SRB1-5 concentration for no-wash and 1x wash experimental conditions;

FIG. 122 is a graph showing the normalized to DMSO control in function of the compound SRB1-5 concentration for cell viability and viral replication;

FIG. 123 is a graph showing the percentage of HCV positive cells in function of the compound SRB1-6 concentration for no-wash and 1x wash experimental conditions;

FIG. 124 is a graph showing the normalized to DMSO control in function of the compound SRB1-6 concentration for cell viability and viral replication;

FIG. 125 is a graph showing the percentage of HCV positive cells in function of the compound SRB1-7 concentration for no-wash and 1x wash experimental conditions;

FIG. 126 is a graph showing the normalized to DMSO control in function of the compound SRB1-7 concentration for cell viability and viral replication;

FIG. 127 is a graph showing the percentage of HCV positive cells in function of the compound SRB1-8 concentration for no-wash and 1x wash experimental conditions;

FIG. 128 is a graph showing the normalized to DMSO control in function of the compound SRB1-8 concentration for cell viability and viral replication;

FIG. 129 is a graph showing the percentage of HCV positive cells in function of the compound SRB1-9 concentration for no-wash and 1x wash experimental conditions;

FIG. 130 is a graph showing the normalized to DMSO control in function of the compound SRB1-9 concentration for cell viability and viral replication; and FIG. 131 is a table showing the effective concentration of each of the tested compositions.

DETAILED DESCRIPTION

Small-molecule compounds have been developed that inhibit the transfer of lipids mediated by the Scavenger receptor class B, type I (SR-BI). These compounds can be described by Formula (I) or a salt or solvate thereof:

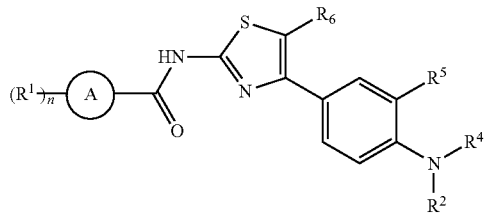

(I)

wherein:

Ⓐ is an aryl or heteroaryl which is not furan;
$R^1$ is halogen, CN, OMe, or $OCF_3$;
$R^2$ is H, $C_1$-$C_6$ alkyl, $SO_2$—$C_1$-$C_6$ alkyl, or C(=O)—$R^3$;
$R^3$ is $C_{1-6}$ alkyl, O—$C_{1-6}$ alkyl, NH—$C_{1-6}$ alkyl, or N($C_{1-6}$ alkyl)$_2$;
$R^4$ is H and $R^5$ is H, or $R^4$ and $R^5$ together are an —$CH_2$—$CH_2$—; —CH=CH— or —$CH_2$—$C(Me)_2$—;
$R^6$ is H or $C_1$-$C_6$ alkyl; and
n is 0, 1, or 2.

In some embodiments, Ⓐ is thiophene, isoxazole, tetrahydrofuran, phenyl, pyridyl, benzofuran, or furanopyridine.

In some embodiments, Ⓐ is a dimethoxy-substituted phenyl. In some embodiments, $R^6$ is H. In some embodiments, $R^4$ and $R^5$ form a ring. In some embodiments, the compound of Formula (I) has the structure:

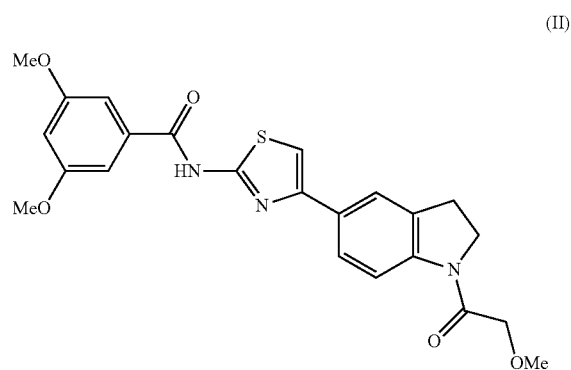 [SMILES: COCC(=O)N1CCc2cc(-c3csc(NC(=O)c4cc(OC)cc(OC)c4)n3)ccc21]

(II)

Other examples of compounds according to Formula (I) are provided in Table I below. Each of the compounds in this table has a potency for modulating (e.g., inhibiting) uptake of lipids via SR-BI (SR-BI-mediated lipid uptake) with an inhibitory concentration $IC_{50}$ of less than 10 μM and a 24-hour cytotoxicity concentration of $IC_{50}$>35 μM.

TABLE I

101

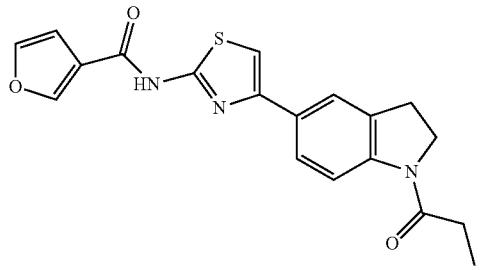 [SMILES: CCC(=O)N1CCc2cc(-c3csc(NC(=O)c4ccoc4)n3)ccc21]

102

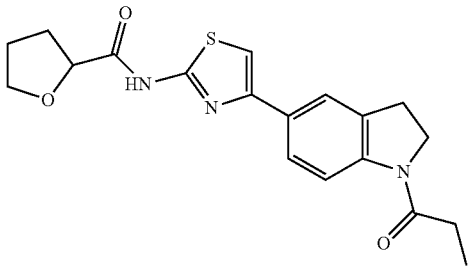 [SMILES: CCC(=O)N1CCc2cc(-c3csc(NC(=O)C4CCCO4)n3)ccc21]

103

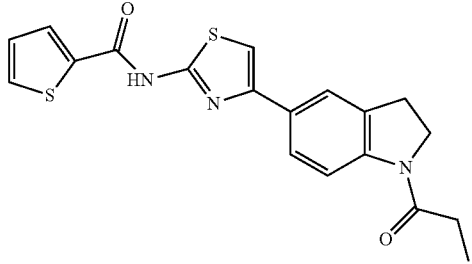 [SMILES: CCC(=O)N1CCc2cc(-c3csc(NC(=O)c4cccs4)n3)ccc21]

104

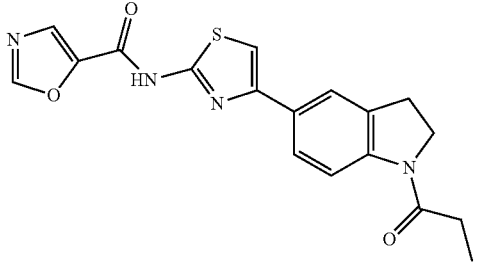 [SMILES: CCC(=O)N1CCc2cc(-c3csc(NC(=O)c4cnco4)n3)ccc21]

TABLE I-continued
| 105 | 106 |
|---|---|
| 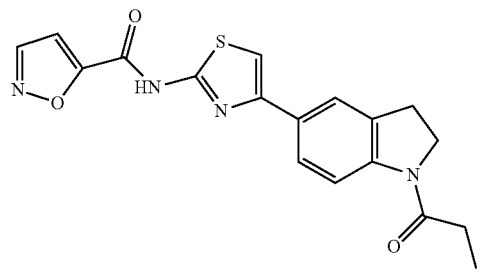 [SMILES: CCC(=O)N1CCc2cc(-c3csc(NC(=O)c4ccno4)n3)ccc21] | 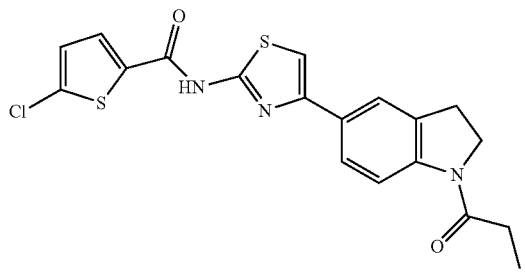 [SMILES: CCC(=O)N1CCc2cc(-c3csc(NC(=O)c4ccc(Cl)s4)n3)ccc21] |
| 107 | 108 |
| 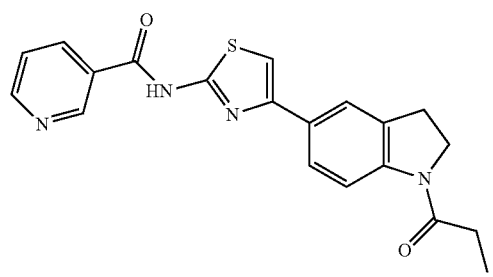 [SMILES: CCC(=O)N1CCc2cc(-c3csc(NC(=O)c4cccnc4)n3)ccc21] | 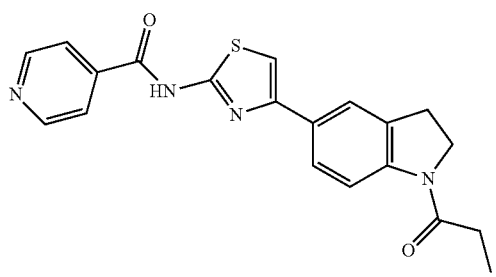 [SMILES: CCC(=O)N1CCc2cc(-c3csc(NC(=O)c4ccncc4)n3)ccc21] |
| 109 | 110 |
| 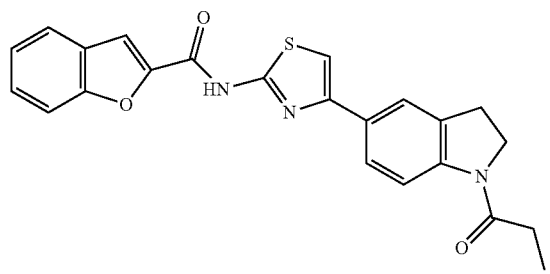 [SMILES: CCC(=O)N1CCc2cc(-c3csc(NC(=O)c4cc5ccccc5o4)n3)ccc21] | 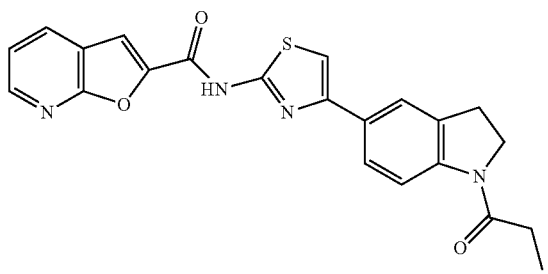 [SMILES: CCC(=O)N1CCc2cc(-c3csc(NC(=O)c4cc5cccnc5o4)n3)ccc21] |
| 111 | 112 |
| 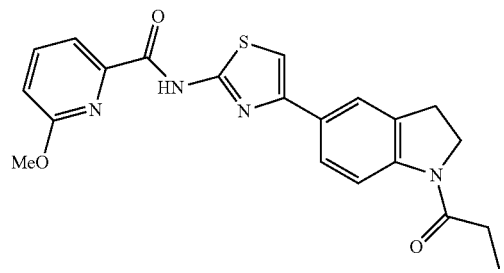 [SMILES: CCC(=O)N1CCc2cc(-c3csc(NC(=O)c4cccc(OC)n4)n3)ccc21] | 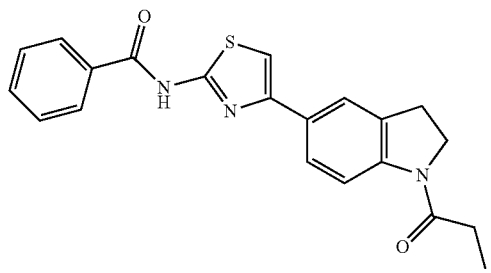 [SMILES: CCC(=O)N1CCc2cc(-c3csc(NC(=O)c4ccccc4)n3)ccc21] |
| 113 | 114 |
| 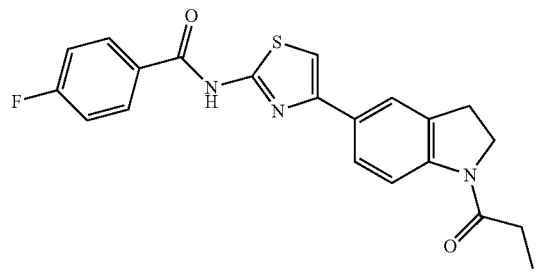 [SMILES: CCC(=O)N1CCc2cc(-c3csc(NC(=O)c4ccc(F)cc4)n3)ccc21] | 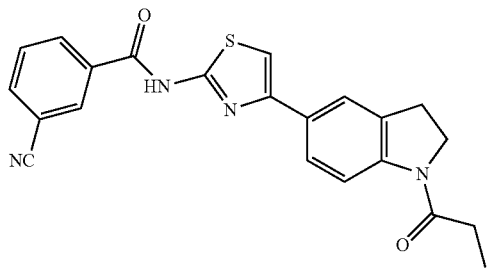 [SMILES: CCC(=O)N1CCc2cc(-c3csc(NC(=O)c4cccc(C#N)c4)n3)ccc21] |

TABLE I-continued
115 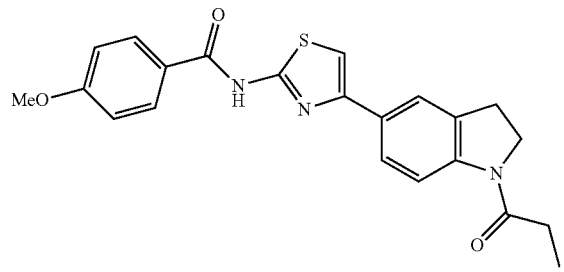 [SMILES: CCC(=O)N1CCc2cc(-c3csc(NC(=O)c4ccc(OC)cc4)n3)ccc21]
116 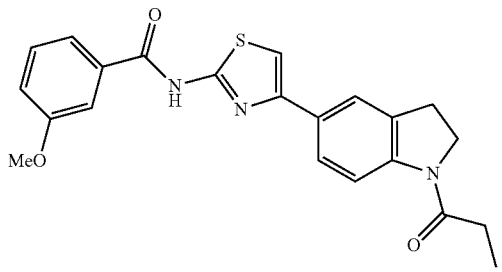 [SMILES: CCC(=O)N1CCc2cc(-c3csc(NC(=O)c4cccc(OC)c4)n3)ccc21]
117 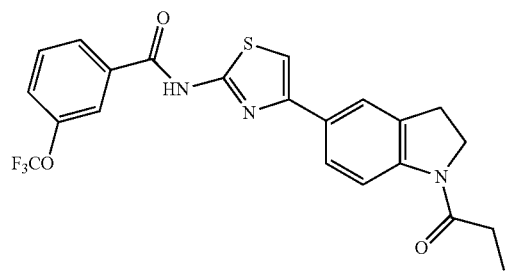 [SMILES: CCC(=O)N1CCc2cc(-c3csc(NC(=O)c4cccc(OC(F)(F)F)c4)n3)ccc21]
118 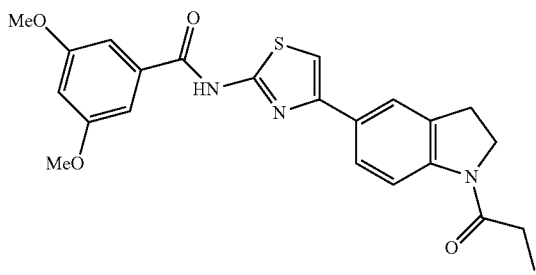 [SMILES: CCC(=O)N1CCc2cc(-c3csc(NC(=O)c4cc(OC)cc(OC)c4)n3)ccc21]
119 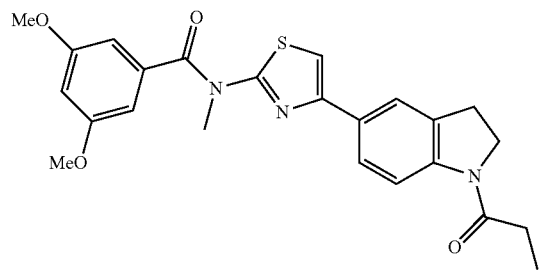 [SMILES: CCC(=O)N1CCc2cc(-c3csc(N(C)C(=O)c4cc(OC)cc(OC)c4)n3)ccc21]
120 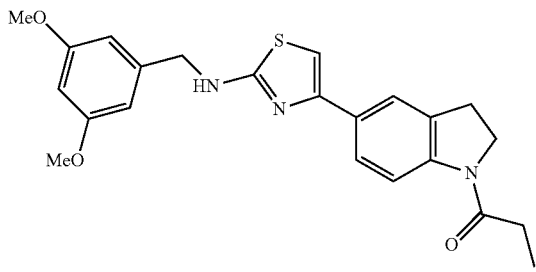 [SMILES: CCC(=O)N1CCc2cc(-c3csc(NCc4cc(OC)cc(OC)c4)n3)ccc21]
121 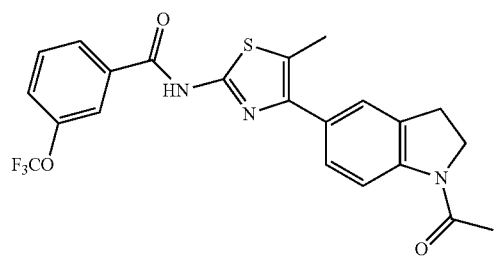 [SMILES: CC(=O)N1CCc2cc(-c3nc(NC(=O)c4cccc(OC(F)(F)F)c4)sc3C)ccc21]
122 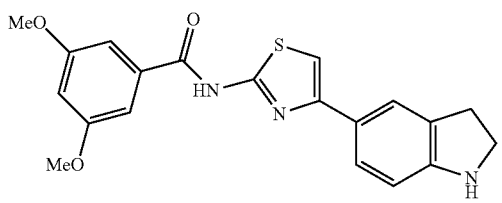 [SMILES: COc1cc(OC)cc(C(=O)Nc2nc(-c3ccc4c(c3)CCN4)cs2)c1]
123 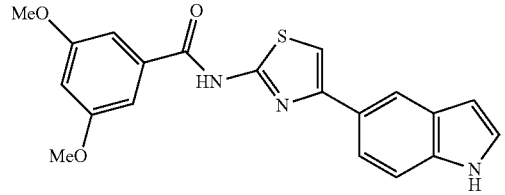 [SMILES: COc1cc(OC)cc(C(=O)Nc2nc(-c3ccc4[nH]ccc4c3)cs2)c1]
124 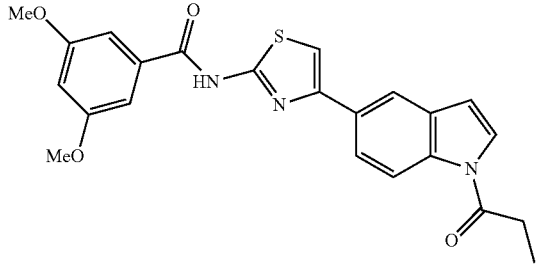 [SMILES: CCC(=O)n1ccc2cc(-c3csc(NC(=O)c4cc(OC)cc(OC)c4)n3)ccc21]

TABLE I-continued
125
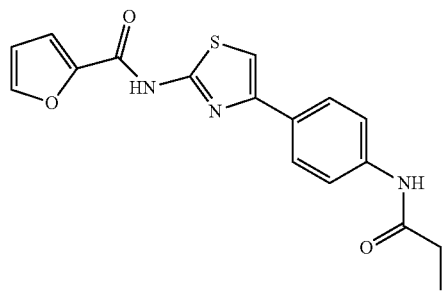 [SMILES: CCC(=O)Nc1ccc(-c2csc(NC(=O)c3ccco3)n2)cc1]
126
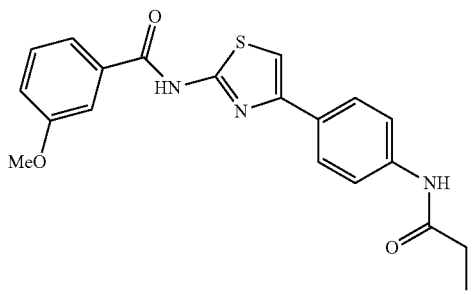 [SMILES: CCC(=O)Nc1ccc(-c2csc(NC(=O)c3cccc(OC)c3)n2)cc1]
127
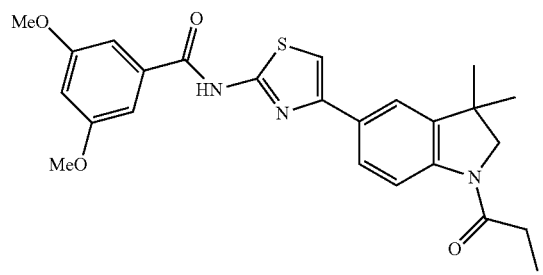 [SMILES: CCC(=O)N1CC(C)(C)c2cc(-c3csc(NC(=O)c4cc(OC)cc(OC)c4)n3)ccc21]
128
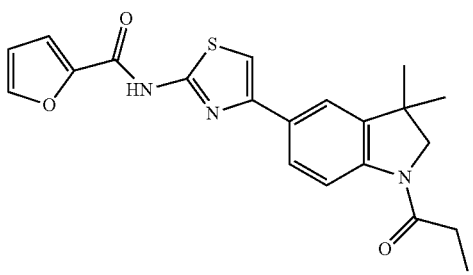 [SMILES: CCC(=O)N1CC(C)(C)c2cc(-c3csc(NC(=O)c4ccco4)n3)ccc21]
129
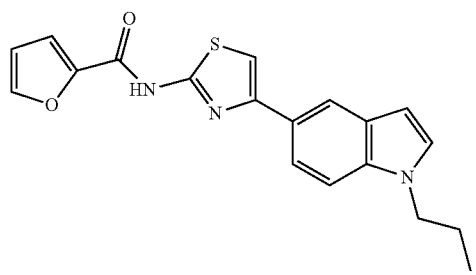 [SMILES: CCCn1ccc2cc(-c3csc(NC(=O)c4ccco4)n3)ccc21]
130
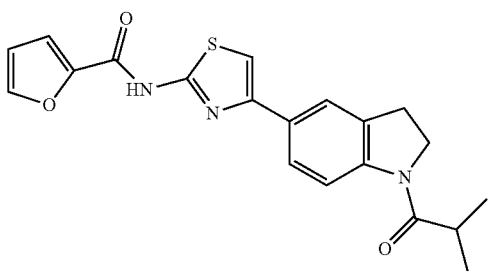 [SMILES: CC(C)C(=O)N1CCc2cc(-c3csc(NC(=O)c4ccco4)n3)ccc21]
131
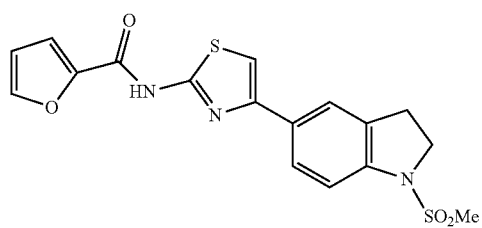 [SMILES: CS(=O)(=O)N1CCc2cc(-c3csc(NC(=O)c4ccco4)n3)ccc21]
132
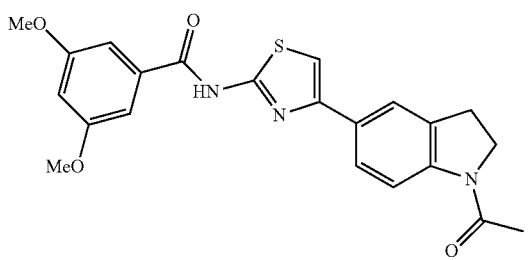 [SMILES: COc1cc(OC)cc(C(=O)Nc2nc(-c3ccc4c(c3)CCN4C(C)=O)cs2)c1]
133
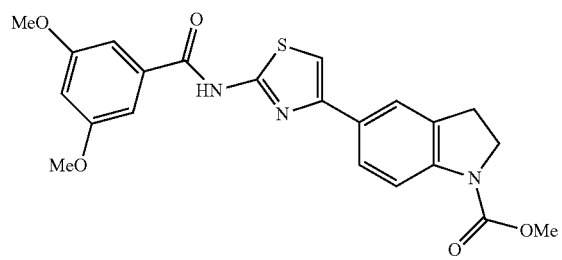 [SMILES: COC(=O)N1CCc2cc(-c3csc(NC(=O)c4cc(OC)cc(OC)c4)n3)ccc21]
134
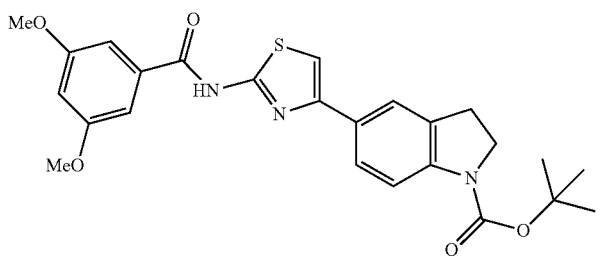 [SMILES: COc1cc(OC)cc(C(=O)Nc2nc(-c3ccc4c(c3)CCN4C(=O)OC(C)(C)C)cs2)c1]

TABLE I-continued

135
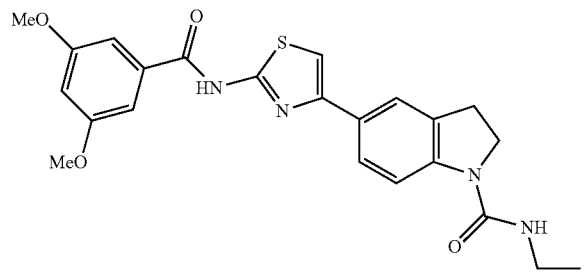 [SMILES: CCNC(=O)N1CCc2cc(-c3csc(NC(=O)c4cc(OC)cc(OC)c4)n3)ccc21]

136
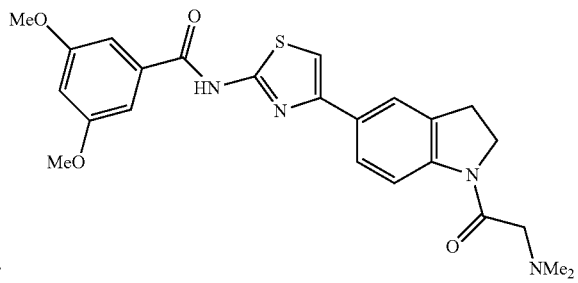

137
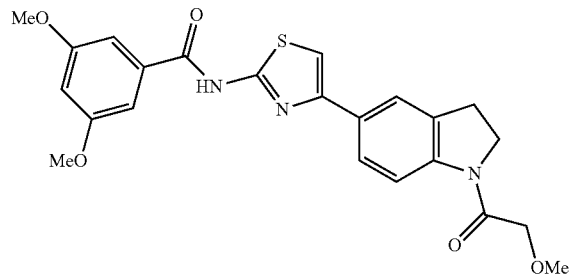 [SMILES: COCC(=O)N1CCc2cc(-c3csc(NC(=O)c4cc(OC)cc(OC)c4)n3)ccc21]

In some embodiments, various salts of these compounds can be used. Preferably, the salt is a pharmaceutically acceptable salt. In some embodiments, various solvates of these compounds can be used.

In some embodiments, compounds that are substantially stereoisomerically pure are used in the methods as described herein. Thus, in some embodiments, the compound of Formula (I) and/or a pharmaceutical composition comprising the compound of Formula (I) is substantially free of other stereoisomers. For example, it contains less than about 20%, 15%, 10%, 5%, 3%, 2%, 1%, 0.5% (w/w or v/v) of other stereoisomer(s).

Scavenger receptor class B, type I (SR-BI) mediates selective uptake of lipids, such as cholesterol, from high-density lipoprotein (HDL) particles, a process that is distinct from endocytic uptake of lipoproteins, such as low-density lipoprotein (LDL). The compounds of the present invention inhibit the transfer of lipids between high-density lipoprotein (HDL) and cells that is mediated by SR-BI. These compounds may inhibit the cellular selective uptake of HDL lipids, such as cholesterol and/or its esters (e.g., cholesteryl ester), as well as the efflux of certain cellular lipids, such as cholesterol, to HDL particles.

At the whole organism level, SR-BI controls the structure and composition of plasma HDL, and the level and fate of HDL cholesterol, including its delivery to the liver and steroidogenic tissues. It is also required for normal endothelial cell function and controlling the structure and function of various blood cells (e.g., red blood cells and platelets). It also influences hepatitis C virus infection and deep vein thrombosis. SR-BI binds HDL and functions as a cell surface transporter to move cholesterol or its esters into or out of cells and as a signaling receptor to control cell function. SR-BI can also interact with a wide variety of other ligands and transport a variety of small molecules.

The compounds as defined by Formula (I) inhibit the transfer of lipids between plasma high-density lipoprotein (HDL) and cells mediated by SR-BI. As noted above, these compounds can inhibit both cellular selective lipid uptake of HDL cholesterol (particularly the esterified form of cholesterol (e.g., cholesteryl ester)) and the efflux of cellular cholesterol to HDL and can be used as a therapeutic agent as well as a probe of the molecular and cellular functions of SR-BI, across diverse areas of physiology and medicine.

Thus, it is an aspect of this invention that the compounds of Formula (I) are administered to inhibit or reduce the transfer of lipids between HDL and cells expressing SR-BI. It is an aspect of this invention that the compounds of Formula (I) are administered to increase the strength of binding of HDL to cells expressing SR-BI. For example, a compound of Formula (I) may be administered to a subject in need thereof in an amount effective to inhibit SR-BI transport of cholesteryl ester or other lipids from HDL into cells or from cells to HDL or other acceptors of said lipids.

These compounds can inhibit the transfer of lipids mediated by the scavenger receptor class B, type I (SR-BI). These compounds can also increase the strength of binding of high-density lipoprotein (HDL) to cells expressing SR-BI, inhibit SR-BI transport of cholesteryl ester or other lipids from HDL into cells, inhibit SR-BI transport of cholesterol or other lipids from cells into HDL, and treat a hepatitis C viral infection.

SR-BI influences multiple facets of lipoprotein/lipid metabolism, and in vitro and in vivo studies (e.g., transgenic and knockout mice) have established a role for SR-BI in many mammalian physiologic and pathophysiologic systems. SR-BI knockout (KO) mice display increased total plasma cholesterol levels and reduced adrenal cholesterol levels. Female KO mice are infertile due to the importance of lipoprotein metabolism in ovarian function and oocyte maturation. Lipoprotein metabolism also impacts endothelial biology, platelet function, bile secretion, steroidogenesis, and cholesterol homeostasis. SR-BI is considered to be a pattern-recognition receptor (PRR), a type of immune recognition receptor for microbial substances, such as lipopolysaccharide (LPS), and has the ability to clear LPS and to suppress stimulation of NF-kB and cytokine stimulation via Toll-like receptors.

As noted above, SR-BI binds HDL and functions as a cell surface transporter to move cholesterol or its esters into or out of cells and as a signaling receptor to control cell function. SR-BI can also interact with and transport a wide variety of other ligands. Thus, in addition to their usefulness as therapeutic agents, in some embodiments of the present invention, the compounds as described herein can be used to map important sites of interaction on SR-BI for these processes, to help identify possible intracellular binding partners, to verify whether SR-BI oligomerizes to mediate HDL interactions, or to improve the understanding of other aspects of SR-BI biology.

SR-BI has a wide variety of functions in physiology and pathophysiology. Thus, some embodiments of the invention provide compounds that modulate (e.g., inhibit or block) SR-BI activity in immune cells to modulate the immune response for example, in the case of sepsis.

Among other things, SR-BI serves as a co-receptor for Hepatitis C Virus (HCV) viral entry. Thus, compounds that can interfere with the interaction of the HCV virus and SR-BI may block or reduce HCV infection. ITX-5061 is a compound currently under clinical review for the treatment of HCV. ITX-5061 has been shown to inhibit HCVcc and HCVpp infection of primary human hepatocytes and/or human hepatoma cell lines (Syder et al., J. Hepatology V. 54(1) January, 2011 48-55) by modulating SR-BI activity. Similarly, the compounds of Formula (I) may also be useful in treating HCV infection.

Thus, in some embodiments of this invention, the compounds of Formula (I) can be administered to inhibit HCV or treat and/or block HCV infection. For example, a compound of Formula (I) may be administered in a dose sufficient to reduce, inhibit or block HCV infection, either alone or in combination with other inhibitors of the HCV lifecycle.

Additionally, the presence of SR-BI can also enhance sporozite invasion efficiency of hepatocytes by the malaria parasite, *Plasmodium falciparum*. Blockade of SR-BI by small molecules, such as the compounds of Formula (I) can aid in the understanding of the precise mechanisms that viruses and pathogens use to enter human cells and cause disease. Thus, it is an aspect of this invention that the compounds of Formula (I) are administered to inhibit or block invasion of the malaria parasite.

Pharmaceutical Compositions

In some embodiments, pharmaceutical compositions are provided that comprise the compounds of Formula (I) and at least one pharmaceutically acceptable carrier and/or excipient. In some embodiments, the pharmaceutical composition may contain a compound which is substantially free of other isomers.

The compounds described herein including pharmaceutically acceptable carriers can be delivered to a patient using a wide variety of routes or modes of administration. Suitable routes of administration include, but are not limited to, inhalation, transdermal, oral, rectal, transmucosal, intestinal, buccal, and parenteral administration, including intramuscular, subcutaneous and intravenous injections.

Proper formulation is dependent upon the route of administration chosen. For example, for oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained, for example, by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added. Examples include cross-linked polyvinyl pyrrolidone, agar, and alginic acid or a salt thereof such as sodium alginate. In some embodiments, the pharmaceutical composition may be formulated as a solid dosage form (e.g., a tablet or capsule), a paste, emulsion, slurry, or ointment.

In other embodiments, the compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions. For injection, the agents of the invention may be formulated in aqueous solutions, preferably in physiologically compatible buffers such as Hanks's solution, Ringer's solution, or physiological saline buffer.

Alternatively, the active ingredient may be in powder form for constitution with a suitable vehicle, e.g., sterile pyrogen-free water, before use.

In some embodiments, pharmaceutical compositions are provided in which the active ingredient can be a compound of Formula (I) contained in the composition in a therapeutically effective amount, i.e., in an amount effective to achieve its intended purpose. The actual amount effective for a particular application will depend, inter alia, on the condition being treated. Determination of an effective amount is well within the capabilities of those skilled in the art, especially in light of the detailed disclosure herein.

For any compound described herein, the therapeutically effective amount can be initially determined from in vitro assays. As is well known in the art, in some cases, therapeutically effective amounts for use in humans can be determined from animal models. A therapeutically effective dose can also be determined from human data for compounds which are known to exhibit similar pharmacological activities. The applied dose can be adjusted based on the relative potency of the administered compound as compared with that of a known compound.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages can range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

Definitions and Abbreviations

The definitions of terms used herein are meant to incorporate the present state-of-the-art definitions recognized for each term in the chemical and pharmaceutical fields. Where appropriate, exemplification is provided. The definitions apply to the terms as they are used throughout this specification, unless otherwise limited in specific instances, either individually or as part of a larger group.

Where stereochemistry is not specifically indicated, all stereoisomers of the compounds provided herein are included within the scope of this disclosure, as pure isomers as well as mixtures thereof. Unless otherwise indicated, individual enantiomers, diastereomers, geometrical isomers, and combinations and mixtures thereof are all encompassed by the present disclosure.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_{1-6}$ means one to six carbons). Examples of saturated hydrocarbon radicals include, but are not limited to, groups such as methyl, ethyl, n-propyl, isopropyl, n-butyl, t-butyl, isobutyl, sec-butyl, cyclohexyl, homologs and isomers of, for example, n-pentyl, n-hexyl, and the like. An unsaturated alkyl group is one having one or more double bonds or triple bonds. Examples of unsaturated alkyl groups include, but are not limited to, vinyl, 2-propenyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." The definition of each expression, e.g. alkyl, m, n, and the like, when it occurs more than once in any structure, is intended to be independent of its definition elsewhere in the same structure.

The terms "alkoxyl" or "alkoxy" refers to an alkyl group, as defined herein, having an oxygen radical attached thereto. In one embodiment, alkoxyl groups include methoxy, ethoxy, propyloxy, tert-butoxy and the like. The alkyl portion of an alkoxy group is sized like the alkyl groups, and can be substituted by the same groups that are suitable as substituents on alkyl groups, to the extent permitted by the available valences.

The term "aryl" means, unless otherwise stated, a substituted or unsubstituted polyunsaturated, aromatic, hydrocarbon substituent which can be a single ring or multiple rings (preferably from 1 to 3 rings) having 3 to 10 or alternatively 3 to 7 members which are fused together or linked covalently.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. Up to two heteroatoms may be consecutive, such as, for example, $-CH_2-NH-OCH_3$ and $-CH_2-O-Si(CH_3)_3$. The term "heteroalkyl" encompass poly(ethylene glycol) and its derivatives.

The term "heteroaryl" refers to aryl groups that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system, such as a benzodioxolyl (e.g., 1,3-benzodioxol-5-yl), benzofuran, isobenzofuran, indole, isoindole, indoxazine, indazole, benzoxazole, and anthranil. In some embodiments, the heteroaryl is a thiophene, isoxazole, tetrahydrofuran, pyridyl, benzofuran, or furanopyridine.

Each of the above terms (e.g., "alkyl," "alkoxy," "aryl" and "heteroaryl") includes both substituted and unsubstituted forms of the indicated radical. Preferred substituents for each type of radical are provided below.

Substituents for the alkyl, and heteroalkyl radicals are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$). In some embodiments, the term "alkyl" will also include groups including acyl (e.g., —C(O)CH$_3$, —C(O)CF$_3$, —C(O)CH$_2$OCH$_3$, and the like).

As used herein, the term "heteroatom" includes oxygen (O), nitrogen (N), sulfur (S) and silicon (Si).

The terms "halo" or "halogen," by themselves or as part of another substituent, mean, unless otherwise stated, a fluorine, chlorine, bromine, or iodine atom.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The phrase "pharmaceutically acceptable" refers to additives or compositions that are physiologically tolerable and do not typically produce an allergic or similar untoward reaction, such as gastric upset, dizziness and the like, when administered to an animal, such as a mammal (e.g., a human). The term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's, The Science and Practice of Pharmacy, (Gennaro, A. R., ed., 19$^{th}$ edition, 1995, Mack Pub. Co.), discloses various carriers used in formulating pharmaceutical compositions and known techniques for the preparation thereof. Except insofar as any conventional carrier medium is incompatible with the compounds provided herein, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc. Excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "pharmaceutical composition" refers to a composition of the compounds of Formula (I) described herein, or pharmaceutically acceptable salts thereof, with other agents such as carriers and/or excipients.

As used herein, the term "patient" is a human or other animal, who is in need of treatment with inhibitor of SR-BI or would receive benefit from inhibition of the transfer of lipids mediated by SR-BI. For example, the patient may be a human or other animal with a bacterial infection, who has been exposed to bacteria, who is at risk of exposure to a bacteria, or who is otherwise in need of antibacterial treatment. The patient may be infected or at risk of infection with hepatitis C virus. Thus, in some embodiments the patient will be in need of the therapeutic treatment as provided herein. Preferred patients are mammals. Often, the human patients considered for the present invention are institutionalized in a primary medical care facility such as a hospital or nursing home. However, any other patient is also included within the scope of the present invention. The treatment of disease associated with the use of antibiotics or cancer chemotherapies or antiviral therapies can occur on an outpatient basis or can be prescribed by a physician for homecare as well.

The terms "salt" and "pharmaceutically acceptable salt" refers to a salt of one or more compounds. Suitable salts and pharmaceutically acceptable salts include acid addition salts which may, for example, be formed by mixing a solution of the compound with a solution of a pharmaceutically acceptable acid, such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

The term "solvate," as used herein, is a molecular or ionic complex of molecules or ions of a solvent with molecules or ions of the compound of Formula (I). When water is the solvent, the molecule is referred to as a "hydrate".

The term "stereoisomers" refers to compounds whose molecules have the same number and kind of atoms and the same atomic arrangement, but differ in their spatial arrangement.

The term "substantially free of", when used to describe a material or compound, means that the material or compound lacks a significant or detectable amount of a designated substance. In some embodiments, the designated substance is present at a level not more than about 1%, 2%, 3%, 4% or 5% (w/w or v/v) of the material or compound. For example, a preparation of a particular stereoisomer is "substantially free of" other stereoisomers if it contains less than about 20%, 15%, 10%, 5%, 3%, 2%, 1%, 0.5% (w/w or v/v) of the other stereoisomers other than the particular stereoisomer designated.

The term "inhibit" or "inhibition" as used herein means to reduce, slow, or stop a process, e.g., the transfer of HDL cholesterol and/or its esters between the the extracellular fluid and the cell or an infection, such as HCV infection. The term "substantially inhibit" as used herein means reducing a process by at least 70%. In some embodiments, SR-BI is inhibited at least 80%, at least 90%, at least 95%, or at least 98%.

The term "substituted" refers to a chemical group, such as alkyl, cycloalkyl aryl, and the like, wherein at least one hydrogen is replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. This disclosure is not intended to be limited in any manner by the permissible substituents of organic compounds. In many embodiments, however, any single substituent has fewer than the 100 total atoms. In many embodiments, however, any single substituent has fewer than the 10 total atoms.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "SR-BI," means a mammalian scavenger receptor class B, type I as well as non-mammalian homologues. In some embodiments, SR-BI is a mammal SR-BI. In some embodiments, SR-BI is a murine or human SR-BI.

The phrase "therapeutically effective amount" as used herein, means an amount sufficient to elicit a desired biological or medicinal response in a cell culture, tissue system, animal, or human. In some embodiments, the response includes alleviation and/or delay of onset of one or more symptoms of the disease, condition, or disorder being treated. A therapeutically effective amount of the composition may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The term "treatment" or "treating" as used herein means any therapeutic intervention in a patient, preferably a human, or any other animal capable of suffering from a disease or condition associated with SR-BI mediated processes. For example, the treatment may be for abnormal lipid metabolism resulting and the treatment would restore physiologically normal metabolism by reducing SR-BI activity. As another example, the treatment may be to prevent or lessen the symptoms or duration of HCV infection. This therapeutic intervention encompasses inhibition by arresting the development of clinical symptoms, e.g., slowing the progression of the disease; and relief, by, for example, causing the regression of clinical symptoms.

The term "about" or "approximately" means within an acceptable error range for the particular value as determined by one of ordinary skill in the art, which will depend in part on how the value is measured or determined—e.g., the limitations of the measurement system, or the degree of precision required for a particular purpose. For example, "about" can mean within 1 or within 2 standard deviations, as per the practice in the art. Alternatively, "about" can mean a range of up to 20%, preferably up to 10%, and more preferably up to 5% of a given value. Where particular values are described in the application and claims, unless otherwise stated, the term "about" means an acceptable error range for the particular value should be assumed.

As used herein and in the appended claims, the singular forms "a," "an," and "the," include plural referents unless the context clearly indicates otherwise. Thus, for example, reference to "a molecule" includes one or more of such molecules, "a resin" includes one or more of such different resins and reference to "the method" includes reference to equivalent steps and methods known to those of ordinary skill in the art that could be modified or substituted for the methods described herein.

While the above description provides examples and specific details of various embodiments, it will be appreciated that some features and/or functions of the described embodiments admit to modification without departing from the scope of the described embodiments. The above description is intended to be illustrative of the invention, the scope of which is limited only by the language of the claims appended hereto.

Examples

Aspects of the applicant's teachings may be further understood in light of the following examples, which should not be construed as limiting the scope of the applicant's teachings in any way or be necessarily indicative to the optimal ways that the invention can be practiced.

The compounds as described in the above Table 1 were synthesized as provided in Scheme 1. By way of example, the synthesis of the compound of Formula (II) (compound 137 (FIG. 1)) is outlined in scheme 1 shown below. In this reaction sequence, indoline was protected with benzenesulfonyl chloride, and the resulting sulfonamide underwent efficient Friedel-Crafts acylation with chloroacetyl chloride. The sulfonamide was then hydrolyzed by heating with concentrated sulfuric acid, and then the crude chloroketone product was condensed with thiourea at an elevated temperature to generate the desired 2-aminothiazole. Protection of the indoline nitrogen occurred with excellent selectivity using Boc2O, then the aminothiazole was acylated with 2,4-dimethoxybenzoyl chloride. The indoline was then deprotected and acylated with 2-methoxyacetyl chloride to generate the final compound. Full experimental details are provided below.

Scheme 1

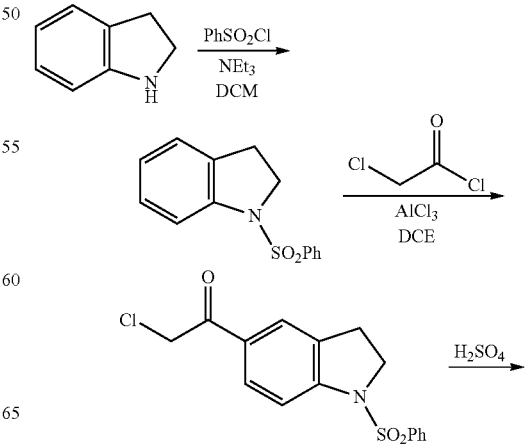

-continued

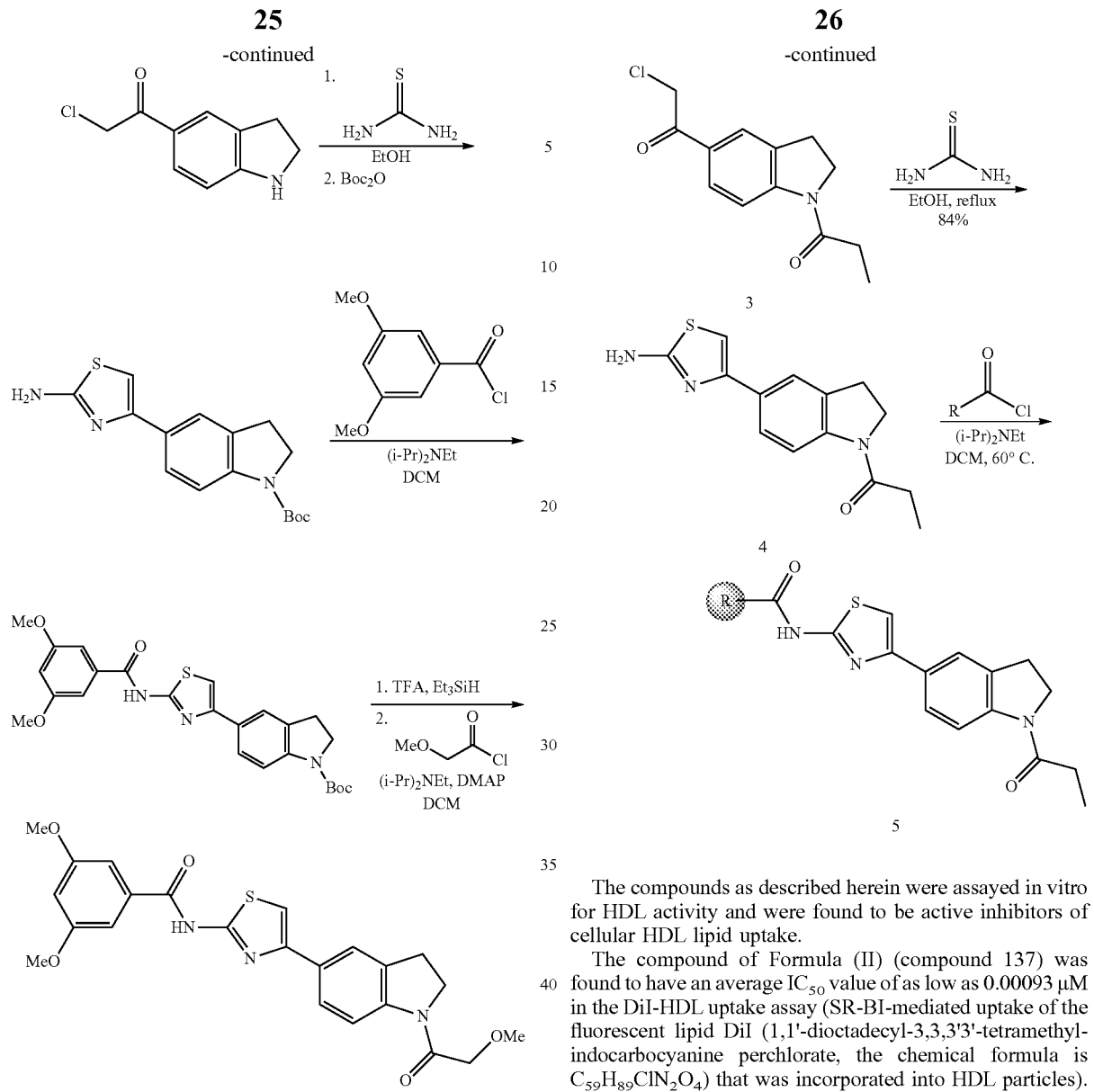

Alternatively, the compounds of the present invention can be synthesized by Scheme 2, as shown below:

Scheme 2

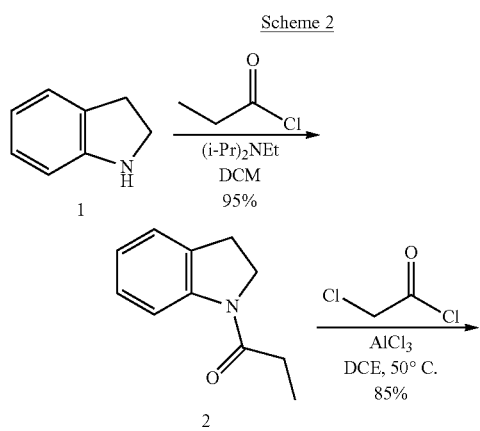

-continued

The compounds as described herein were assayed in vitro for HDL activity and were found to be active inhibitors of cellular HDL lipid uptake.

The compound of Formula (II) (compound 137) was found to have an average $IC_{50}$ value of as low as 0.00093 µM in the DiI-HDL uptake assay (SR-BI-mediated uptake of the fluorescent lipid DiI (1,1'-dioctadecyl-3,3,3'3'-tetramethyl-indocarbocyanine perchlorate, the chemical formula is $C_{59}H_{89}ClN_2O_4$) that was incorporated into HDL particles).

In a binding assay, $^{125}$I-HDL binding to cells (4° C. or 37° C.) was measured for 2 h in the absence (total activity) or presence (nonspecific activity) of a 40-fold excess of unlabeled HDL. Stably transfected cells were seeded in the wells of 24-well plates (50,000 cells per well) in Ham's F12 medium containing 2 mM L-glutamine, 50 units/mL penicillin per 50 µg/mL streptomycin (medium A) supplemented with 5% (vol/vol) FBS and 0.25 mg/mL G418 (medium B) on day 0, and binding assays were performed on day 2. The cells were washed twice with prewarmed (37° C.) medium A plus 0.5% (wt/vol) BSA (medium C) prior to adding $^{125}$I-HDL. For binding assays performed at 4° C., the assay plates were removed from the incubator, precooled for 30 min on ice in a cold room (4° C.), and then washed twice with cold (4° C.) medium C supplemented with 10 mM Hepes, pH 7.4, prior to adding $^{125}$I-HDL. Specific binding or uptake is the difference between total and nonspecific activities. In assays using small molecule inhibitors (all incubations at 37° C.), immediately prior to incubation with $^{125}$I-HDL, the cells were washed twice with medium A, preincubated with the small molecules for 1 h, and then incubated with radiolabeled lipoproteins as described above, all in medium C plus 0.5% (vol/vol) DMSO in the presence of the indicated concentrations of small molecules. $IC_{50}$ for the compound of Formula (II) is 0.0057 μM, with a measured range of 0.00093-0.006 μM.

Compound reversibility was tested by measuring the cellular uptake of DiI from DiI-HDL (all incubations at 37° C.) in ldlA7 cells that were stably transfected with cDNA encoding murine SR-BI. On day 0, 50,000 cells were plated in 96-well dishes per well (Costar, black with clear, flat bottom) in Ham's F12 medium containing 2 mM L-glutamine, 50 units/mL penicillin per 50 μg/mL streptomycin (medium A) supplemented with 5% (vol/vol) FBS and 0.25 mg/mL G418 (medium B). On day 2, the cells were washed twice with prewarmed (37° C.) medium A. The cells were then preincubated with the tested compounds in 200 μL per well of medium A plus 0.5% (wt/vol) BSA plus 0.5% (vol/vol) DMSO (medium C) for 1 hr. The 1 hr preincubation was followed by either a 0 or 4 hr incubation in medium C in the absence of compound. The cells were then incubated in medium C (200 μL per well) containing 10 μg protein per mL of DiI-HDL at 37° C. for 2 h to measure DiI uptake. After 2 hr incubation, cells were washed rapidly two times with 150 μL ice-cold wash buffer [0.9% NaCl, 50 mM Tris.HCl, pH 7.4, plus 0.5% (wt/vol) BSA] and once with 150 μL PBS. Then 50 μL PBS was added and fluorescence measurements made using a Molecular Devices SpectraMax fluorescence plate reader (excitation at 515 nm, emission at 575 nm, bottom read mode). DiI uptake was also measured in the presence of a 40-fold excess of unlabeled HDL to determine nonspecific (SR-BI-independent) uptake. $IC_{50}$ for the compound of Formula (II) is 0.315 μM.

The compound of Formula (II) shows no apparent cytotoxicity after 24 hours of treatment ($EC_{50}$=>35 μM). The selectivity of this compound was found to be greater than 1000. The compound of Formula (II) has been shown to inhibit efflux of cholesterol and it does not inhibit endocytosis of transferrin.

The compound of formula (II) was also tested for the in vitro inhibition of HCV. Huh-7.5 cells were seeded in a 24-well plates (50,000 cells/well) and incubate over night. The medium was changed to compound/solvent containing medium 2 hours prior to infection (200 μL/well) with a reporter HCV virus called Jc1 378-1 TagRFP. A dilute virus stock was used to infect at a MOI of 0.1 (7,500 IU/well) in 10 μL medium. 10 μL of virus dilution was added to the wells containing compound/solvent (thereby dilution the compounds by only ~5%). Infections were incubated for 4 hours before washing off the inoculum 1× with 500 μL medium. Fresh compound/solvent containing medium was added to the cells (500 μL/well), and further incubated for 48-72 hours. Cells were harvested at 48-72 hpi and viral replication was determined by fixing the cells and measuring replication by FACS (fluorescence activated cell sorting). Controls having antibodies that neutralize HCV by blocking E2 (2 μg/mL) and controls having antibodies that block a HCV receptor CD81 (2 μg/mL) were used.

Figures 1, 2:
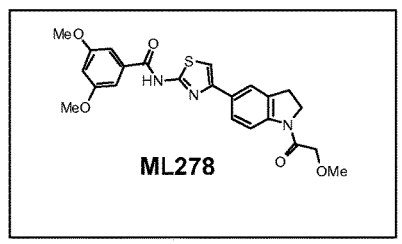
FIG. 1 is a drawing showing the molecular representation of the probe ML278.
FIG. 2 is a table showing the properties of the probe ML278.

Cell viability and viral replication for the compound of formula (II) is shown in FIG. 2. This compound was determined to have an $EC_{50}$=44 nM and $EC_{90}$ of about 500 nM for Huh-7.5 cells infected with Jc1 378-1 TagRFP.

Further Experimental Results

Using a cell-based DiI-HDL uptake assay, we performed a high-throughput screen (HTS) of the NIH MLPCN compound library. Of the 319,533 compounds tested, 3,046 compounds (0.96%) were classified as inhibitors of DiI-HDL uptake. MLS001217863 (SID49678600, CID24761960) was identified in the primary HTS as an inhibitor. It had potent activity in the primary assay, a low hit rate in other MLPCN screens, and possessed structural properties suitable for analog synthesis. Structure/activity relationship (SAR) studies identified a probe (CID53377439/ML278), that shows low nanomolar inhibition of HDL uptake through SR-BI and high micromolar activity in the cytotoxicity assay. ML278 was tested for lipid efflux inhibition, modulation of HDL binding to SR-BI, and inhibition of endocytosis. ML278 functions by inhibiting both SR-BI-mediated lipid uptake and efflux of free cholesterol to HDL particles.

The compounds of the present invention inhibit the transfer of lipids between high-density lipoprotein (HDL) and cells mediated by the HDL receptor Scavenger receptor class B, type I (SR-BI). ML278 inhibits both cellular selective lipid uptake of HDL cholesteryl ester and efflux of cellular cholesterol to HDL. This probe will enable deeper understanding of the molecular and cellular functions of SR-BI, across diverse areas of physiology and medicine, and represents a novel lead for further optimization prior to use in in vivo studies.

SR-BI influences multiple facets of lipoprotein/lipid metabolism, and in vitro and in vivo studies (e.g., transgenic and knock out mice) have established a role for SR-BI in many mammalian physiologic and pathophysiologic systems. SR-BI knock out (KO) mice display increased total plasma cholesterol levels and reduced adrenal cholesterol levels. Female KO mice are infertile due to the importance of lipoprotein metabolism in ovarian function and oocyte maturation. Lipoprotein metabolism also impacts endothelial biology, platelet function, bile secretion, steroidogenesis, and cholesterol homeostasis. SR-BI is considered to be a pattern-recognition receptor (PRR), a type of immune recognition receptor for microbial substances, such as lipopolysaccharide (LPS), and has the ability to clear LPS and to suppress stimulation of NF-kB and cytokine stimulation via Toll-like receptors (TLRs). Further, SR-BI serves as a co-receptor for Hepatitis C (HCV) viral entry, and interference with compound (e.g., ITX-5061) or blocking antibodies can reduce cellular infection. Additionally, the presence of SR-BI enhances sporozoite invasion efficiency of hepatocytes by the malaria parasite, *Plasmodium falciparum*. Thus, ML278 will be a useful tool with which to further explore the contributions of SR-BI in each of these diverse areas in vitro and in vivo.

At the molecular level, SR-BI controls the structure and composition of plasma HDL, and levels and fates of HDL cholesterol, including delivery to the liver and steroidogenic tissues. SR-BI binds HDL and functions as a cell surface transporter to move cholesterol or its esters into or out of cells and as a signaling receptor to control cell function. SR-BI can also interact with and transport a wide variety of other ligands. A new probe could be used to map important sites of interaction on SR-BI for these processes, to help identify possible intracellular binding partners, to verify whether SR-BI oligomerizes to mediate HDL interactions, or to improve our knowledge of other aspects of SR-BI biology.

ML278 may represent a significant improvement over prior SR-BI inhibitors. Blocker of lipid transport-1 (BLT-1) has nanomolar potency but binds SR-BI irreversibly and is extremely toxic to cells, which has limited the use of the compound to short term in vitro assays. ML278 overcomes the major limitations of BLT-1: specifically it is a reversible binder of SR-BI and is not cytotoxic. Further, ML278 is more potent than ITX-5061, a previously described compound that disrupts HDL uptake.

Scavenger receptor class B, type I (SR-BI) is a member of the CD36 superfamily. Each member contains a large extracellular domain flanked by two internal membrane-spanning domains that are adjacent to short amino and carboxy-terminal intracellular tails. CD36 family members maintain about 30% amino acid sequence identity but differ in subcellular localization and ligand preference. For example, CD36/SCARB3 is 29% identical to SR-BI and can bind HDL but is incapable of HDL uptake. There are several isoforms of SR-BI with the predominant one being isoform 1 (NP_058021). Isoform 2 of SR-BI differs by a 40 amino acid sequence in the C-terminus that is encoded by an alternative exon and has a reduced efficiency in selective uptake of HDL (2). SR-BI mediates selective uptake of cholesterol from high-density lipoprotein (HDL) particles through a poorly understood process that is dramatically different from classic cellular endocytic uptake of lipoproteins (e.g., low-density lipoprotein (LDL), via LDL receptors). New tools are required to enhance our understanding of SR-BI function and mechanism of action, both in vitro and in vivo. Recent disappointments in attempts to develop HDL-focused pharmaceutical agents with other molecular targets highlight the importance of developing a deeper and broader understanding of all aspects of HDL metabolism including those mediated by SR-BI. Given the central role of SR-BI in lipid transfer and metabolism, inhibitors of SR-BI function will be useful tools to further probe the mechanisms of SR-BI, both in vitro and in vivo, and may also have clinical utility, such as in the inhibition of pathogen cell entry (e.g., HCV).

Figure 3:
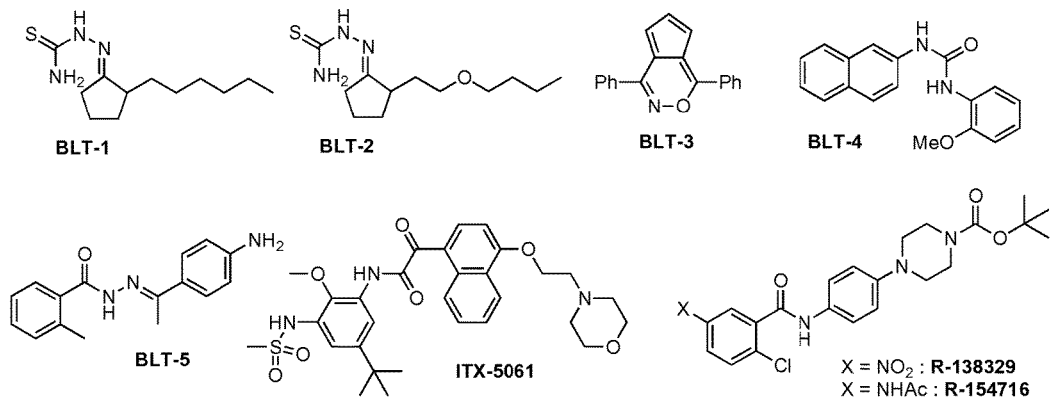
FIG. 3 is a drawing showing the molecular representations of the reported inhibitors of SR-BI.

Several small-molecule inhibitors of SR-BI have been discovered. (See FIG. 3.) Krieger and coworkers identified five compounds (BLTs 1-5) that block lipid transport selectively via SR-BI, with nanomolar to micromolar potencies (12, 14-16). Assays with purified SR-BI reconstituted into liposomes show that BLTs directly act on SR-BI (17). However, these probes exhibit an unacceptable level of cellular toxicity. The diabetes drug glyburide, a potent inhibitor of the sulfonylurea receptors SUR1 and SUR2, was also found to have activity at SR-BI, though it was a relatively weak inhibitor of cholesterol efflux. Researchers at Sankyo discovered that the protected piperazines R-138329 and R-154716 increased HDL-cholesterol in both mice and hamsters, presumably by inhibiting SR-BI-mediated uptake of HDL. Recently, a p38 MAP kinase inhibitor (ITX-5061) was reported to have similar in vivo effects and appears to be a moderate inhibitor of SR-BI-mediated cholesterol uptake. ITX-5061 is also an inhibitor of HCV entry into cells, and is presently in Phase II trials as a HCV antiviral treatment. This compound was prepared in our laboratories and was profiled in our assays of interest. Finally, ITX-7650 has been described as an inhibitor of cholesterol uptake and HCV infection, but the structure remains undisclosed.

A major goal of the proposed work is to identify a new SR-BI inhibitor that will provide a substantial improvement over the existing tool compounds under at least one of the following categories: 1) increased potency and reversibility; 2) reduced cellular toxicity; 3) new insights into mechanism; and 4) a unique activity profile (e.g., direct inhibition of ligand binding, differential influence on selective uptake and free cholesterol efflux).

Materials and Reagents
DiI-HDL, custom purified HDL particles derived from human blood were prepared by and labeled with 1,1'-dioctadecyl-3,3,3',3'-tetramethylindocarbocyanine perchlorate (DiI; Catalog No. D-282; Invitrogen, Carlsbad, Calif.).

Alexa 488 HDL, human HDL particles labeled with the Alexa Fluor® 488 Protein Labeling Kit (Catalog No. A-10235, Invitrogen; Carlsbad, Calif.) were likewise purified and labeled.

CellTiter-Glo® Luminescent Cell Viability Assay was purchased from Promega (Catalog No. G7573; Madison, Wis.).

Radiolabeled cholesterol [1,2-$^3$H(N)]—, 1 mCi (37 MBq) was obtained from PerkinElmer-NEN (Catalog No. NET139001MC; Waltham, Mass.).

Alexa Fluor-594 conjugated human transferrin (Catalog No. T-13343) was obtained from Invitrogen.

Cell Lines
The following cell lines were used in this study:
ldlA[mSR-BI] is a Chinese hamster ovary (CHO) cell line that overexpresses murine SR-BI, isoform 1 (NP_058021) and was obtained from the Assay Provider (Krieger Laboratory). This cell line was used for the primary assay and several secondary assays. A variant of this cell line expressing mutant SR-BI, where a cysteine required for interaction with BLT-1 is mutated to serine (C384S SR-BI), was used in several secondary assays.

[ldlA7] is the parental cell line to ldlA[mSR-BI]cells, and does not overexpress SR-BI, and can be used to rule out compound activity independent of SR-BI. This cell line was obtained from the Assay Provider.

Assays
DiI-HDL Uptake Assay (Primary Assay AID Nos. 488896, 493194, 540354 588392, 588553, 588548, 588754, 588828, 588833)

ldlA[mSR-BI]cells were plated into 384-well plates at 30 μl per well and incubated overnight. As a measurable surrogate for cholesterol uptake, human HDL particles were treated with the lipophilic fluorescent dye DiI and exposed to ldlA[mSR-BI]cells in lipoprotein-free media (Ham's F12/0.5% fatty acid-free Bovine Serum Albumin (BSA)/25 mM HEPES pH 7.4 plus 10 μg protein/ml DiI-HDL). Cells took up the DiI via SR-BI over 3 hours in the presence of compound. After significant uptake of the DiI, the cells became fluorescent. The level of fluorescence correlates with the amount of DiI uptake and can be measured with a standard plate reader (here a PerkinElmer EnVision plate reader was used). The uptake of lipid (represented by DiI) was inhibited by the positive control compound BLT-1 or with an excess of HDL untreated with DiI. Primary HTS data were analyzed in Genedata Screener Assay Analyzer, and were normalized against DMSO and the positive control (1 μM BLT-1). For the HTS, the average of two replicates was used to rank order activity and to choose compounds for retests. For dose studies, percent (%) activity was determined for each concentration and the concentration response curves (CRCs) were generated with Genedata Condeseo.

Fluorescence Quencher Counterscreen (Secondary Assay (SA) 2: AID Nos. 588403, 540326)

The primary assay for this project measures a reduction in fluorescence by potential inhibitors. One possible explanation for the loss of signal in the primary assay is the compounds have inherent fluorescence-quenching properties and reduce signal in a dose-dependent manner without actually altering the uptake of the fluorescent substrate. We developed an assay where compounds were pinned into assay buffer containing DiI-HDL without any cells. The compounds were incubated with DiI-HDL at 5 μg protein/ml in Ham's/25 mM HEPES/0.5% fatty acid-free BSA media for 30 minutes. Then, assay plates were measured with the identical settings for the primary assay. Compounds that quench DiI fluorescence led to a dose-dependent loss of signal in this assay. Any compound that altered fluorescence or had an $IC_{50}$ value of <30 μM was not considered for further studies.

Cell Cytotoxicity Assay (SA 1: AID Nos. 540246, 588829, 588826, 588830, 588842, 602126)

It is possible that a compound will cause cells to decrease HDL-mediated DiI uptake due to nonspecific consequences of cellular toxicity, representing a second class of false positive hits. The cells were treated with compounds for 3 hours or 24 hours, and then cell viability was measured using the CellTiter-Glo Assay (Promega), a luciferase-based reagent that measures cellular ATP levels. The compounds were tested at different concentrations to determine $IC_{50}$ values. Compounds that were toxic after 3 hours with an $IC_{50}$ value of less than 30 μM were excluded from additional studies. Compounds that were active in the primary assay but toxic below 30 μM at 24 hours (but nontoxic at 3 hours) were still considered. None of our preferred scaffolds showed cytotoxicity at either time point (e.g., see FIGS. 8C, 8D). Data were normalized against DMSO and the positive control (1 μM BLT-1) in Genedata Assay Analyzer. Curves were generated with Genedata Condeseo and showed percent (%) activity for the individual doses.

HDL Binding Assay (SA 6: AID Nos. 588777, 588810)

HDL binding was assessed using Alexa Fluor 488-labeled HDL particles. For this assay, the Alexa 488 dye was covalently bound to apolipoprotein components of the HDL particle via primary amines; thus, no transfer of the fluorophore to cell membranes occurs. In this manner, direct binding of the HDL particles to SR-BI can be measured. As a positive control, BLT-1, which is known to increase binding of HDL to SR-BI, was used at 1 μM (12). It is possible that a compound can reduce binding of HDL to the receptor, and this would lead to a decrease in signal. This assay is used to characterize the mechanism of action of a particular compound; therefore, any outcome in the assay is acceptable. Data were normalized against DMSO and the positive control (1 μM BLT-1) in Genedata Assay Analyzer. Curves were generated with Genedata Condeseo and showed percent (%) activity for the individual doses.

Cholesterol Efflux Assay (SA 4: AID Nos. 588818, 602152)

SR-BI also mediates bidirectional flux (e.g. efflux) of unesterified or 'free' cholesterol (FC) between cells and HDL or other acceptors. In vivo, the greatest SR-BI-mediated selective uptake occurs in the liver and steroidogenic organs. This assay is used to determine if the compounds alter the efflux of FC to HDL. Compounds that do and do not inhibit efflux in a dose-dependent manner will be of value.

On Day 0, 50,000 cells per well were plated in 24-well plates. On the following day, the media was removed and [$^3$H]cholesterol in lipoprotein-deficient media was added. On Day 1, the medium was replaced with Ham's F12 medium supplemented with 10% bovine lipoprotein deficient serum with 1 μCi/ml [1,2-$^3$H]cholesterol (40-60 Ci/mmol). On Day 3, the cells were washed to remove serum and incubated in Ham's F12 plus 1% fatty acid-free BSA. On Day 4, the cells were washed and pretreated with compounds for 1 hour. Subsequently, the cells were incubated for an additional 2 hours with the same concentrations of small molecules and with unlabeled HDL (final HDL concentration of 100 μg protein/ml). The medium was collected to determine released cholesterol, and the cells were lysed. The amount of [$^3$H]cholesterol in the medium and cells was determined using liquid scintillation counting. Total cellular [$^3$H]cholesterol was calculated as the sum of the radioactivity in the efflux medium plus the radioactivity in the cells and was used to calculate the [$^3$H]cholesterol efflux (percent of total [$^3$H]cholesterol released into the medium).

Mutant SR-BI Cholesterol Efflux Assay (SA 10: AID Nos. 588843, 602138)

BLT-1 is known to interact at cysteine 384 of SR-BI (16). If the cysteine is mutated to serine, BLT-1 can no longer bind and shows no ability to inhibit cholesterol uptake. This assay is used to determine if the compounds work in a similar fashion to BLT-1 and require Cys384 to alter the efflux of free cholesterol to HDL. Compounds that do and do not inhibit efflux in a dose-dependent manner will be of value.

On Day 0, 50,000 cells expressing murine SR-BI with the C384S mutation per well were plated in 24-well plates. On the following day, the media was removed and [$^3$H]cholesterol in lipoprotein-deficient media was added. On Day 1, the medium was replaced with Ham's F12 medium supplemented with 10% bovine lipoprotein deficient serum with 1 μCi/ml [1,2-$^3$H]cholesterol (40-60 Ci/mmol). On Day 3, the cells were washed to remove serum and incubated in Ham's F12 plus 1% fatty acid-free BSA. On Day 4, the cells were washed and pretreated with compounds for 1 hour. Subsequently, the cells were incubated for an additional 2 hours with the same concentrations of small molecules and with unlabeled HDL (final HDL concentration of 100 μg protein/ml). The medium was collected to determine released cholesterol, and the cells were lysed. The amount of [$^3$H] cholesterol in the medium and within cells was calculated using liquid scintillation counting. Total cellular [$^3$H]cholesterol was determined as the sum of the radioactivity in the efflux medium plus the radioactivity in the cells and was used to calculate the [$^3$H]cholesterol efflux (percent of total [$^3$H]cholesterol released into the medium).

DiI-HDL Uptake Assay in the Absence of SR-BI (SA 7: AID No. 588825)

In the primary assay, the cell line used to measure DiI-HDL uptake lacks the LDL receptor and overexpresses SR-BI. In this assay, the parental CHO cell line [ldlA7], which lacks the LDL receptor but does not overexpress SR-BI, was used to determine if inhibitors work via non-SR-BI-mediated mechanisms. As in the primary assay, 10 μg protein/ml of DiI-HDL was used to measure DiI uptake into the cells after 3 hours of incubation with different concentrations of compound. Little to no uptake of DiI-HDL was observed in these cells, and the only signal observed was minimal background staining.

Transferrin Endocytosis Assay (SA 3: AID No. 602134)

This assay measures the endocytosis of an independent ligand, transferrin, which is not taken up via SR-BI but by clathrin-mediated endocytosis. This assay provides a measure of the selectivity of the inhibitors. Alexa-594-labeled transferrin is taken into the cell via endocytosis and localization of labeled transferrin was quantitated in the various intracellular compartments. If a compound inhibits endocytosis, the labeled transferrin will not enter the cell leading to a decrease of fluorescent signal. Inhibitors of interest should act selectively at SR-BI and should have no activity in this assay.

Figure 22:
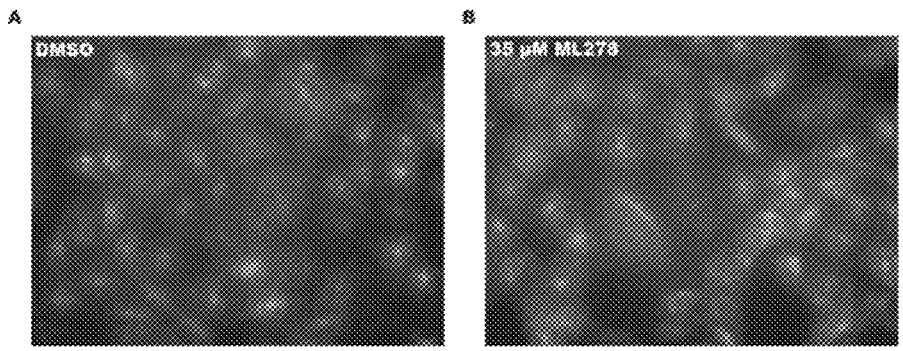
FIG. 22 are images showing that ML278 does not inhibit endocytosis of transferrin.

Cells were pre-treated with compound for 3 hours and then treated with the Alexa-594 transferrin reagent for 30 minutes (Catalog No. T-13343; Invitrogen) in serum-free media. Plates of cells were then placed onto ice, washed with ice cold PBS, and then fixed with 4% paraformaldehyde. In addition, the nuclei were stained with 300 nM 4',6-diamidino-2-phenylindole (DAPI) (Catalog No. 21490; Invitrogen). The cells were imaged with the Molecular Devices IXM microscope (FIG. 22). Translocation measurements were performed using MetaExpress software and normalized for cell number.

DiI-HDL Uptake Assay with Washout (SA 5: AID No. 588831)

This is a modification of the primary assay where cells are treated with compound prior to the addition of DiI-HDL but no compound is present during the DiI-HDL treatment period. ldlA[mSR-BI]cells were plated into 384-well plates at 30 µl per well and incubated overnight. Cells were treated with compound for 3 hours, then media were removed and the cells were washed with PBS before fresh lipoprotein-free media (Ham's F12/0.5% fatty acid-free Bovine Serum Albumin [BSA]/25 mM HEPES pH 7.4) was added with 10 g protein/ml DiI-HDL. Cells took up the DiI via SR-BI over 3 hours in the absence of compound. After significant uptake of the DiI, the cells became fluorescent. The level of fluorescence correlates with the amount of DiI uptake and can be measured with a standard plate reader. The uptake of lipid (represented by DiI) was inhibited by the compound BLT-1.

DiI-HDL Uptake Assay with Extended Washout (SA 5: AID No. 602154)

This is another modification of the primary assay where cells are pretreated with compound but no compound is present during a 4-hour washout period or the subsequent 3-hour DiI-HDL treatment period. This protocol allows us to distinguish between an irreversible inhibitor and a reversible inhibitor with a slow "off-rate". ldlA[mSR-BI]cells were plated into 384-well plates at 30 µl per well and incubated overnight. Cells were treated with compound for 3 hours, then were washed four times with PBS, once with lipoprotein-free media (Ham's F12/0.5% fatty acid-free Bovine Serum Albumin [BSA]/25 mM HEPES pH 7.4), and then returned to the incubator with lipoprotein-free media for 4 hours. Media were then removed and cells were washed with PBS before fresh lipoprotein-free media (Ham's F12/0.5% fatty acid-free Bovine Serum Albumin [BSA]/25 mM HEPES pH 7.4) was added with 10 g protein/ml DiI-HDL. Cells took up the DiI via SR-BI over 3 hours in the absence of compound. After significant uptake of the DiI, the cells became fluorescent. The level of fluorescence correlates with the amount of DiI uptake and can be measured with a standard plate reader. The uptake of lipid (represented by DiI) was inhibited by the compound BLT-1 or with an excess of HDL untreated with DiI.

2.1.11 Lipid Transport Assay in Liposomes (SA 11: AID No. 602155)

Figure 21:
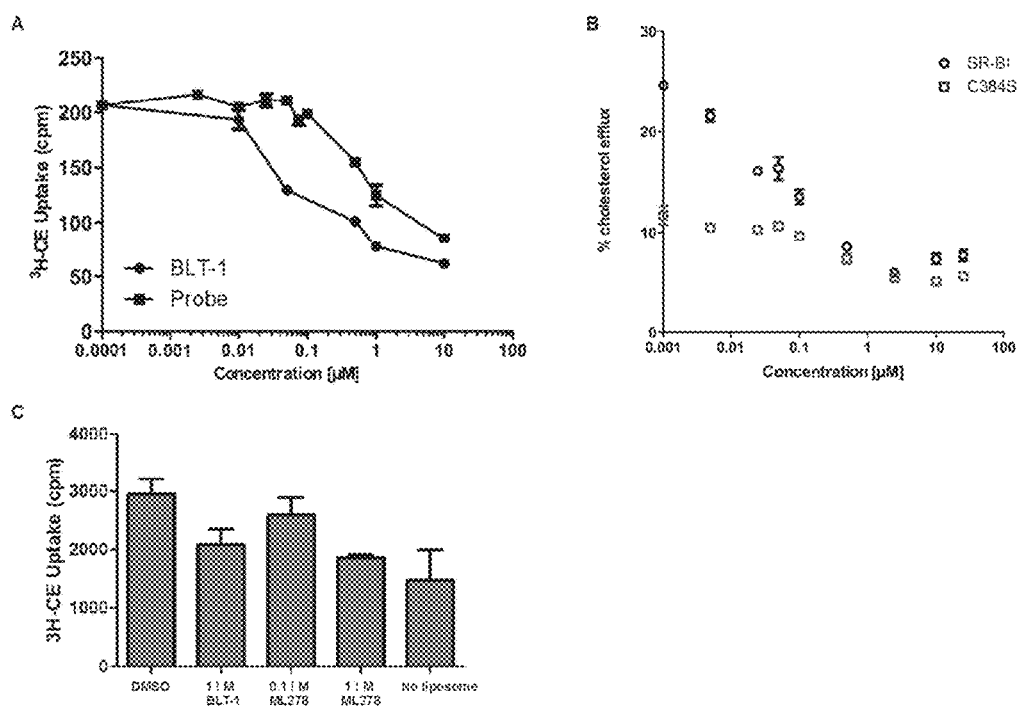
FIG. 21A is a drawing showing the ML278 activity in assay AID 588836.
FIG. 21B is a drawing showing the ML278 activity in assay AID 602152 and AID 602138.
FIG. 21C is a drawing showing the SR-BI liposome assay AID 602155.

This assay provides extra confirmation of activity via SR-BI by measuring the uptake of [$^3$H]cholesteryl ester ([$^3$H]CE) into liposomes loaded with purified SR-BI (FIG. 21C). For the purification of C-terminally epitope-tagged murine SR-BI (mSR-BI-t1) with uniform, truncated N-linked oligosaccharide chains, we overexpressed mSR-BI-t1 in HEK293S cells. The mSR-BI-t1 was expressed in an N-acetylglucosaminyltransferase I (GnTI)-defective HEK293S derivative, HEK293S GnTI(2), which generates a glycoprotein with uniform, truncated N-linked oligosaccharide chains under the control of a tetracycline-inducible promoter. mSR-BI-t1 was immunoaffinity purified to virtual homogeneity, and the detergent-solubilized receptor was reconstituted into liposomes as described previously (15). Briefly, 20 µg of SR-BI (or an equivalent volume of protein-free buffer to generate control liposomes that are devoid of SR-BI) was reconstituted into liposomes by acetone precipitation. SR-BI liposomes were washed once by resuspension of the acetone precipitate in protein-free assay medium followed by a centrifugation step for 25 min and 48,000 g at 4° C. The pellet was first reconstituted in assay medium without protein, and then an equal volume of assay medium with 1% fatty acid-free BSA was added to yield liposomes at a nominal final concentration of 18 ng SR-BI/ml. In each reaction, 30 ml were preincubated together with 30 ml of assay medium containing 0.5% fatty Acid-free BSA, 1% DMSO, and the indicated compounds for 60 min at 37° C. Subsequently, 20 µl of [$^3$H]CE-HDL (five replicates per sample) were added to a final concentration of 10 µg protein/ml. Incubation was continued for 4 hours at 37° C., and then SR-BI selective uptake of [$^3$H]CE into liposomes was determined using the previously described filter binding assays (15). The 100% of control value represents receptor-specific activity in SR-BI-t1-containing liposomes in the presence of 0.5% DMSO without compounds, and the 0% of control value represents background selective uptake in control liposomes devoid of SR-BI-t1.

Radioactive HDL Uptake Assay (wild type SR-BI) (SA 8: AID No. 588836)

The goal of this assay is to verify compounds that disrupt the lipid uptake from HDL particles to SR-BI scavenger receptor-expressing cells using an alternative means of labeling HDL particles and avoiding any type of fluorescence measurement. To measure this binding event, HDL particles are labeled with [$^3$H]cholesteryl ester and added to mSR-BI expressing cells. Cells take up the radioactive lipids from HDL via SR-BI in 2 to 3 hours. After significant uptake of the lipids from HDL, the radiolabel can be detected by liquid scintillation counting. The level of radioactivity correlates with the amount of HDL lipid uptake. The uptake of lipid from the HDL particles particles can be inhibited by the compound BLT-1 or when co-treated with an excess of unlabeled HDL. The ldlA[mSR-BI]-expressing cells utilized in the assay are from a Chinese Hamster Ovary (CHO) cell line lacking expression of the LDL receptors and overexpressing the scavenger receptor, SR-BI. Inhibitors of SR-BI and HDL lipid uptake will have a reduction in liquid scintillation counts.

Radioactive HDL Uptake Assay (mutant SR-BI) (SA 9: AID No. 588837)

BLT-1 is known to interact at cysteine 384 of SR-BI (16). If the cysteine is mutated to serine, BLT-1 can no longer bind and shows no ability to inhibit cholesterol uptake. This assay is used to determine if the compounds work in a similar fashion to BLT-1 and require Cys384 to alter the binding of HDL particles and uptake of the lipid to the mutant SR-BI scavenger receptor, using an alternative means of labeling HDL-cholesterol particles and avoiding any type of fluorescence measurement. To measure this lipid uptake event, HDL particles are labeled with [$^3$H]cholesteryl ester and added to C384S SR-BI cells. Cells take up HDL lipids via the mutant SR-BI in 2 to 3 hours. After significant uptake of the HDL lipid, the radiolabel can be detected by liquid scintillation counting. The level of radioactivity correlates with the amount of HDL lipid uptake. The uptake of lipid from the HDL particles can be inhibited by the compound BLT-1 or when co-treated with an excess of unlabeled HDL. The mSR-BI cells utilized in the assay are a CHO cell line lacking expression of the LDL receptors and overexpressing the mutant scavenger receptor, C384S SR-BI.

Probe Chemical Characterization

Figure 4:
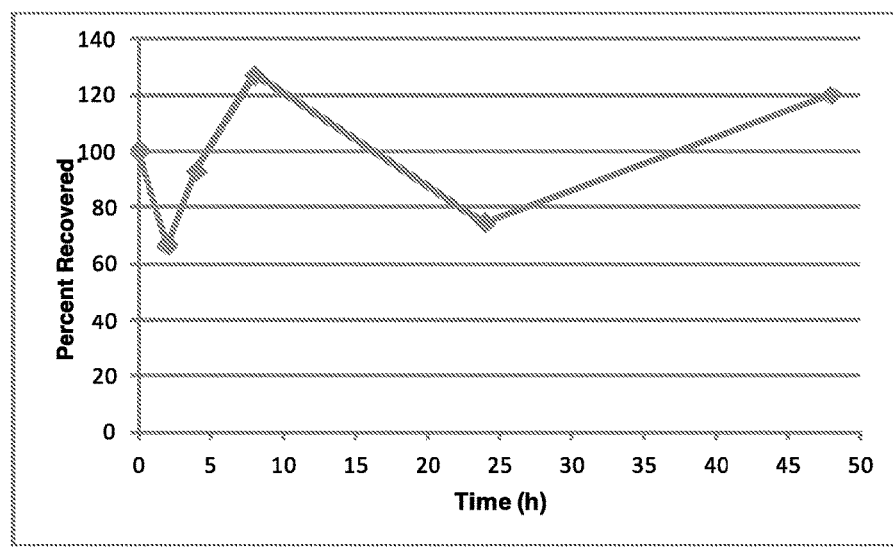
FIG. 4 is a graph showing the recovery of undissolved probe (ML278) from PBS buffer (pH 7.4, 23° C.)
Figures 5, 6:
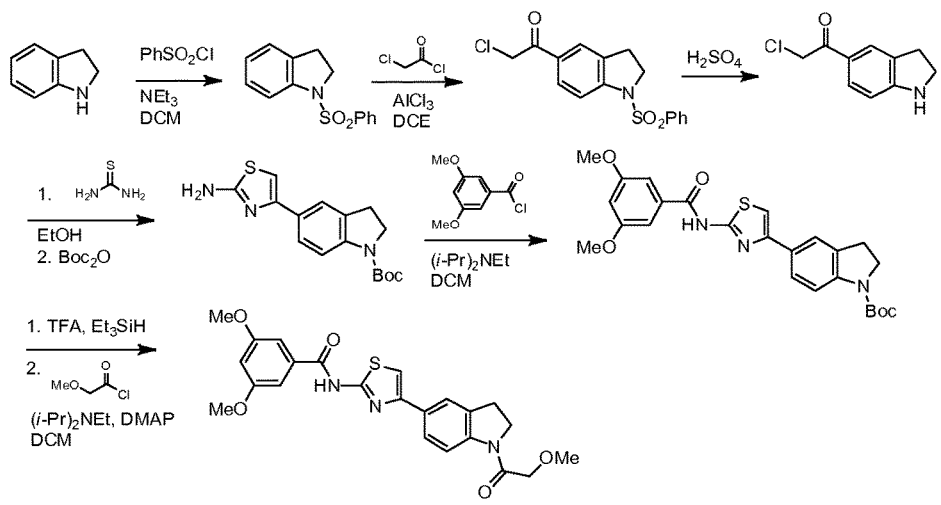
FIG. 5 is a table showing the summary of known probe (ML278) properties computed from structure.
FIG. 6 is a diagram showing the synthesis of probe (ML278)

The probe (ML278) was prepared as described in Section 2.3, and was analyzed by UPLC, $^1$H and $^{13}$C NMR spectroscopy, and high-resolution mass spectrometry. The data obtained from NMR and mass spectrometry were consistent with the structure of the probe, and UPLC analysis showed purity of >95%. Characterization data ($^1$H NMR spectra and UPLC chromatograms) of the probe are provided The solubility of ML278 was determined to be 0.57 µM in Phosphate buffered saline (PBS; pH 7.4, 23° C.) solution with 1% DMSO. The stability of the probe in PBS (1% DMSO) was measured over 48 hours. We noticed that the concentration of the probe fluctuated through the course of the assay (data not shown). We believe that this fluctuation is due to the low solubility of the probe. Thus, we decided to determine the amount of undissolved probe present in the well after it was treated with PBS for a given length of time, relative to the amount of undissolved probe at the start of the assay. The wells were centrifuged and the supernatant was removed after various time points, then acetonitrile was added to dissolve the remaining solid in the wells, and the amount of probe was quantified. From these results, the probe seems to be stable to PBS (FIG. 4). The stability of the probe was confirmed by measuring stability in human plasma, with >99% remaining after a 5-hour incubation period. Plasma protein binding (PPB) studies showed that it was 93.5% bound in human plasma. FIG. 5 provides a tablular summary of Known Probe (ML278) Properties Computed from Structure.

Probe Preparation

The probe was prepared using the sequence outlined in scheme 1 illustrated in FIG. 6, which was designed for flexibility in producing analogs with diverse indoline N-substituents. A streamlined route to the probe (or a specific analog) is anticipated by alternatively starting the synthesis by N-acylating indoline with the desired building block (e.g., methoxyacetyl chloride). Such a synthesis has been tested in the production of analogs with the indoline N-propionyl substitution pattern. In the sequence described in Scheme 1, indoline was protected with benzenesulfonyl chloride, and the resulting sulfonamide underwent efficient Friedel-Crafts acylation with chloroacetyl chloride. The sulfonamide was then hydrolyzed by heating with concentrated sulfuric acid, and then the crude chloroketone product was condensed with thiourea at elevated temperature to generate the desired 2-aminothiazole. Protection of the indoline nitrogen occurred with excellent selectivity using $Boc_2O$, then the aminothiazole was acylated with 2,4-dimethoxybenzoyl chloride. The indoline was then deprotected and acylated with 2-methoxyacetyl chloride to generate the final probe.

Probe 278 had the following attributes: (1) an $IC_{50}$ value as low as 0.00093 µM in the DiI-HDL uptake assay; (2) no apparent cytotoxicity after 24 hours of treatment ($EC_{50}$=>35 µM); (3) Inhibits efflux of cholesterol; (4) did not inhibit endocytosis of transferring and (5) was a reversible inhibitor.

To identify novel inhibitors, SR-BI-mediated lipid uptake was measured in an engineered cell line that minimized potential uptake by other mechanisms, including via the LDL receptor (1). ldlA[mSR-BI]cells overexpress murine isoform 1 and selectively take up HDL lipid at similar levels as "has been reported for cultured mouse adrenal cells, perfused organs, and liver, adrenal gland and ovary in vivo" (1). This primary cell-based assay was used in a pilot screen that identified BLTs 1 through 5 (12). The assay was slightly modified from the original protocol of Nieland et al. to increase throughput and to ease automation procedures. Briefly, the plate reader was switched to a Perkin-Elmer EnVision, several washing steps were eliminated, and the cell number per well was reduced without impacting the robustness of the assay. The automated assay was first tested with a validation set of 2,240 compounds. These compounds were tested in duplicate with in-plate neutral (DMSO) and positive controls (1 µM BLT-1). Robustness, reproducibility, and variability parameters were analyzed before initiating the full HTS. The HTS was run over the course of several weeks. Data were normalized relative to controls, and plate patterns were corrected using a multiplicative algorithm in Genedata Assay Analyzer. For each compound, the average of the two replicates was determined and used for subsequent analysis.

Determination of hits required several criteria: only assay plates with a Z' greater than 0.3 were accepted for analysis, compounds needed to reach 70% inhibition relative to 1 µM BLT-1, and score in fewer than 10% of HTS assays listed in PubChem. In total, 319,533 compounds were screened. Of these, 3,046 compounds were considered active (a hit rate of 0.96%), 613 were inconclusive, and 315,055 were inactive. Compounds were clustered based upon chemical structure using a customized script in Pipeline Pilot. Clusters were rated based upon structural liabilities and ranked accordingly. Substructures were analyzed and compared to inactive compounds to identify inactive analogs. Representatives from the more desirable clusters were selected for retest. In addition, a small number of inactive analogs were chosen to provide initial structure/activity relationship (SAR) data during the retest studies. Of these, 573 compounds were retested over a range of concentrations to validate activity, and 186 compounds showed dose-dependent inhibition of DiI-HDL uptake.

Since active compounds produce a decrease in signal in the primary assay, confirmation was required that the reduction in fluorescence was not a result of quenching by the compound. Compounds were tested in the presence of DiI-HDL in a cell-free version of the primary assay. Of the compounds that were active in the primary assay, 127 were found to quench the DiI signal while 59 showed no alteration of fluorescence in the quenching assay.

All available dry powder samples of the remaining, non-quenching compounds were procured from commercial sources and purities were determined. The compounds obtained were then retested in the primary assay and in the cytotoxicity assays. We wanted to rule out any compounds that were cytotoxic, especially in the 3-hour time span of the primary DiI-HDL uptake assay. Therefore, compounds were tested in ldlA[mSR-BI]cells for cytotoxicity at 3 hours and 24 hours using the CellTiter-Glo assay (Promega) that measures cellular ATP as a marker of cell viability. Of these, 11 compounds showed an $IC_{50}$ value of less than 35 µM and were excluded from further consideration. Approximately 44 compounds had an $IC_{50}$ value below 10 µM in the primary DiI-HDL assay. Fifteen chemical scaffolds showed potencies below 1 µM, and three of these were prioritized for follow-up studies. Compounds were screened for inhibition of endocytosis using labeled transferrin, which is known to bind the transferrin receptor, enter cells by clathrin-mediated endocytosis, and move to endosomes before being recycled to the cell surface. The BLT compounds have also been tested for potential interference with endocytosis and show no such activity.

Figure 7:
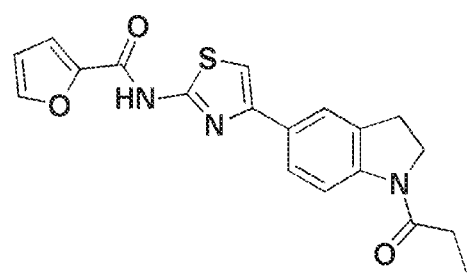
FIG. 7 is a drawing showing the molecular representation of the indoline-thiazole scaffold of MLS001217863.

Neither the original hit described in this report, MLS001217863 (FIG. 7, SID49678600, CID24761960), nor ML278 (FIG. 1, AID No. 602134) affected endocytosis of transferrin, indicating that they are not grossly perturbing cellular membrane trafficking pathways independent of SR-BI. The indoline-thiazole scaffold of CID24761960 registered an $IC_{50}$ value in the primary assay of 0.035 µM (FIG.

8, AID No. 540354), and was prioritized for further development. Analogs were designed and synthesized, eventually leading to the more potent probe, ML278 (see Section 3.4)

In the primary HTS, compounds were active if they decreased DiI-HDL uptake as measured by fluorescence. The positive control, BLT-1 (1 μM), caused a decrease in uptake that led to over a 2.2-fold reduction in signal. Compounds with greater than 70% activity of the positive control were considered actives and chosen for confirmation studies (see Section 3.4 for details).

Figure 9:
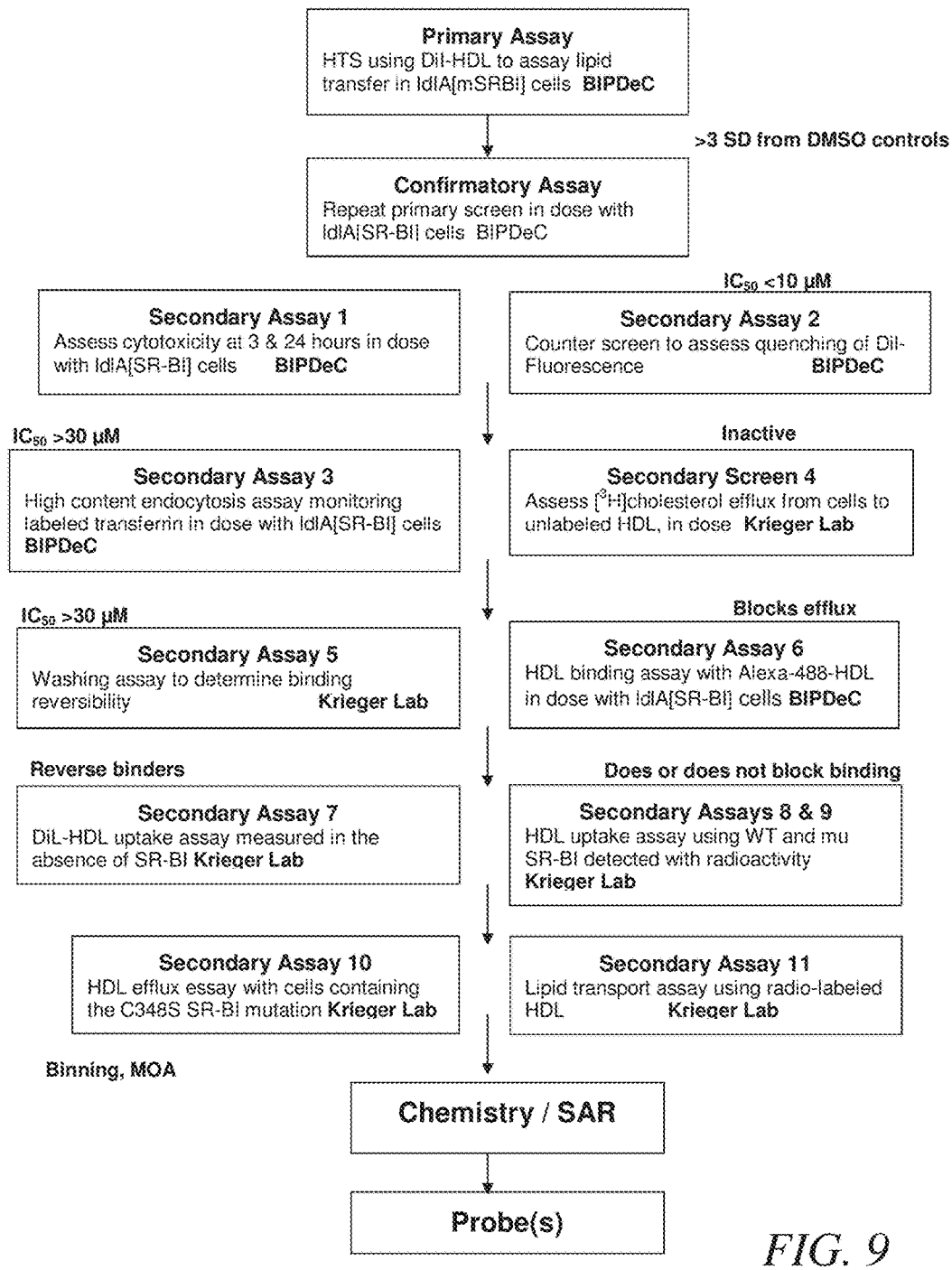
FIG. 9 is a diagram showing the critical path for probe development.

FIG. 9 displays the critical path for probe development. To explore SAR, numerous analogs were synthesized and tested. Selected results are shown in the figures.

Dose Response Curves for the Probe (ML278) are provided in FIG. 10. Probe 1 (ML278) has no apparent chemical liabilities, which is also supported by its good plasma stability previously discussed above.

Figure 23:
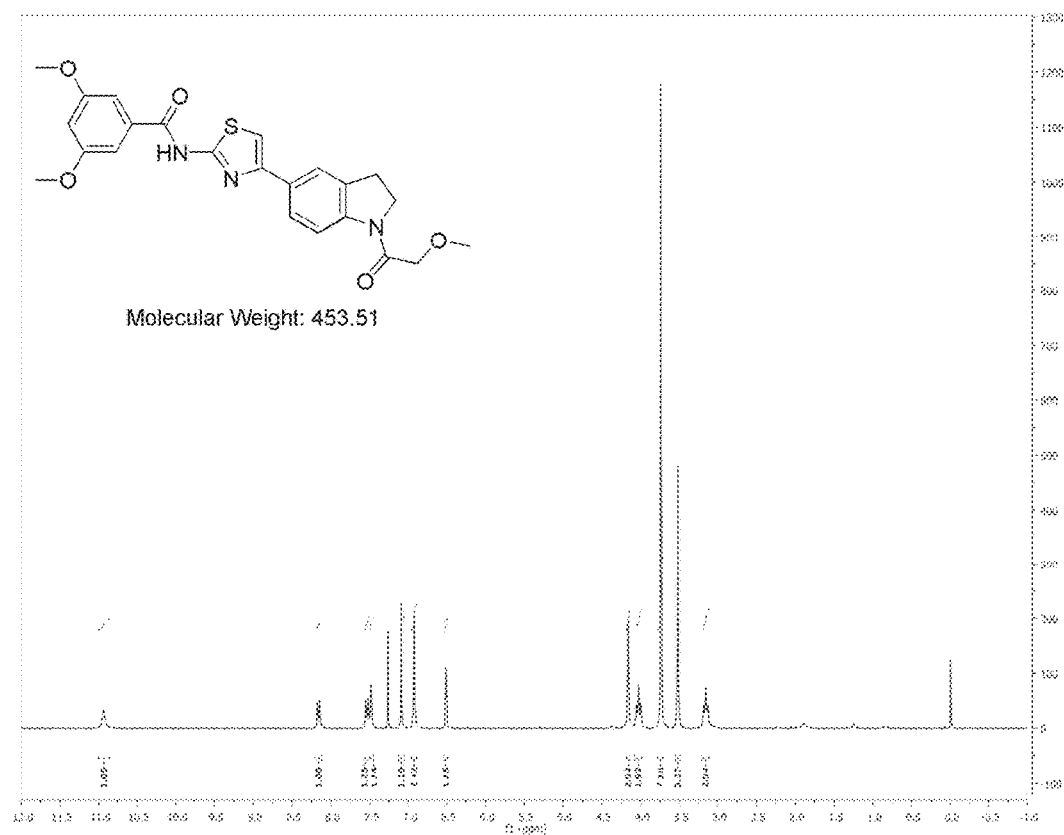
FIG. 23 is a graph showing the chemical characterization data for probe 1 (ML278), $^1$H-NMR spectrum.
Figure 24:
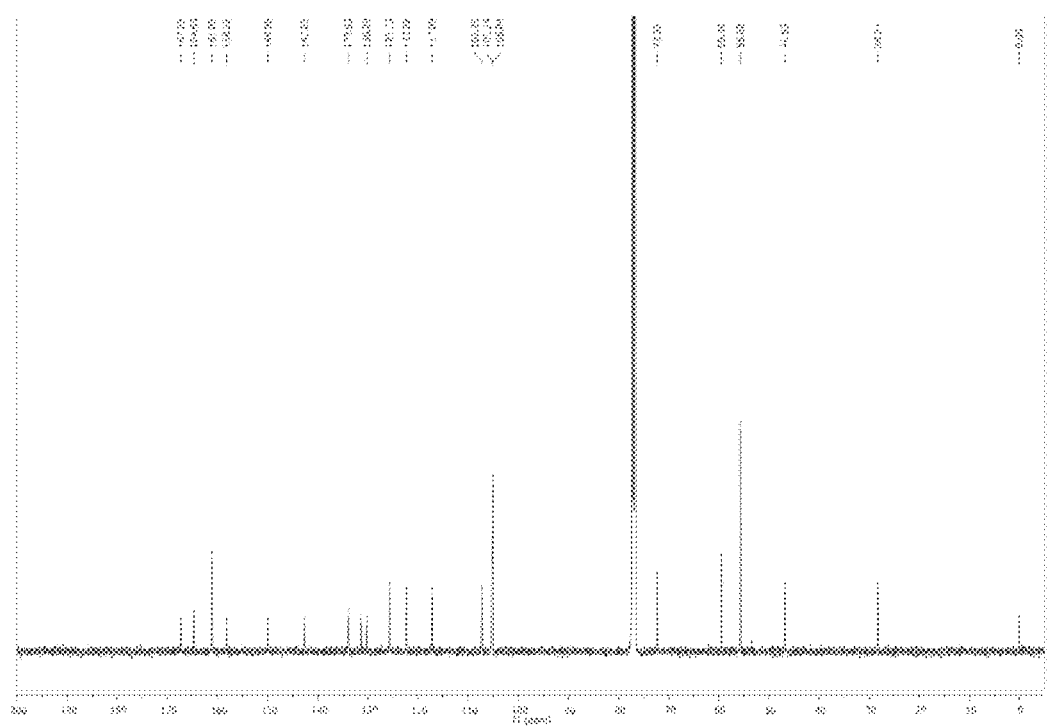
FIG. 24 is a graph showing the chemical characterization data for probe 1 (ML278), $^{13}$C-NMR spectrum.
Figure 25:
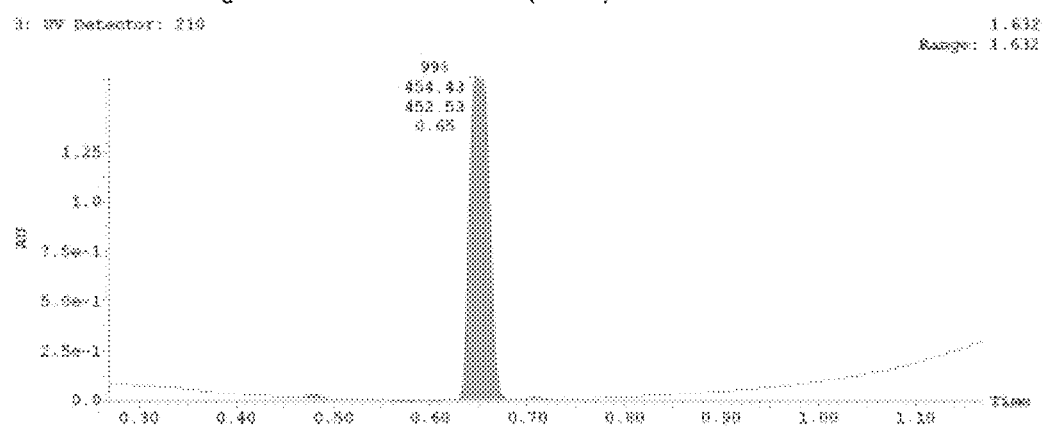
FIG. 25 is a graph showing the chemical characterization data for probe 1 (ML278), UPLC-MS chromatogram.
Figure 26C:
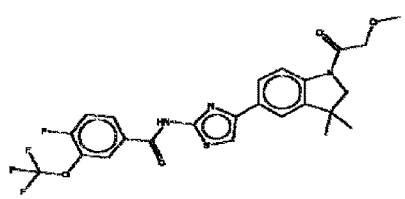
FIG. 26C is a table showing the SAR analysis of additional analogs (cont'd)
Figure 26D:
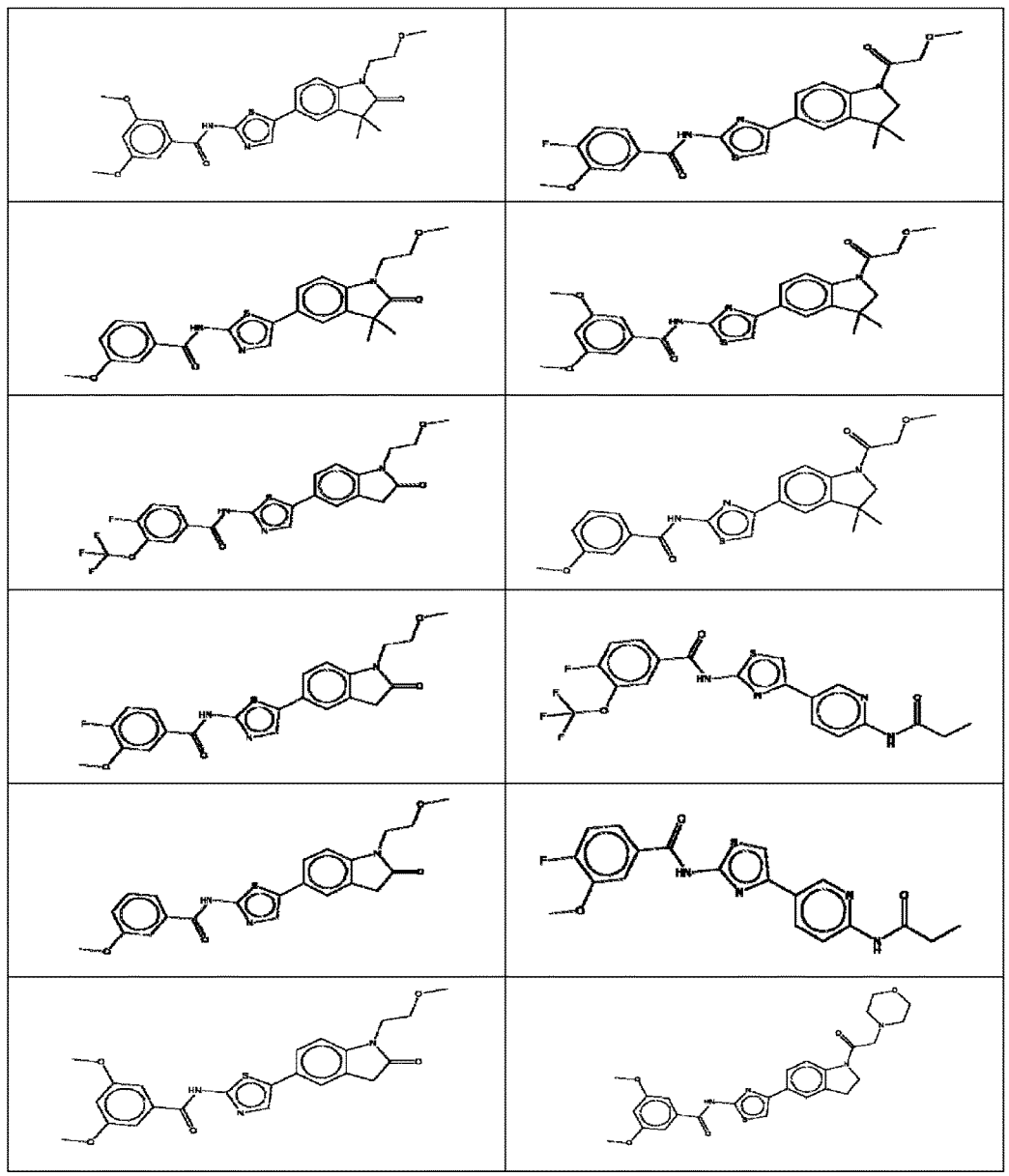
FIG. 26D is a table showing additional analogs.
Figure 27:
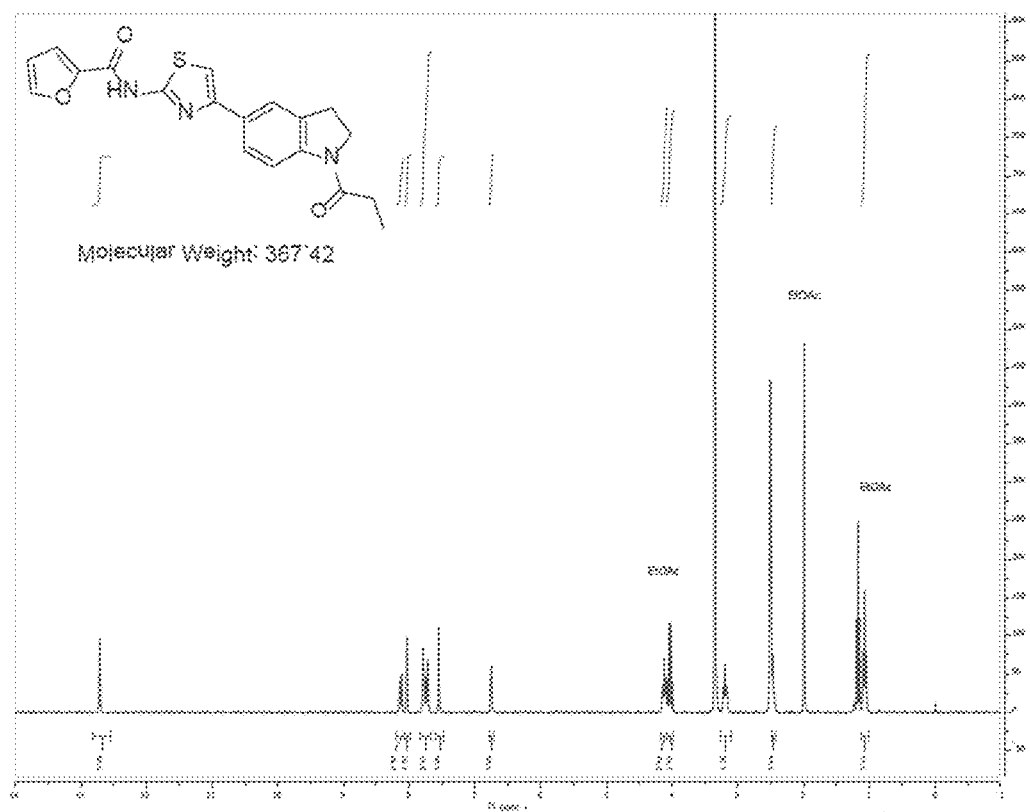
FIG. 27 is a graph showing the chemical characterization data for analog CID 24761960, $^1$H-NMR spectrum.
Figure 28:
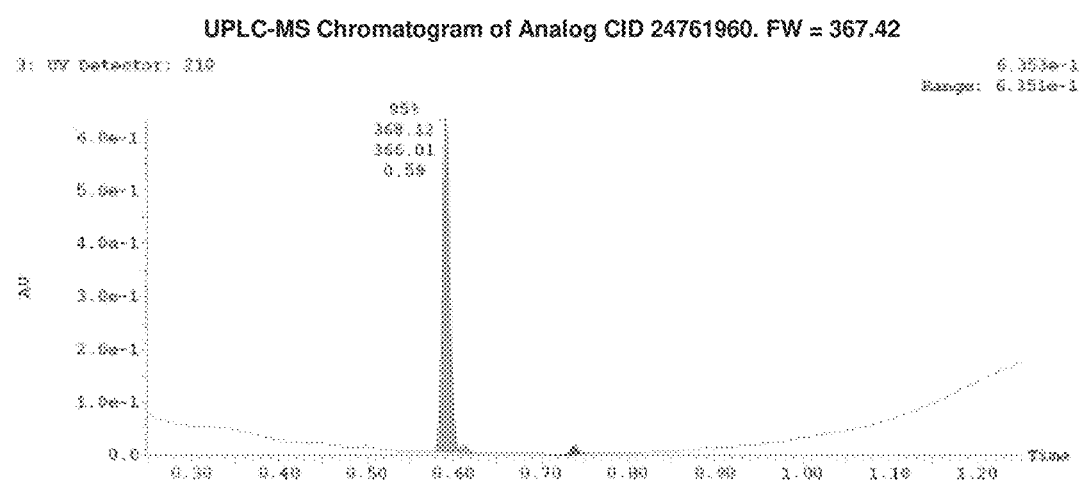
FIG. 28 is a graph showing the chemical characterization data for analog CID 24761960, UPLC-MS chromatogram.
Figure 29:
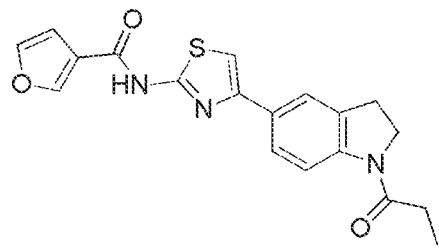
FIG. 29 is a graph showing the chemical characterization data for analog CID 53262914, $^1$H-NMR spectrum.
Figure 30:
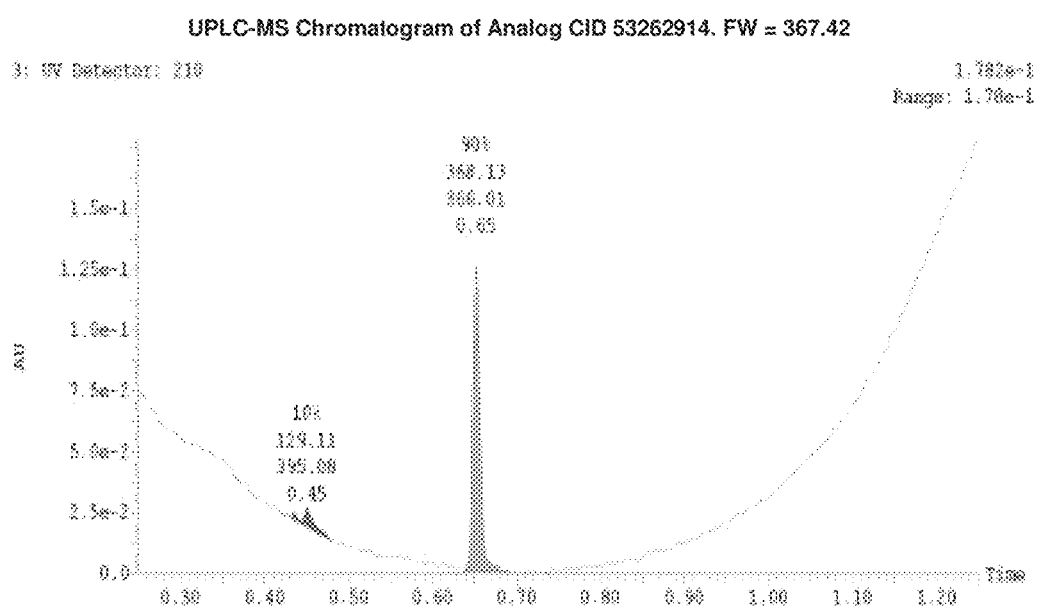
FIG. 30 is a graph showing the chemical characterization data for analog CID 53262914, UPLC-MS chromatogram.
Figure 31:
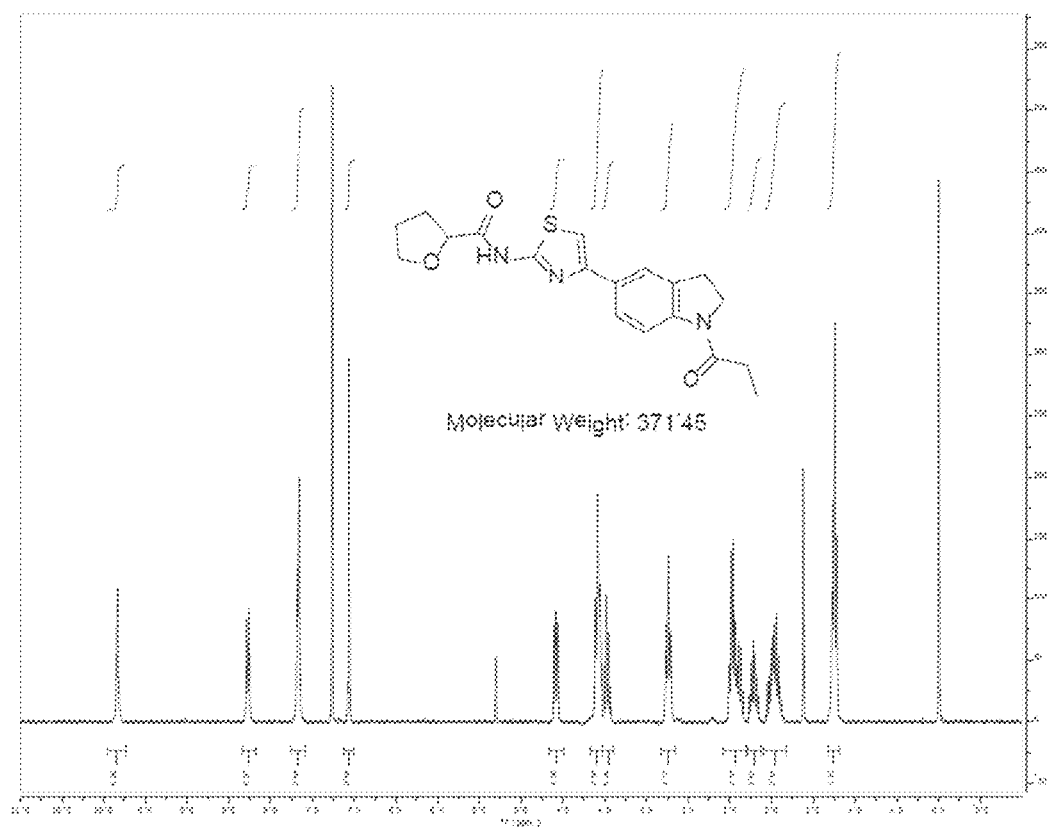
FIG. 31 is a graph showing the chemical characterization data for analog CID 53347982, $^1$H-NMR spectrum.
Figure 32:
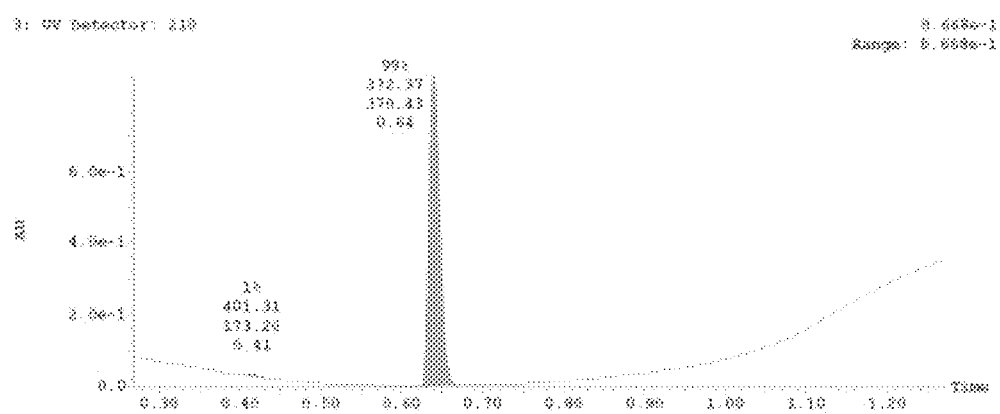
FIG. 32 is a graph showing the chemical characterization data for analog CID 53347982, UPLC-MS chromatogram.
Figure 33:
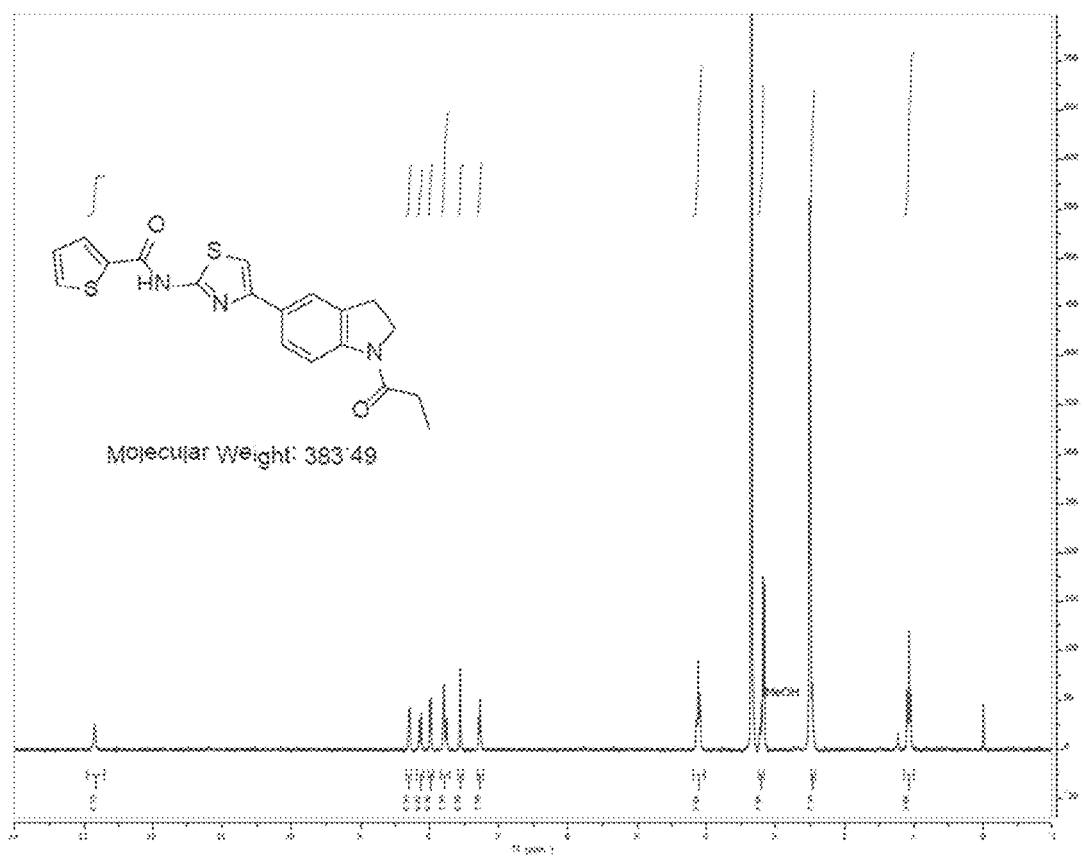
FIG. 33 is a graph showing the chemical characterization data for analog CID 53348009, $^1$H-NMR spectrum.
Figure 34:
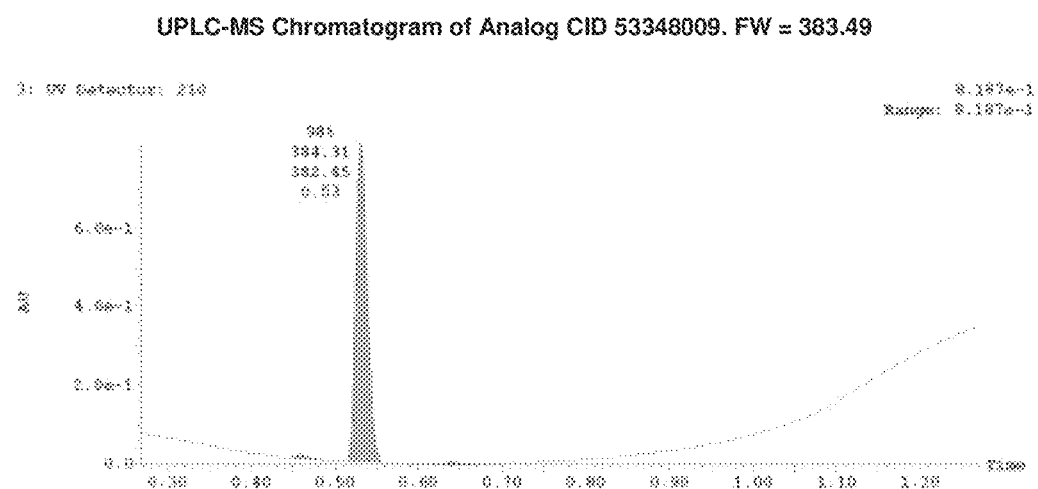
FIG. 34 is a graph showing the chemical characterization data for analog CID 53348009, UPLC-MS chromatogram.
Figure 35:
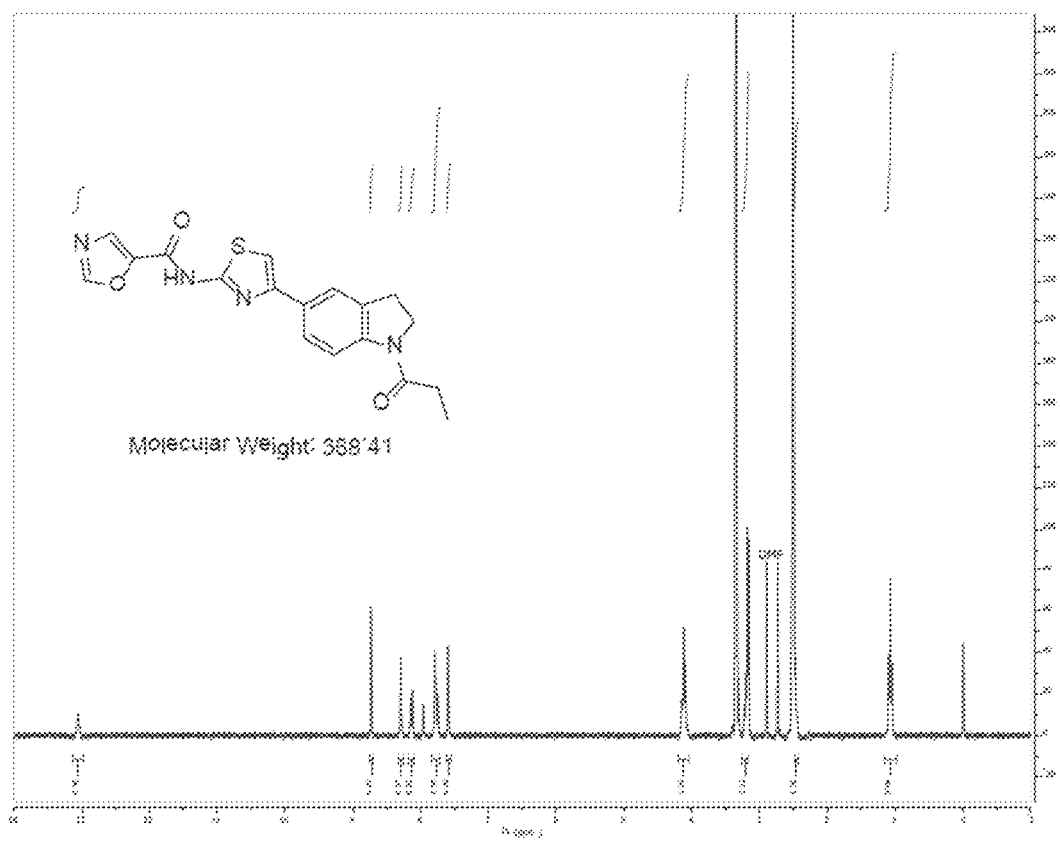
FIG. 35 is a graph showing the chemical characterization data for analog CID 53262916, $^1$H-NMR spectrum.
Figure 36:
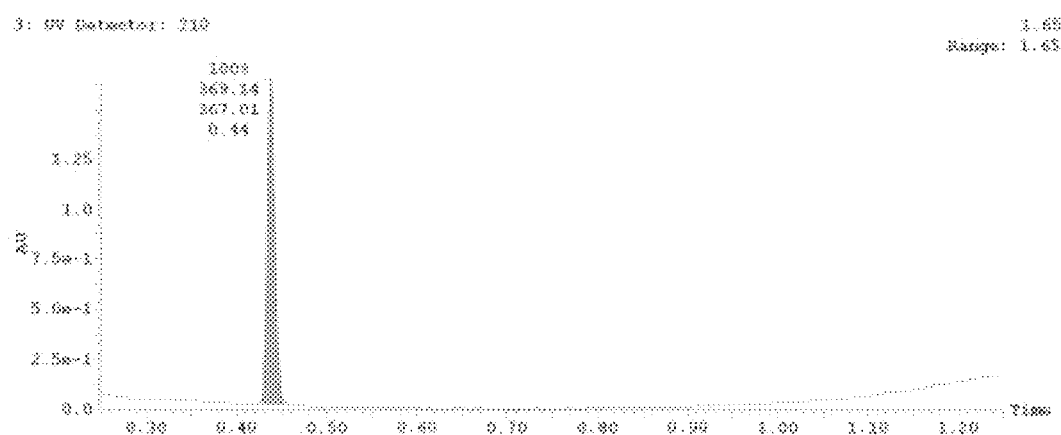
FIG. 36 is a graph showing the chemical characterization data for analog CID 53262916, UPLC-MS chromatogram.
Figure 37:
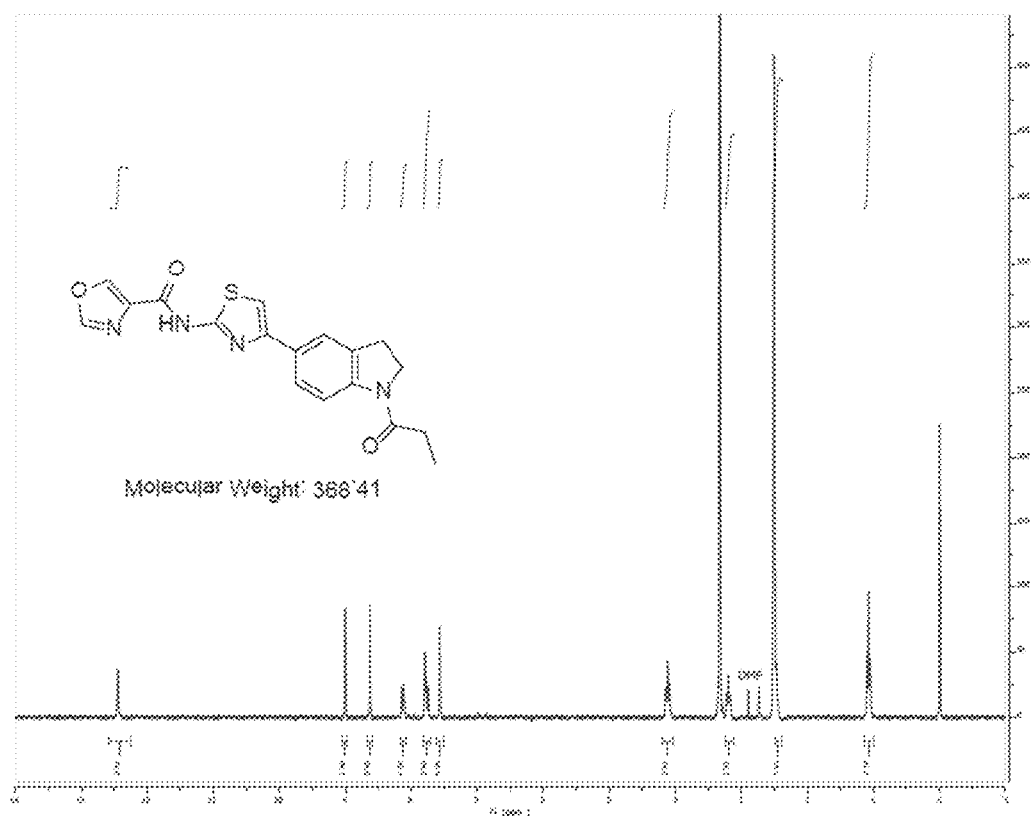
FIG. 37 is a graph showing the chemical characterization data for analog CID 53347968, $^1$H-NMR spectrum.
Figure 38:
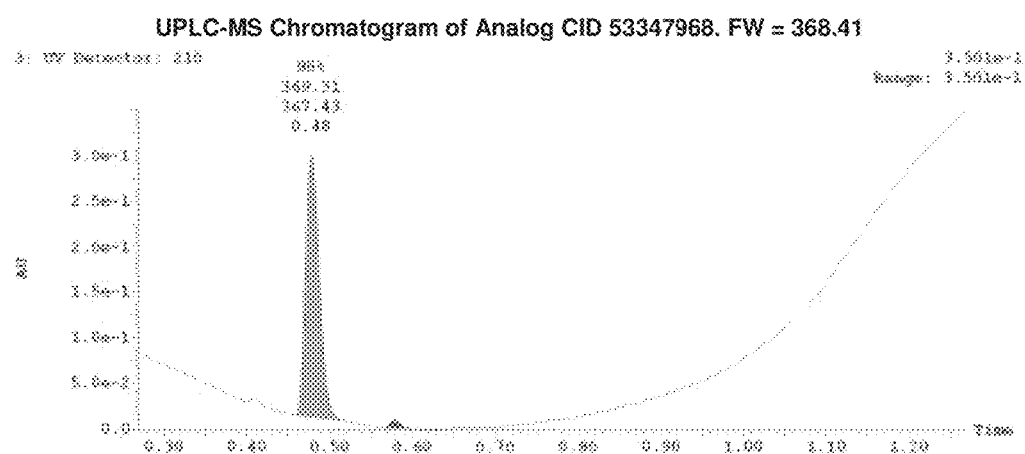
FIG. 38 is a graph showing the chemical characterization data for analog CID 53347968, UPLC-MS chromatogram.
Figure 39:
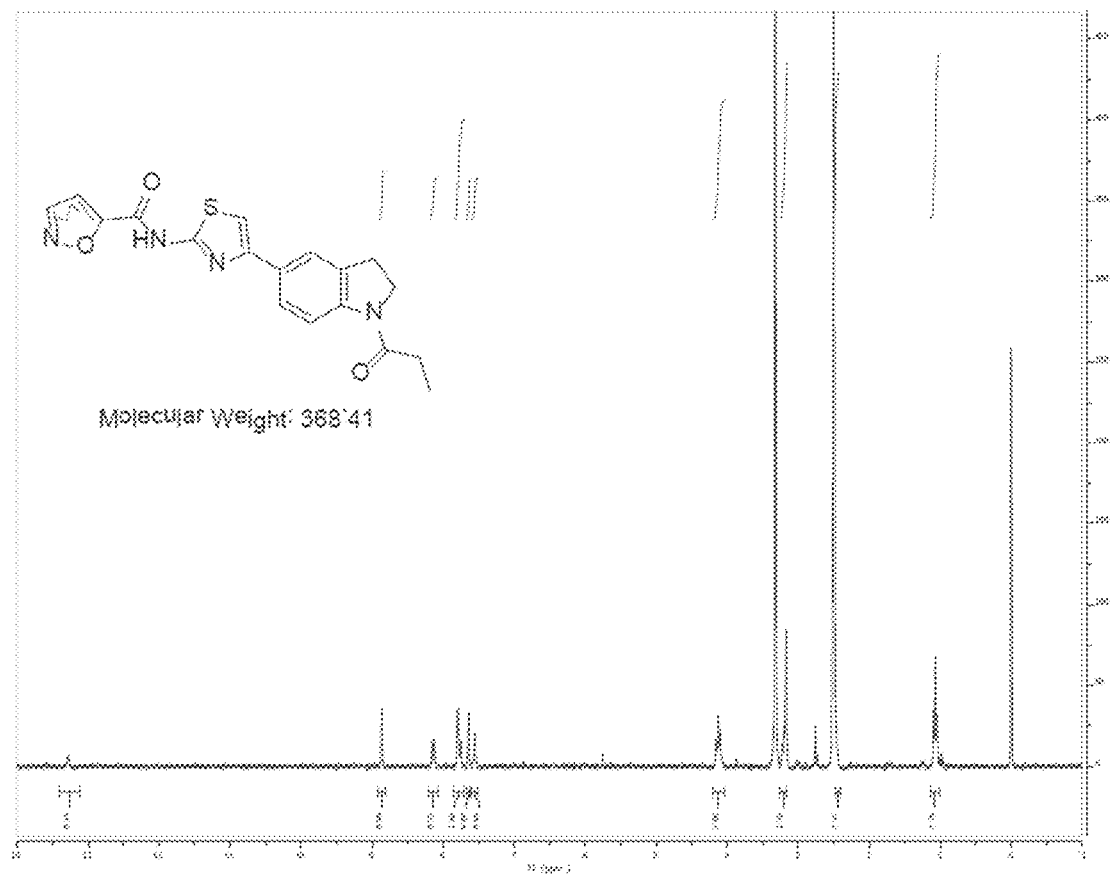
FIG. 39 is a graph showing the chemical characterization data for analog CID 53347974, $^1$H-NMR spectrum.
Figure 40:
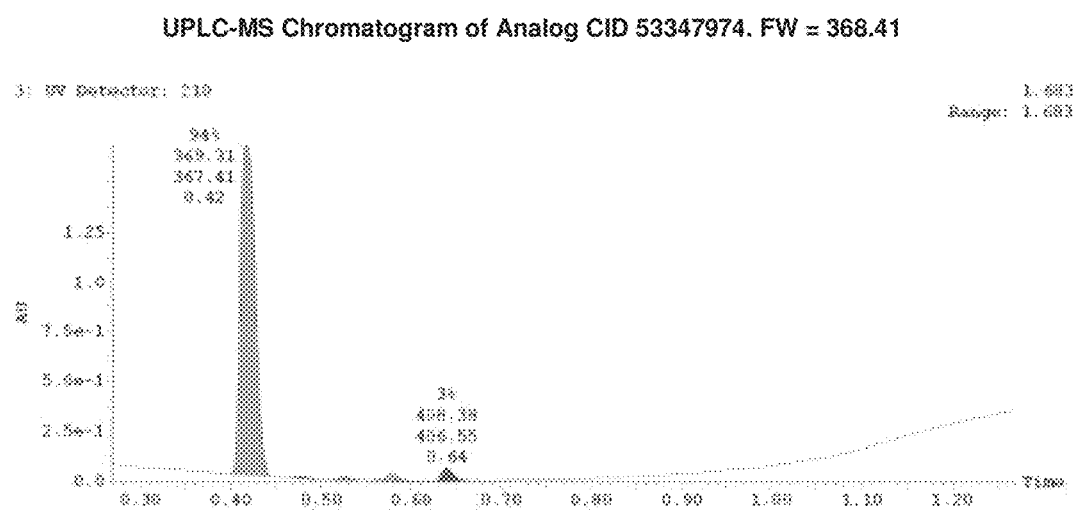
FIG. 40 is a graph showing the chemical characterization data for analog CID 53347974, UPLC-MS chromatogram.
Figure 41:
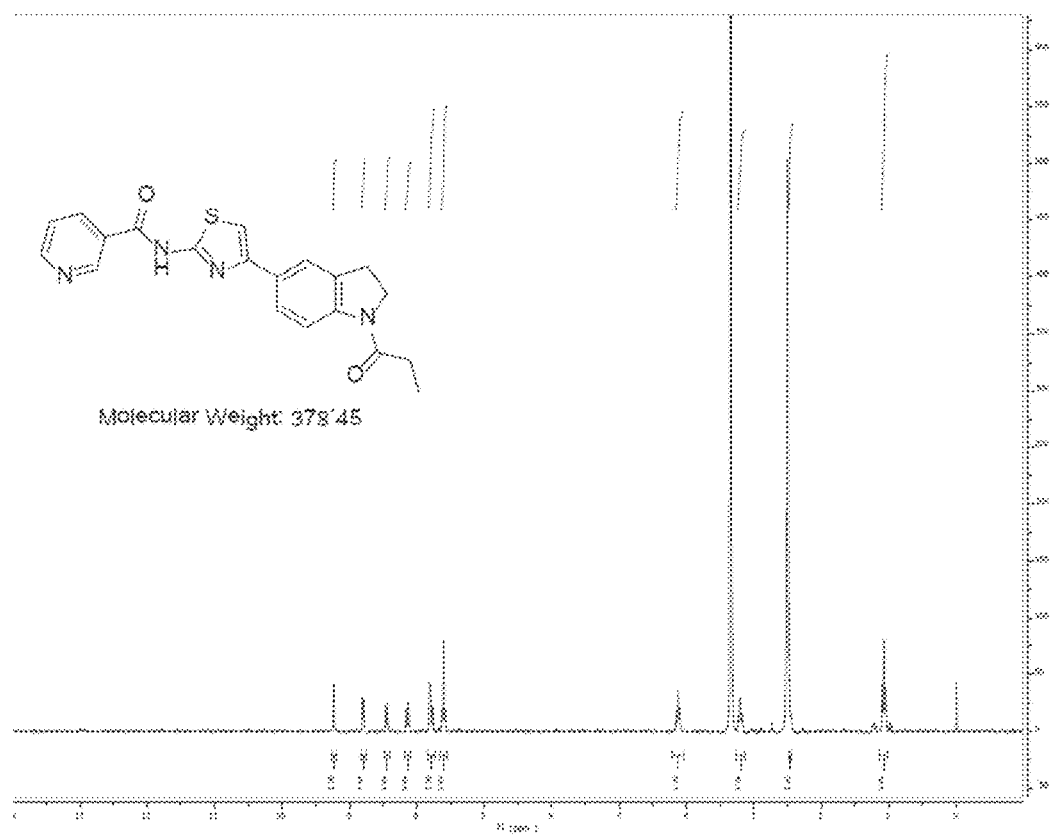
FIG. 41 is a graph showing the chemical characterization data for analog CID 53262919, $^1$H-NMR spectrum.
Figure 42:
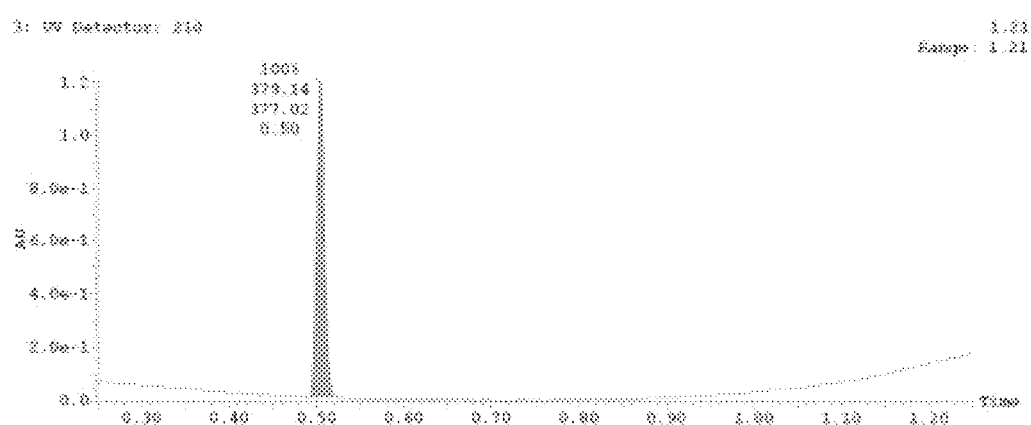
FIG. 42 is a graph showing the chemical characterization data for analog CID 53262919, UPLC-MS chromatogram.
Figure 43:
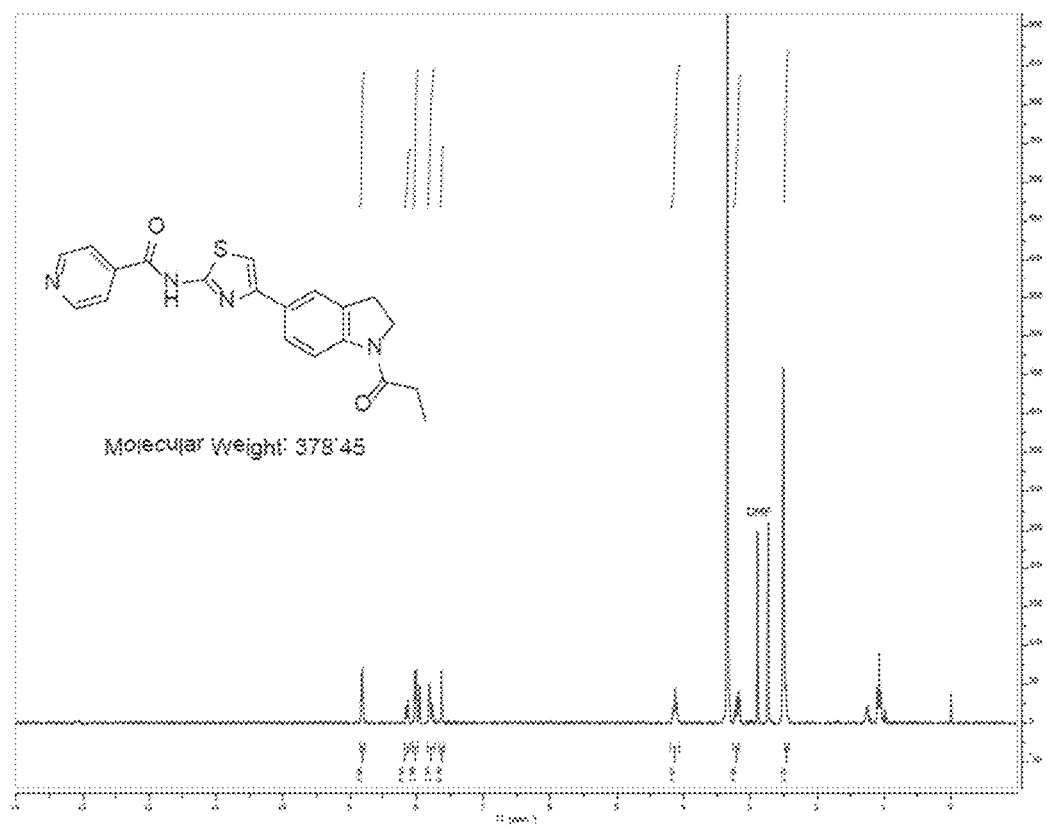
FIG. 43 is a graph showing the chemical characterization data for analog CID 53262921, $^1$H-NMR spectrum.
Figure 44:
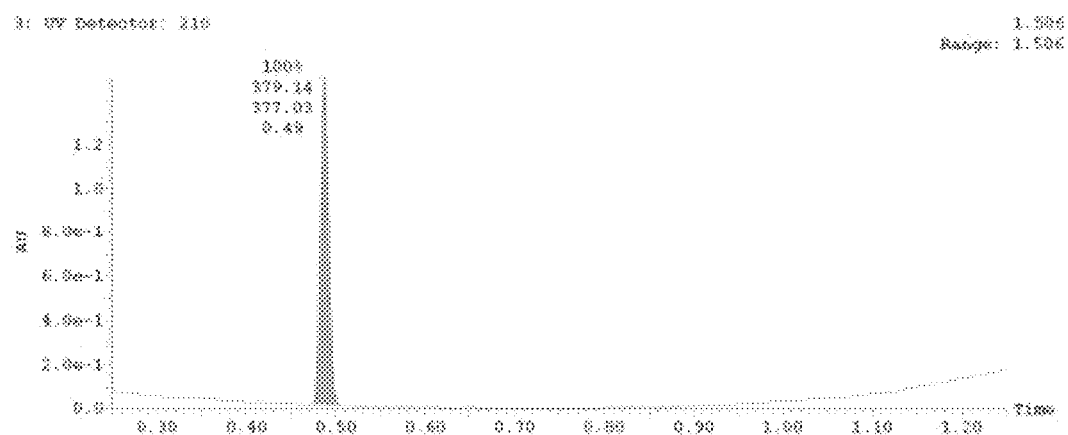
FIG. 44 is a graph showing the chemical characterization data for analog CID 53262921, UPLC-MS chromatogram.
Figure 45:
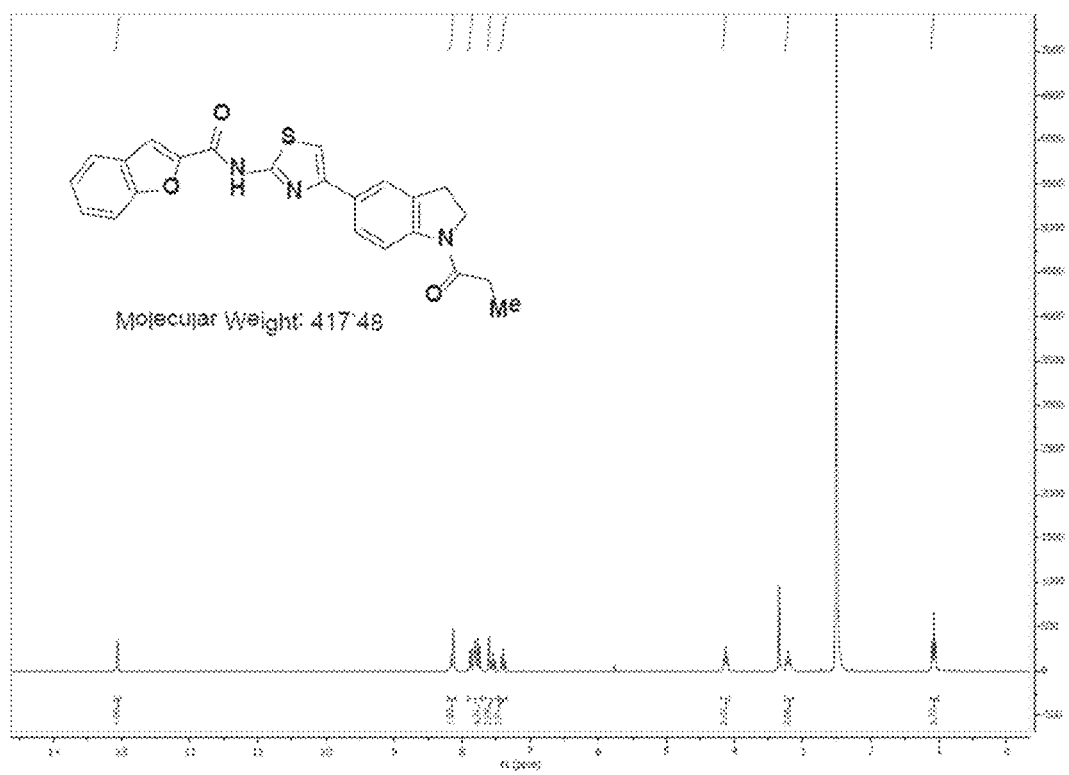
FIG. 45 is a graph showing the chemical characterization data for analog CID 53393838, $^1$H-NMR spectrum.
Figure 46:
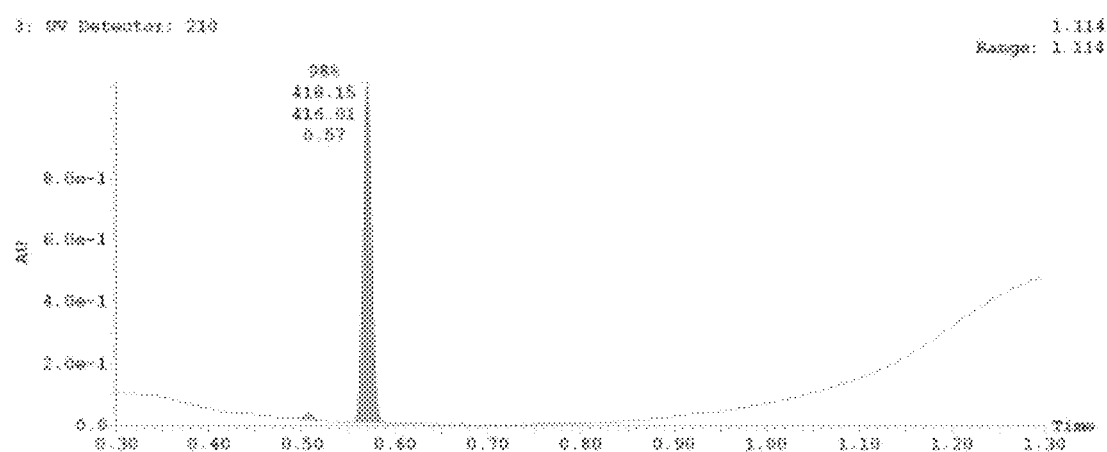
FIG. 46 is a graph showing the chemical characterization data for analog CID 53393838, UPLC-MS chromatogram.
Figure 47:
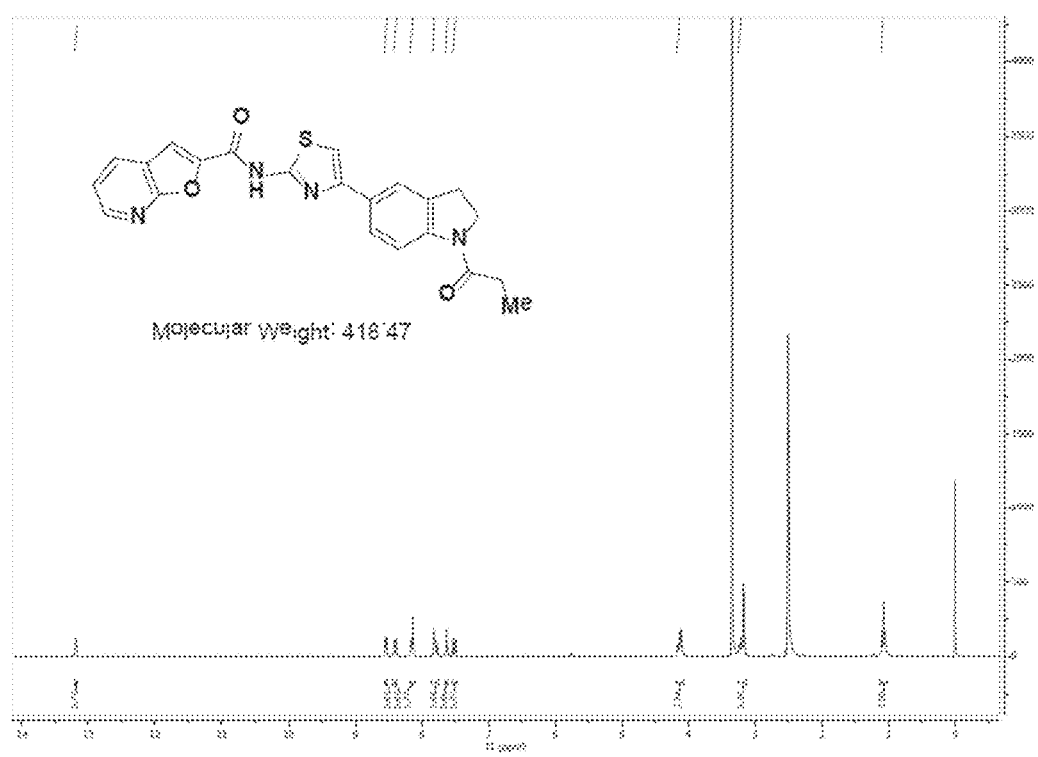
FIG. 47 is a graph showing the chemical characterization data for analog CID 53377424, $^1$H-NMR spectrum.
Figure 48:
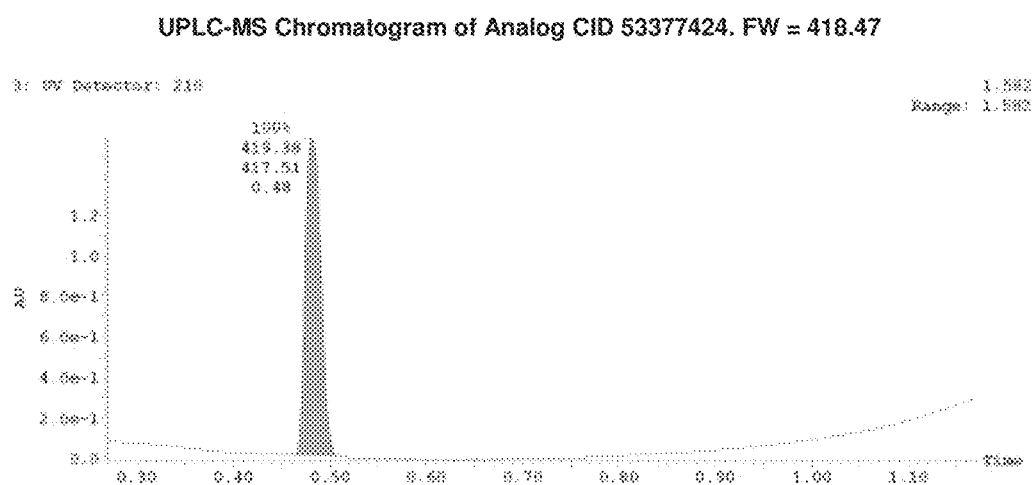
FIG. 48 is a graph showing the chemical characterization data for analog CID 53377424, UPLC-MS chromatogram.
Figure 49:
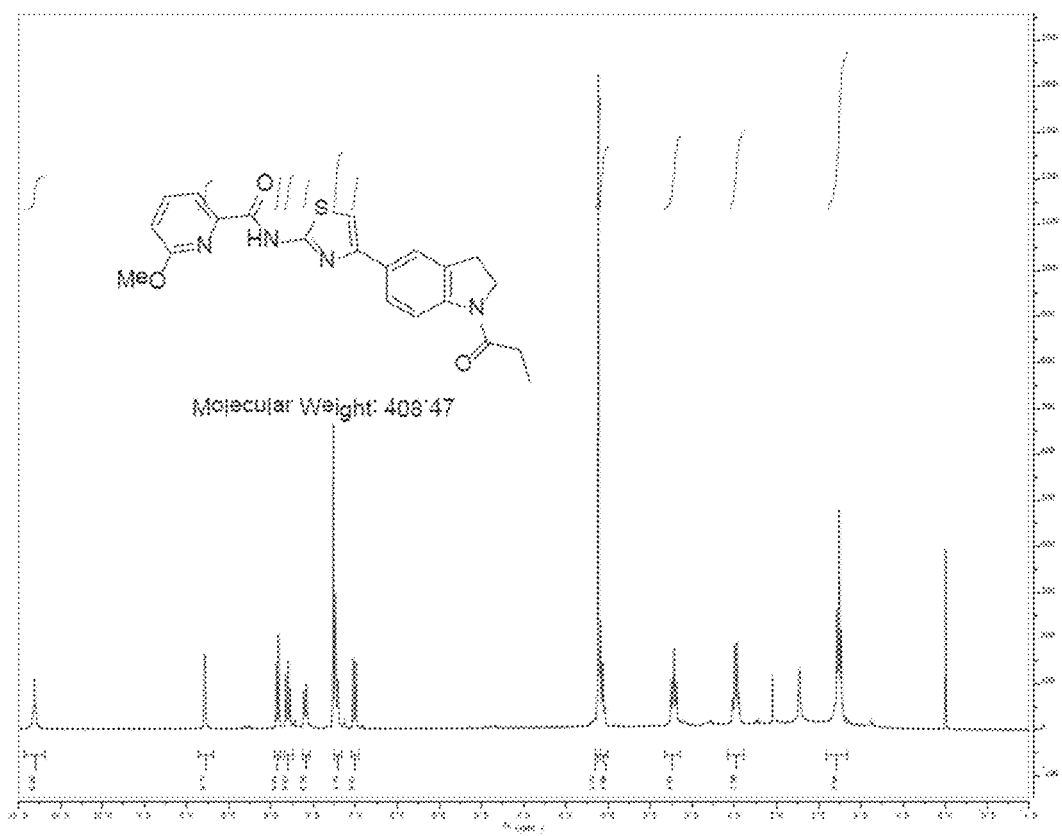
FIG. 49 is a graph showing the chemical characterization data for analog CID 53347952, $^1$H-NMR spectrum.
Figure 50:
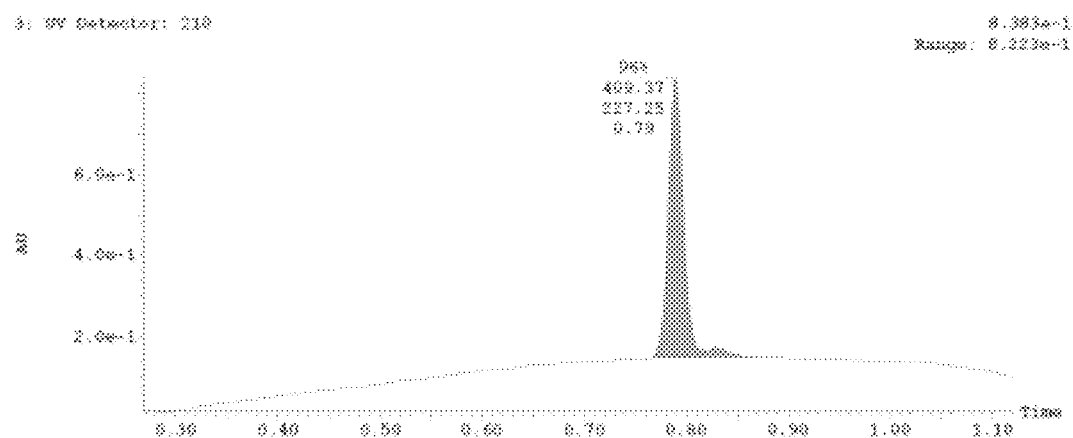
FIG. 50 is a graph showing the chemical characterization data for analog CID 53347952, UPLC-MS chromatogram.
Figure 51:
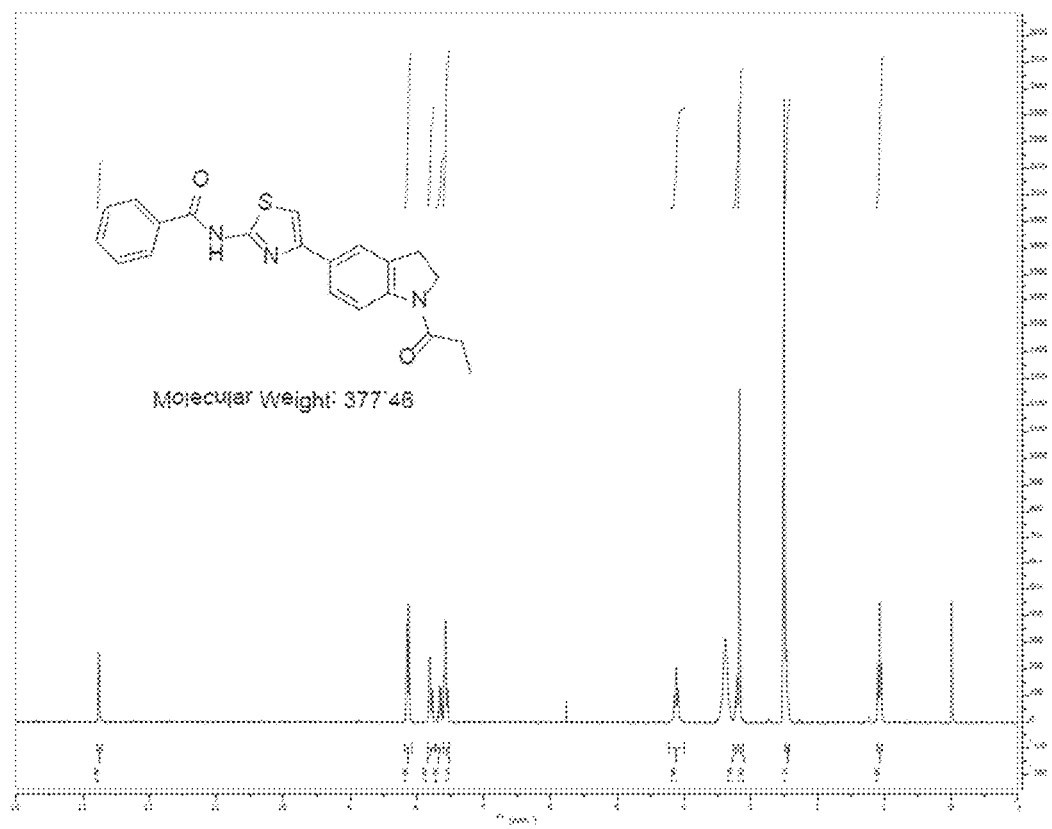
FIG. 51 is a graph showing the chemical characterization data for analog CID 53262918, $^1$H-NMR spectrum.
Figure 52:
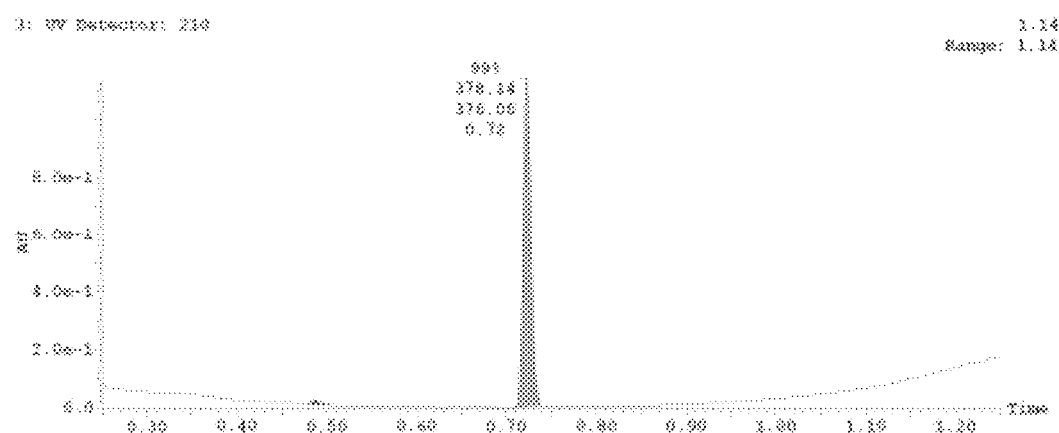
FIG. 52 is a graph showing the chemical characterization data for analog CID 53262918, UPLC-MS chromatogram.
Figure 53:
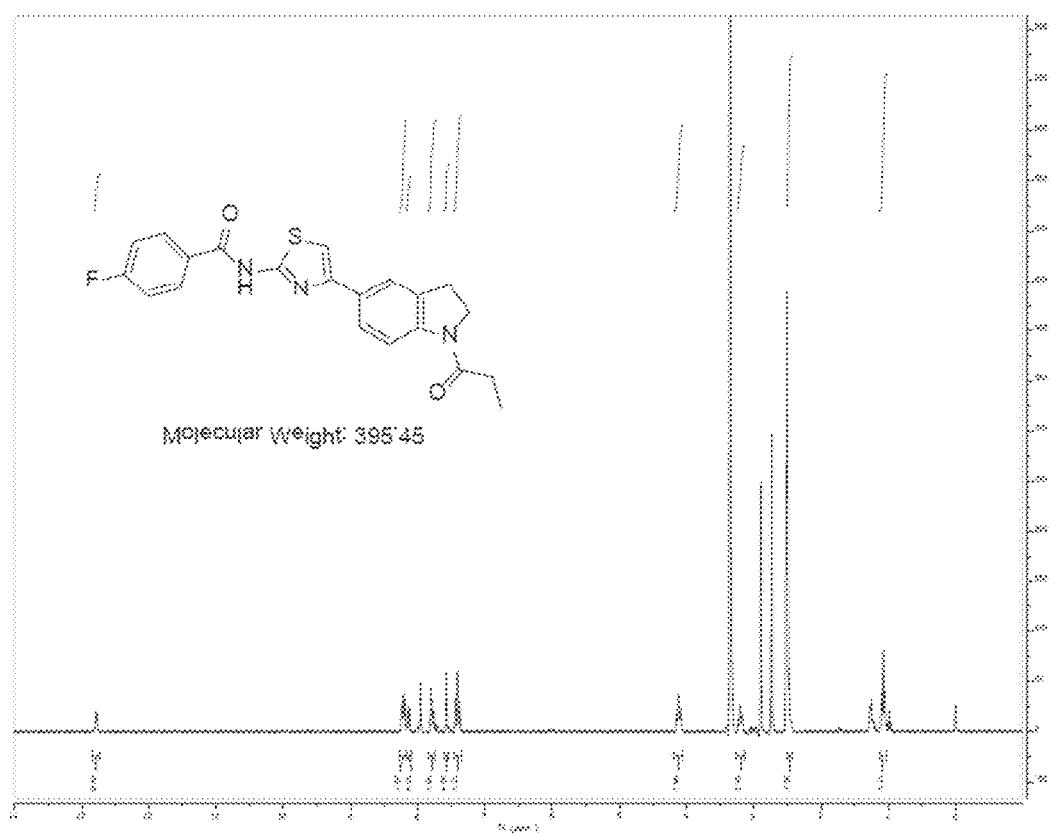
FIG. 53 is a graph showing the chemical characterization data for analog CID 1458888, $^1$H-NMR spectrum.
Figure 54:
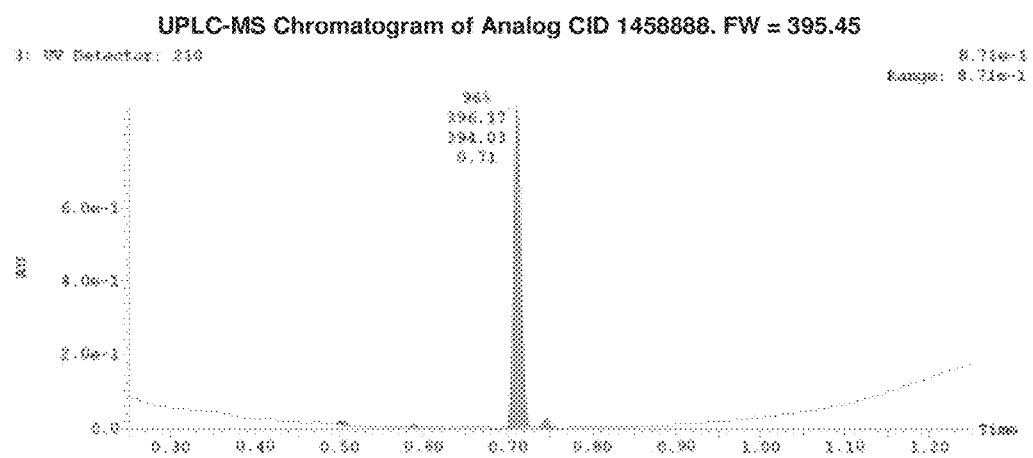
FIG. 54 is a graph showing the chemical characterization data for analog CID 1458888, UPLC-MS chromatogram.
Figure 55:
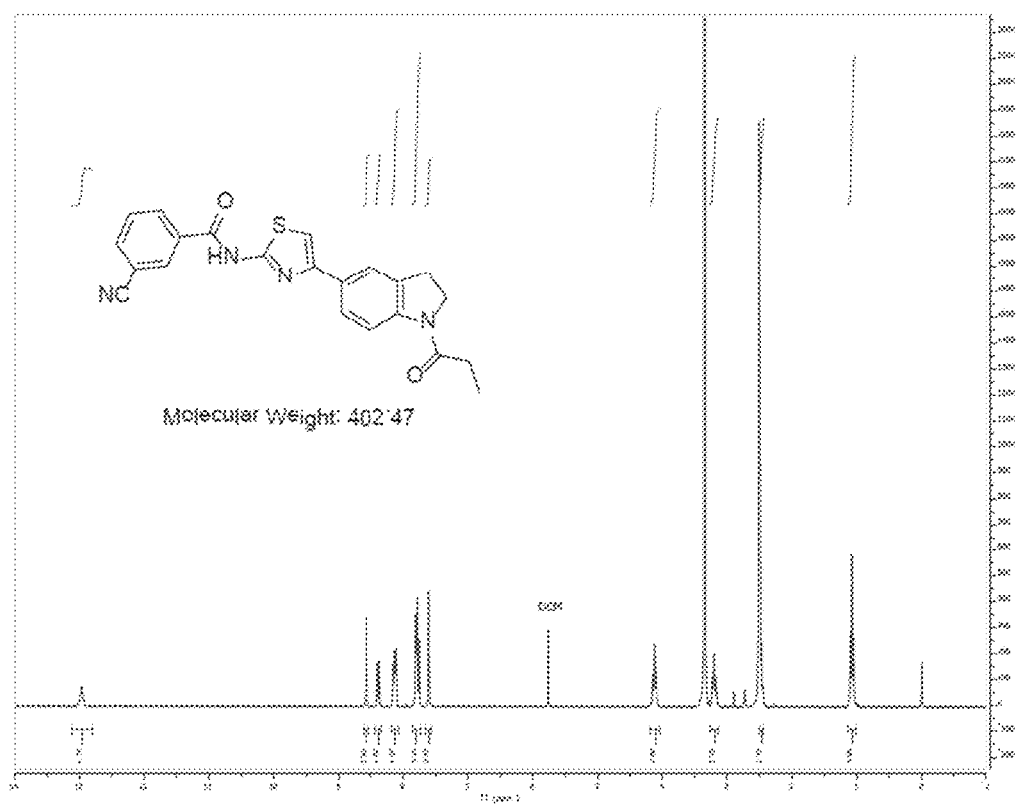
FIG. 55 is a graph showing the chemical characterization data for analog CID 53347958, $^1$H-NMR spectrum.
Figure 56:
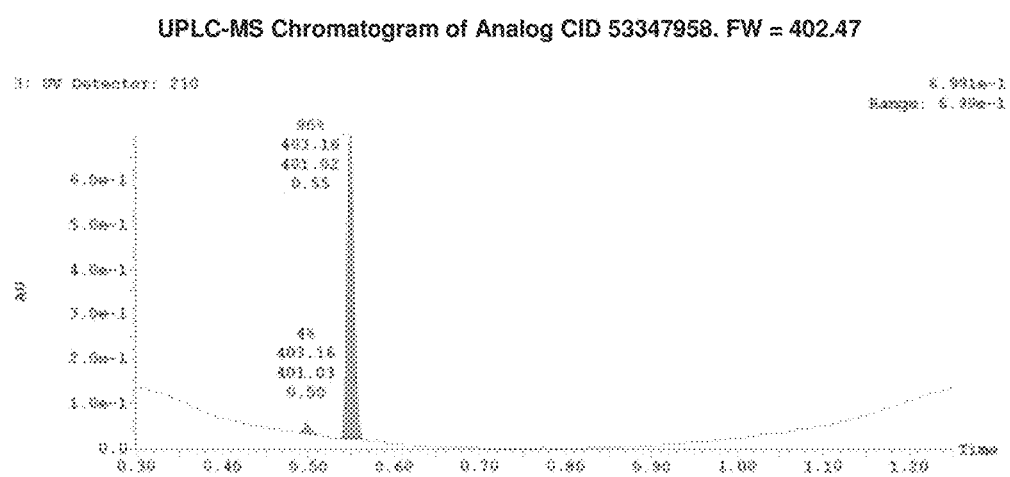
FIG. 56 is a graph showing the chemical characterization data for analog CID 53347958, UPLC-MS chromatogram.
Figure 57:
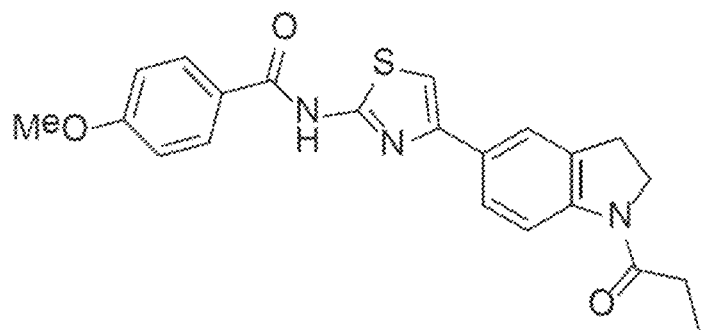
FIG. 57 is a graph showing the chemical characterization data for analog CID 53262913, $^1$H-NMR spectrum.
Figure 58:
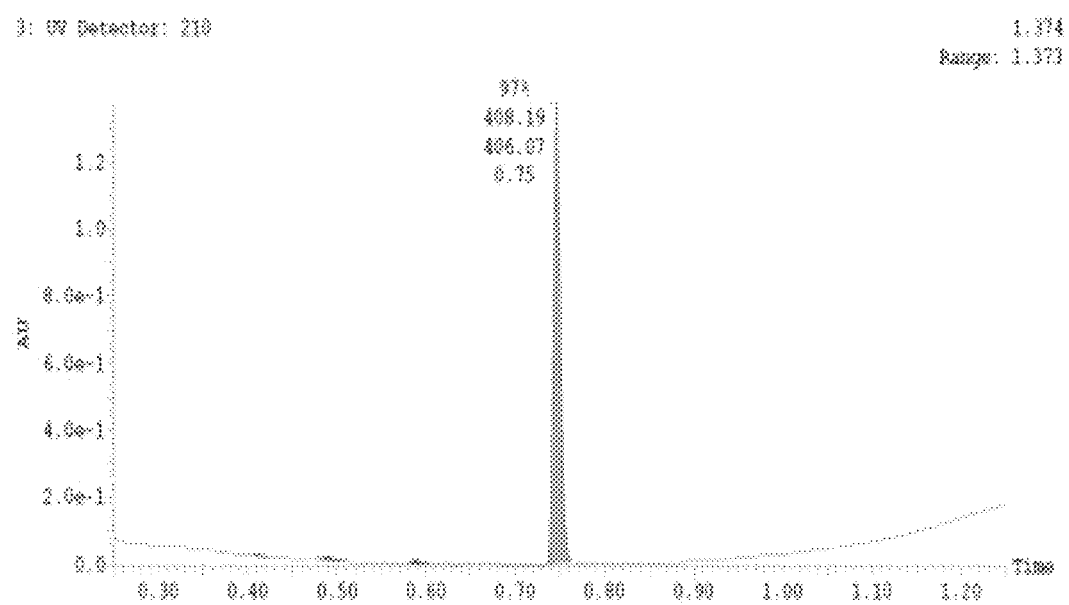
FIG. 58 is a graph showing the chemical characterization data for analog CID 53262913, UPLC-MS chromatogram.
Figure 59:
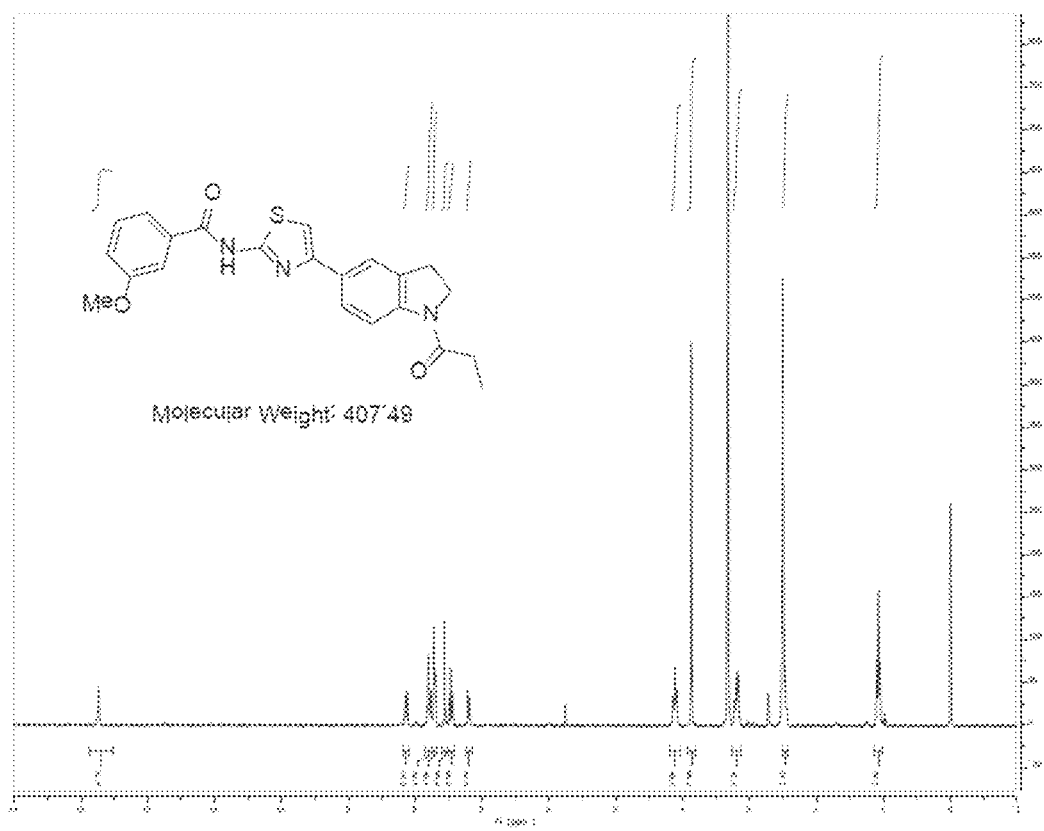
FIG. 59 is a graph showing the chemical characterization data for analog CID 1458885, $^1$H-NMR spectrum.
Figure 60:
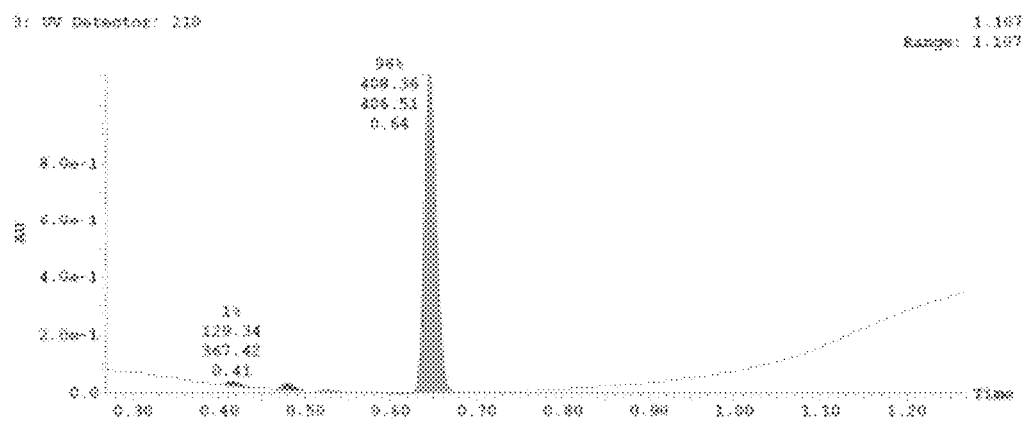
FIG. 60 is a graph showing the chemical characterization data for analog CID 1458885, UPLC-MS chromatogram.
Figure 61:
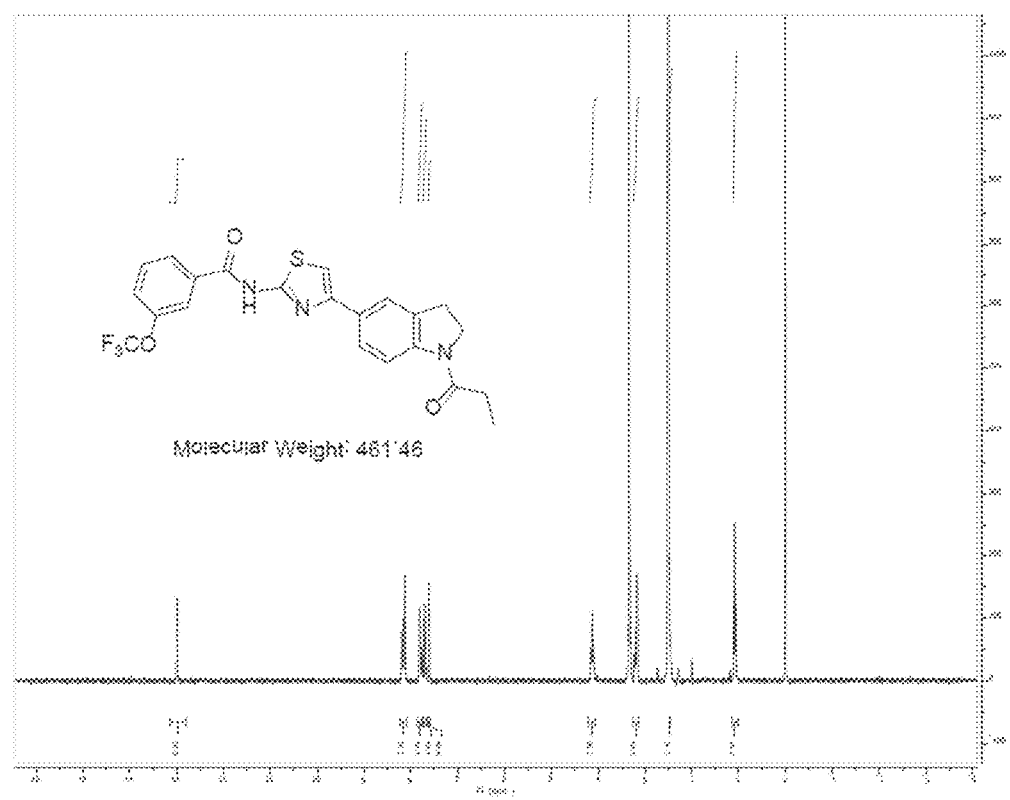
FIG. 61 is a graph showing the chemical characterization data for analog CID 53347940, $^1$H-NMR spectrum.
Figure 62:
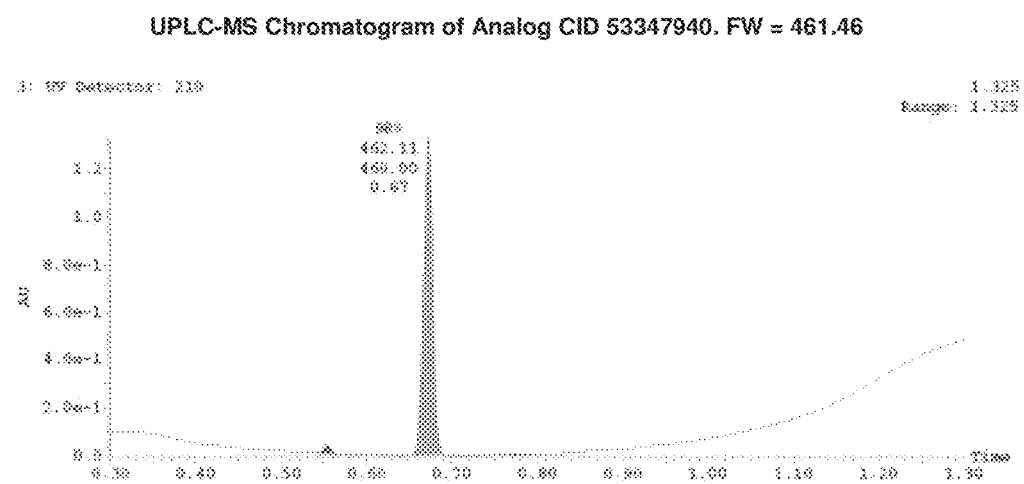
FIG. 62 is a graph showing the chemical characterization data for analog CID 53347940, UPLC-MS chromatogram.
Figure 63:
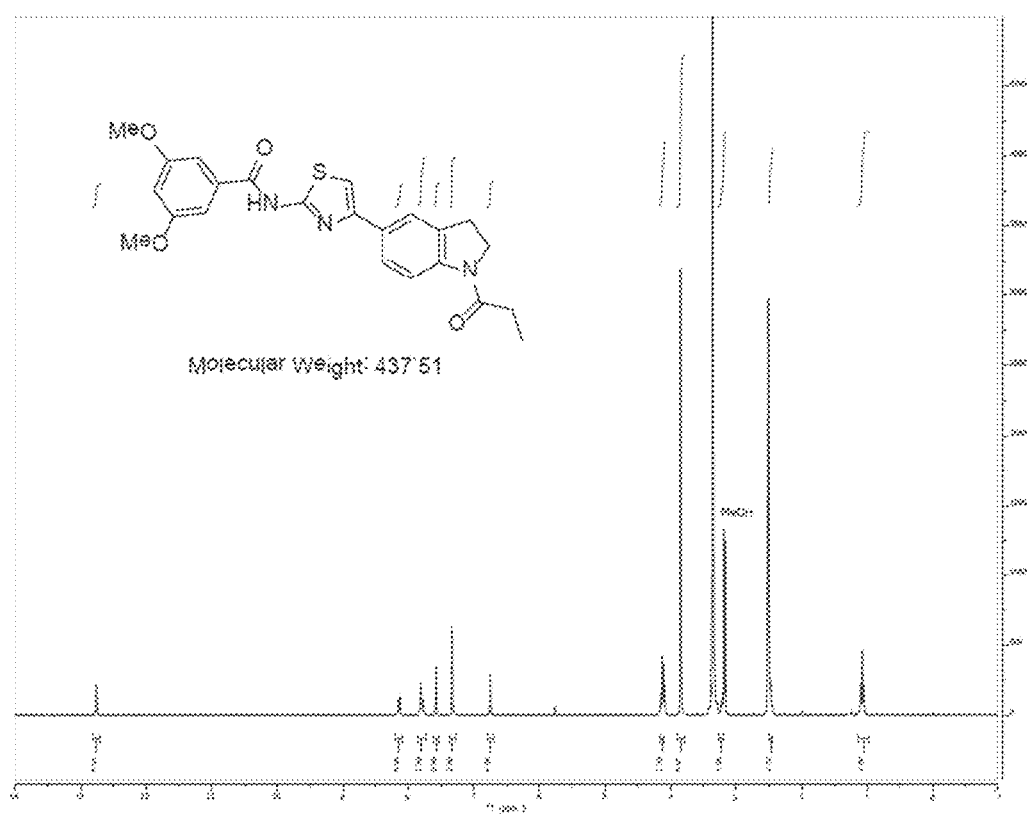
FIG. 63 is a graph showing the chemical characterization data for analog CID 53347941, $^1$H-NMR spectrum.
Figure 64:
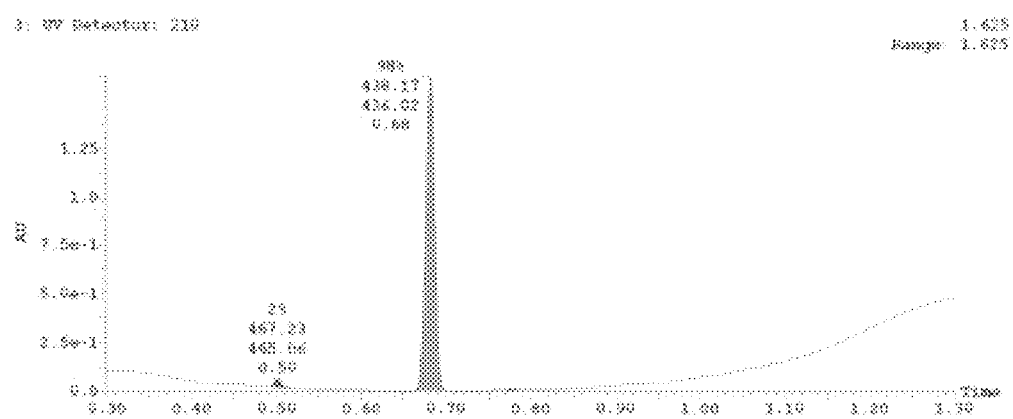
FIG. 64 is a graph showing the chemical characterization data for analog CID 53347941, UPLC-MS chromatogram.
Figure 65:
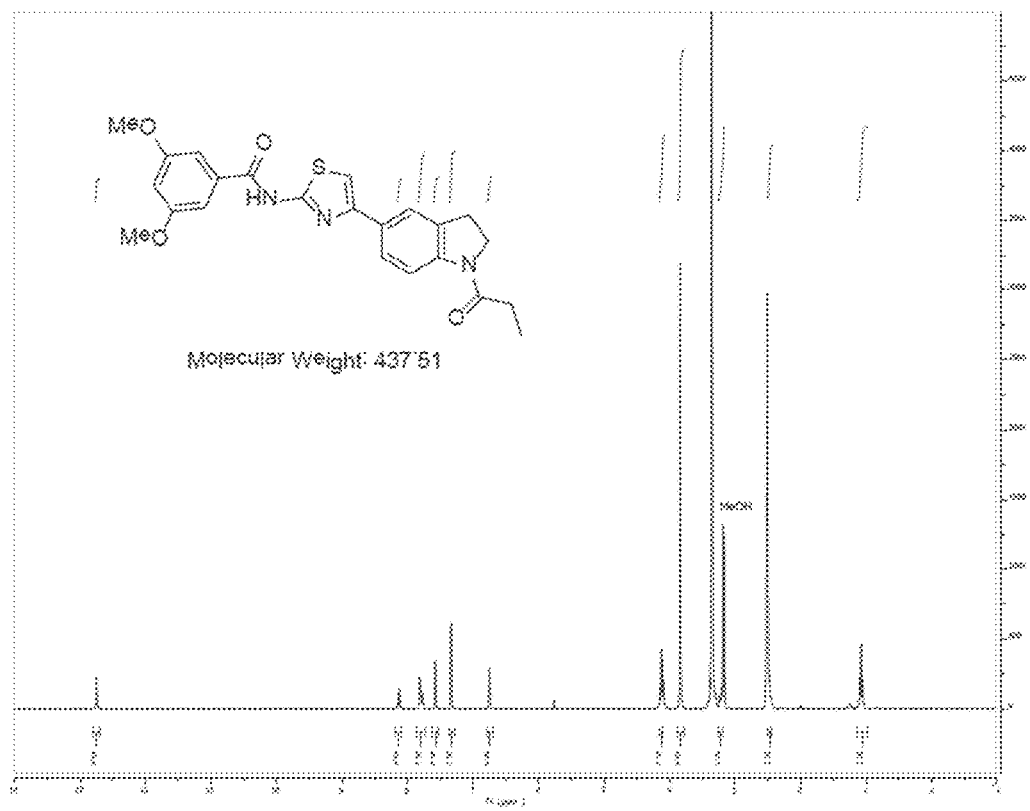
FIG. 65 is a graph showing the chemical characterization data for analog CID 53347941, $^1$H-NMR spectrum.
Figure 66:
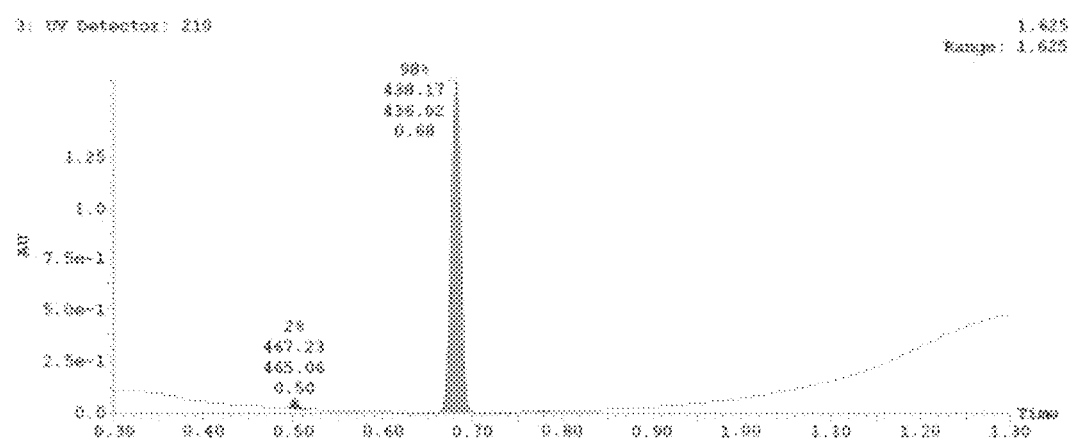
FIG. 66 is a graph showing the chemical characterization data for analog CID 53347941, UPLC-MS chromatogram.
Figure 67:
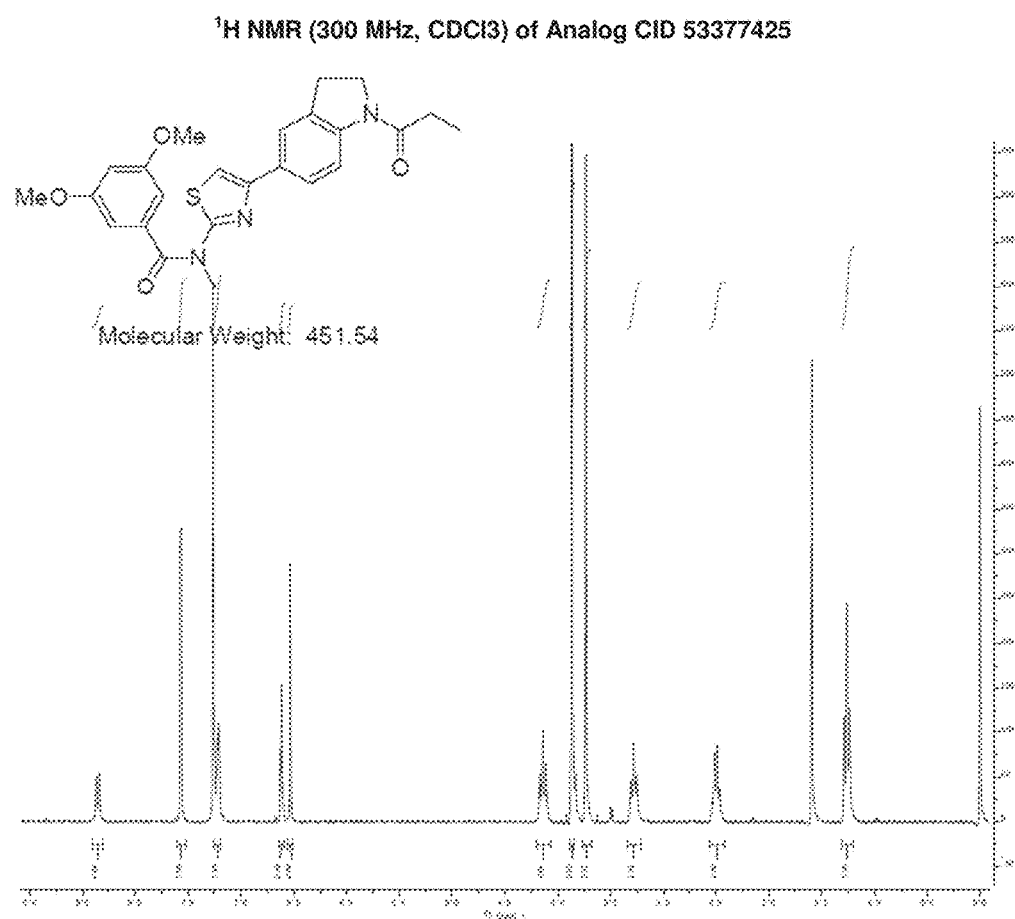
FIG. 67 is a graph showing the chemical characterization data for analog CID 53377425, $^1$H-NMR spectrum.
Figure 68:
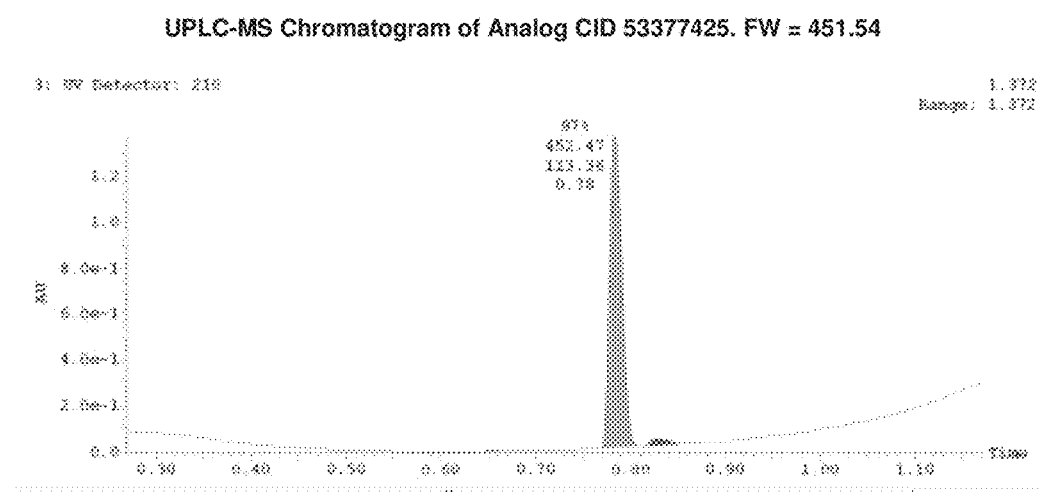
FIG. 68 is a graph showing the chemical characterization data for analog CID 53377425, UPLC-MS chromatogram.
Figure 69:
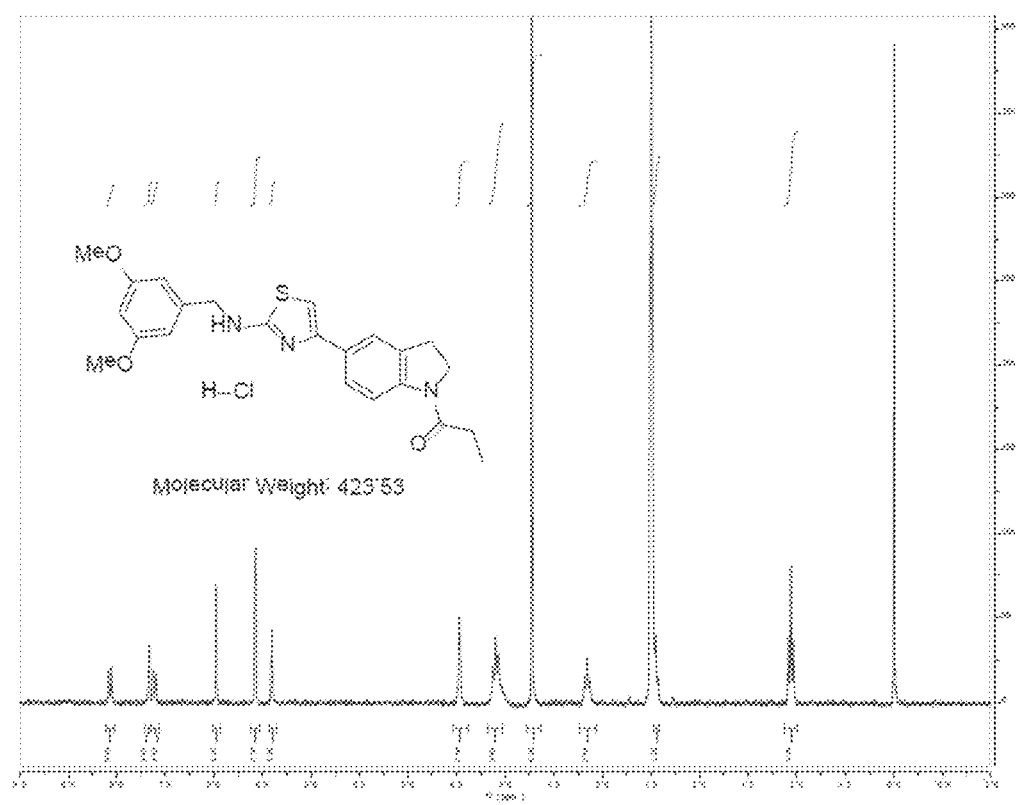
FIG. 69 is a graph showing the chemical characterization data for analog CID 53393842, $^1$H-NMR spectrum.
Figure 70:
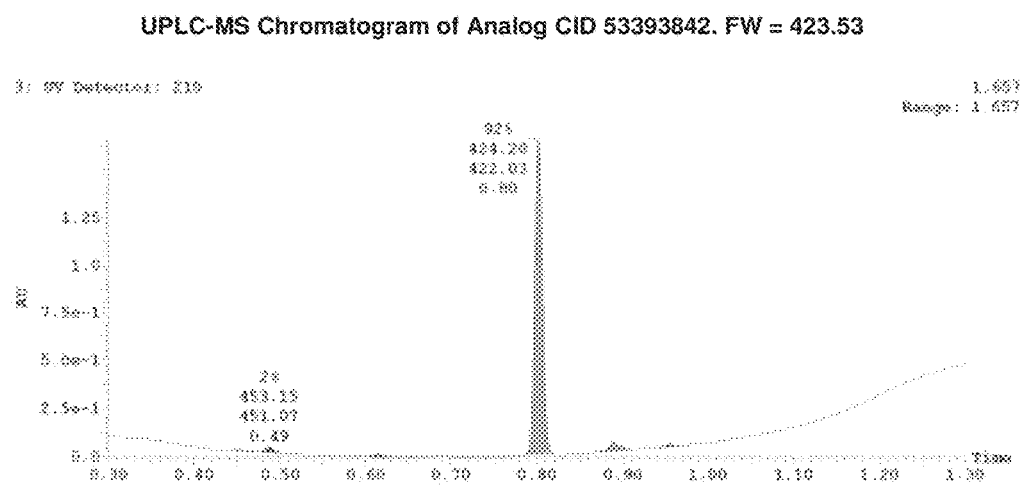
FIG. 70 is a graph showing the chemical characterization data for analog CID 53393842, UPLC-MS chromatogram.
Figure 71:
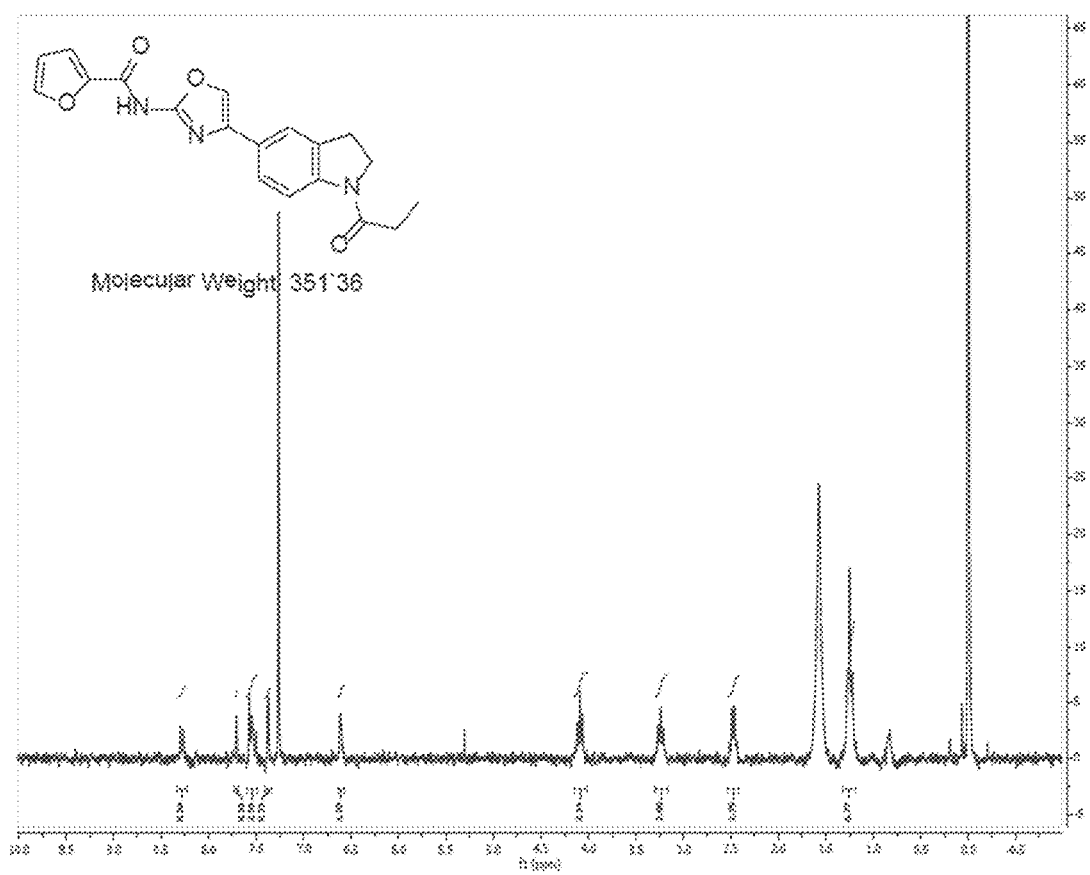
FIG. 71 is a graph showing the chemical characterization data for analog CID 53347969, $^1$H-NMR spectrum.
Figure 72:
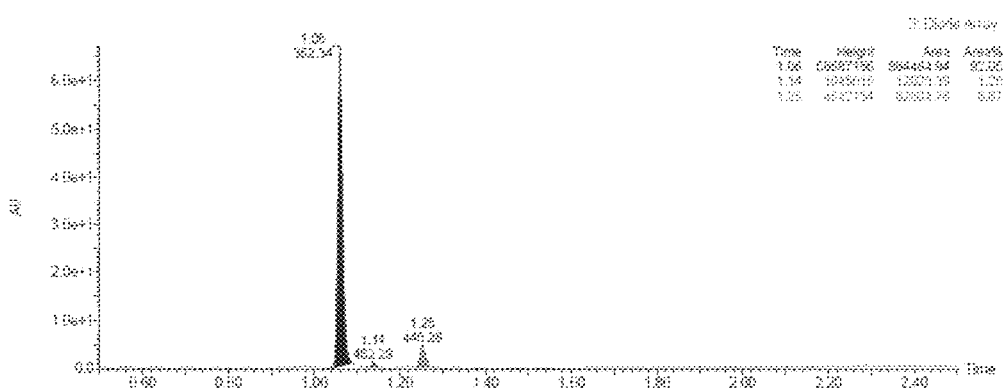
FIG. 72 is a graph showing the chemical characterization data for analog CID 53347969, LC-MS chromatogram.
Figure 73:
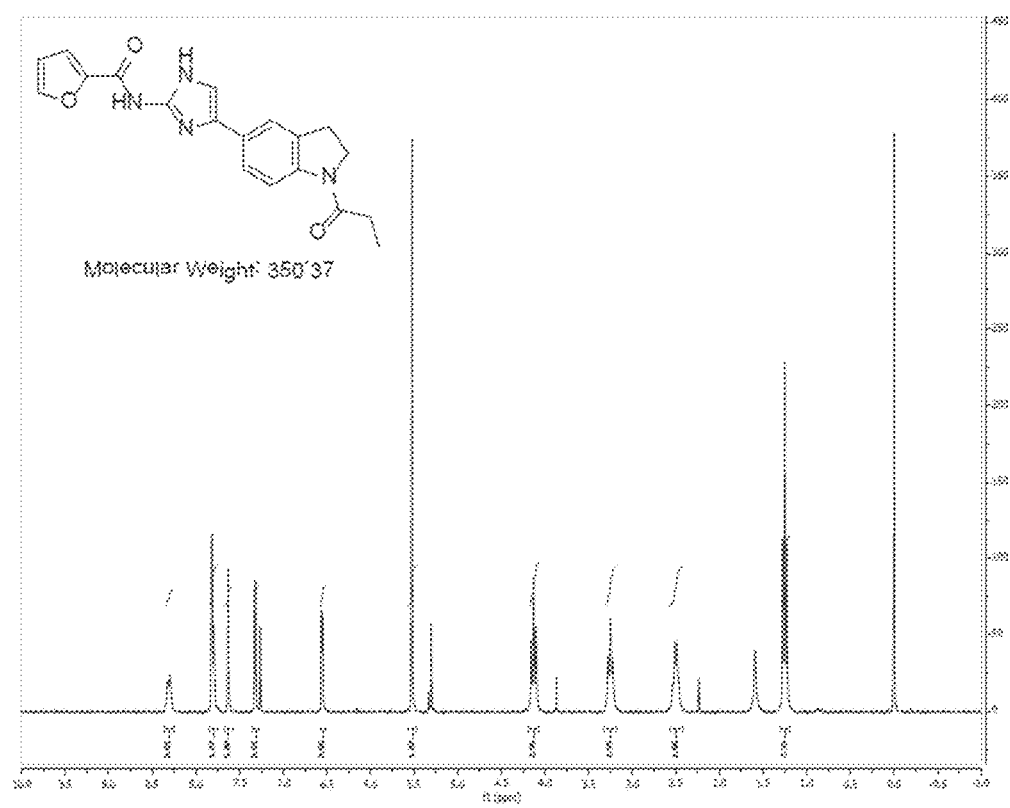
FIG. 73 is a graph showing the chemical characterization data for analog CID 53347964, $^1$H-NMR spectrum.
Figure 74:
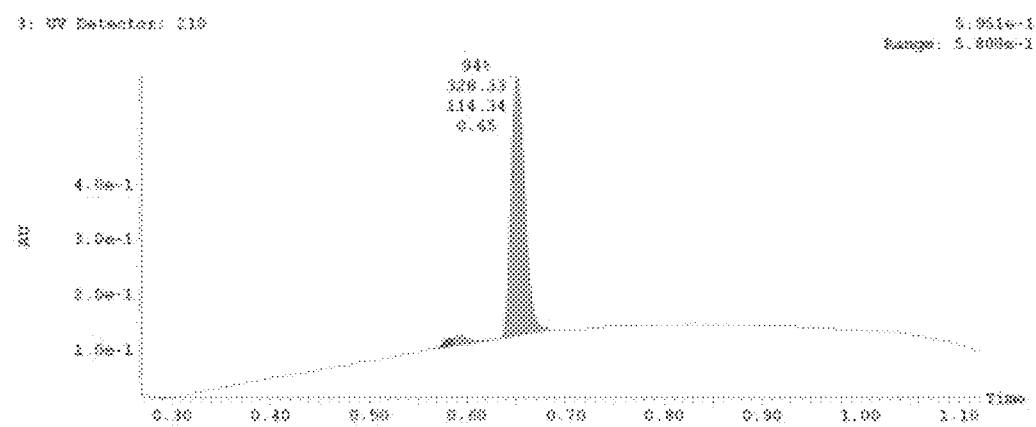
FIG. 74 is a graph showing the chemical characterization data for analog CID 53347964, UPLC-MS chromatogram.
Figure 75:
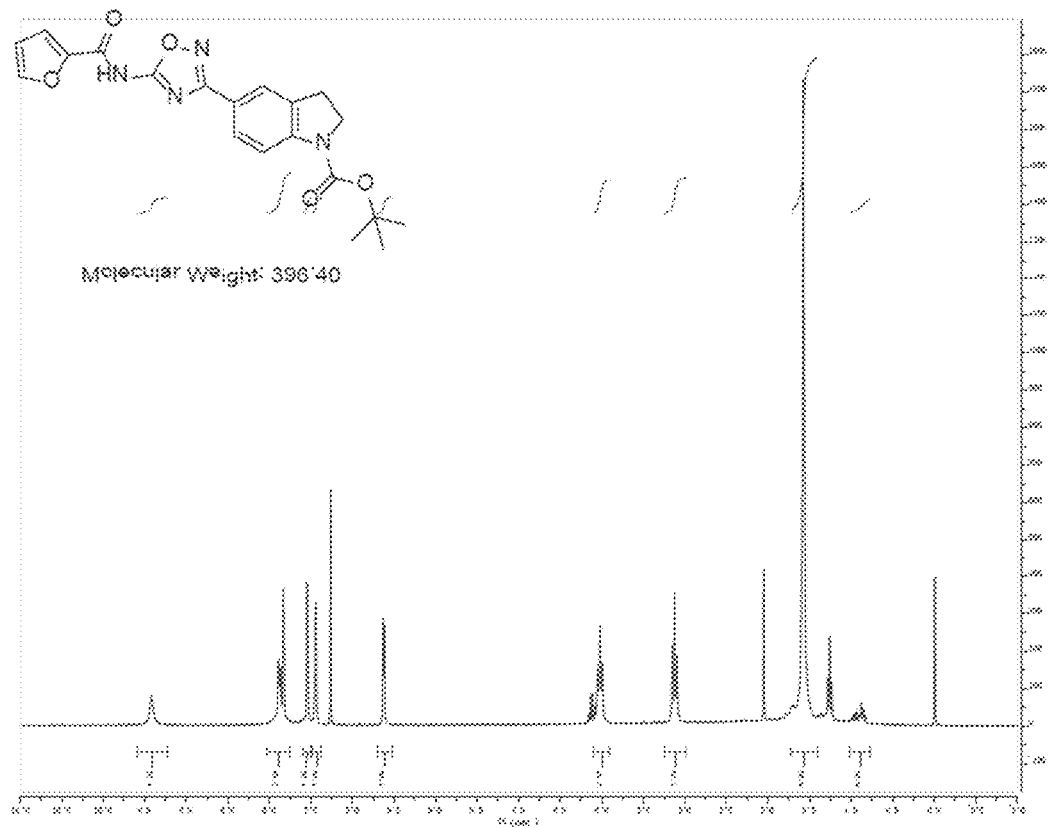
FIG. 75 is a graph showing the chemical characterization data for analog CID 53377423, $^1$H-NMR spectrum.
Figure 76:
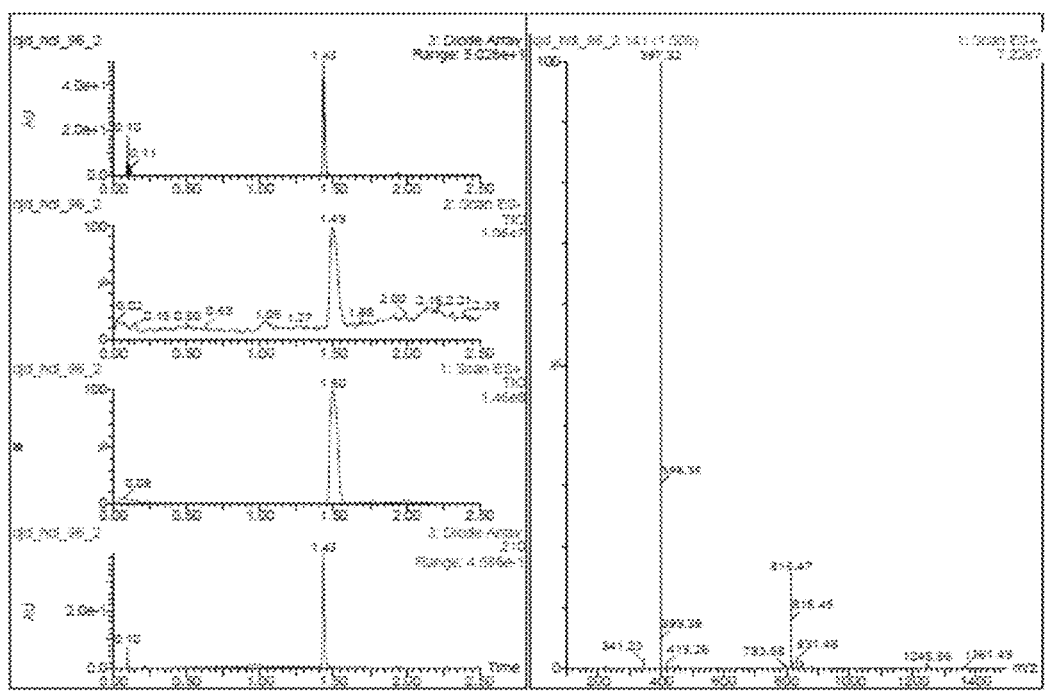
FIG. 76 is a graph showing the chemical characterization data for analog CID 53377423, UPLC-MS chromatogram.
Figure 77:
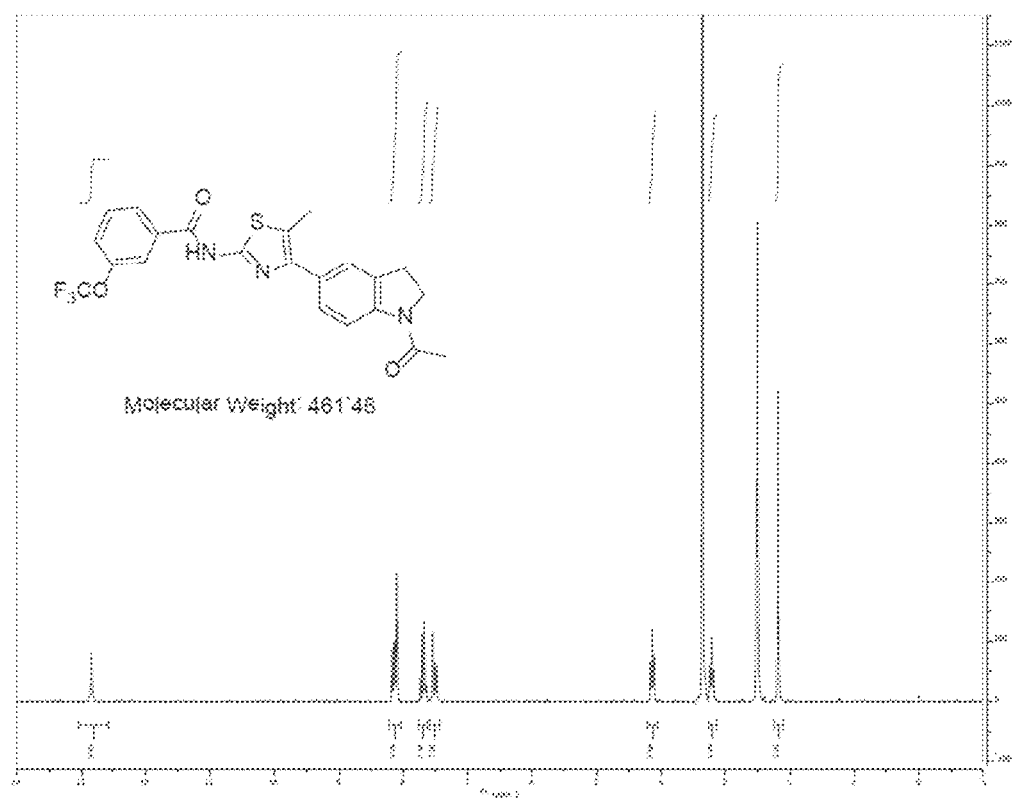
FIG. 77 is a graph showing the chemical characterization data for analog CID 53393834, $^1$H-NMR spectrum.
Figure 78:
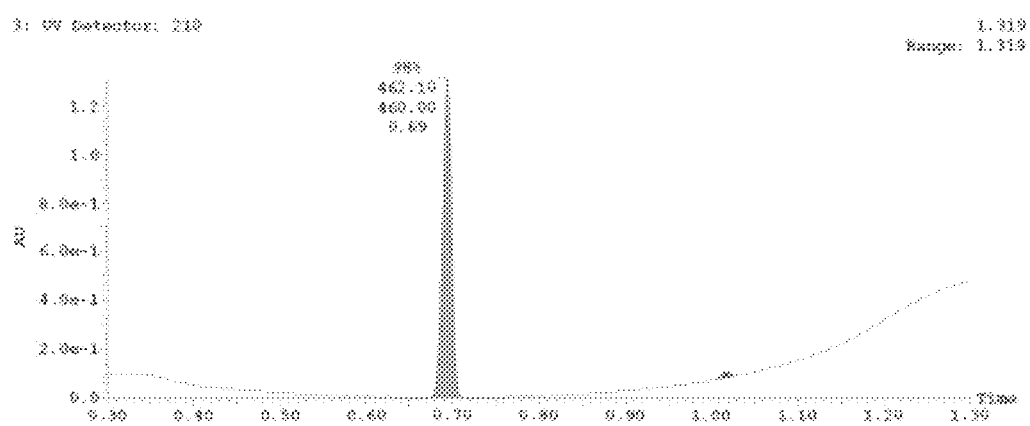
FIG. 78 is a graph showing the chemical characterization data for analog CID 53393834, UPLC-MS chromatogram.
Figure 79:
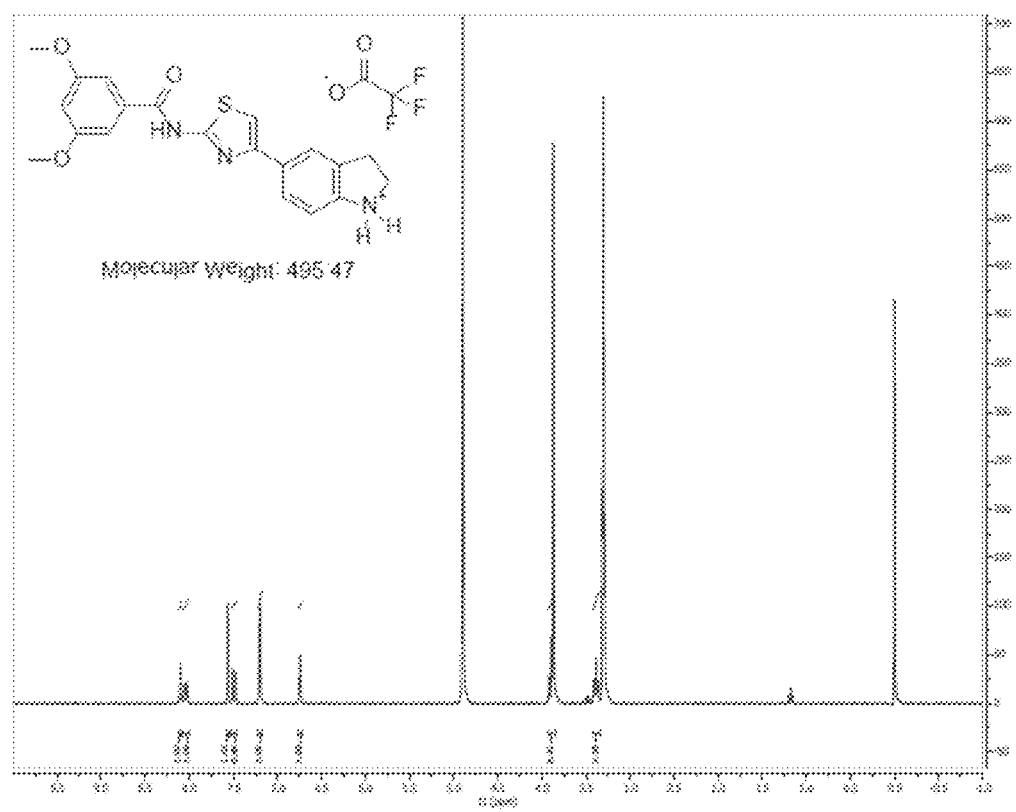
FIG. 79 is a graph showing the chemical characterization data for analog CID 53377450, $^1$H-NMR spectrum.
Figure 80:
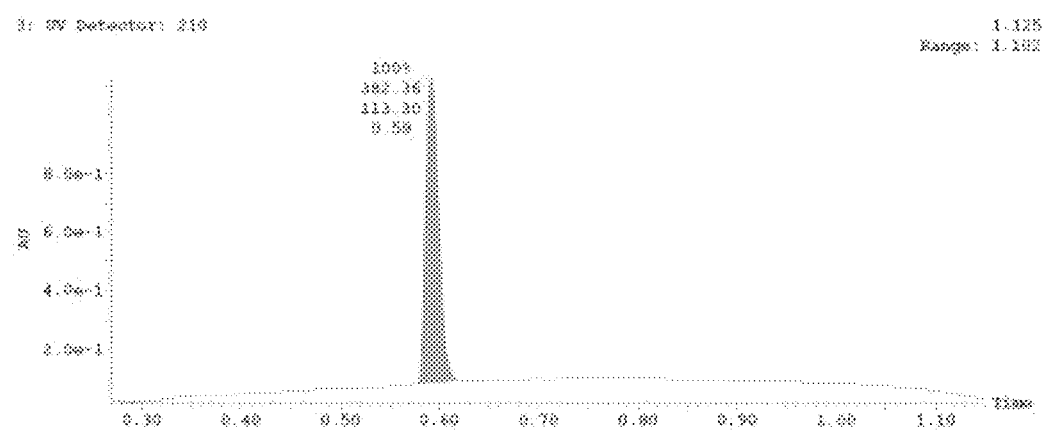
FIG. 80 is a graph showing the chemical characterization data for analog CID 53377450, UPLC-MS chromatogram.
Figure 81:
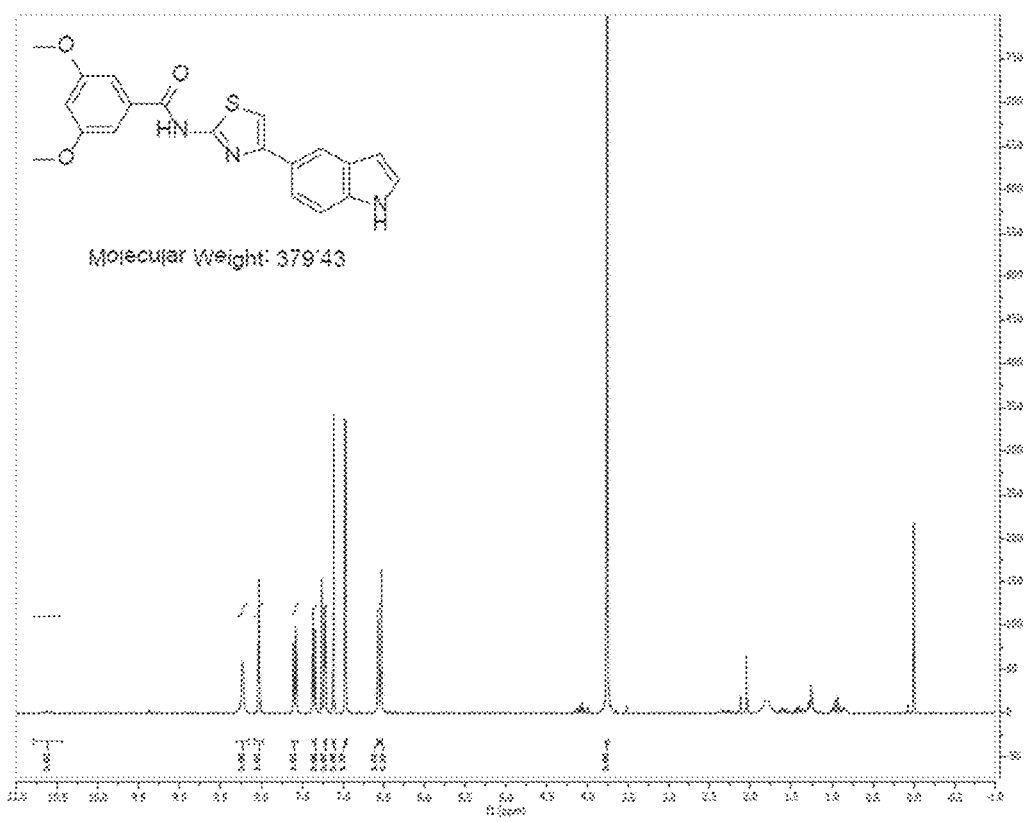
FIG. 81 is a graph showing the chemical characterization data for analog CID 53377427, $^1$H-NMR spectrum.
Figure 82:
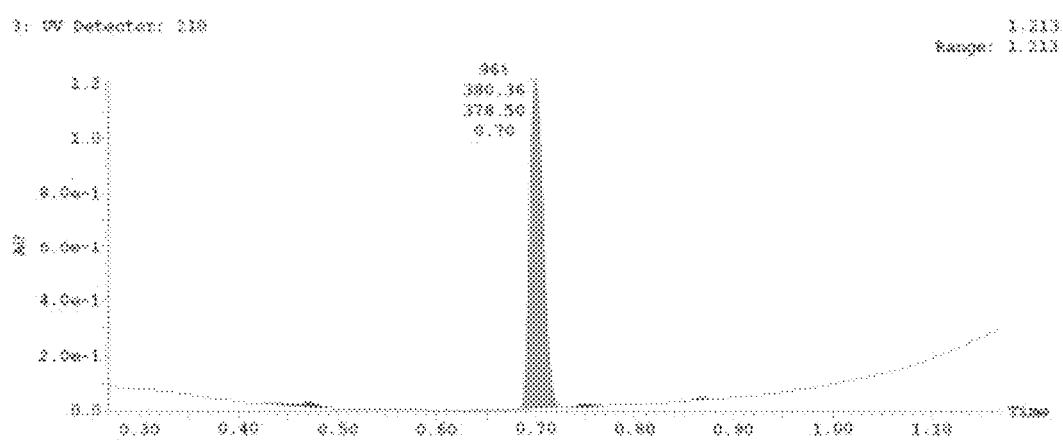
FIG. 82 is a graph showing the chemical characterization data for analog CID 53377427, UPLC-MS chromatogram.
Figure 83:
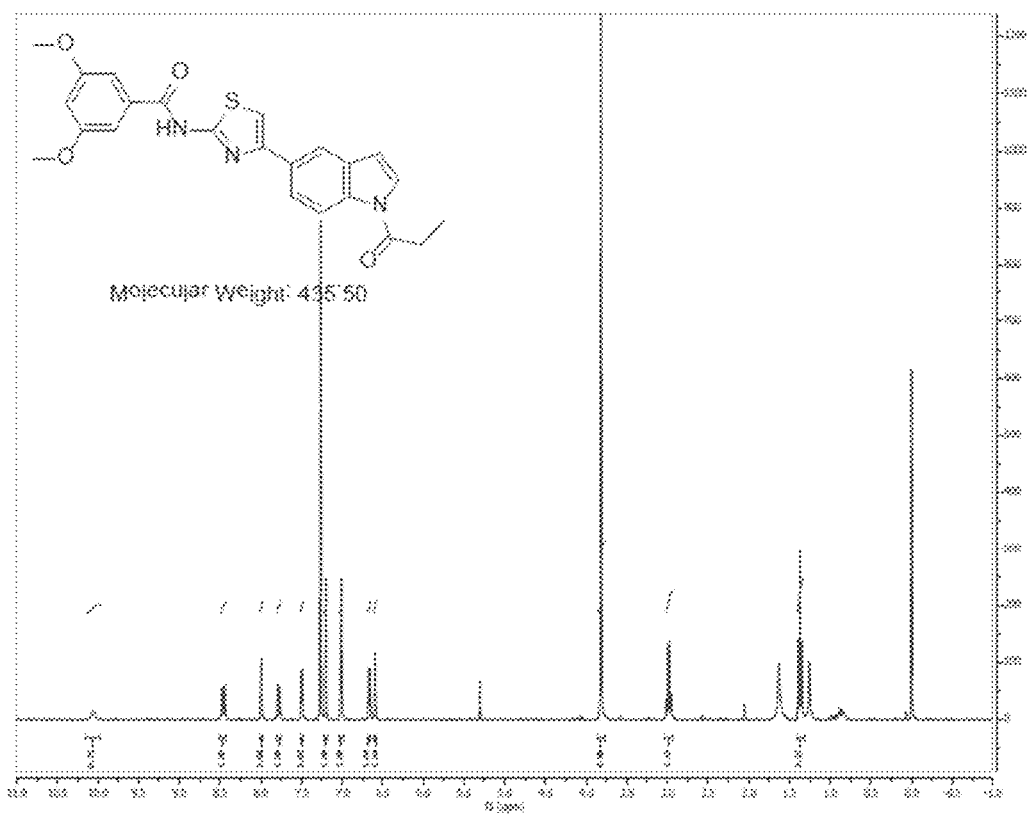
FIG. 83 is a graph showing the chemical characterization data for analog CID 53393833, $^1$H-NMR spectrum.
Figure 84:
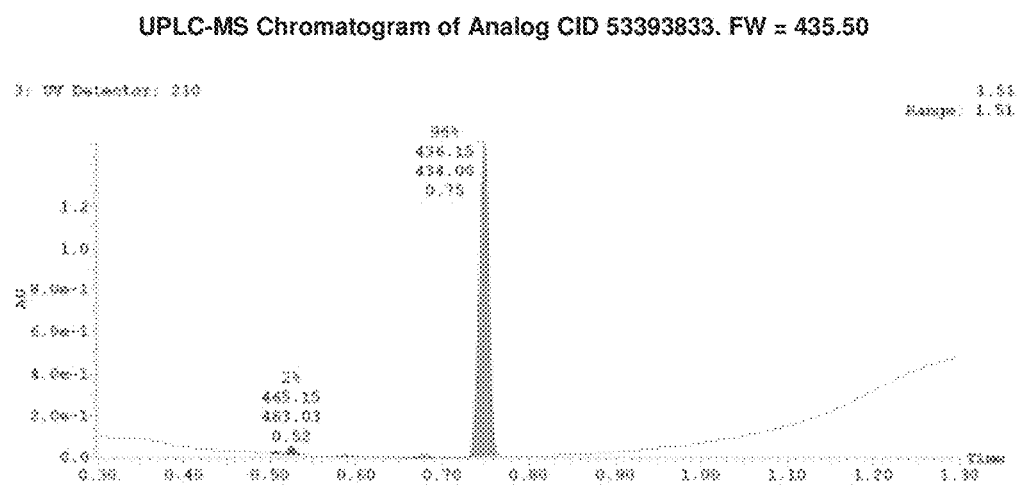
FIG. 84 is a graph showing the chemical characterization data for analog CID 53393833, UPLC-MS chromatogram.
Figure 85:
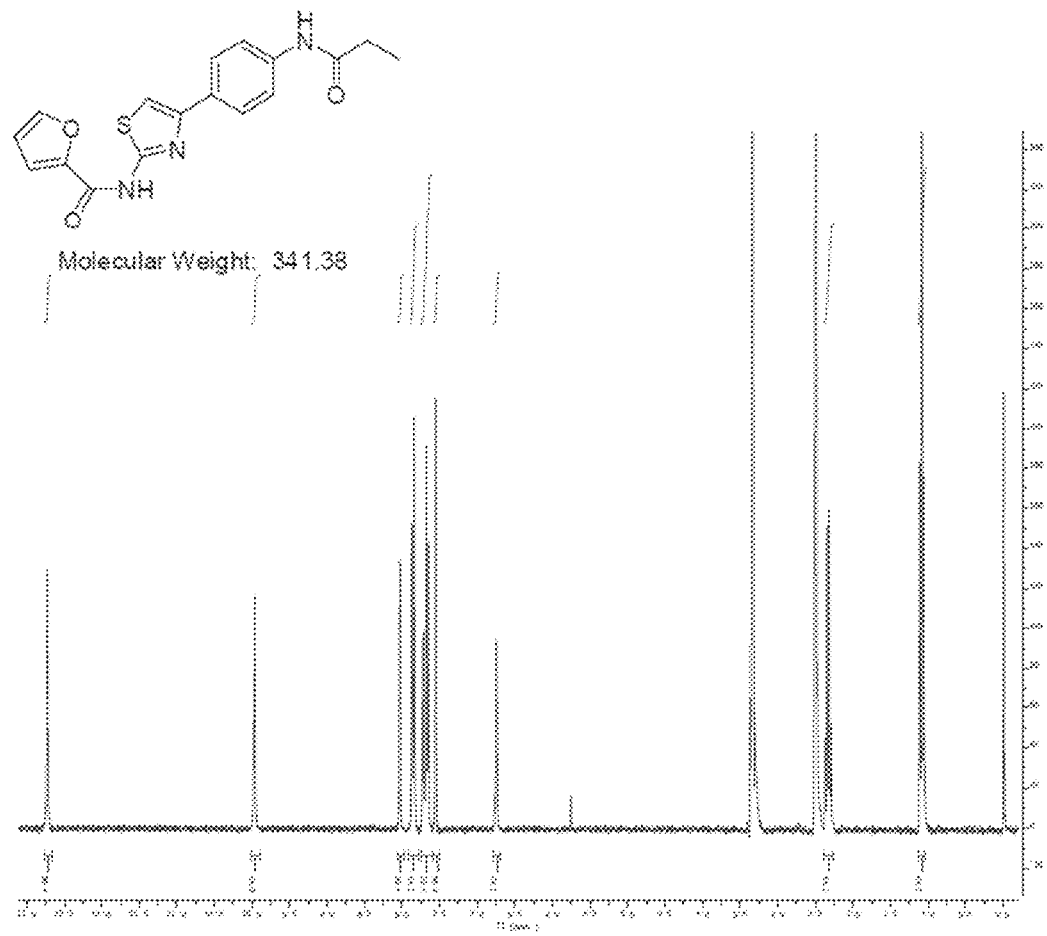
FIG. 85 is a graph showing the chemical characterization data for analog CID 53377433, $^1$H-NMR spectrum.
Figure 86:
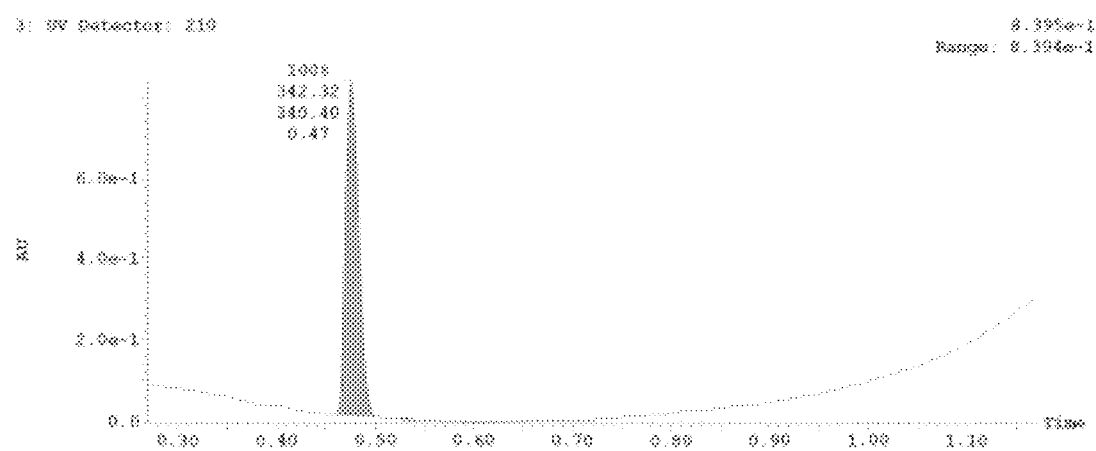
FIG. 86 is a graph showing the chemical characterization data for analog CID 53377433, UPLC-MS chromatogram.
Figure 87:
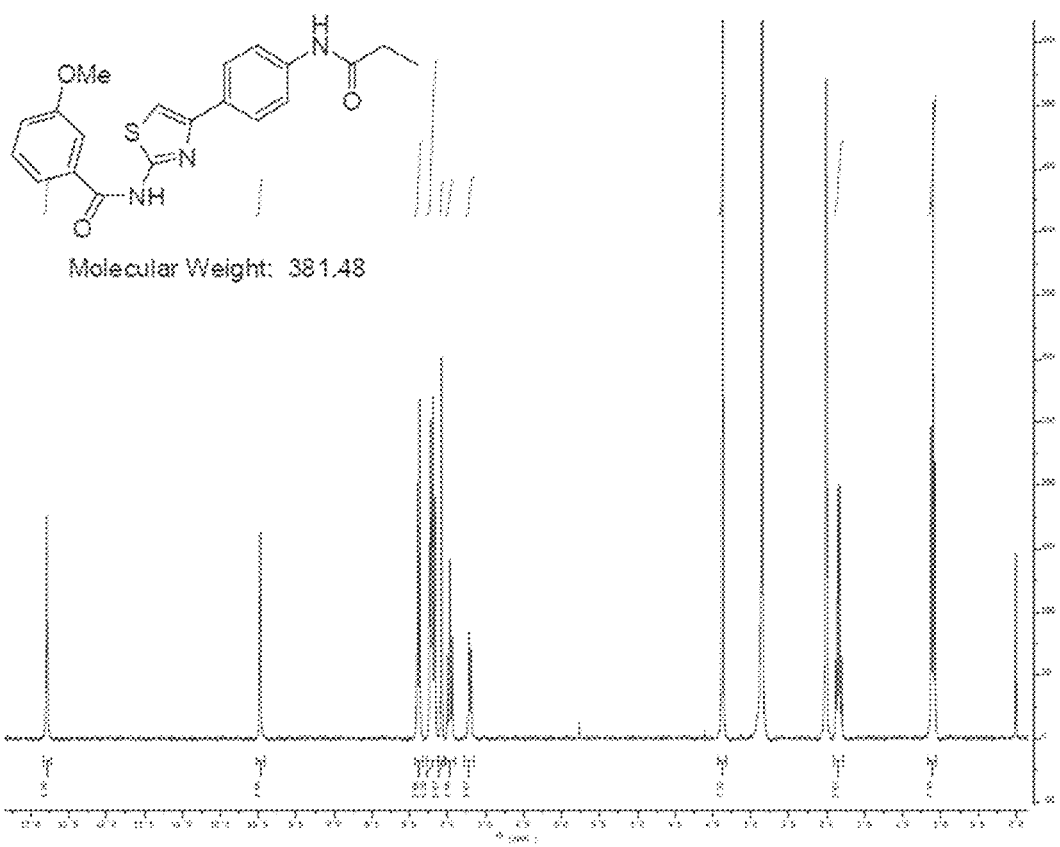
FIG. 87 is a graph showing the chemical characterization data for analog CID 53377426, $^1$H-NMR spectrum.
Figure 88:
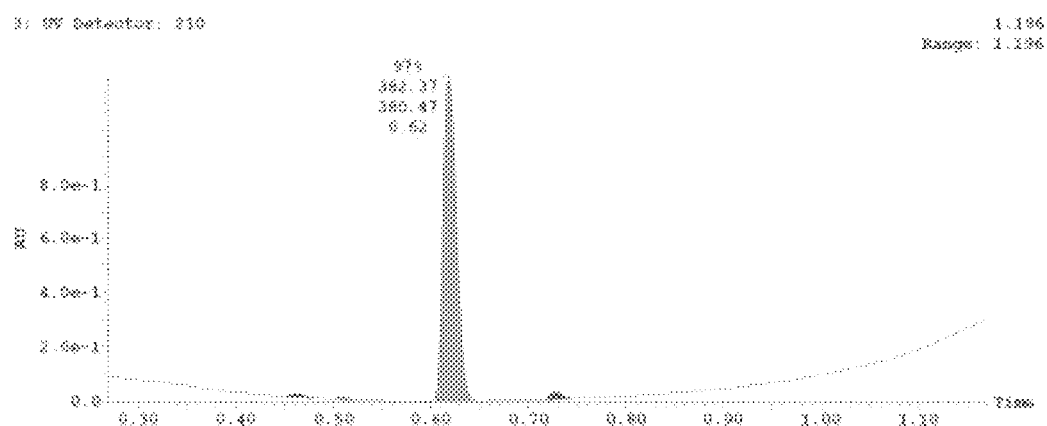
FIG. 88 is a graph showing the chemical characterization data for analog CID 53377426, UPLC-MS chromatogram.
Figure 89:
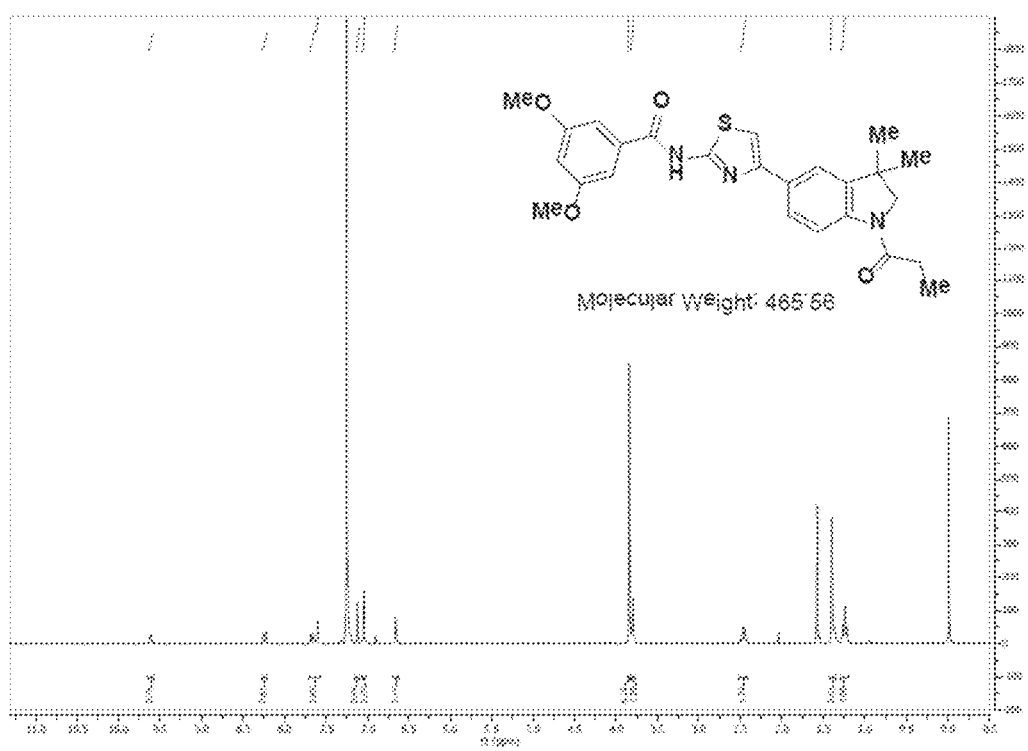
FIG. 89 is a graph showing the chemical characterization data for analog CID 53393841, $^1$H-NMR spectrum.
Figure 90:
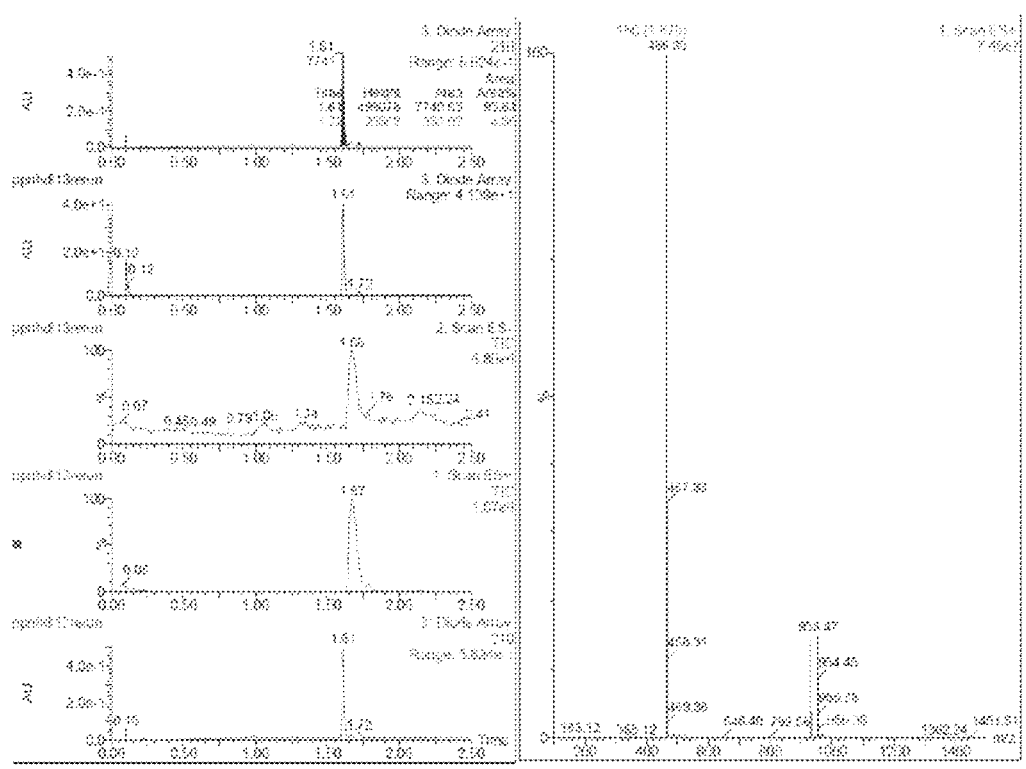
FIG. 90 is a graph showing the chemical characterization data for analog CID 53393841, UPLC-MS chromatogram.
Figure 91:
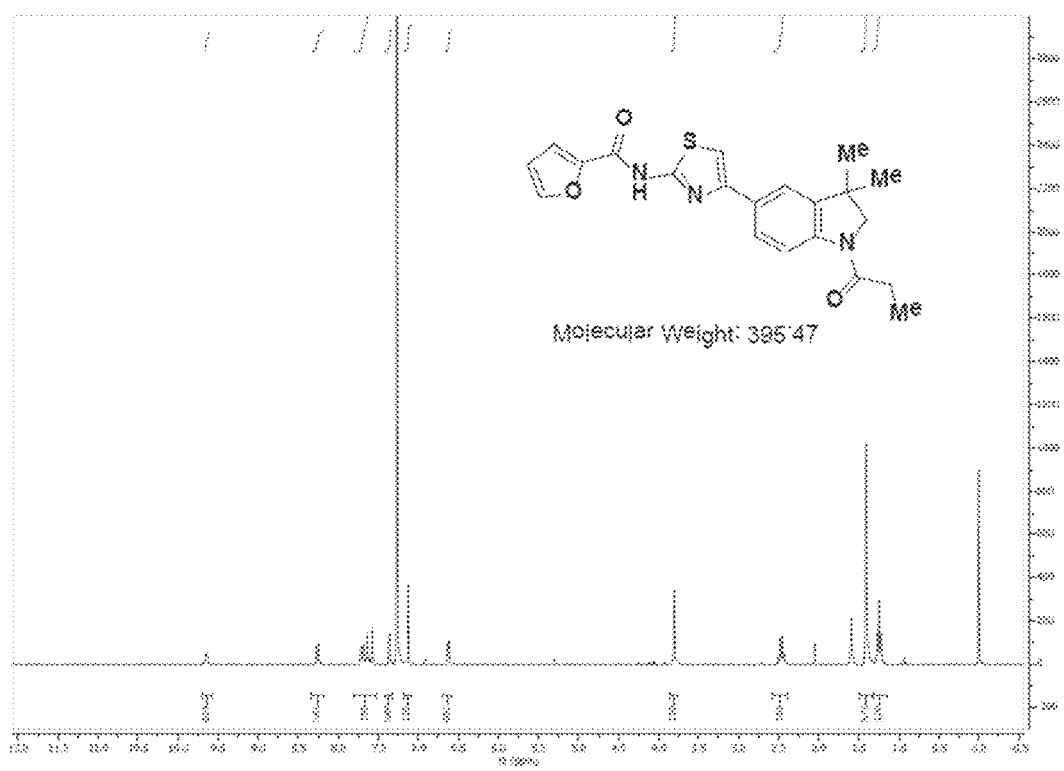
FIG. 91 is a graph showing the chemical characterization data for analog CID 53393840, $^1$H-NMR spectrum.
Figure 92:
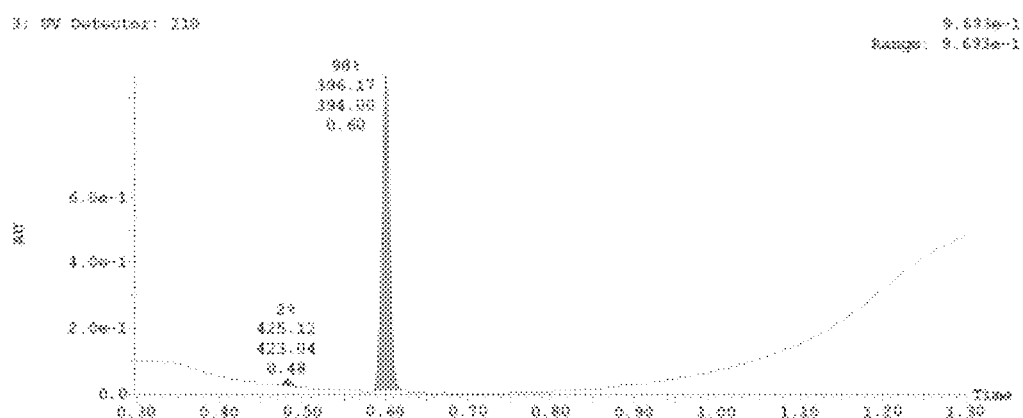
FIG. 92 is a graph showing the chemical characterization data for analog CID 53393840, UPLC-MS chromatogram.
Figure 93:
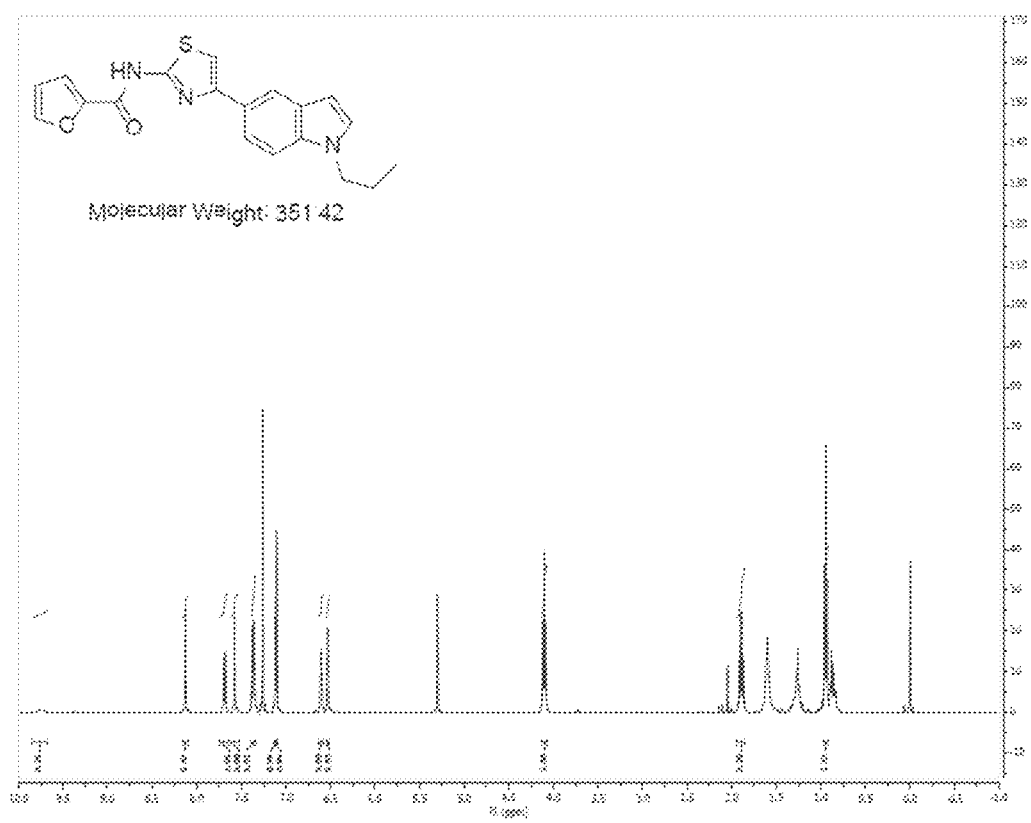
FIG. 93 is a graph showing the chemical characterization data for analog CID 53347949, $^1$H-NMR spectrum.
Figure 94:
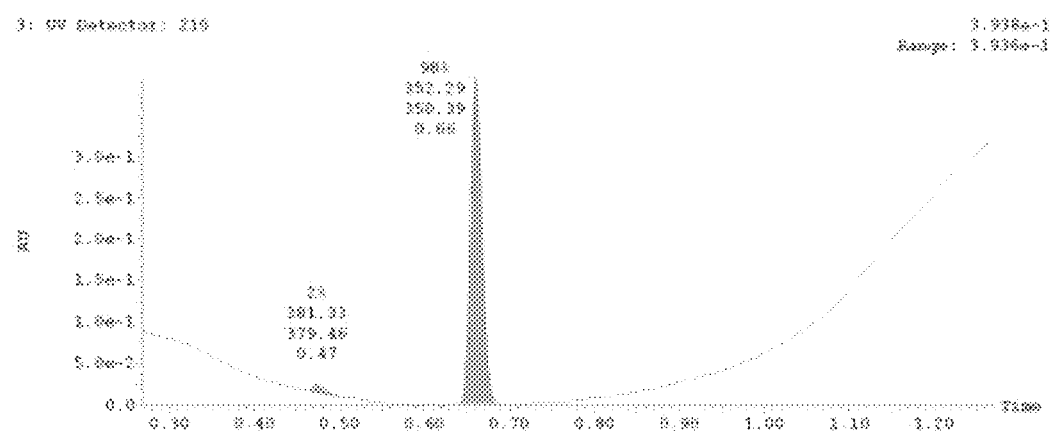
FIG. 94 is a graph showing the chemical characterization data for analog CID 53347949, UPLC-MS chromatogram.
Figure 95:
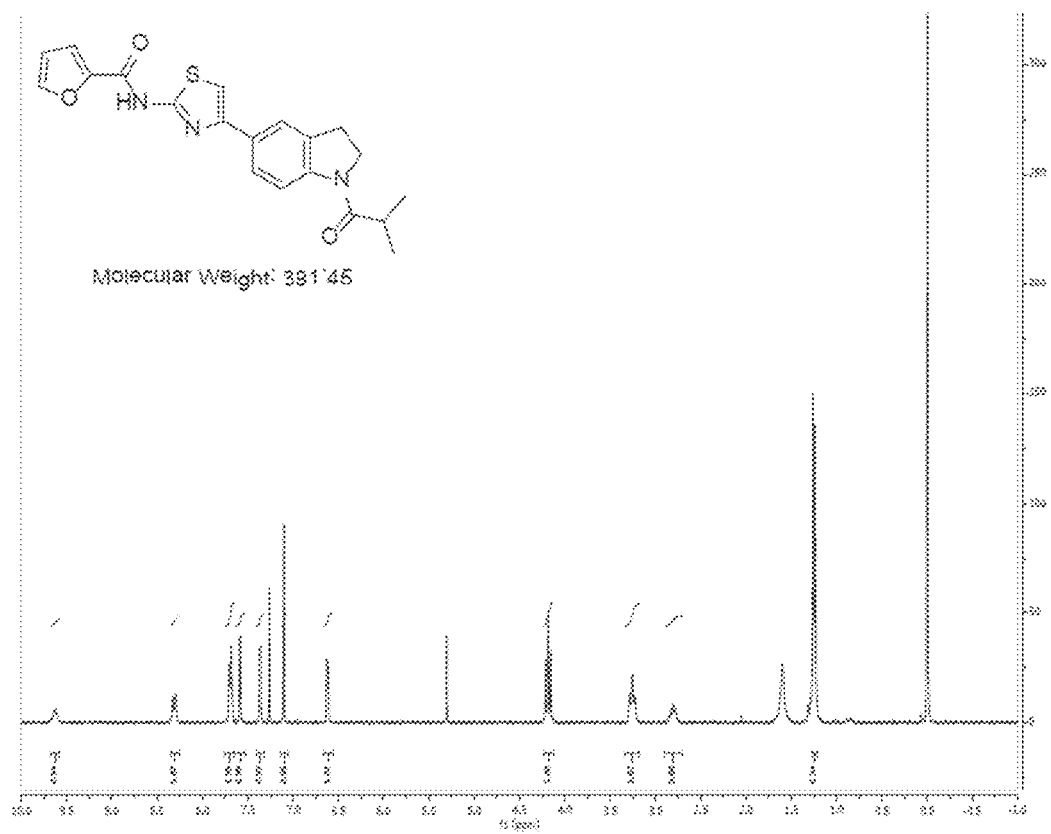
FIG. 95 is a graph showing the chemical characterization data for analog CID 53348001, $^1$H-NMR spectrum.
Figure 96:
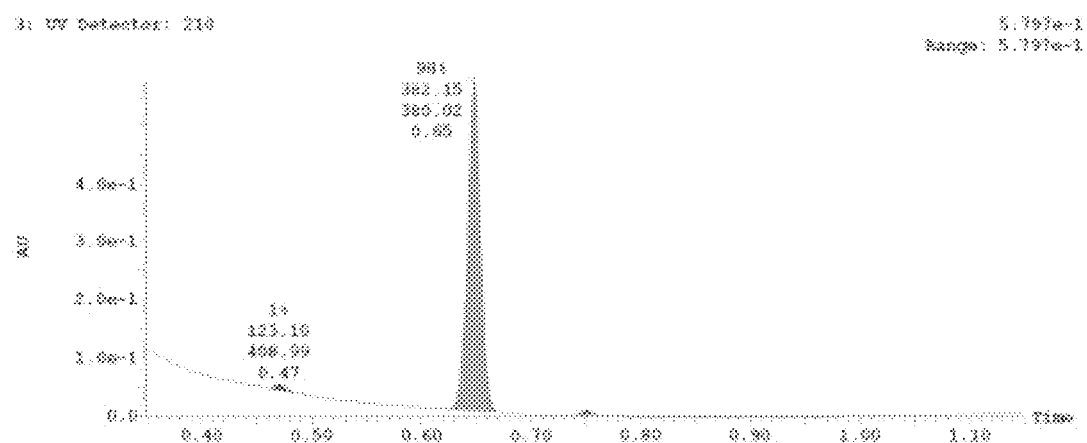
FIG. 96 is a graph showing the chemical characterization data for analog CID 53348001, UPLC-MS chromatogram.
Figure 97:
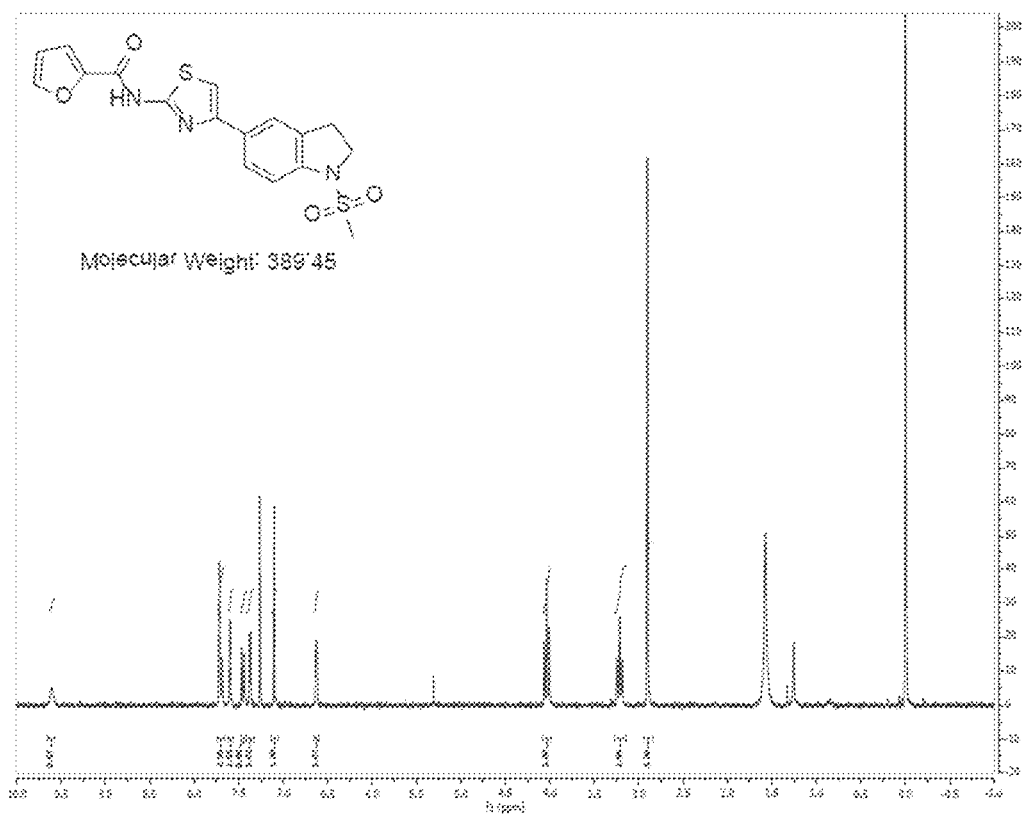
FIG. 97 is a graph showing the chemical characterization data for analog CID 43816465, $^1$H-NMR spectrum.
Figure 98:
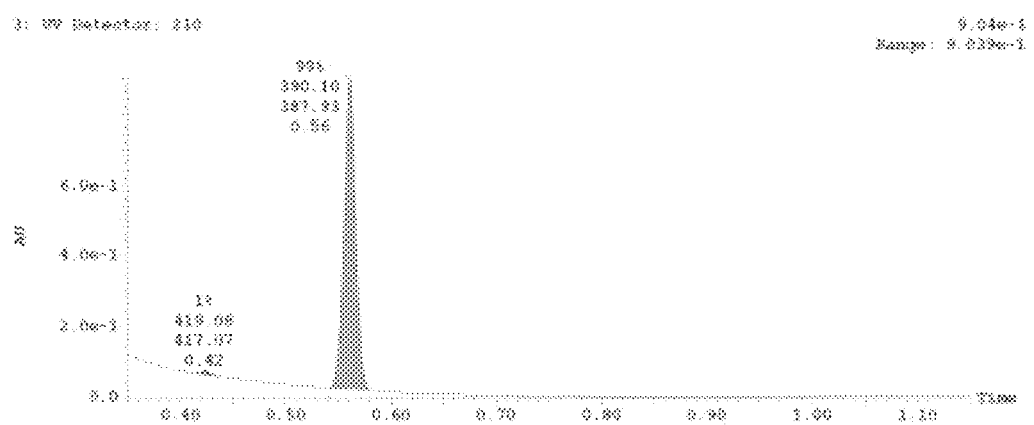
FIG. 98 is a graph showing the chemical characterization data for analog CID 43816465, UPLC-MS chromatogram.
Figure 99:
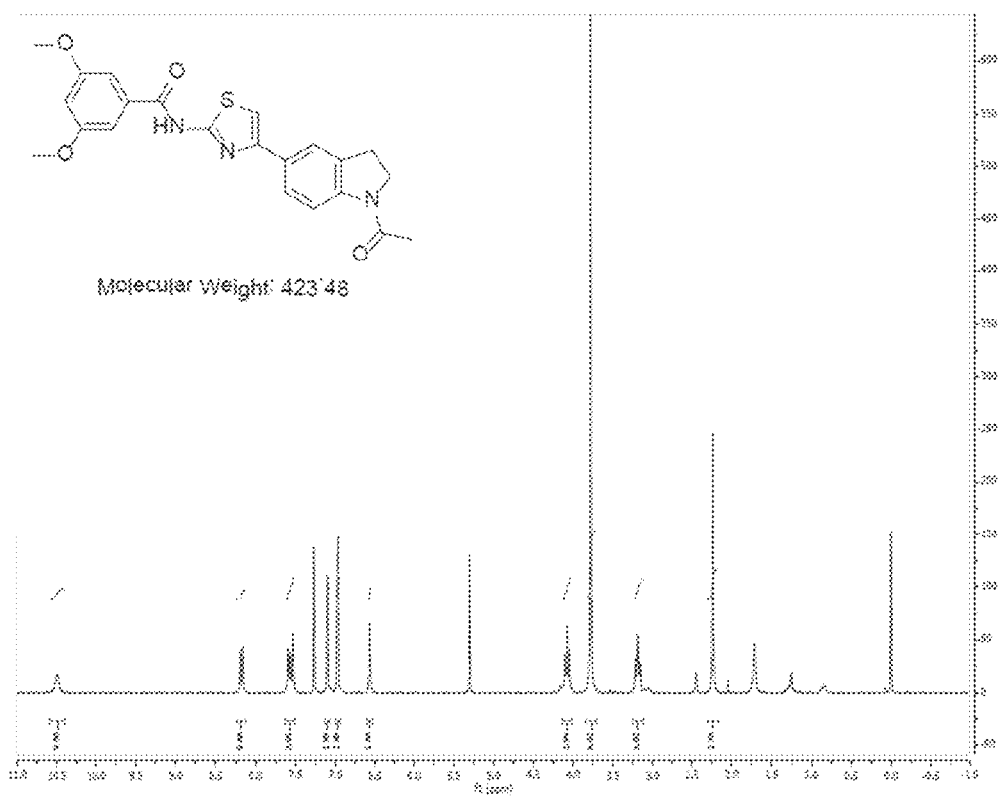
FIG. 99 is a graph showing the chemical characterization data for analog CID 53377441, $^1$H-NMR spectrum.
Figure 100:
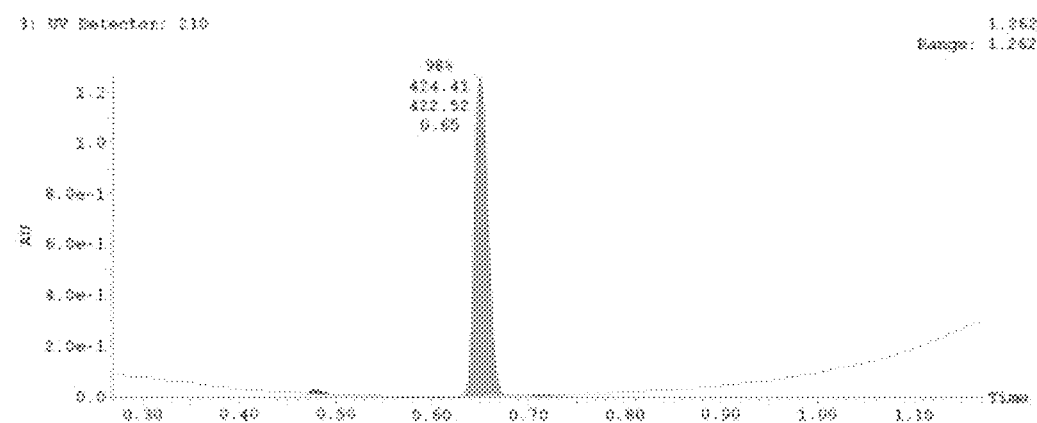
FIG. 100 is a graph showing the chemical characterization data for analog CID 53377441, UPLC-MS chromatogram.
Figure 101:
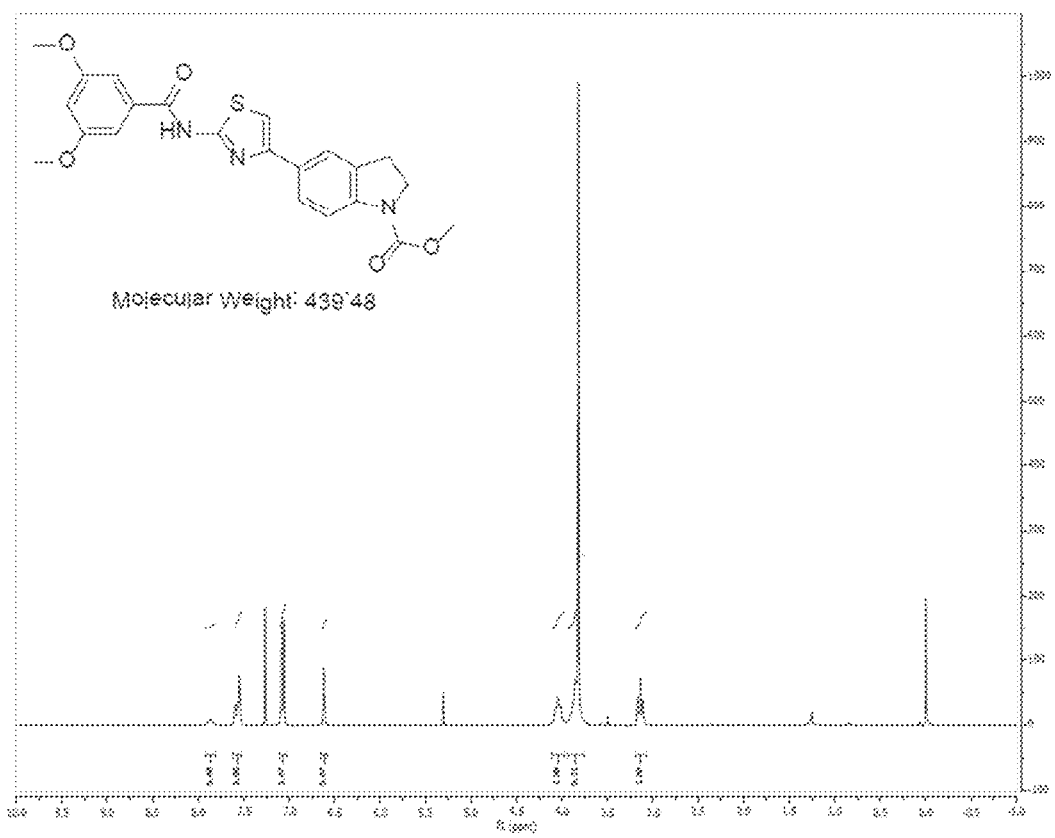
FIG. 101 is a graph showing the chemical characterization data for analog CID 53377444, $^1$H-NMR spectrum.
Figure 102:
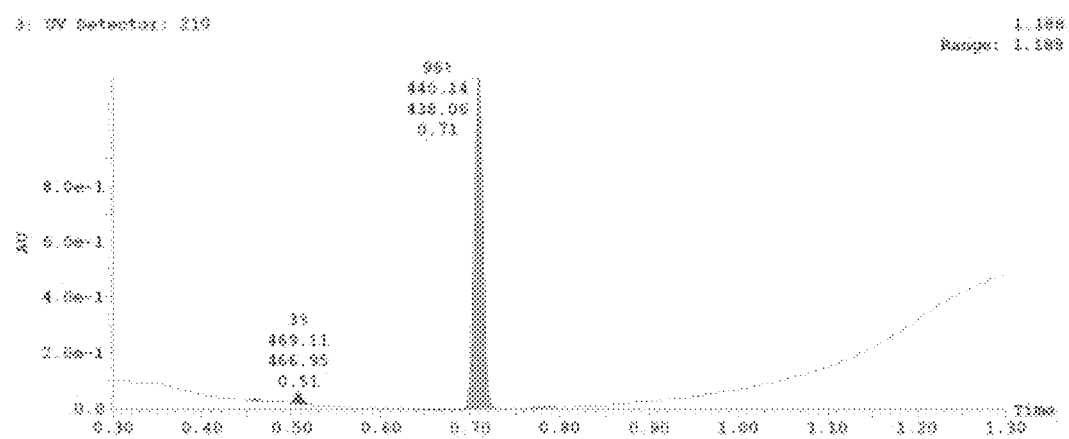
FIG. 102 is a graph showing the chemical characterization data for analog CID 53377444, UPLC-MS chromatogram.
Figure 103:
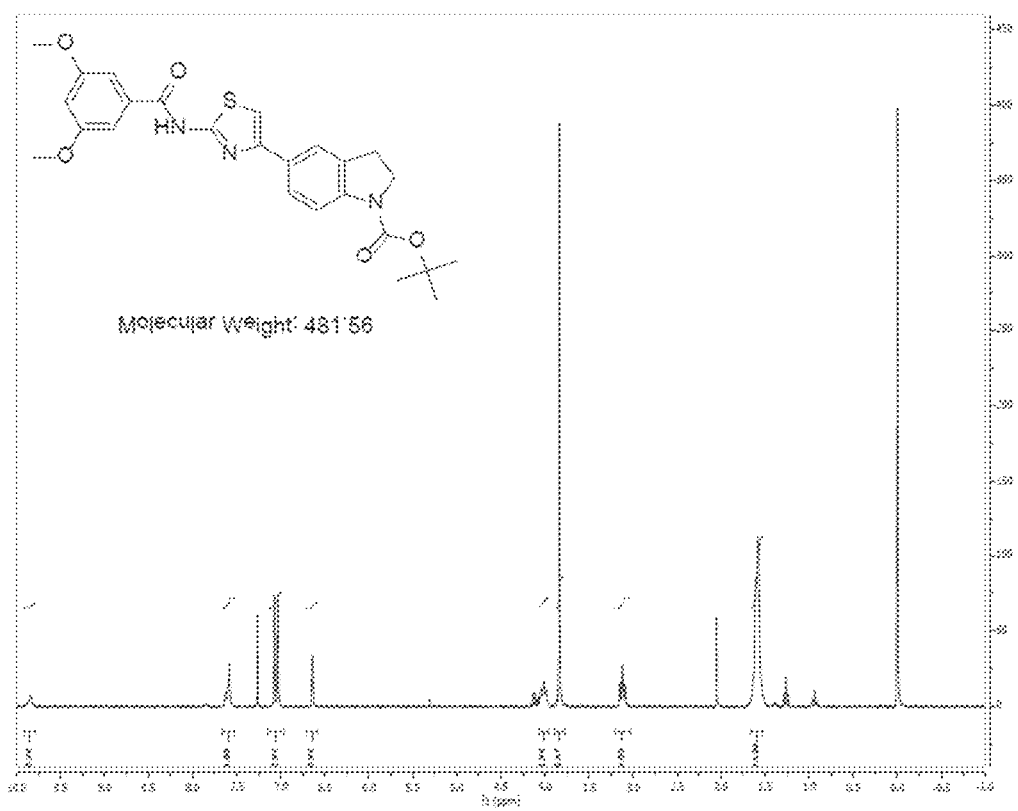
FIG. 103 is a graph showing the chemical characterization data for analog CID 53377409, $^1$H-NMR spectrum.
Figure 104:
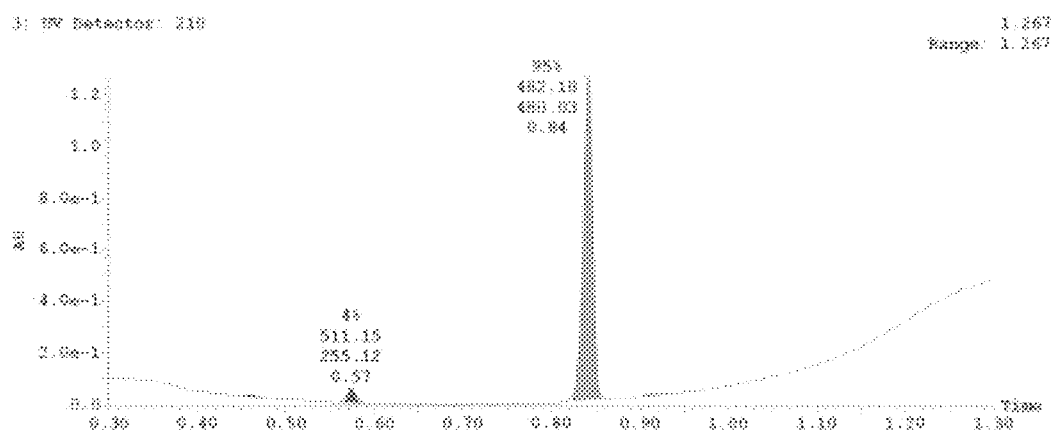
Figure 105:
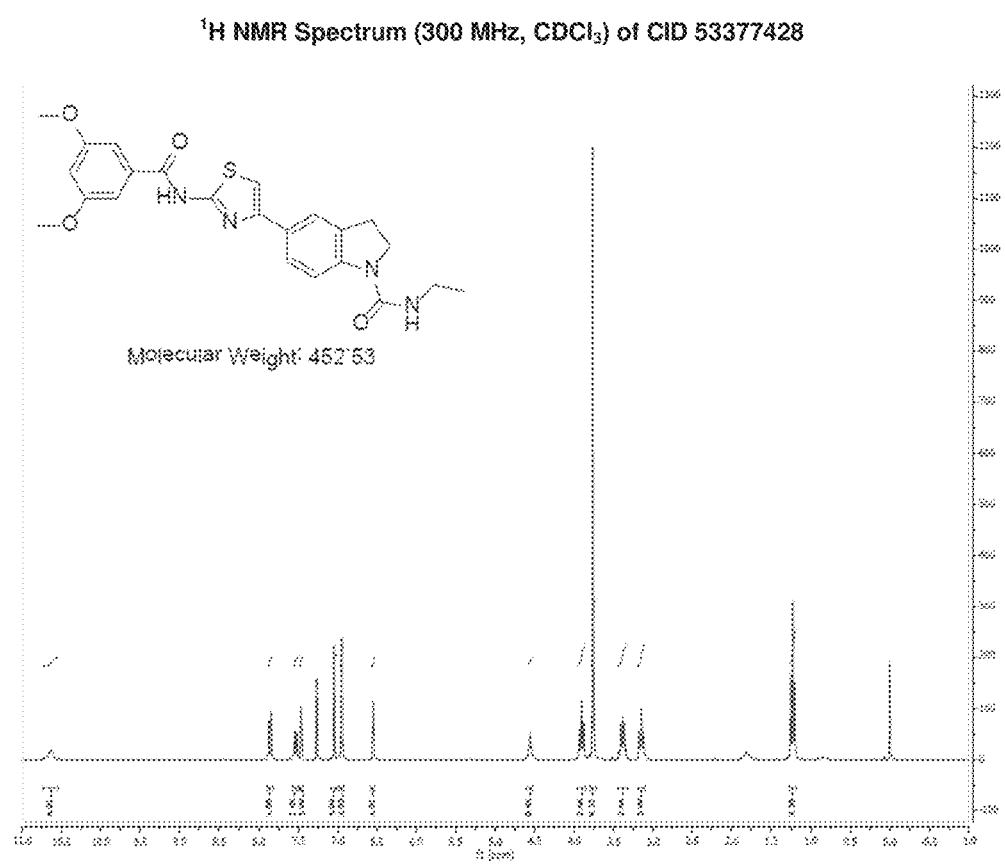
Figure 106:
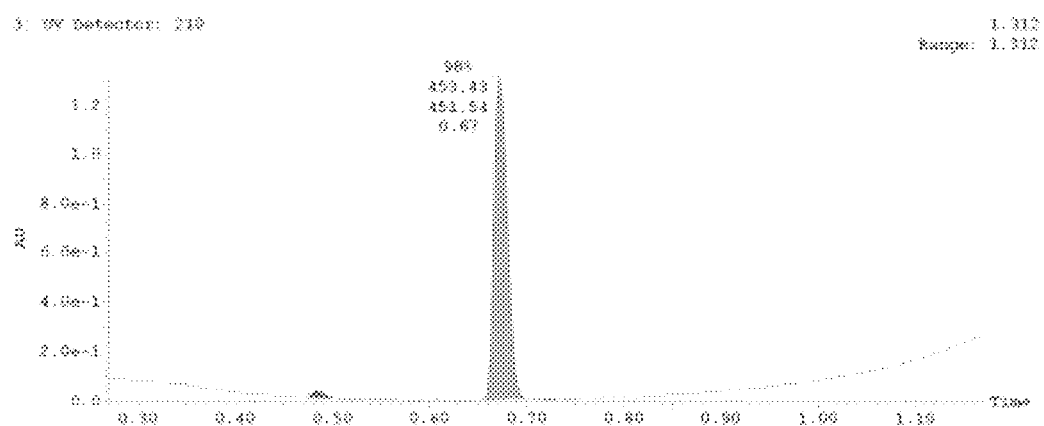

The biological assay data of the probe and analogs are presented in FIGS. 11-16B. Characterization data ($^1$H NMR spectra and UPLC chromatograms) of these analogs are provided in FIGS. 23-106.

The hit compound showed good potency (average $IC_{50}$ for HDL-mediated lipid uptake=0.0057 μM, range=0.00093-0.006 μM). A large number of furan replacements were prepared, allowing the SAR at the western end of the molecule to be explored. This was also a priority due to the possible metabolic and toxicity liabilities presented by the furan. The position of the furan oxygen is critical, as the 3-substituted analog was >150-fold less active. Disappointingly, the racemic tetrahydrofuran also had relatively weak activity, as did the 2-thiophene analog. Introduction of a nitrogen heteroatom into the ring also decreased activity significantly. Certain pyridyl analogs showed moderate activity; the 2-pyridyl analog was insoluble in DMSO and could not be tested. The benzofuran analog showed a drop in activity relative to the hit furan (0.26 μM), though the 7-azabenzofuran showed reasonable potency ($IC_{50}$=0.14 μM). It should be noted that almost all of the compounds in this report showed no significant cytotoxicity at 24 hours.

A representative series of western aryl analogs of the hit compound is presented in the figures. A hydrogen bond acceptor at the 3-position of the benzamide appears to be critical for high potency as the 3-methoxybenzamide was the first analog we observed with activity ($IC_{50}$=0.038 μM) equivalent or superior to the furan. The 3-trifluoromethoxy analog also had decent activity ($IC_{50}$=0.11 μM). Addition of a second methoxy group gave the most potent analog yet prepared ($IC_{50}$=0.033 μM), and we fixed the 3,5-dimethoxybenzamide moiety in order to explore SARs at other parts of the molecule. However, some of these analogs exploring other SARs were prepared before the discovery of the high potency of 3,5-dimethoxybenzamide, therefore some of the entries in the subsequent SAR tables also have the furan substituent at the western portion.

Analogs with modified benzamide moieties were prepared to explore the requirements for the amide functional group. Amide N-methylation reduced the potency >50-fold. Reductive amination of 3,5-dimethoxybenzaldehyde with the 5-substituted 2-aminothiazole (used to prepare all of the analogs thus described) gave a secondary amine, which also had reduced activity. Using numerous multistep synthetic approaches, several replacements for the central thiazole ring were prepared. Oxazole, imidizole, and oxadiazole analogs of the furan hit all poorly inhibited HDL-mediated lipid uptake, indicating that the thiazole is critical for activity. The Boc-protected indoline of the oxadiazole is analogous to a thiazole compound with a Boc group in the same position, which showed outstanding potency. Finally, a 5-methyl thiazole analog (showed good potency ($IC_{50}$=0.040 μM), suggesting that substituted central heterocycles are tolerated and could enable additional modifications in the future.

Next, modifications to the indoline ring were explored (FIG. 15). Removal of the acyl group from the indoline maintained some activity ($IC_{50}$=0.11 μM), but was approximately 3-fold less potent than the analogous propionamide. The related N-unsubstituted indole also showed decreased activity relative to its propionamide derivative ($IC_{50}$=0.10 μM). Several aniline analogs were prepared, which correspond to removal of the bridging ethylene of the indoline system. The 3-methoxybenzamide showed good potency ($IC_{50}$=0.066 μM) demonstrating that the indoline ring is not strictly required for activity. Preliminary results with substituted indolines are very promising, as several 3,3-dimethylindolines showed very good activity ($IC_{50}$=0.008 μM for the 3,5-dimethoxybenzamide analog. Thus, modification of the indoline ring could facilitate attractive new compounds in future medicinal chemistry campaigns.

Figures 16B, 17:
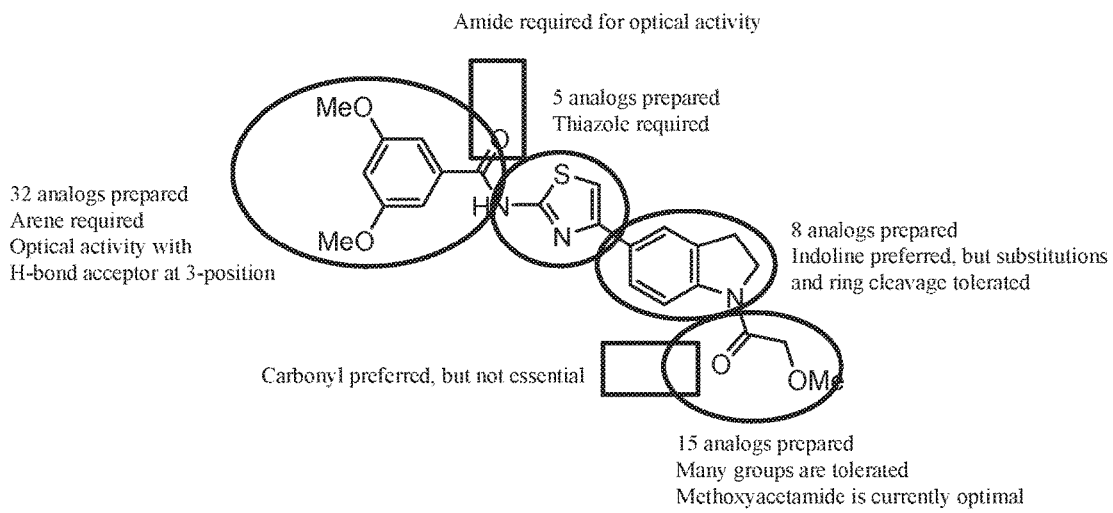
FIG. 16B is a table showing the SAR analysis of probe 1 eastern N-substituent (select analogs (cont'd))
FIG. 17 is a diagram showing the summary of SAR performed.

Finally, the nature of the indoline N-substituent was explored in detail (FIGS. 16A-16B). Removal of the amide oxygen caused the activity to drop off substantially (indole N-propyl analog). Replacement of the ethyl amide substituent with an isopropyl group gave a moderate drop in activity as did the replacement of the amide with a sulfonamide. A variety of other functionalities could also be introduced which maintained or improved activity, including an acetamide (, carbamates, and a urea (. The Boc carbamate was extremely potent ($IC_{50}$=0.9 nM), and is the most potent compound we have tested thus far. Several substituted amides were additionally prepared in an attempt to improve the water solubility of this series (typically <1 μM in PBS). The measured solubilities were surprisingly low, but the methoxy-substituted amide had acceptable solubility (0.57 μM) for a compound with outstanding potency (avg. $IC_{50}$=2 nM), and has been nominated here as the probe (ML278).

The primary assay and several of the secondary assays are cell-based experiments. The compound is active in cells and the effective $IC_{50}$ value for the probe in the primary assay (averaging 0.002 μM over multiple assays and compound batches) is well below the measured PBS solubility (0.57 μM). This inhibition of uptake was confirmed with a non-fluorescent, radiolabeled version of the assay with an average $IC_{50}$ value of 1 μM (AID No. 588836, FIG. 21A). Since SR-BI is a cell-surface receptor (and the compound is presumed to act on the extracellular surface), cell permeability is not an issue, though the probe is expected to have reasonable permeability. ML278 showed no cytotoxicity at 24 hours (FIGS. 19 & 20, AID No. 540326). The precise mode of action for the probe is not known but several supplemental assays suggest a direct interaction with SR-BI. The probe shows no effect on the endocytosis of transferrin, at concentrations up to 35 μM (FIG. 19, AID No. 602134).

Numerous synthetic analogs were prepared and investigated SAR at five different parts of the peptide scaffold (illustrated in FIG. 17), leading to the identification of the probe (ML278). In summary, 62 analogs were prepared and screened, leading to a probe with slightly improved solubility and improved potency (>20-fold) over the original hit. The furan of the hit, which is a potential toxicophore, was also replaced.

FIG. 18 presents a comparison of the activity and selectivity profile of the probe (ML278) with the probe criteria decided upon in the chemical probe development plan (CPDP).

The performance of ML278 was compared with BLT-1, the prior art compound ITX-5061, and another probe ML279. These results are presented in FIGS. 19 and 20. ML278 outperformed both BLT-1 and ITX-5061. BLT-1 is a potent inhibitor of SR-BI-mediated lipid uptake and of free cholesterol efflux. It is a nonreversible covalent modifier of SR-BI and is toxic to cells. In contrast, ML278 is a reversible inhibitor of HDL uptake (AID Nos. 588831, 602154) and shows no cytotoxicity in [ldlA]mSR-BI cells. As discussed earlier, ITX-5061 is an SR-BI inhibitor that is currently in Phase 1b clinical trial for HCV infection. We synthesized ITX-5061 and tested it in multiple assays. In every experiment, ML278 outperformed ITX-5061, with approximately 15-fold higher potency ML278 is also more potent than ML279.

ML278 and selected analogs were tested in several secondary assays that address possible mechanisms of action. In addition to binding of HDL particles and uptake of esterified cholesterol into the cell, SR-BI also plays a role in the efflux of free cholesterol (FC) from the cell to recipient HDL particles. Compounds were tested to determine if there was an impact on efflux from cells. Similar to BLT-1, ML278 reduces efflux of FC from cells by up to 50% during the course of the assay (FIG. 21B). Unlike BLT-1, ML278 was shown to be a reversible inhibitor in the DiI uptake assay. In experiments where cells were pre-treated with compounds for 2 hours, washed with PBS and then incubated with DiI-HDL without compound, ML278 showed no inhibition at the $IC_{50}$ concentration (AID No. 588831) and had an $IC_{50}$ value of 0.3 µM compared to 0.006 µM when compound is present during DiI-HDL exposure (AID No. 588833 versus AID No. 588831). The residual activity of ML278 is likely due to its lipophilic nature, as it we expect it to wash out of cell membranes slowly. In comparison, BLT-1 registers an $IC_{50}$ value of 600 pM after a 4-hour washout period (AID No. 602154), reflecting the progression of its covalent reaction with cysteine 384 of SR-BI (16).

ML278 was tested for efflux in a cell line that only expresses a mutant form of the protein where Cys384 is converted to a serine residue. In this mutant background, BLT-1 does not significantly reduce uptake of HDL or efflux of cholesterol. Conversely, ML278 can reduce uptake and efflux in the mutant background suggesting that the compound might work at a different site on the receptor that does not involve Cys384 (FIG. 21B). However, the comparison between ML278 and BLT-1 is complicated by the fact that ML278 is not a covalent inhibitor. Characterization of BLT-1 as a covalent inhibitor was not made until after the bulk of this project was completed. We also assessed binding of HDL to SR-BI using Alexa-488 labeled HDL particles. Similar to BLT-1, ML278 increases binding of HDL to the receptor. Further studies need to be performed to determine the nature of this tertiary interaction. When comparing the activity of ML278 in the DiI-HDL and radiolabeled versions of the uptake assay there is a large difference in potency ($IC_{50}$ of 0.002 µM and 1 µM, respectively). This is distinct from BLT-1 which shows equal potency in the both uptake assays. This difference may be a result of how ML278 interacts with SR-BI.

ML278 was also tested with SR-BI in purified liposomes. These data suggest a direct interaction between the probe and SR-BI. These data support results in [ldlA7] cells where SR-BI is required for compound activity.

Our initial assays focused on SR-BI relative to cholesterol metabolism. SR-BI also has roles in immunity and acts as a co-receptor for malaria and hepatitis C virus infection. We plan to test ML278 for its ability to reduce or prevent in vitro infection of cells with these two pathogens. Compounds will be tested in collaboration with researchers at the National Institute of Allergy and Infectious Diseases (NIAID) and at the Broad Institute. If activity is found for HCV, in vivo models of HCV infection have been developed. It is important to note that either mouse or human SR-BI can mediate in vivo HCV infection. Therefore, our probe developed for murine SR-BI will likely inhibit the human homologue and may be applicable to preventing human HCV infection.

All reagents and solvents were purchased from commercial vendors and used as received. NMR spectra were recorded on a Bruker 300 MHz or Varian UNITY INOVA 500 MHz spectrometer as indicated. Proton and carbon chemical shifts are reported in parts per million (ppm; δ) relative to tetramethylsilane, $CDCl_3$ solvent, or $d_6$-DMSO ($^1$H δ 0, $^{13}$C δ 77.16, or $^{13}$C δ 39.5, respectively). NMR data are reported as follows: chemical shifts, multiplicity (obs.=obscured, app=apparent, br=broad, s=singlet, d=doublet, t=triplet, m=multiplet, comp=complex overlapping signals); coupling constant(s) in Hz; integration. Unless otherwise indicated, NMR data were collected at 25° C. Flash chromatography was performed using 40-60 µm Silica Gel (60 Å mesh) on a Teledyne Isco Combiflash $R_f$ system. Tandem liquid chromatography/mass spectrometry (LCMS) was performed on a Waters 2795 separations module and Waters 3100 mass detector. Analytical thin layer chromatography (TLC) was performed on EM Reagent 0.25 mm silica gel 60-F plates. Visualization was accomplished with UV light and aqueous potassium permanganate ($KMnO_4$) stain followed by heating. High-resolution mass spectra were obtained at the MIT Mass Spectrometry Facility with a Bruker Daltonics APEXIV 4.7 Tesla Fourier Transform Ion Cyclotron Resonance mass spectrometer. Compound purity and identity were determined by UPLC-MS (Waters, Milford, Mass.). Purity was measured by UV absorbance at 210 nm. Identity was determined on a SQ mass spectrometer by positive electrospray ionization. Mobile Phase A consisted of either 0.1% ammonium hydroxide or 0.1% trifluoroacetic acid in water, while mobile Phase B consisted of the same additives in acetonitrile. The gradient ran from 5% to 95% mobile Phase B over 0.8 minutes at 0.45 ml/min. An Acquity BEH C18, 1.7 µm, 1.0×50 mm column was used with column temperature maintained at 65° C. Compounds were dissolved in DMSO at a nominal concentration of 1 mg/ml, and 0.25 µl of this solution was injected.

Synthesis Details

A detailed description of the synthesis scheme for ML278 is provided below:

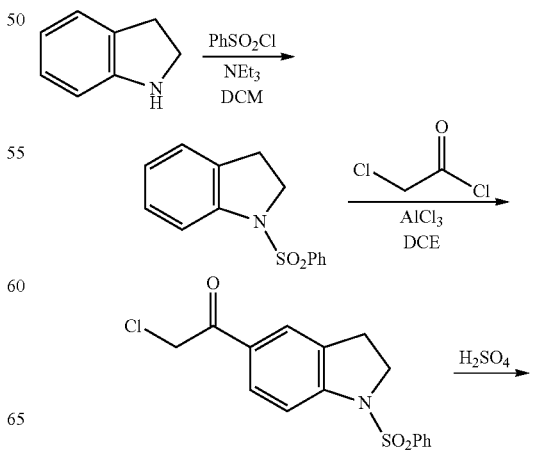

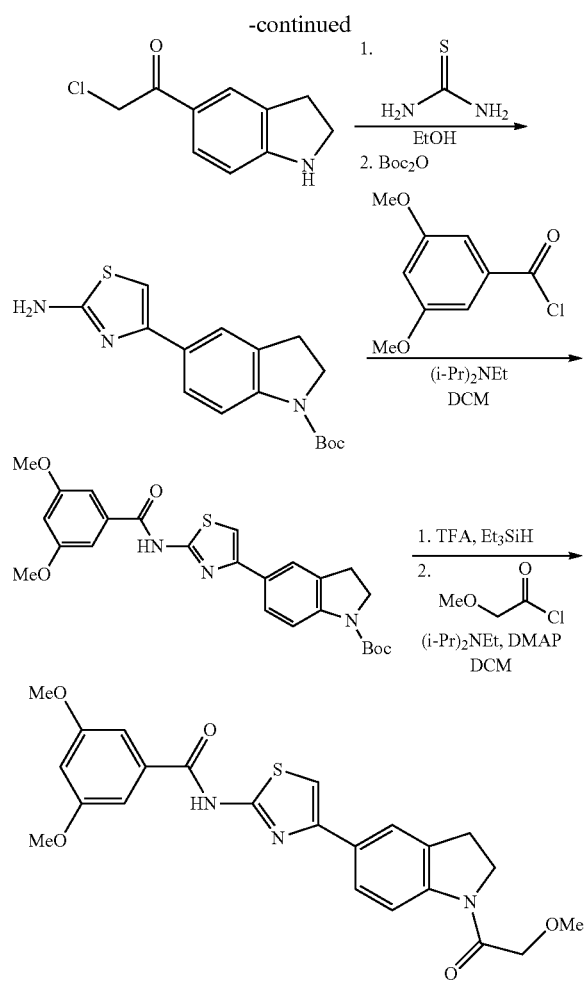

1-(Phenylsulfonyl)indoline

Indoline (1.4 ml, 12.6 mmol) was placed in a round-bottom flask equipped with a magnetic stirbar and dissolved in dichloromethane (42.0 ml). After cooling to 0° C., triethylamine (3.5 ml, 25.2 mmol) was added to the solution, followed by benzenesulfonyl chloride (1.7 ml, 13.3 mmol). The reaction was stirred for 30 minutes while warming to room temperature. Saturated sodium bicarbonate solution (aqueous, 30 ml) was added to quench the reaction. The layers were separated, and the aqueous layer was extracted with dichloromethane (3×25 ml). The combined organics were washed with brine (25 ml), then shaken over magnesium sulfate, filtered, and concentrated under reduced pressure to give a light tan solid. The crude material was purified by column chromatography over silica gel (hexanes/ethyl acetate: 100/0 to 80/20) to give the title compound as a light pink solid (3.00 g, 92%). $^1$H NMR (300 MHz, CDCl$_3$): δ 7.82-7.77 (m, 2H), 7.66 (d, J=8.0 Hz, 1H), 7.55 (t, J=7.4 Hz, 1H), 7.44 (t, J=7.9 Hz, 2H), 7.20 (t, J=7.8 Hz, 1H), 7.08 (d, J=7.4 Hz, 1H), 6.98 (t, J=7.4 Hz, 1H), 3.93 (t, J=8.4 Hz, 2H), 2.89 (t, J=8.4 Hz, 2H); MS (ESI$^+$): 260 (M+H).

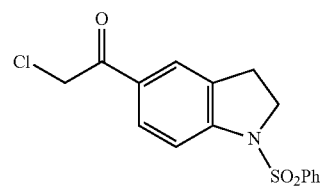

2-Chloro-1-(1-(phenylsulfonyl)indolin-5-yl)ethanone

A round-bottom flask was charged with a magnetic stirbar and anhydrous aluminum chloride (1.70 g, 12.7 mmol) then placed under nitrogen atmosphere. Anhydrous 1,2-dichloroethane (28 ml) was added to produce a pale yellow suspension. Chloroacetyl chloride (1.0 ml, 12.7 mmol) was added slowly by syringe. The mixture was stirred at room temperature for 30 minutes. A solution of 1-(phenylsulfonyl)indoline (3.00 g, 11.6 mmol) in anhydrous 1,2-dichloroethane (8.0 ml) was slowly added to the reaction by syringe. The syringe was rinsed twice with anhydrous 1,2-dichloroethane (3.0 ml), and the rinses were added to the reaction. The reaction, now a dark green mixture, was heated to 50° C. and stirred for 4 hours. Additional portions of aluminum chloride (1.30 g, 9.7 mmol) and chloroacetyl chloride (0.75 ml, 9.5 mmol) were dissolved in anhydrous 1,2-dichloroethane (10 ml) and added to the reaction. After stirring 2 more hours at 50° C., 5 ml of anhydrous 1,2-dichloroethane containing another 0.8 g (6.0 mmol) of aluminum chloride and 0.5 ml (6.4 mmol) of chloroacetyl chloride was added. Stirring at 50° C. was continued for another hour to complete the reaction. The dark red mixture was slowly poured into ice water (approx. 250 ml) and further diluted with dichloromethane (200 ml). The resulting cloudy, orange mixture was stirred while warming to room temperature, after which the layers were separated and the aqueous phase was extracted with dichloromethane (3×100 ml). The combined organic layers were washed with water (100 ml) and brine (100 ml), then shaken over magnesium sulfate, filtered, and concentrated under reduced pressure to give a brown solid (3.91 g). The crude material was purified by column chromatography over silica gel (hexanes/ethyl acetate: 100/0 to 0/100) to give the title compound as a tan solid (3.41 g, 88%). $^1$H NMR (300 MHz, CDCl$_3$): δ 7.87-7.81 (m, 3H), 7.75-7.69 (m, 2H), 7.65-7.57 (m, 1H), 7.54-7.47 (m, 2H), 4.63 (s, 2H), 4.01 (t, J=8.6 Hz, 2H), 3.05 (t, J=8.6 Hz, 2H); MS (ESI$^+$): 336 (M+H).

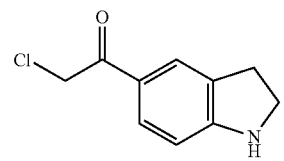 [SMILES: O=C(CCl)c1ccc2c(c1)CCN2]

2-Chloro-1-(indolin-5-yl)ethanone

A microwave tube was charged with a magnetic stirbar and 2-chloro-1-(1-(phenylsulfonyl)indolin-5-yl)ethanone (3.26 g, 9.54 mmol). Concentrated sulfuric acid (9.0 ml) was added, and the resulting suspension was microwaved for 10 minutes at 100° C. The reaction was carefully poured into ice water (500 ml). The dark mixture was stirred while warming to room temperature then treated with 10% (w/v) aqueous sodium hydroxide (approximately 200 ml) until the pH>10. This mixture was then extracted with dichloromethane (3×250 ml). The combined extracts were washed with brine (200 ml), then shaken over magnesium sulfate, filtered, and concentrated under reduced pressure to give a brown solid (1.52 g). This material was used immediately without further purification. $^1$H NMR (300 MHz, CDCl$_3$): δ 7.72 (d, J=1.2 Hz, 1H), 7.69 (dd, J=8.3, 1.6 Hz, 1H), 6.54 (d, J=8.2 Hz, 1H), 4.60 (s, 2H), 3.70 (t, J=8.6 Hz, 2H), 3.09 (t, J=8.6 Hz, 2H); MS (ESI$^+$): 196 (M+H).

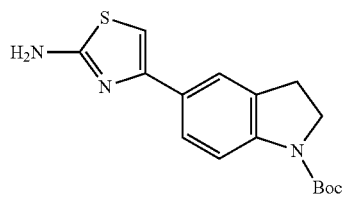 [SMILES: CC(C)(C)OC(=O)N1CCc2cc(-c3csc(N)n3)ccc21]

tert-Butyl 5-(2-aminothiazol-4-yl)indoline-1-carboxylate

2-Chloro-1-(indolin-5-yl)ethanone (1.52 g, 7.75 mmol) was placed in a microwave vial and dissolved in anhydrous ethanol (30.0 ml) to give an opaque, black solution. Thiourea (0.66 g, 8.67 mmol) was added and the resulting mixture was microwaved for 30 minutes at 120° C. 4-(N,N-Dimethylamino)pyridine (95.0 mg, 0.78 mmol) and N,N-diisopropylethylamine (1.5 ml, 9.3 mmol) were added to the reaction mixture. Neat di-tert-butyl dicarbonate (2.0 ml, 8.52 mmol) was added last, and the reaction was stirred at room temperature for 1 hour. The opaque, red-brown mixture was concentrated under reduced pressure to give a red-brown solid. This material was partitioned between water (50 ml) and ethyl acetate (75 ml) and stirred at room temperature until everything dissolved. The layers were separated and the aqueous phase was extracted with ethyl acetate (3×50 ml). The combined organic extracts were shaken over magnesium sulfate, filtered, and concentrated under reduced pressure to give an orange-brown solid. The crude material was purified by column chromatography over silica gel (hexanes/ethyl acetate: 100/0 to 40/60) to give the title compound as an orange solid (1.72 g, 56% over three steps). $^1$H NMR (300 MHz, d$_6$-DMSO): δ 7.61 (s, 1H), 7.60 (d, J=8.1 Hz, 1H), 6.99 (s, 1H), 6.85 (s, 1H), 3.92 (t, J=8.7 Hz, 2H), 3.07 (t, J=8.7 Hz, 2H), 1.51 (s, 9H); MS (ESI$^+$): 318 (M+H).

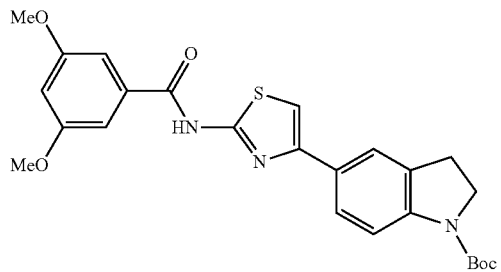 [SMILES: COc1cc(OC)cc(C(=O)Nc2nc(-c3ccc4c(c3)CCN4C(=O)OC(C)(C)C)cs2)c1]

tert-Butyl 5-(2-(3,5-dimethoxybenzamido)thiazol-4-yl)indoline-1-carboxylate

In a round-bottom flask equipped with a magnetic stirbar, tert-butyl 5-(2-aminothiazol-4-yl)indoline-1-carboxylate (0.500 g, 1.58 mmol) was combined with 4-(N,N-dimethylamino)pyridine (19.0 mg, 0.16 mmol). Dichloromethane (4.0 ml) was added to produce an orange suspension that was cooled to 0° C. N,N-Diisopropylethylamine (0.33 ml, 1.89 mmol) was added followed by a solution of 3,5-dimethoxybenzoyl chloride (0.35 g, 1.73 mmol) in dichloromethane (1.00 ml). The bright orange mixture was stirred for 1 hour while warming to room temperature. The resulting clear, red-brown solution was diluted with saturated sodium bicarbonate solution (aqueous, 10 ml) and dichloromethane (10 ml). The layers were separated, and the aqueous phase was extracted with dichloromethane (3×10 ml). The combined organics were washed with brine (10 ml) then shaken over magnesium sulfate, filtered, and concentrated under reduced pressure to give a thick, orange-brown oil. This material was purified by column chromatography over silica gel (hexanes/ethyl acetate: 100/0 to 70/30) to give the title compounds as a light yellow solid (0.51 g, 67%). $^1$H NMR (300 MHz, CDCl$_3$): δ 9.84 (s, 1H), 7.60 (d, J=12.2 Hz, 1H), 7.58 (s, 1H), 7.07 (s, 1H), 7.04 (s, 1H), 7.03 (s, 1H), 6.64 (t, J=2.2 Hz, 1H), 4.01 (t, J=8.7 Hz, 2H), 3.84 (s, 6H), 3.12 (t, J=8.7 Hz, 2H), 1.58 (s, 9H); MS (ESI$^+$): 482 (M+H).

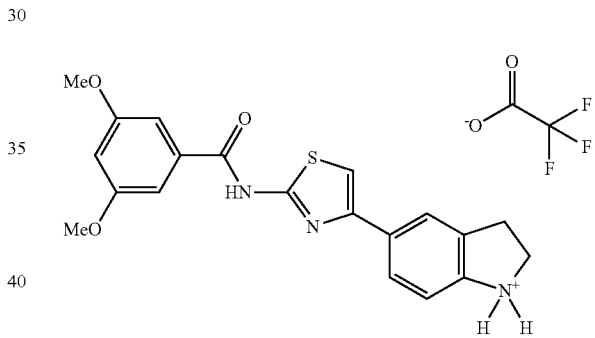

N-(4-(Indolin-5-yl)thiazol-2-yl)-3,5-dimethoxybenzamide, trifluoroacetic acid salt tert-Butyl 5-(2-(3,5-dimethoxybenzamido)thiazol-4-yl) indoline-1-carboxylate (0.38 g, 0.79 mmol) was placed in a round-bottom flask with a magnetic stirbar and dissolved in dichloromethane (5.3 mL) to give a clear, yellow solution. Triethylsilane (1.3 ml, 7.93 mmol) was added followed by 2,2,2-trifluoroacetic acid (1.2 ml, 15.9 mmol), and the reaction quickly turned light orange and produced a gas. The reaction was stirred at room temperature for 1 hour. The light pink reaction was concentrated under reduced pressure to give a rose-colored solid. The crude material was suspended in diethyl ether (10 ml) and filtered. The collected solids were washed with additional diethyl ether and air dried on the filter to give the title compound as light purple solid (0.36 g, 93%). $^1$H NMR (300 MHz, CD$_3$OD): δ 8.05 (s, 1H), 7.99 (d, J=10.0 Hz, 1H), 7.51 (s, 1H), 7.39 (d, J=8.3 Hz, 1H), 7.20 (s, 1H), 7.20 (s, 1H), 6.74 (s, 1H), 3.87 (s, 6H), 3.85 (t, J=7.8 Hz, 2H), 3.35 (t, J=7.7 Hz, 2H); MS (ESI$^+$): 382 (M+H).

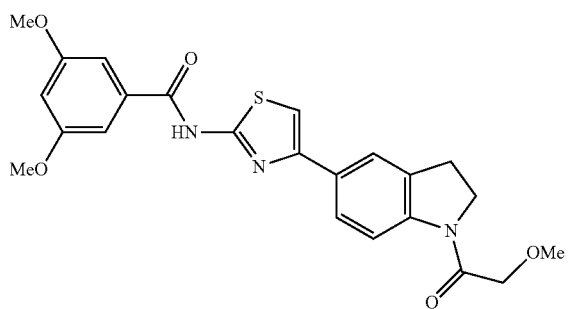 [SMILES: COCC(=O)N1CCc2cc(-c3csc(NC(=O)c4cc(OC)cc(OC)c4)n3)ccc21]

3,5-Dimethoxy-N-(4-(1-(2-methoxyacetyl)indolin-5-yl)thiazol-2-yl)benzamide (PROBE)

A round-bottom flask equipped with a magnetic stirbar was charged with 5-(2-(3,5-dimethoxybenzamido)thiazol-4-yl)indolinium 2,2,2-trifluoroacetate (75.0 mg, 0.15 mmol). Dichloromethane (1.5 ml) was added to produce a purple suspension that was cooled to 0° C. 4-(N,N-Dimethylamino)pyridine (1.8 mg, 0.015 mmol) was added, followed by N,N-diisopropylethylamine (79 µl, 0.45 mmol) to give a clear, dark solution. 2-Methoxyacetyl chloride (15 µl, 0.17 mmol) was added last. The reaction was warmed to room temperature and stirred for 1 hour. The cloudy, tan mixture was diluted with dichloromethane (2 ml) and quenched with saturated sodium bicarbonate (aqueous, 2 ml). The layers were separated, and the aqueous portion was extracted with additional hot ethyl acetate (5×3 ml). The combined organic layers were shaken over magnesium sulfate, filtered, and concentrated under reduced pressure to give a light tan solid. The crude material was purified by column chromatography over silica gel (dichloromethane/methanol: 100/0 to 97/3) to give the title compound as an off-white solid (54.3 mg, 79%). $^1$H NMR (500 MHz, CDCl$_3$): δ 10.14 (s, 1H), 8.23 (d, J=8.3 Hz, 1H), 7.63 (d, J=8.4 Hz, 1H), 7.60 (s, 1H), 7.11 (s, 1H), 7.01 (d, J=1.9 Hz, 3H), 6.61 (t, J=2.0 Hz, 1H), 4.18 (s, 2H), 4.07 (t, J=8.3 Hz, 2H), 3.81 (s, 8H), 3.53 (s, 4H), 3.22 (t, J=8.2 Hz, 2H). $^{13}$C NMR (126 MHz, CDCl$_3$): δ 167.2, 164.6, 161.1, 158.2, 150.0, 142.7, 133.9, 131.4, 130.3, 125.7, 122.2, 117.1, 107.3, 105.2, 105.0, 72.3, 59.4, 55.6, 46.8, 28.2. HRMS (ESI$^+$): calculated for C$_{23}$H$_{24}$N$_3$O$_5$S [M+H]454.1437. found 454.1420.

In Vitro Testing with Cells Infected with HCV

A series of tests were conducted using the compound of Formula II ML278), other known inhibitors of SRB1 and controls with cells infected with hepatitis C virus (HCV). The cells (Huh-7.5 cells infected with Jc1 378-1 TagRFP (MOI=0.1) 3 dpi) were treated with the following SR-BI compounds and controls:

| | |
|---|---|
| SRB1-1—Enantiomer of probe 2 (negative control) | 10 uM |
| SRB1-2—R-154716 | 10 uM |
| SRB1-3—Comparative compound | 1 uM |
| SRB1-4—Comparative compound | 10 uM |
| SRB1-5—Comparative compound | 10 uM |
| SRB1-6—Comparative compound | 10 uM |
| SRB1-7—Probe 1 (ML278) | 0.5 uM |
| SRB1-8—BLT-1 (Irreversible inhibitor of SR-BI) | 1 uM |
| SRB1-9—ITX-5061 | 0.5 uM |
| anti-CD81 | 10 ug/mL |
| anti-SR-BI | 10 ug/mL |

Figure 107:
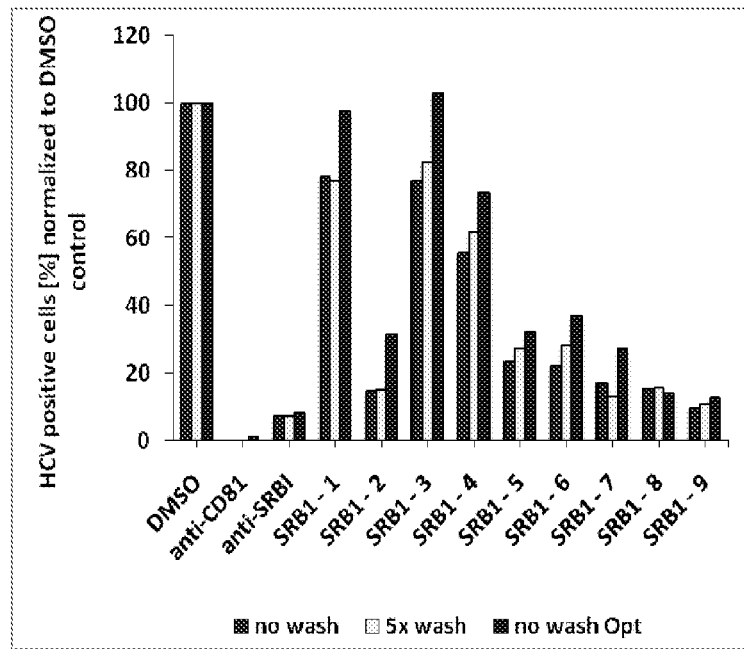
Figure 108:
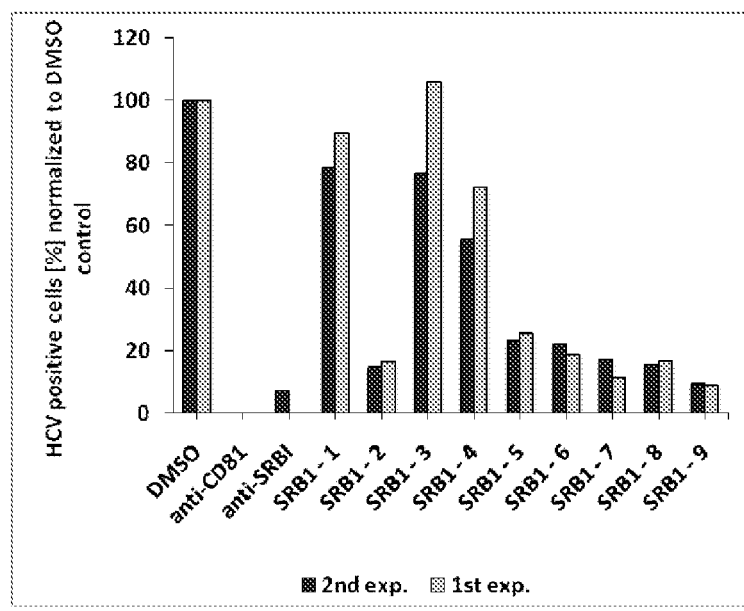

Three different infection protocols were followed: (1) no wash—virus inoculum was removed 4 hpi and fresh medium containing compounds added without washing cells; (2) 5× wash—virus inoculum was removed 4 hpi, cells were washed 5× with PBS and fresh medium containing compounds added; and (3) no wash Opt—infection were performed in serum-free OptiMem; virus inoculum was removed 4 hpi and fresh medium containing compounds added without washing cells. FIG. 107 provides a comparison of the three different infection set-ups. FIG. 108 provides a comparison of two independent experiments. The data indicate that the compound of Formula II (SRB1-7) inhibited viral replication along with SRB1-2, 6, 7, 8 and 9.

Figure 109:
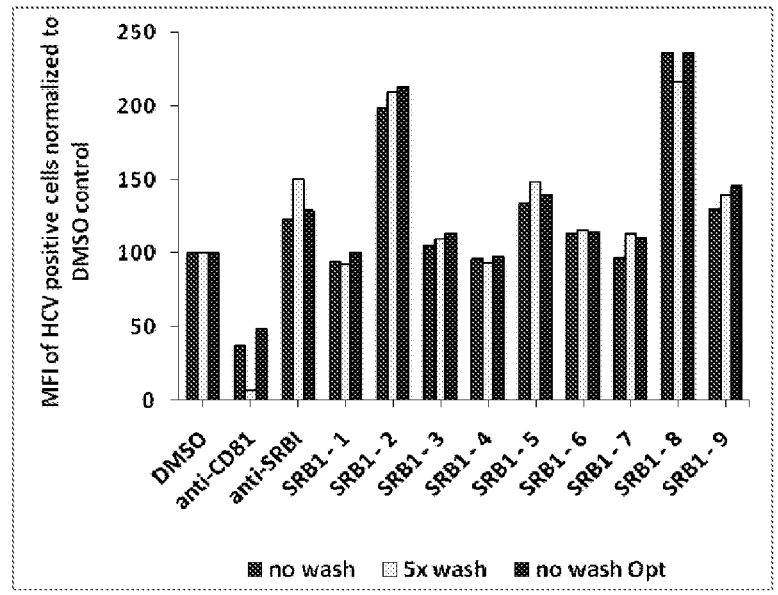
Figure 110:
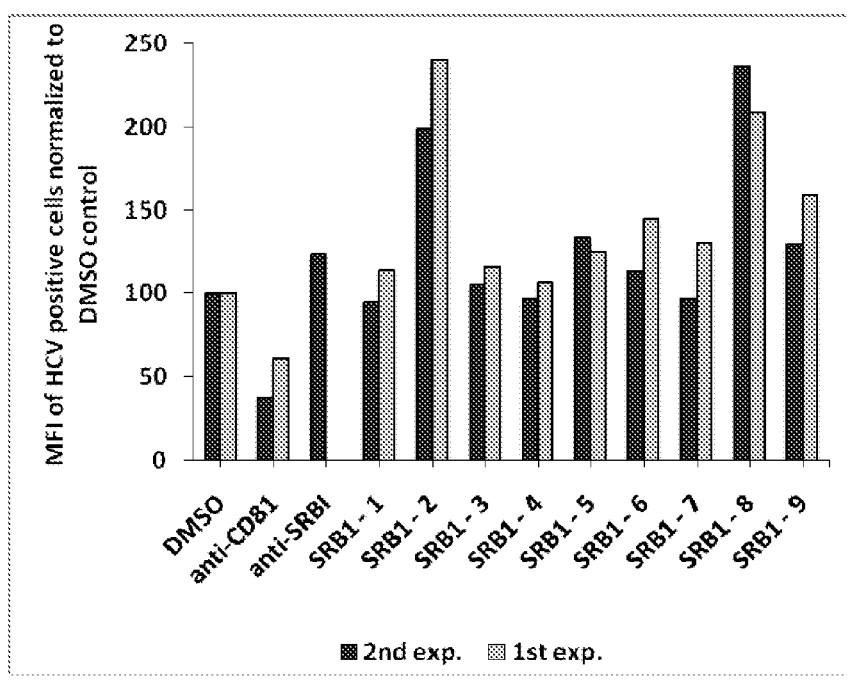

FIGS. 109 and 110 provide another measure of the compound of Formula II (SRB1-7) in terms of fluorescence intensity of HCV positive cells (normalized to a DMSO control). The data show that SRB1-5 can also inhibit virus assembly/egress.

Figure 111:
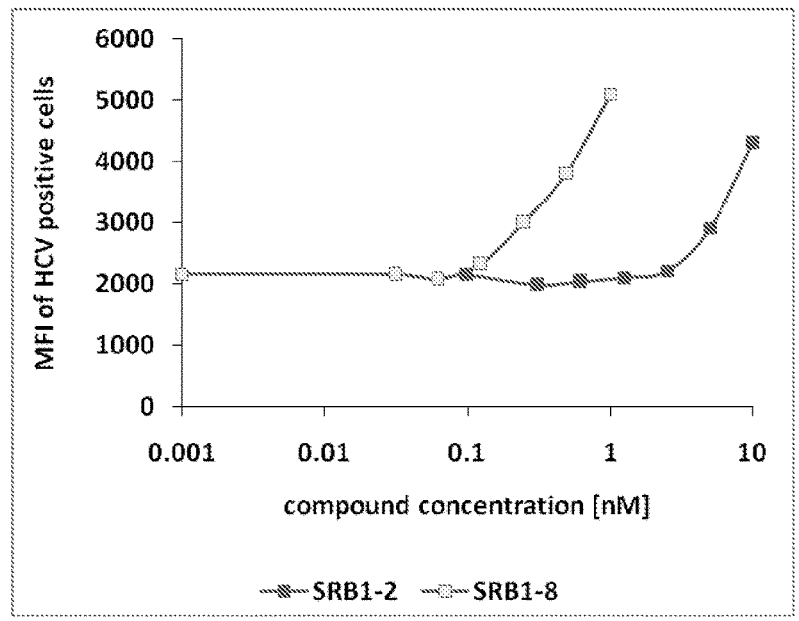
Figure 112:
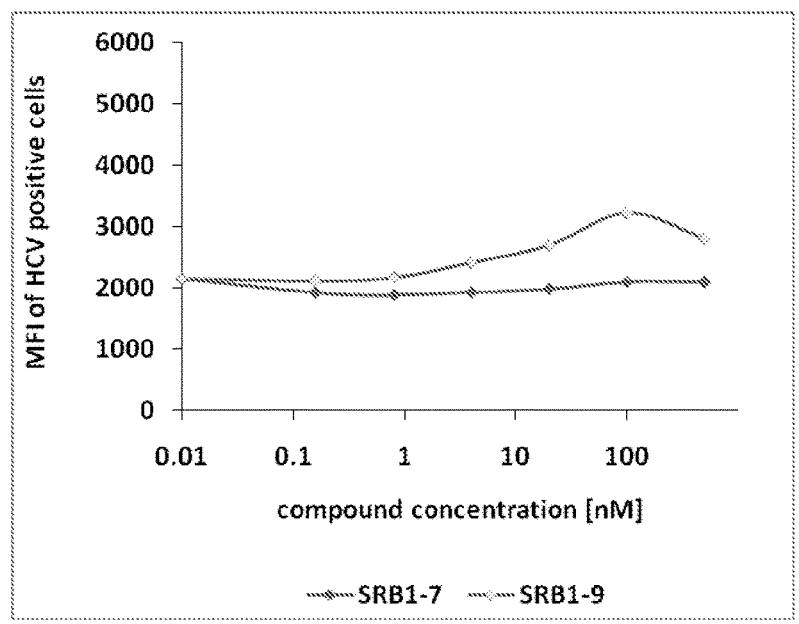

The data also suggest infections performed in serum-free Optimem do not increase compounds potency. FIGS. 111-112 provide dose dependence data for various tested compounds.

The experiments indicate that (1) wash steps to remove virus inoculum post infection does not affect compound's potency nor does performing infections in serum free medium (OptiMEM) enhance compound's viral inhibition and (2) SRBI compounds 2/5/6/7/8/9 were able to inhibit HCV replication. Interestingly, treatment with compounds 2 and 8 resulted in increased mean fluorescence intensity (MFI) of HCV positive cells in a dose dependent manner, which correlated to their inhibitory effect. In contrast, this increase was not seen with other compounds e.g. 7 and 9.

Figure 113:
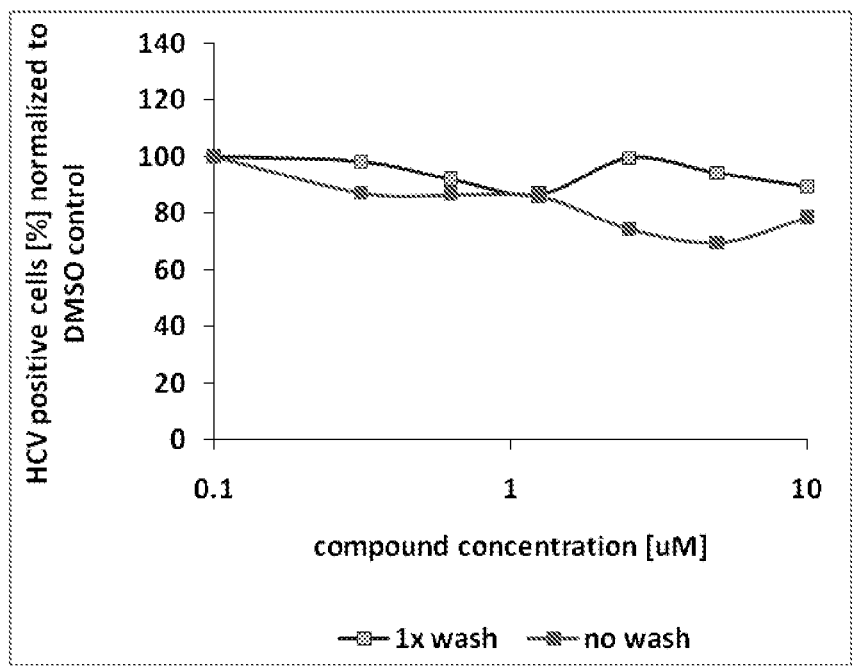
Figure 114:
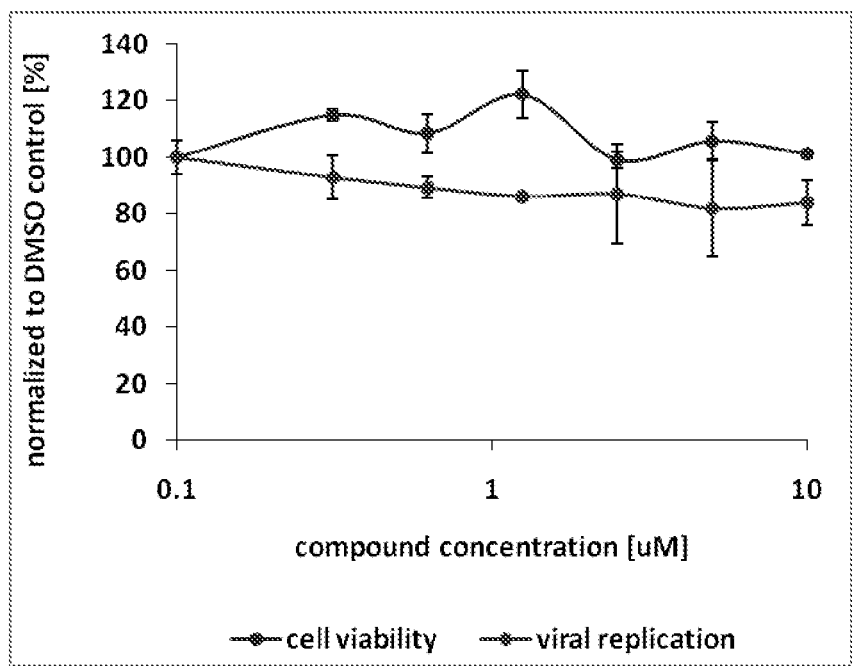
Figure 115:
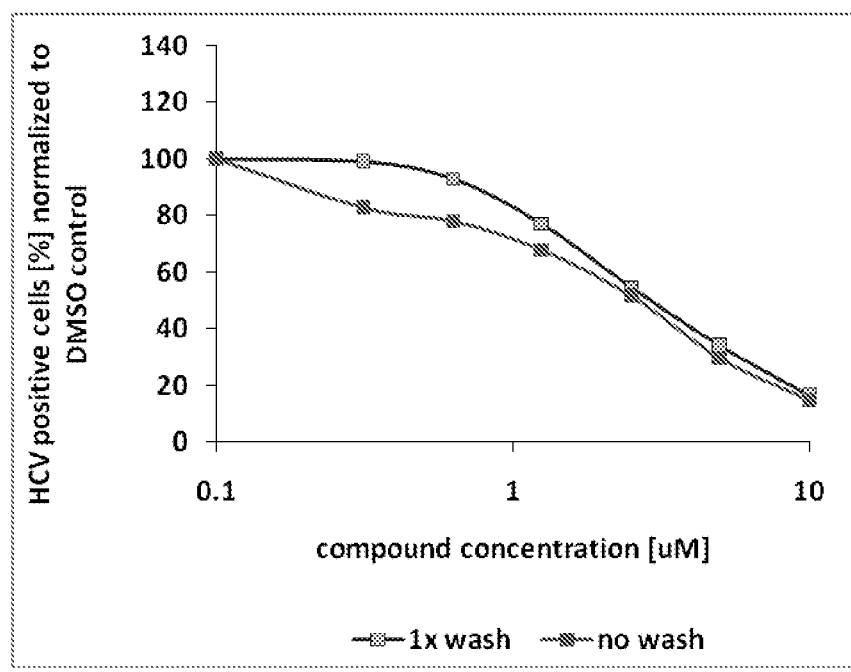

FIGS. 113-114 provide further experimental results for test compound SBR1-1; FIGS. 115-116 provide further experimental results for test compound SBR1-2; FIGS. 117-118 provide further experimental results for test compound SBR1-3; FIGS. 119-120 provide further experimental results for test compound SBR1-4; FIGS. 121-122 provide further experimental results for test compound SBR1-5; FIGS. 123-124 provide further experimental results for test compound SBR1-6; FIGS. 125-126 provide further experimental results for test compound SBR1-7; FIGS. 127-128 provide further experimental results for test compound SBR1-8; and FIGS. 129-130 provide further experimental results for test compound SBR1-9.

FIG. 131 provides tabular data for the effective concentrations (EC$_{50}$ and EC$_{90}$) of each of the tested compositions.

The section headings used herein are for organizational purposes only and are not to be construed as limiting the subject matter described in any way. All patents, patent applications, cited references and any other publications noted herein for whatever reason are specifically incorporated in their entirety by reference. While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:
1. A compound of the formula:

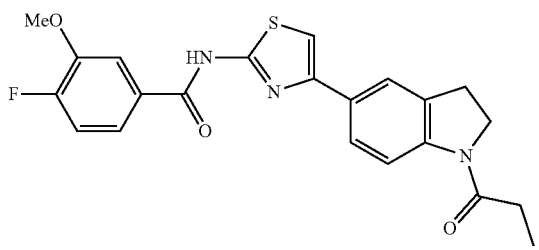 [SMILES: CCC(=O)N1CCc2cc(-c3csc(NC(=O)c4ccc(F)c(OC)c4)n3)ccc21]

or a salt or solvate thereof.

2. A compound of the formula:

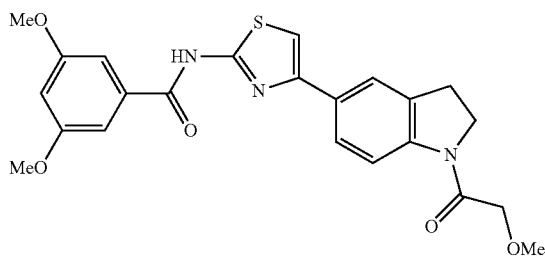 [SMILES: COCC(=O)N1CCc2cc(-c3csc(NC(=O)c4cc(OC)cc(OC)c4)n3)ccc21]

or a salt or solvate thereof.

3. A method of inhibiting Scavenger receptor class B, type I (SR-BI) lipid transport activity comprising exposing said receptor to a compound of the formula

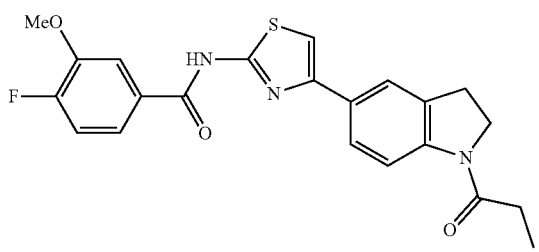 [SMILES: CCC(=O)N1CCc2cc(-c3csc(NC(=O)c4ccc(F)c(OC)c4)n3)ccc21]

or a salt or solvate thereof.

4. A method of inhibiting Scavenger receptor class B, type I (SR-BI) lipid transport activity comprising exposing said receptor to a compound of the formula:

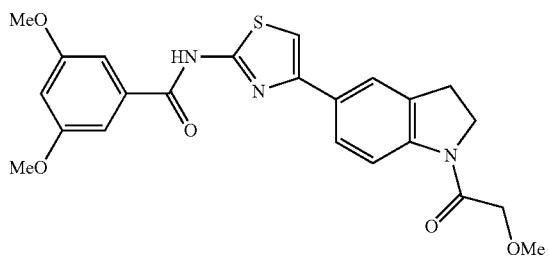 [SMILES: COCC(=O)N1CCc2cc(-c3csc(NC(=O)c4cc(OC)cc(OC)c4)n3)ccc21]

or a salt or solvate thereof.

5. The method of claim 3 or 4, wherein said lipid transport activity is determined by measuring the binding of $^{125}$I-HDL or Alexa-labeled HDL to cells.

6. The method of claim 3 or 4, wherein said method comprises increasing the strength of binding of high-density lipoprotein (HDL) to cells.

7. The method of claim 3 or 4, wherein said method comprises inhibiting SR-BI transport of cholesteryl ester or other lipids from high-density lipoprotein (HDL) into cells expressing SR-BI.

8. The method of claim 3 or 4, wherein said method comprises inhibiting transport of cholesterol or other lipids from cells expressing SR-BI into high-density lipoprotein (HDL).

9. A method of treating a hepatitis C viral infection, comprising administering to a subject in need thereof an effective amount of a compound of the formula:

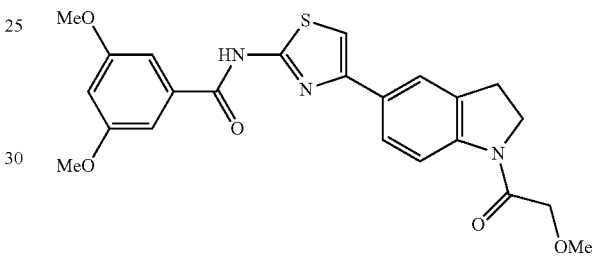

or a salt or solvate thereof.

10. A method of treating a hepatitis C viral infection, comprising administering to a subject in need thereof an effective amount of a compound of the formula:

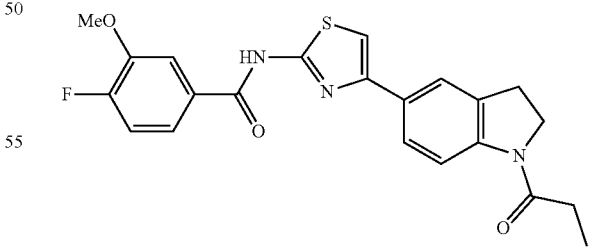

or a salt or solvate thereof.

* * * * *